(12) United States Patent
Blake et al.

(10) Patent No.: US 7,902,373 B2
(45) Date of Patent: Mar. 8, 2011

(54) NICOTINAMIDE DERIVATIVES

(75) Inventors: Tanisha D. Blake, Florissant, MO (US);
Bruce C. Hamper, Kirkwood, MO (US); Wei Huang, Wildwood, MO (US);
James R. Kiefer, Jr., Ballwin, MO (US);
Joseph B. Moon, Saint Louis, MO (US);
Bradley E. Neal, Saint Louis, MO (US);
Kirk L. Olson, Canton, MI (US);
Matthew J. Pelc, Ballwin, MO (US);
Barbara A. Schweitzer, Webster Groves, MO (US); Atli Thorarensen, Dardenne Praire, MO (US); John I. Trujillo, Saint Charles, MO (US);
Steven R. Turner, Labadie, MO (US)

(73) Assignee: Pfizer Inc, New York, NY (US)

( * ) Notice: Subject to any disclaimer, the term of this patent is extended or adjusted under 35 U.S.C. 154(b) by 20 days.

(21) Appl. No.: 11/954,799

(22) Filed: Dec. 12, 2007

(65) Prior Publication Data
US 2008/0146569 A1 Jun. 19, 2008

Related U.S. Application Data

(60) Provisional application No. 60/891,650, filed on Feb. 26, 2007, provisional application No. 60/870,777, filed on Dec. 19, 2006.

(51) Int. Cl.
*A01N 43/40* (2006.01)
*C07D 213/62* (2006.01)
(52) U.S. Cl. ........................................ 546/300; 514/340
(58) Field of Classification Search .................. 514/340; 546/300
See application file for complete search history.

(56) References Cited

U.S. PATENT DOCUMENTS

| | | | |
|---|---|---|---|
| 6,395,753 B1 | 5/2002 | Kodama et al. | 514/318 |
| 2005/0165028 A1 | 7/2005 | Norman et al. | 514/256 |
| 2005/0288286 A1 | 12/2005 | Flynn et al. | 514/235.2 |
| 2006/0100245 A1 | 5/2006 | Bakthavatchalam et al. | 514/332 |

FOREIGN PATENT DOCUMENTS

| | | |
|---|---|---|
| JP | 2004002248 | 1/2004 |
| JP | 2004051600 | 2/2004 |
| JP | 2007051121 | 1/2007 |
| WO | WO 9736901 | 10/1997 |
| WO | WO 9827064 | 6/1998 |
| WO | WO 9827064 | * 8/1998 |
| WO | WO 9918086 | 4/1999 |
| WO | WO 03045912 | 6/2003 |
| WO | WO 2004006956 | 1/2004 |
| WO | WO 2004031180 | 4/2004 |
| WO | WO 2004081005 | 9/2004 |
| WO | WO 2005009539 | 2/2005 |
| WO | WO 2005072681 | 8/2005 |
| WO | WO 2005094805 | 10/2005 |
| WO | WO 2007003934 | 1/2007 |
| WO | WO 2007007778 | 1/2007 |
| WO | WO 2007041634 | 4/2007 |

OTHER PUBLICATIONS

"Bioisosterism: A Rational Approach in Drug Design", Patani et. al., Chem. Rev. 1996, 3147-3176.*
Kosuke Aritake et al., Journal of Biological Chemistry, 281(22), pp. 15277-15286, 2006.
Patani et al., Chem. Rev. 1996, 96, pp. 3147-3176.

* cited by examiner

*Primary Examiner* — Janet L Andres
*Assistant Examiner* — Heidi Reese
(74) *Attorney, Agent, or Firm* — Jennifer A. Kispert; Robert T. Ronau

(57) ABSTRACT

The present invention relates to compounds of formula (I)

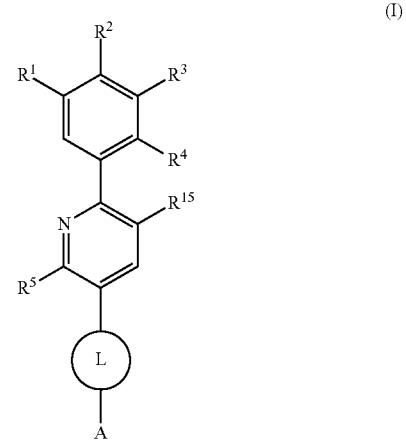

(I)

and pharmaceutically acceptable salts and solvates thereof, wherein the substituents are as defined herein, compositions containing such compounds and the uses of such compounds for the treatment of various diseases and conditions such as asthma.

6 Claims, No Drawings

NICOTINAMIDE DERIVATIVES

The present invention relates to pharmaceutically active compounds which are useful in the treatment of allergic and respiratory conditions and diseases. More particularly, the present invention relates to nicotinamide derivatives, and pharmaceutically acceptable salts and solvates thereof, and their use for treating prostaglandin $D_2$ mediated diseases including, but not limited to, allergic rhinitis, nasal congestion, rhinorrhea, perennial rhinitis, nasal inflammation, asthma of all types, chronic obstructive pulmonary diseases, allergic conjunctivitis, atopic dermatitis and other forms of lung inflammation. The invention also relates to pharmaceutical compositions comprising the nicotinamide derivatives.

Prostaglandin $D_2$ ($PGD_2$) is a metabolite of arachidonic acid. $PGD_2$ promotes sleep, inhibits platelet aggregation, relaxes smooth muscle contraction, induces bronchoconstriction and attracts inflammatory cells including Th2 cells, eosinophils and basophils. Both lipocalin-type PGD synthase (L-PGDS) and hematopoietic PGDS (H-PGDS) convert $PGH_2$ to $PGD_2$.

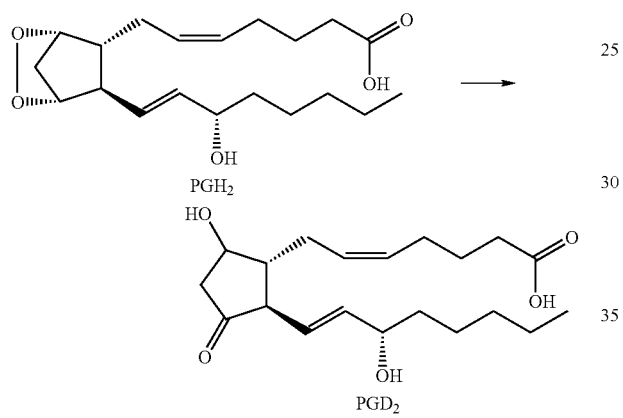

L-PGDS, also known as glutathione-independent PGDS or brain PGDS, is a 26 kDa secretory protein that is expressed by meningeal cells, epithelial cells of the choroid plexus and oligodendrocytes in the brain. L-PGDS secreted into cerebrospinal fluid is thought to be the source of $PGD_2$ in the central nervous system. In addition, epithelial cells in the epididymis and Leydig cells in the testis express L-PGDS and are thought to be the source of $PGD_2$ found in the seminal fluid. L-PGDS belongs to the lipocalin superfamily that consists of lipophilic ligand carrier proteins such as retinol- and retinoic acid-binding proteins.

In contrast, H-PGDS is a 26 kDa cytosolic protein that is responsible for the synthesis of $PGD_2$ in immune and inflammatory cells including mast cells, antigen-presenting cells and Th2 cells. H-PGDS is the only vertebrate member of the sigma class of glutathione S-transferases (GSTs). While both H- and L-PGDS convert $PGH_2$ to $PGD_2$, the mechanism of catalysis and specific activity of the enzymes are quite different.

The production of $PGD_2$ by H-PGDS is thought to play a pivotal role in airway allergic and inflammatory processes and induces vasodilatation, bronchoconstriction, pulmonary eosinophil and lymphocyte infiltration, and cytokine release in asthmatics. $PGD_2$ levels increase dramatically in bronchoalveolar lavage fluid following allergen challenge and the observation that patients with asthma exhibit bronchoconstriction upon inhalation of $PGD_2$ underscores the pathologic consequences of high levels of $PGD_2$ in the lung. Treatment with $PGD_2$ produces significant nasal congestion and fluid secretion in man and dogs, and $PGD_2$ is 10 times more potent than histamine and 100 times more potent than bradykinin in producing nasal blockage in humans, demonstrating a role for $PGD_2$ in allergic rhinitis.

Several lines of evidence suggest that PGDS is an excellent target for allergic and respiratory diseases or conditions. H-PGDS overexpressing transgenic mice show increased allergic reactivity accompanied by elevated levels of Th2 cytokines and chemokines as well as enhanced accumulation of eosinophils and lymphocytes in the lung. In addition, $PGD_2$ binds to two GPCR receptors, DP1 and CRTH2. Antigen-induced airway and inflammatory responses are strongly decreased in DP1-receptor null mice and recent evidence shows that $PGD_2$ binding to CRTH2 mediates cell migration and the activation of Th2 cells, eosinophils, and basophils in vitro and likely promotes allergic disease in vivo. Finally, several published reports link H-PGDS gene polymorphisms with atopic asthma. For example, Aritake et al., Structural and Functional Characterization of HQL-79, and Orally Selective inhibitor of Human Hematopoietic Prostaglandin D Synthase, *Journal of Biological Chemistry* 2006, 281(22), pp. 15277-15286, provides a rational basis for believing that inhibition of H-PGDS is an effective way of treating several allergic and non-allergic diseases.

Compounds have now been found that are effective for treating allergic and respiratory diseases. The compounds are inhibitors of H-PGDS, and at expected efficacious doses, do not significantly inhibit L-PGDS or kinases.

The invention therefore provides a compound of formula (I):

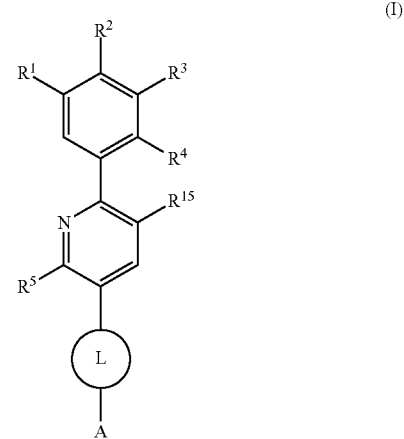

or a pharmaceutically acceptable salt or solvate thereof, wherein:

$R^1$, $R^3$ and $R^4$ are independently H, F, Cl, —$CHF_2$, —$CF_3$, —OH, —$CH_2OH$, —$CH_2CH_2OH$, —C≡N, —$CH_2C$≡N, —$CH_2CH_2C$≡N, $C_1$-$C_5$ alkyl, —C(O)$OR^{16}$, —NC(O)$R^{16}$, —$NSO_2R^{16}$, —C(O)$R^{16}$, or —$OCH_3$;

$R^2$ is H or F;

$R^5$ is H, —$NH_2$, —OH or —$CH_3$;

$R^{15}$ is H, F, Cl, —$CH_3$ or —$OCH_3$;

$R^{16}$ is $C_1$-$C_5$ alkyl;

L is —C(O)NH—, —NHC(O)— or —$CH_2$NHC(O)—;

A is:

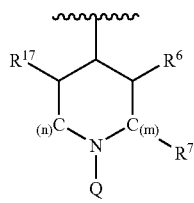

wherein: n is 0 or 1;
m is 0 or 1;
$R^6$ is H or OH and $R^{17}$ is H, or $R^6$ and $R^{17}$ form a bridge across the ring;
$R^7$ is absent when m is 0 and is (—H,—H), =O, (—H,—F) or (—H,—OCH$_3$) when m is 1; or
$R^6$ and $R^7$, where both are present, together with the bonds with which they are attached, form a carbocyclic or heterocyclic ring system such that a bicyclic nitrogen-containing heterocyclic system is formed;
Q is $C_1$-$C_6$ alkyl, —CH$_2$CF$_3$, —C(O)CH$_2$CH$_3$, —C(O)CH$_2$CH$_2$CH$_3$, —C(O)CH(CH$_3$)$_2$, —OCH$_3$, —CH$_2$OCH$_3$ or —CO$_2$CH$_2$CH$_3$, or Q is represented by the formula:

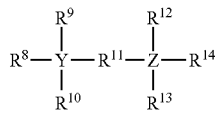

wherein: $R^8$ is a bond, —CH$_2$—, —CH$_2$CH$_2$—, or —CO$_2$CH$_2$CH$_2$—;
Y is a bond, H, $C_3$-$C_7$ cycloalkyl, phenyl, 5-7 membered heterocyclyl or 5-6 membered heteroaryl;
$R^9$ is not present, or $R^9$ is H, F, Cl, =O, =N, —C≡N, —CH$_2$C≡N, —CH$_2$CH$_2$C≡N or $C_1$-$C_6$ alkyl;
$R^{10}$ is not present, or $R^{10}$ is H, F, Cl, Br, —NH$_2$, —CH$_3$, —CH$_2$CH$_3$, —CF$_3$, —OH, —OCH$_3$, —OCH(CH$_3$)$_2$, —CH$_2$OCH$_3$, —C(O)NH$_2$, =O, —CO$_2$CH$_2$CH$_3$, —NHCH$_2$CH$_2$OH, —NHCO$_2$CH$_3$, —NHCO$_2$CH$_2$CH$_3$, —NHCO$_2$C(CH$_3$)$_2$CH$_3$, —N(CH$_3$)$_2$, or heteroaryl substituted with methyl;
$R^{11}$ is not present or $R^{11}$ is a bond, H, —CH$_2$—, —NH—, —CH$_2$CH$_2$—, —OCH$_2$—, —CO—, —CO$_2$CH$_2$CH$_2$—, —C(O)NH—, —C(O)NHCH$_2$—, —C(O)NHCH$_2$CH$_2$—, —NHCO$_2$—, —NHCO$_2$CH$_2$—, —NHCO$_2$CH$_2$CH$_2$— or —NHCO$_2$C(CH$_3$)$_2$CH$_2$—;
Z is not present, or Z is a bond, H, $C_1$-$C_3$ alkyl, $C_3$-$C_7$ cycloalkyl, phenyl, 5-7 membered heterocyclyl or 5-6 membered heteroaryl;
$R^{12}$ is not present, or $R^{12}$ is H, F, Cl, —CH$_3$, —CH$_2$CH$_3$, —OCH$_3$, —CO$_2$CH$_2$CH$_3$, —NHCO$_2$CH$_3$, —NHCO$_2$CH$_2$CH$_3$ or —NHCO$_2$C(CH$_3$)$_2$CH$_3$;
$R^{13}$ is not present, or $R^{13}$ is H, F, Cl, —CH$_3$, —CH$_2$CH$_3$, —OCH$_3$, —CO$_2$CH$_2$CH$_3$—NHCO$_2$CH$_3$, —NHCO$_2$CH$_2$CH$_3$ or NHCO$_2$C(CH$_3$)$_2$CH$_3$;
$R^{14}$ is not present, or $R^{14}$ is H, =O, —OH, $C_1$-$C_6$alkyl, —CH$_3$, —CF$_3$, —OCH$_3$, —OCH$_2$CH$_3$, —OCH(CH$_3$)$_2$, —O(CH$_2$)$_2$OH, —CO$_2$CH$_2$CH$_3$, F, Cl, Br, =N, —C≡N, —N(CH$_3$)$_2$, —C(O)CH$_3$, —C(O)NH$_2$, —CH$_2$CH$_2$OH, —C(O)NHCH$_3$, —C(O)N(CH$_3$)$_2$, ($C_1$-$C_3$)alkylsulfonyl, aminosulfonyl, ($C_1$-$C_3$)alkylaminosulfonyl, 2-methylbutanolyl, 1-methoxy-2-methyl butanyl, 2-methylhex-5-ene-2-yl, —N(CH$_3$)$_2$, N-ethyl-N-methylethanaminyl, 5-6 membered cycloalkyl, 5-7 membered heterocyclyl, 5-6 membered heteroaryl or phenyl, wherein each cyclic system is optionally substituted with H, —CH$_3$, or —C≡N, and wherein when $R^{14}$ is cycloalkyl, heterocyclyl, phenyl or heteroaryl, and when Z is a cycloalkyl, heterocyclyl, phenyl or heteroaryl, $R^{14}$ and Z may form a bicyclic ring system,
and wherein when Y is a cyclic system and $R^{11}$ and is not present, Y and Z may form a saturated, partially unsaturated or aromatic bicyclic carbocyclic or heterocyclic ring system or a saturated, partially unsaturated or aromatic spiro-fused carbocyclic or heterocyclic ring system;

with the proviso that the compound is not ethyl 4-{[(2-methyl-6-phenylpyridin-3-yl)carbonyl]amino}piperidine-1-carboxylate.

A preferred compound of formula (I) is a compound of formula (Ia):

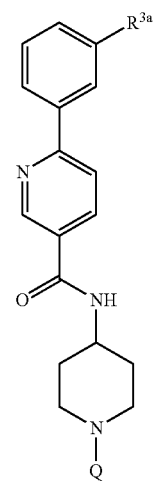

(Ia)

or a pharmaceutically acceptable salt thereof, wherein:
$R^{3a}$ is H or F; and
Q is —CH$_2$CF$_3$ or 5-(morpholin-4-ylcarbonyl)pyridin-2-yl.

In an embodiment of the present invention, a compound of formula (Ia) is provided wherein $R^{3a}$ is H and Q is —CH$_2$CF$_3$.

In another embodiment of the present invention, a compound of formula (Ia) is provided wherein $R^{3a}$ is F and Q is —CH$_2$CF$_3$.

In another embodiment of the present invention, a compound of formula (Ia) is provided wherein $R^{3a}$ is F and Q is 5-(morpholin-4-ylcarbonyl)pyridin-2-yl.

In another embodiment of the present invention, a compound of formula (Ia) is provided wherein $R^{3a}$ is H and Q is 2-(5-morpholine-4-carbonyl)pyridinyl-2-yl.

Referring to a compound of formula (I), Q is preferably $C_1$-$C_6$ alkyl, —CH$_2$CF$_3$, —C(O)CH$_2$CH$_3$, —C(O)CH$_2$CH$_2$CH$_3$, —C(O)CH(CH$_3$)$_2$, —OCH$_3$, —CH$_2$OCH$_3$, —CO$_2$CH$_2$CH$_3$, —(CH$_2$)$_r$-A$^1$, —(CH$_2$)$_r$-A$^1$—B, —(CH$_2$)$_r$-A$^1$—B-A$^2$ or —(CH$_2$)$_r$—CO-A$^1$, wherein:

A$^1$ is (a) phenyl; (b) naphthyl; (c) a five-membered aromatic heterocyclic group containing either (i) 1-4 nitrogen atoms or (ii) 0-3 nitrogen atoms and 1 oxygen or 1 sulphur atom; (d) a six-membered aromatic heterocyclic group containing 1-3 nitrogen atoms; (e) a nine-membered bicyclic aromatic heterocyclic group containing either (i) 1-5 nitrogen atoms or (ii) 0-4 nitrogen atoms and 1 oxygen or 1 sulphur atom; (f) a ten-membered bicyclic aromatic heterocyclic group containing 1-6 nitrogen atoms; (g) a five- or six-membered saturated or partially unsaturated heterocyclic group containing one or two nitrogen or oxygen groups; (h) a $C_3$-$C_6$ cycloalkyl or cycloalkenyl group, optionally benzo-fused; each of said groups (a)-(h) being optionally substituted by one or more of $C_1$-$C_6$ alkyl, $C_1$-$C_6$ fluoroalkyl, $C_3$-$C_6$ cycloalkyl, hydroxy($C_3$-$C_6$ cycloalkyl), $C_1$-$C_6$ alkenyl, —$(CH_2)_p$OH, —$(CH_2)_p$CN, halo, oxo, —$(CH_2)_p$NR$^{18}$R$^{19}$, —$(CH_2)_p$CONR$^{18}$R$^{19}$, —$(CH_2)_p$OR$^{18}$, —$(CH_2)_p$COR$^{18}$ and —$(CH_2)_p$COOR$^{18}$, wherein p is 0-3 and R$^{18}$ and R$^{19}$ are each H or $C_1$-$C_6$ alkyl optionally substituted with —OH or $C_1$-$C_6$ alkoxy;

r is 0 or 1;

B is $C_1$-$C_6$ alkylene or $C_1$-$C_6$ cycloalkylene, wherein one or two —$CH_2$— groups of said $C_1$-$C_6$ alkylene or $C_1$-$C_6$ cycloalkylene may each be replaced with a group independently selected from —NH—, —CO— and —O—;

A$^2$ is (a) phenyl; (b) naphthyl; (c) a five-membered aromatic heterocyclic group containing either (i) 1-4 nitrogen atoms or (ii) 0-3 nitrogen atoms and 1 oxygen or 1 sulphur atom; (d) a six-membered aromatic heterocyclic group containing 1-3 nitrogen atoms; (e) a nine-membered bicyclic aromatic heterocyclic group containing either (i) 1-5 nitrogen atoms or (ii) 0-4 nitrogen atoms and 1 oxygen or 1 sulphur atom; (f) a ten-membered bicyclic aromatic heterocyclic group containing 1-6 nitrogen atoms; (g) a five- or six-membered saturated or partially unsaturated heterocyclic group containing one or two nitrogen or oxygen groups; (h) a $C_3$-$C_6$ cycloalkyl or cycloalkenyl group, optionally benzo-fused; each of said groups (a)-(h) being optionally substituted by one or more of $C_1$-$C_6$ alkyl, $C_1$-$C_6$ fluoroalkyl, $C_3$-$C_6$ cycloalkyl, hydroxy($C_3$-$C_6$ cycloalkyl), $C_1$-$C_6$ alkenyl, —$(CH_2)_p$OH, —$(CH_2)_p$CN, halo, —$(CH_2)_p$NR$^{18}$R$^{19}$, —$(CH_2)_p$CONR$^{18}$R$^{19}$, —$(CH_2)_p$OR$^{18}$, —$(CH_2)_p$COR$^{18}$ and —$(CH_2)_p$COOR$^{18}$, wherein p is 0-3 and R$^{18}$ and R$^{19}$ are each H or $C_1$-$C_6$ alkyl optionally substituted with —OH or $C_1$-$C_6$ alkoxy;

Compounds in which Q is —$(CH_2)_r$-A$^1$, optionally substituted as described above, are particularly preferred, especially where r is 0. For example, Q may be optionally substituted tetrazolyl, such as ($C_1$-$C_6$ alkyl)tetrazolyl. More specifically Q may be methyltetrazolyl such as 1-methyltetrazol-5-yl.

In general, suitable choices for Q include isopropyl, (trifluoromethyl)methyl, 1-oxo-butan-1-yl, ethoxycarbonyl and the following (Me=methyl, Et=ethyl):

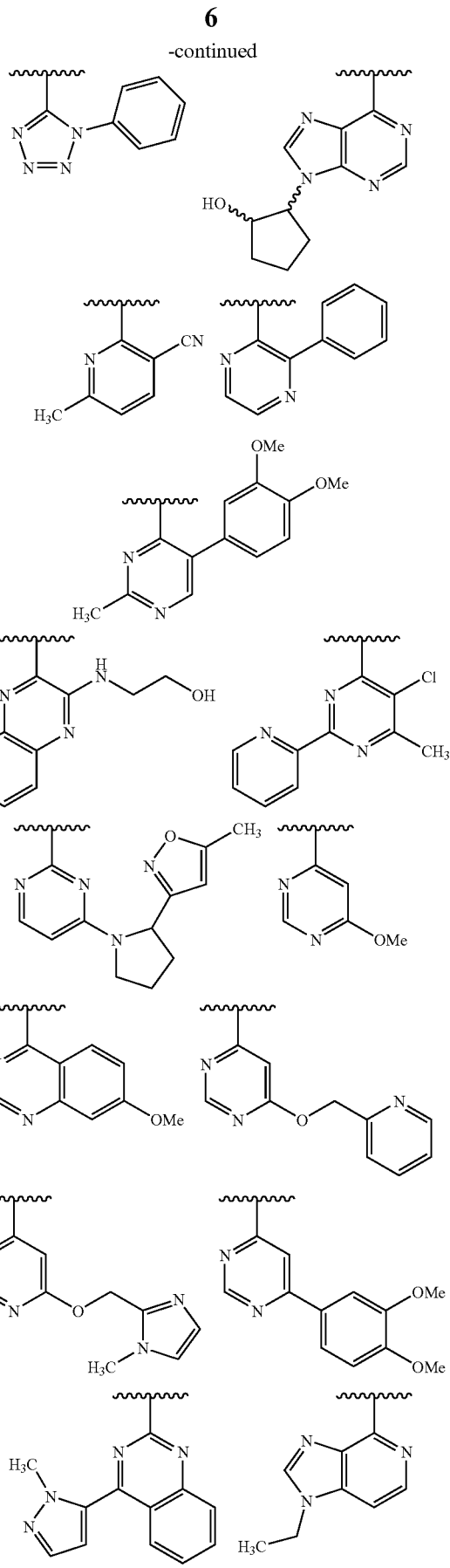

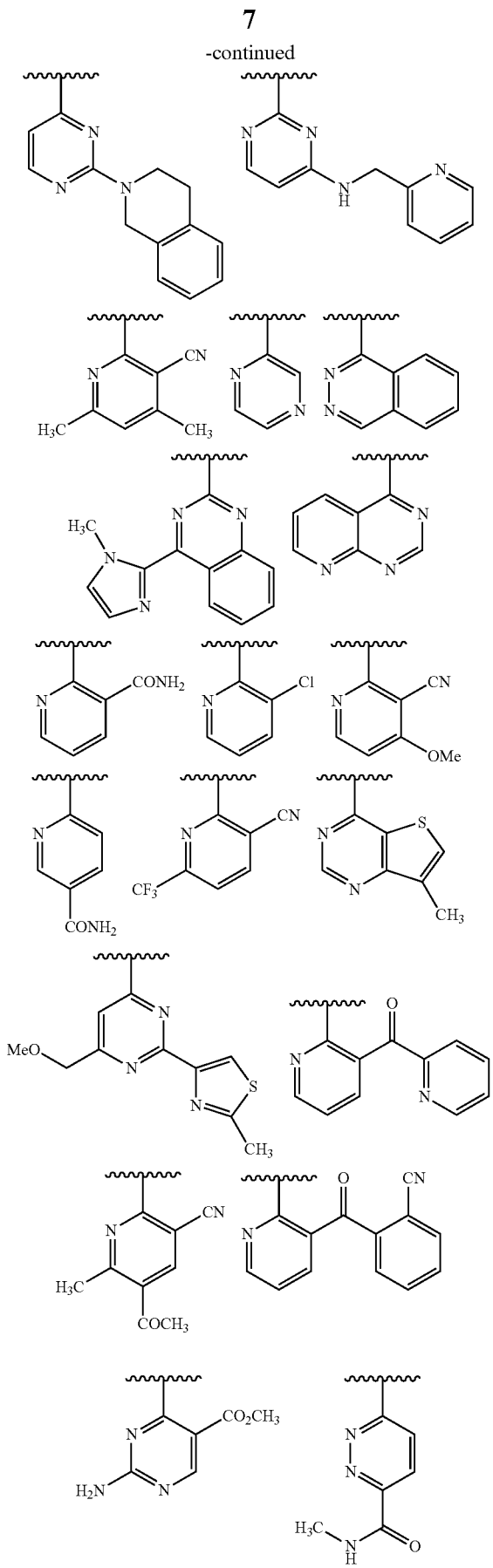
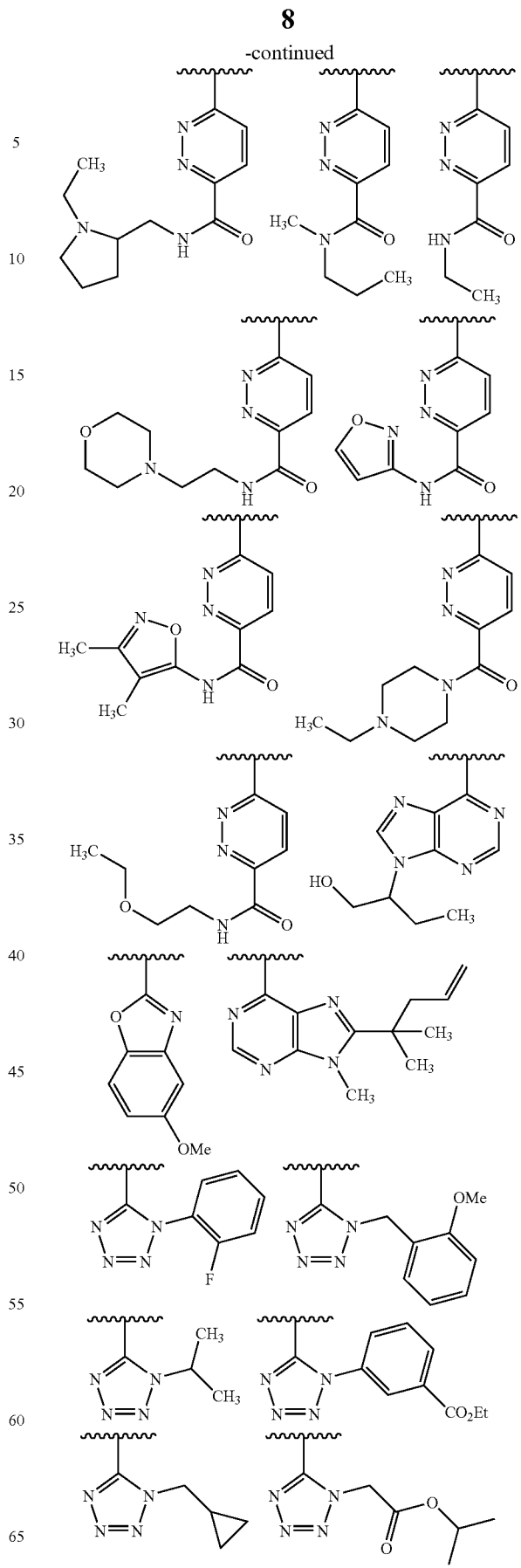

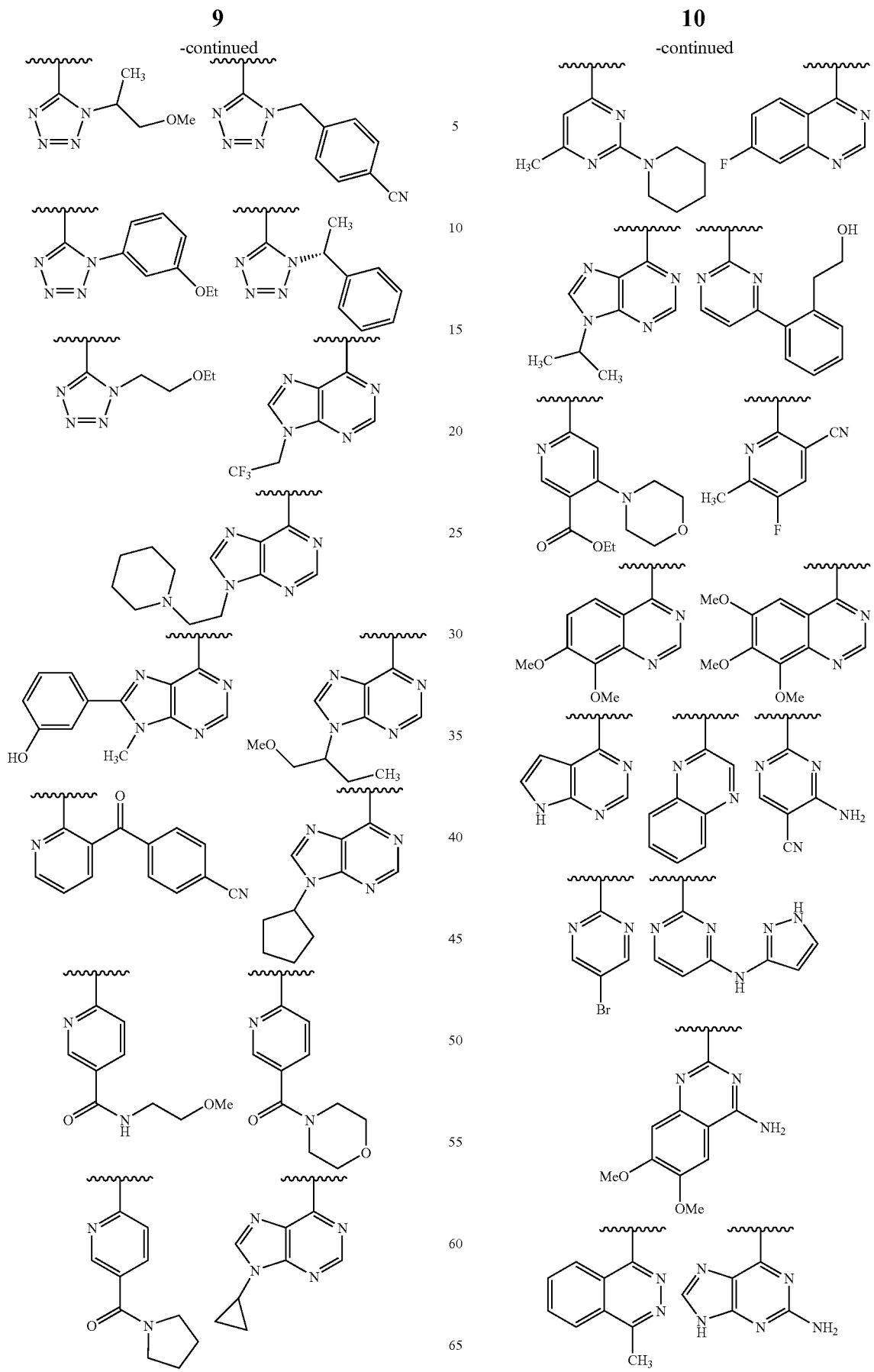

-continued
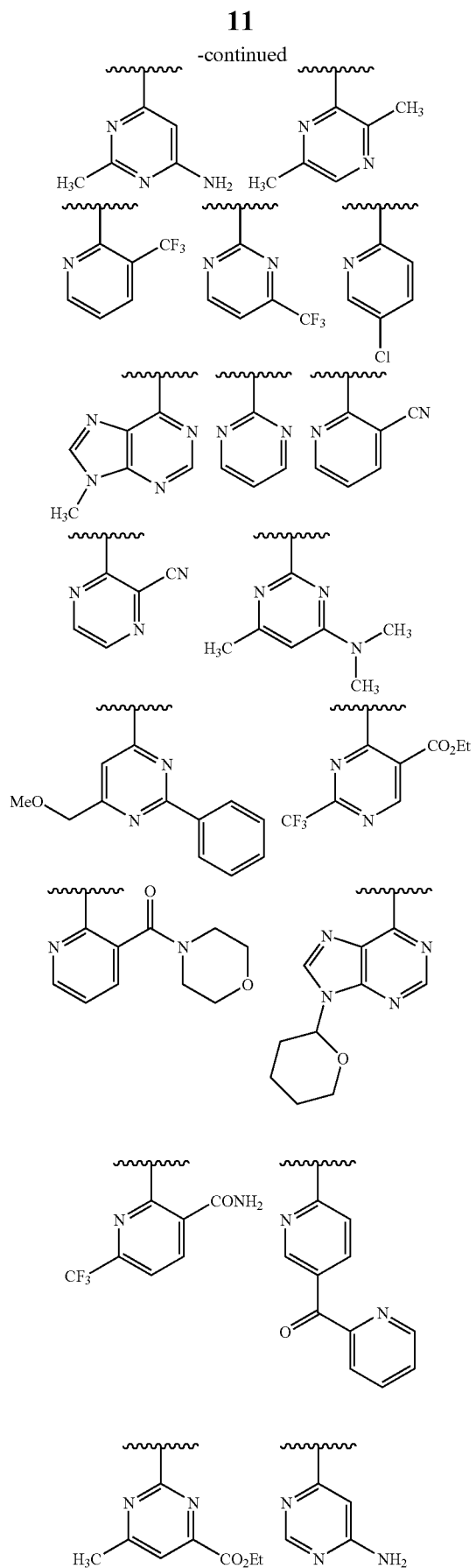
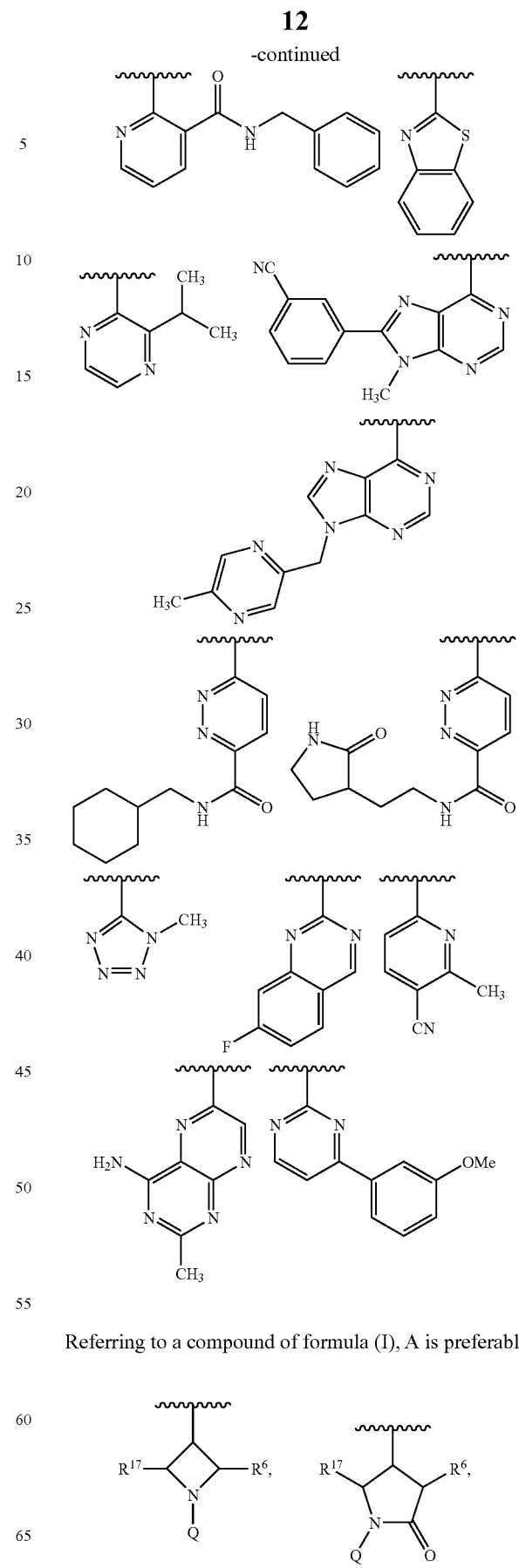
Referring to a compound of formula (I), A is preferably:
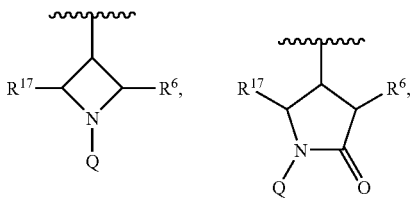

-continued

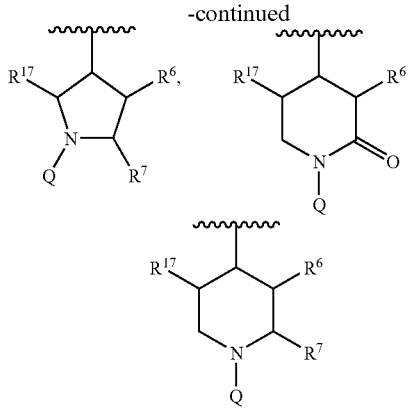

wherein: R⁶ is H or OH and R¹⁷ is H, or R⁶ and R¹⁷ form a zero, one or two carbon bridge (preferably a zero carbon bridge) across the ring; and
R⁷ is H; or
R⁶ and R⁷, where both are present, together with the bonds with which they are attached, form a carbocyclic or heterocyclic ring system such that a bicyclic nitrogen-containing heterocyclic system is formed.

Most preferably, A is:

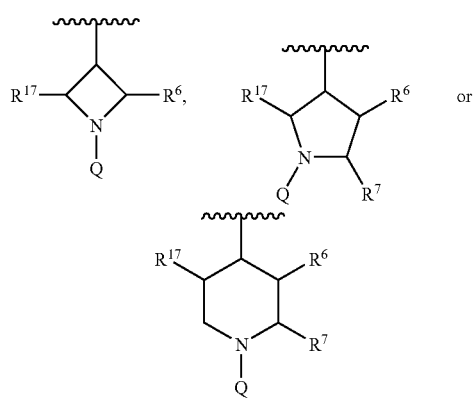

wherein: R⁶ is H and R⁷ is H, or R⁶ and R¹⁷ form a zero, one or two carbon bridge (preferably a zero carbon bridge) across the ring; and
R⁷ is H.

In one embodiment, the invention provides a compound of formula (I), or a pharmaceutically acceptable salt or solvate thereof, in which Q is represented by the formula:

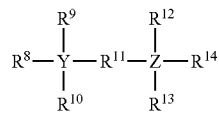

wherein R⁸, R⁹, R¹⁰, R¹¹, R¹², R¹³, R¹⁴, Y and Z are as defined above.

In another embodiment, the invention provides a compound of Formula (I), or a pharmaceutically acceptable salt or solvate thereof, in which A, L, R², R⁵ and R¹⁵ are as defined above and R¹, R³ and R⁴ are independently H, F, Cl, CHF₂, CF₃, or OH. In a preferred aspect of this embodiment, Q is represented by the formula:

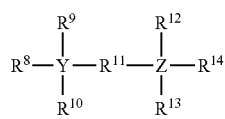

wherein R⁸, R⁹, R¹⁰, R¹¹, R¹², R¹³, R¹⁴, Y and Z are as defined above.

In another embodiment, the invention provides a compound of Formula (III):

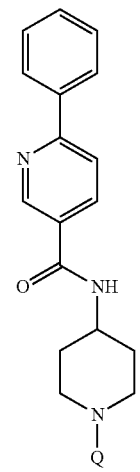

(III)

or a pharmaceutically acceptable salt or solvate thereof, wherein Q is as defined above for a compound of formula (I).

In a preferred group of compounds of formula (III), Q is:

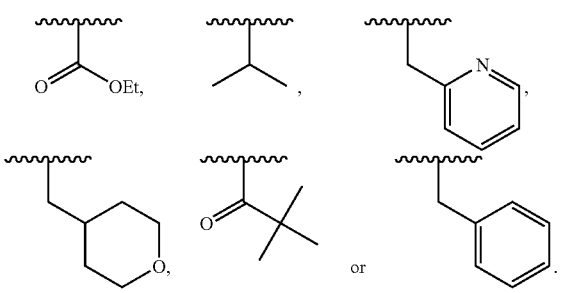

In another embodiment, the invention provides a compound of Formula (IV):

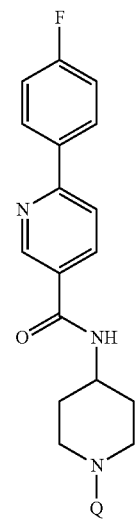

(IV)

or a pharmaceutically acceptable salt or solvate thereof, wherein Q is as defined above for a compound of formula (I).

In a preferred group of compounds of formula (IV), Q is:

[structures: propanoyl, 2-pyridylmethyl, ethyl (CH₃), or benzyl]

In another embodiment, the invention provides a compound of Formula (V):

(V)

[structure showing 3-methoxyphenyl-pyridine-carboxamide-piperidine-Q]

or a pharmaceutically acceptable salt or solvate thereof, wherein Q is as defined above for a compound of formula (I).

In a preferred group of compounds of formula (V), Q is:

[structures: propanoyl, 2-pyridylmethyl, ethyl (CH₃), benzyl, —C(O)OEt, or isobutyl]

In another embodiment, the invention provides a compound of Formula (VI):

(VI)

[structure showing 3-methylphenyl-pyridine-carboxamide-piperidine-Q]

or a pharmaceutically acceptable salt or solvate thereof, wherein Q is as defined above for a compound of formula (I).

In a preferred group of compounds of formula (VI), Q is:

[structures: propanoyl, ethyl (CH₃), benzyl, or isobutyl]

In another embodiment, the invention provides a compound of Formula (VII):

(VII)

[structure showing 3-fluorophenyl-pyridine-carboxamide-piperidine-Q]

or a pharmaceutically acceptable salt or solvate thereof, wherein Q is as defined above for a compound of formula (I).

In another embodiment, the invention provides a compound of Formula (VIII):

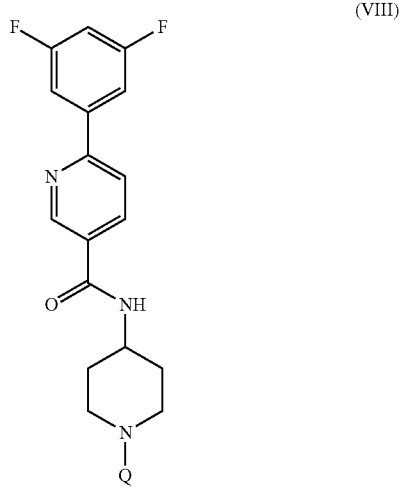

(VIII)

or a pharmaceutically acceptable salt or solvate thereof, wherein Q is as defined above for a compound of formula (I).

In a preferred group of compounds of formula (VIII), Q is carboxylate or (trifluoromethyl)methyl.

In another embodiment, the invention provides a compound of Formula (IX):

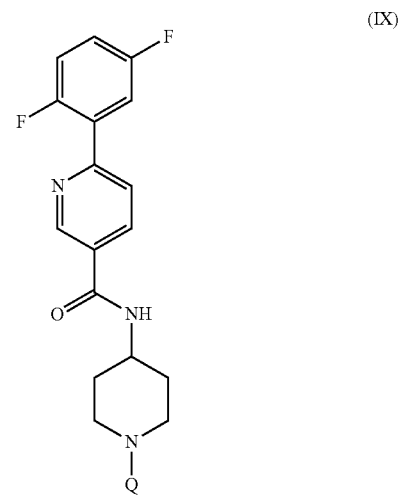

(IX)

or a pharmaceutically acceptable salt or solvate thereof, wherein Q is as defined above for a compound of formula (I).

In another embodiment, the invention provides a compound of Formula (X):

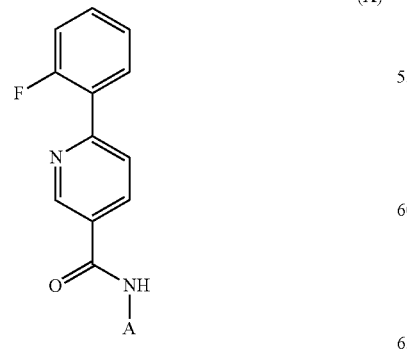

(X)

or a pharmaceutically acceptable salt or solvate thereof, wherein A is as defined above for a compound of formula (I).

In another embodiment, the invention provides a compound of Formula (XII):

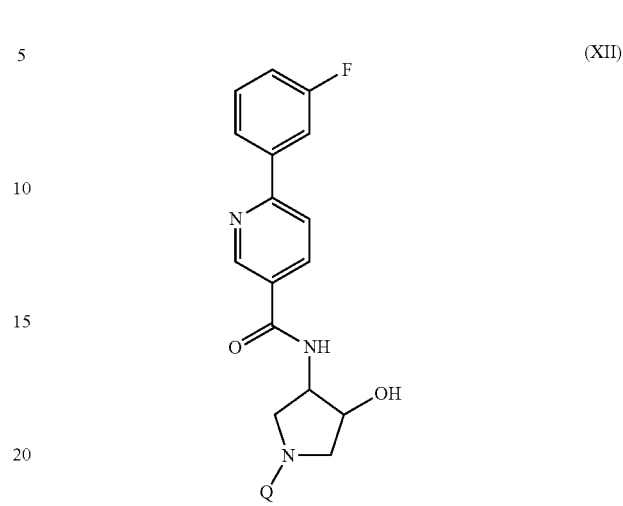

(XII)

or a pharmaceutically acceptable salt or solvate thereof, wherein Q is as defined above for a compound of formula (I).

In another embodiment, the invention provides a compound of Formula (XIII):

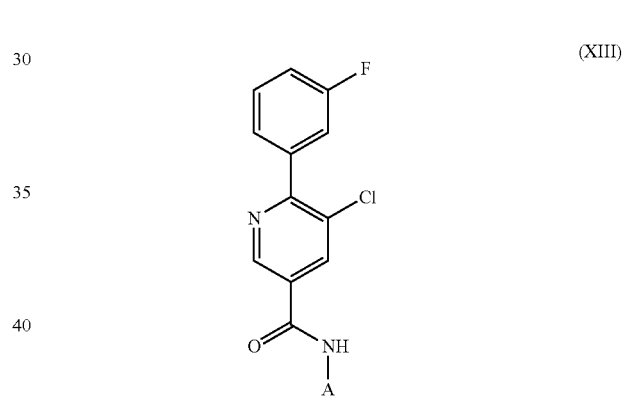

(XIII)

or a pharmaceutically acceptable salt or solvate thereof, wherein A is as defined above for a compound of formula (I).

In another embodiment, the present invention provides a compound of Formula (Ib):

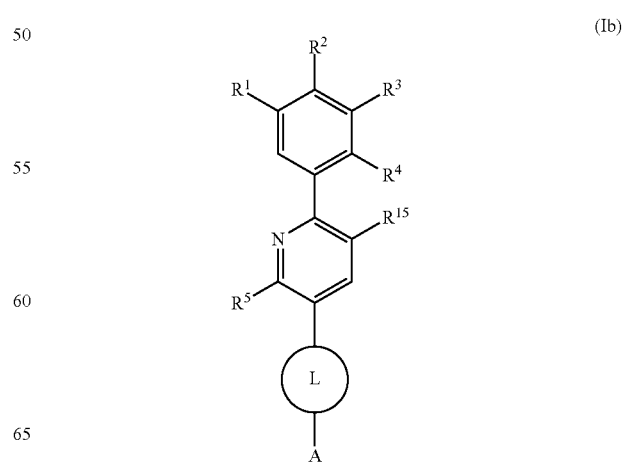

(Ib)

or a pharmaceutically acceptable salt or solvate thereof, wherein:

$R^1$, $R^3$ and $R^4$ are independently H, F, Cl, —$CHF_2$, —$CF_3$, —OH, —$CH_2OH$, —$CH_2CH_2OH$, —C≡H, —$CH_2$C≡N, —$CH_2CH_2$C≡N, $C_1$-$C_5$ alkyl, $C(O)OR^{16}$, —$NC(O)R^{16}$, —$NS(O)_2R^{16}$, —$C(O)R^{16}$, or —$OCH_3$;

$R^2$ is H or F;

$R^5$ is H, —$NH_2$, —OH or —$CH_3$;

$R^{15}$ is H, F, Cl, —$CH_3$ or —$OCH_3$;

L is —C(O)NH—, —NHC(O)— or —$CH_2NHC(O)$—; and

A is selected from the group consisting of:

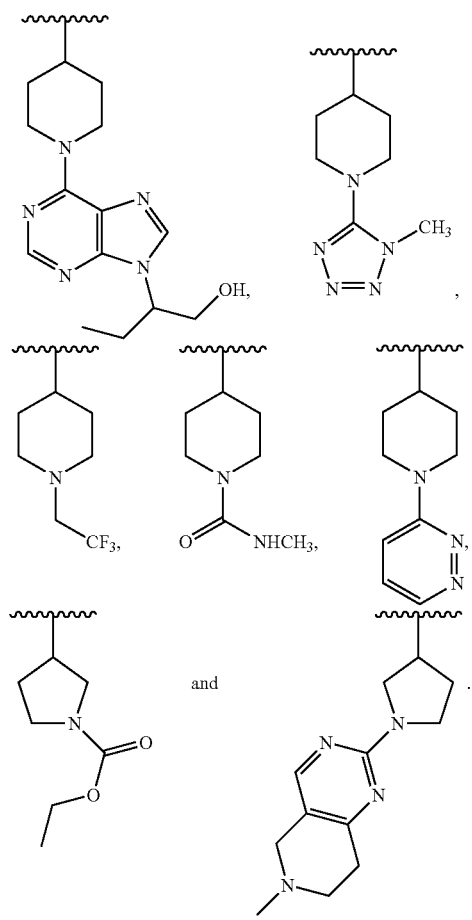

In another embodiment, the invention provides a compound selected from the group consisting of:
6-(3-fluorophenyl)-N-(1-{9-[1-(hydroxymethyl)propyl]-9H-purin-6-yl}piperidin-4-yl)nicotinamide; fluorophenyl)-N-[1-(1-methyl-1H-tetrazol-5-yl)piperidin-4-yl]nicotinamide; and
6-(3-fluorophenyl)-N-{1-[5-(morpholin-4-ylcarbonyl)pyridin-2-yl]piperidin-4-yl}nicotinamide;
and the pharmaceutically acceptable salts and solvates thereof.

In another embodiment, the invention provides 6-(3-fluoro-phenyl)-N-[1-(1-methyl-1H-tetrazol-5-yl)-piperidin-4-yl]-nicotinamide, and pharmaceutically acceptable salts and solvates thereof.

The present invention also provides: a method of treating a disease or condition mediated at least in part by prostaglandin $D_2$ produced by H-PGDS, in a subject in need of such treatment, comprising administering to the subject a therapeutically effective amount of a compound of formula (I), or a pharmaceutically acceptable salt or solvate thereof; the use of a compound of formula (I), or a pharmaceutically acceptable salt or solvate thereof, for the manufacture of a medicament for treating a disease or condition mediated at least in part by prostaglandin $D_2$ produced by H-PGDS; a compound of formula (I), or a pharmaceutically acceptable salt or solvate thereof, for use as a medicament; a compound of formula (I), or a pharmaceutically acceptable salt or solvate thereof, for use in the treatment of a disease or condition mediated at least in part by prostaglandin $D_2$ produced by H-PGDS; a pharmaceutical composition comprising a compound of formula (I), or a pharmaceutically acceptable salt or solvate thereof, and a pharmaceutically acceptable excipient; a pharmaceutical composition for the treatment of a disease or condition mediated at least in part by prostaglandin $D_2$ produced by H-PGDS comprising a compound of formula (I), or a pharmaceutically acceptable salt or solvate thereof.

The diseases and conditions mediated at least in part by prostaglandin $D_2$ produced by H-PGDS include allergy and allergic inflammation. Important diseases and conditions of this kind are allergic respiratory conditions such as allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, airways disease that is associated with pulmonary hypertension, acute lung injury, bronchiectasis, sinusitis, allergic conjunctivitis or atopic dermatitis, particularly asthma or chronic obstructive pulmonary disease.

Types of asthma include atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

Included in the use of the compounds of formula (I) for the treatment of asthma, is palliative treatment for the symptoms and conditions of asthma such as wheezing, coughing, shortness of breath, tightness in the chest, shallow or fast breathing, nasal flaring (nostril size increases with breathing), retractions (neck area and between or below the ribs moves inward with breathing), cyanosis (gray or bluish tint to skin, beginning around the mouth), runny or stuffy nose, and headache.

Other important diseases and conditions mediated at least in part by prostaglandin $D_2$ produced by H-PGDS are arthritis (especially rheumatoid arthritis), irritable bowel diseases (such as Crohns disease and ulcerative colitis), irritable bowel syndrome, inflammatory pain, skin inflammation and irritation (such as eczema), niacin-induced skin flushing and cealic type disease (e.g. as a result of lactose intolerance).

The present invention also provides any of the uses, methods or compositions as defined above wherein the compound of formula (I), or pharmaceutically acceptable salt or solvate thereof, is used in combination with another pharmacologically active compound, particularly one of the compounds listed in Table 1 below. Specific combinations useful according to the present invention include combinations comprising a compound of formula (I), or a pharmaceutically acceptable salt or solvate thereof, and (i) a glucocorticosteroid or DAGR (dissociated agonist of the corticoid receptor); (ii) a $\beta_2$ agonist, an example of which is a long-acting $\beta_2$ agonist; (iii) a muscarinic M3 receptor antagonist or an anticholinergic agent; (iv) a histamine receptor antagonist, which may be an H1 or an H3 antagonist; (v) a 5-lypoxygenase inhibitor; (vi) a thromboxane inhibitor; or (vii) an $LTD_4$ inhibitor. Generally, the compounds of the combination will be administered together as a formulation in association with one or more pharmaceutically acceptable excipients.

TABLE I (a) 5-Lipoxygenase activating protein (FLAP) antagonists
(b) Leukotriene antagonists (LTRAs) including antagonists of $LTB_4$, $LTC_4$, $LTD_4$, and $LTE_4$
(c) Histamine receptor antagonists including H1 and H3 antagonists
(d) $\alpha_1$- and $\alpha_2$-Adrenoceptor agonist vasoconstrictor sympathomimetic agents for decongestant use
(e) Muscarinic M3 receptor antagonists or anticholinergic agents
(f) PDE inhibitors, e.g. PDE3, PDE4 and PDE5 inhibitors, such as theophylline
(g) Sodium cromoglycate
(h) COX inhibitors, including both non-selective and selective COX-1 or COX-2 inhibitors (such as NSAIDs)
(i) Glucocorticosteroids or DAGR (dissociated agonists of the corticoid receptor)
(j) Monoclonal antibodies active against endogenous inflammatory entities
(k) β2 agonists, including long-acting β2 agonists
(l) Integrin antagonists
(m) Adhesion molecule inhibitors, including VLA-4 antagonists
(n) Kinin-$B_1$- and $B_2$-receptor antagonists
(o) Immunosuppressive agents, including inhibitors of the IgE pathway, and cyclosporin;
(p) Inhibitors of matrix metalloproteases (MMPs), such as., MMP9, and MMP12
(q) Tachykinin $NK_1$, $NK_2$ and $NK_3$ receptor antagonists
(r) Protease inhibitors, such as elastase inhibitors, chymase and cathepsin G;
(s) Adenosine A2a receptor agonists and A2b antagonists
(t) Inhibitors of urokinase
(u) Compounds that act on dopamine receptors, such as D2 agonists
(v) Modulators of the NFκB pathway, such as IKK inhibitors
(w) Modulators of cytokine signaling pathways such as syk kinase, JAK kinase inhibitors, p38 kinase, SPHK-1 kinase, Rho kinase, EGF-R or MK-2
(x) Agents that can be classed as mucolytics or anti-tussive, and mucokinetics;
(y) Antibiotics;
(z) Antivirals;
(aa) Vaccines
(bb) Chemokines
(cc) Epithelial sodium channel (ENaC) blockers or Epithelial sodium channel (ENaC) inhibitors
(dd) P2Y2 Agonists and other Nucleotide receptor agonists
(ee) Inhibitors of thromboxane
(ff) Niacin
(gg) Inhibitors of 5-lypoxygenase (5-LO)
(hh) Adhesion factors including VLAM, ICAM, and ELAM Besides being useful for human treatment, compounds of formula (I) are also useful for veterinary treatment of companion animals, exotic animals and farm animals.

When used in the present application, the following abbreviations have the meanings set out below:

HATU is N,N,N',N'-tetramethyl-O-(7-azabenzotriazol-1-yl)uronium hexafluorophosphate;
HOBt is 1-hydroxybenzotriazole;
BOP is (benzotriazol-1-yloxy)tris(dimethylamino)phosphonium hexafluorophosphate;
HBTU is N,N,N',N'-tetramethyl-O-(1H-benzotriazol-1-yl)uronium hexafluorophosphate;
TBTU is O-(benzotriazol-1-yl)-N,N,N',N'-tetramethyluronium tetrafluoroborate;
DIPEA is N,N-diisopropylethylamine;
TEA is triethylamine;
TFA is trifluoroacetic acid;
DCM is dichloromethane;
DMA is N,N-dimethylacetamide;
EDC/EDAC is N-(3-Dimethylaminopropyl)-N'-ethylcarbodiimide hydrochloride;
NMM is 4-methylmorpholine;
DCC is N,N'-dicyclohexylcarbodiimide;
HOAt is 1-hydroxy-7-azabenzotriazole;
Me is methyl;
Et is ethyl;
EtOAc is ethyl acetate;
$CDCl_3$ is deuterochloroform;
$CH_2Cl_2$ is dichloromethane;
iPr is isopropyl; and
$CO_2Et$ is ethyl carboxylate.

Unless otherwise defined herein, scientific and technical terms used in connection with the present invention shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well known and commonly used in the art.

The phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect preventative, palliative, supportive, restorative or curative treatment. The term treatment encompasses any objective or subjective improvement in a subject with respect to a relevant condition or disease.

The term "preventive treatment," as used herein to describe the present invention, means that the compound, pharmaceutical composition or combination is administered to a subject to inhibit or stop the relevant condition from occurring in a subject, particularly in a subject or member of a population that is significantly predisposed to the relevant condition.

The term "palliative treatment," as used herein to describe the present invention, means that the compound, pharmaceutical composition or combination is administered to a subject to remedy signs and/or symptoms of a condition, without necessarily modifying the progression of, or underlying etiology of, the relevant condition.

The term "supportive treatment," as used herein to describe the present invention, means that the compound, pharmaceutical composition or combination is administered to a subject as a part of a regimen of therapy, but that such therapy is not limited to administration of the compound, pharmaceutical composition or combination. Unless otherwise expressly stated, supportive treatment may embrace preventive, palliative, restorative or curative treatment, particularly when the compounds or pharmaceutical compositions are combined with another component of supportive therapy.

The term "restorative treatment," as used herein to describe the present invention, means that the compound, pharmaceutical composition or combination is administered to a subject to modify the underlying progression or etiology of a condition. Non-limiting examples include an increase in forced expiratory volume in one second (FEV 1) for lung disorders, inhibition of progressive nerve destruction, reduction of biomarkers associated and correlated with diseases or disorders, a reduction in relapses, improvement in quality of life and the like.

The term "curative treatment," as used herein to describe the present invention, means that compound, pharmaceutical composition or combination is administered to a subject for the purpose of bringing the disease or disorder into complete remission, or that the disease or disorder is undetectable after such treatment.

The term "alkyl", alone or in combination, means an acyclic alkyl radical, linear or branched, preferably containing from 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like. Where no specific substitution is specified, alkyl radicals can be optionally substituted with groups consisting of hydroxy, methoxy, amino, cyano, chloro, and fluoro. Examples of such substituted alkyl radicals include chloroethyl, hydroxyethyl, cyanobutyl, aminopentyl and the like.

The carbon atom content of various hydrocarbon-containing moieties is indicated by a prefix designating a lower and upper number of carbon atoms in the moiety, that is, the prefix $C_{i-j}$ indicates a moiety of the integer "i" to the integer "j" carbon atoms, inclusive. Thus, for example, '$C_{1-6}$ alkyl' or '$C_1$-$C_6$ alkyl' refers alkyl of one to six carbon atoms, inclusive.

The term "hydroxyl," as used herein, means an OH radical.

The terms 'heterocycle', 'heterocylic ring system' and 'heterocyclyl' refer to a saturated or unsaturated mono- or multi-ring cycloalkyl wherein one or more carbon atoms is replaced by N, S or O. This includes, for example, the following structures:

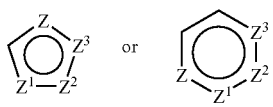

wherein Z, $Z^1$, $Z^2$ and $Z^3$ are C, S, O, or N, with the proviso that one of Z, $Z^1$, $Z^2$ or $Z^3$ is other than carbon, but is not O or S when attached to another Z atom by a double bond or when attached to another O or S atom. Wherein Z, $Z^1$, $Z^2$ or $Z^3$ is S or N, the atom may be substituted by oxygen to form a sulfinyl (S=O), sulfonyl (S(=O)$_2$), or N-oxide (N$^+$—O$^-$) radical. The term "heterocycle" also includes fully saturated ring structures such as piperazinyl, dioxanyl, tetrahydrofuranyl, oxiranyl, aziridinyl, morpholinyl, pyrrolidinyl, piperidinyl, thiazolidinyl, and others. The term "heterocycle" or also includes partially unsaturated ring structures such as dihydrofuranyl, pyrazolinyl, imidazolinyl, pyrrolinyl, chromanyl, dihydrothiophenyl, and others.

The term 'heteroaryl' refers to an aromatic heterocyclic group. Heteroaryl is preferably: (a) a five-membered aromatic heterocyclic group containing either (i) 1-4 nitrogen atoms or (ii) 0-3 nitrogen atoms and 1 oxygen or 1 sulphur atom; (b) a six-membered aromatic heterocyclic group containing 1-3 nitrogen atoms; (c) a nine-membered bicyclic aromatic heterocyclic group containing either (i) 1-5 nitrogen atoms or (ii) 0-4 nitrogen atoms and 1 oxygen or 1 sulphur atom; or (d) a ten-membered bicyclic aromatic heterocyclic group containing 1-6 nitrogen atoms; each of said groups (a)-(d) being optionally substituted by one or more of $C_1$-$C_6$ alkyl, $C_1$-$C_6$ fluoroalkyl, $C_3$-$C_6$ cycloalkyl, hydroxy($C_3$-$C_6$ cycloalkyl), $C_1$-$C_6$ alkenyl, —(CH$_2$)$_p$OH, —(CH$_2$)$_p$CN, halo, oxo, —(CH$_2$)$_p$NR$^{18}$R$^{19}$, —(CH$_2$)$_p$CONR$^{18}$R$^{19}$, —(CH$_2$)$_p$OR$^{18}$, —(CH$_2$)$_p$COR$^{18}$ and —(CH$_2$)$_p$COOR$^{18}$, wherein p is 0-3 and R$^{18}$ and R$^{19}$ are each H or $C_1$-$C_6$ alkyl optionally substituted with —OH or $C_1$-$C_6$ alkoxy. Examples of "heteroaryl" include pyridyl, pyrimidinyl, pyridazinyl, pyrazinyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl (optionally substituted as specified above).

A preferred non-aromatic heterocyclic group is a five- or six-membered saturated or partially unsaturated heterocyclic group containing one or two nitrogen or oxygen groups, optionally substituted by one or more of $C_1$-$C_6$ alkyl, $C_1$-$C_6$ fluoroalkyl, $C_3$-$C_6$ cycloalkyl, hydroxy($C_3$-$C_6$ cycloalkyl), $C_1$-$C_6$cycloalkyl), $C_1$-$C_6$ alkenyl, —(CH$_2$)$_p$OH, —(CH$_2$)$_p$CN, halo, oxo, —(CH$_2$)$_p$NR$^{18}$R$^{19}$, —(CH$_2$)$_p$CONR$^{18}$R$^{19}$, —(CH$_2$)$_p$OR$^{18}$, —(CH$_2$)$_p$COR$^{18}$ and —(CH$_2$)$_p$COOR$^{18}$, wherein p is 0-3 and R$^{18}$ and R$^{19}$ are each H or $C_1$-$C_6$ alkyl optionally substituted with —OH or $C_1$-$C_6$ alkoxy. Preferred examples of non-aromatic heterocyclic groups include azetidinyl, pyrrolidinyl, tetrahydrofuranyl, piperdininyl, piperazinyl and morpholinyl (optionally substituted as specified above).

In either "heterocyle" or "heteroaryl," the point of attachment to the molecule of interest can be at the heteroatom or elsewhere within the ring.

The term "nitrogen-containing heterocycle," or "nitrogen containing heteroaryl," as used herein to describe the present invention, means a heterocyclic or heteroaryl group, respectively, that comprises at least one nitrogen atom. Such substitutents may also be referred to herein as "heterocycle containing at least one nitrogen," and "heteroaryl containing at least one nitrogen."

The term "cycloalkyl" or "carbocyclyl" means a mono- or multi-ringed cycloalkyl wherein each ring contains three to seven carbon atoms, preferably three to six carbon atoms. 'Cycloalkyl' is preferably a monocyclic cycloalkyl containing from three to seven carbon atoms. Examples include cyclopropyl, cyclobutyl, cyclopentyl, cyclohexyl, and cycloheptyl.

The term "oxo" means a doubly bonded oxygen.

The term "alkoxy" means a radical comprising an alkyl radical that is bonded to an oxygen atom, such as a methoxy radical. More preferred alkoxy radicals are "lower alkoxy" radicals having one to about ten carbon atoms. Still more preferred alkoxy radicals have one to about six carbon atoms. Examples of such radicals include methoxy, ethoxy, propoxy, isopropoxy, butoxy and tert-butoxy.

The term "aryl" means a fully unsaturated mono- or multi-ring cycloalkyl having a cyclic array of p-orbitals containing 4n+2 electrons, including, but not limited to, substituted or unsubstituted phenyl, naphthyl, or anthracenyl optionally fused to a carbocyclic radical wherein aryl is optionally substituted with one or more substituents selected from the group consisting of: (a) halo; (b) $C_{1-6}$alkoxy optionally substituted by halo and phenyl; (c) $C_{1-6}$alkyl optionally substituted by halo; (d) phenyl; (e) O-phenyl; (f) cyano; (g) nitro; (h) hydroxyl, or any two adjacent substituents taken together constitute a group of the formula —O(CH$_2$)$_m$O— where m is 1-3.

The symbols

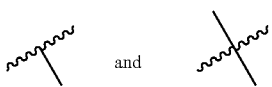

denote the point of attachment of a substituent.

As used herein, the terms "co-administration", "co-administered" and "in combination with", referring to a combination of a compound of formula (I) and one or more other therapeutic agents, is intended to mean, and does refer to and include the following:

simultaneous administration of such a combination of a compound of formula (I) and a further therapeutic agent to a patient in need of treatment, when such components are formulated together into a single dosage form which releases said components at substantially the same time to said patient, substantially simultaneous administration of such a combination of a compound of formula (I) and a further therapeutic agent to a patient in need of treatment, when such components are formulated apart from each other into separate dosage forms which are taken at substantially the same time by said patient, whereupon said components are released at substantially the same time to said patient, sequential administration of such a combination of a compound of formula (I) and a further therapeutic agent to a patient in need of treatment, when such components are formulated apart from each other into separate dosage forms which are taken at consecutive times by said patient with a significant time interval between each administration, whereupon said components are released at substantially different times to said patient; and sequential administration of such a combination of a compound of formula (I) and a further therapeutic agent to a patient in need of treatment, when such components are formulated together into a single dosage form which releases said components in a controlled manner whereupon they are concurrently, consecutively, and/or overlappingly administered at the same and/or different times by said patient, where each part may be administered by either the same or different route.

The term 'excipient' is used herein to describe any ingredient other than a compound of formula (I). The choice of excipient will to a large extent depend on factors such as the particular mode of administration, the effect of the excipient on solubility and stability, and the nature of the dosage form. The term "excipient" encompasses diluent, carrier or adjuvant.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, naphatlene-1,5-disulfonic acid and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of formula (I) may be prepared by one or more of three methods:

(i) by reacting the compound of formula (I) with the desired acid or base;

(ii) by removing an acid- or base-labile protecting group from a suitable precursor of the compound of formula (I) or by ring-opening a suitable cyclic precursor, for example, a lactone or lactam, using the desired acid or base; or (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) may also exist in unsolvated and solvated forms. The term 'solvate' is used herein to describe a molecular complex comprising the compound of formula (I), or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of formula (I) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) (also referred to as compounds of the invention) include references to salts, solvates, multi-component complexes and liquid crystals thereof and to solvates, multi-component complexes and liquid crystals of salts thereof.

Also included within the scope of the invention are all polymorphs and crystal habits of compounds of formula (I), prodrugs and isomers thereof (including optical, geometric and tautomeric isomers) as hereinafter defined and isotopically-labeled forms thereof.

As indicated, so-called 'prodrugs' of the compounds of formula (I) are also within the scope of the invention. Thus certain derivatives of a compound of formula (I) which may have little or no pharmacological activity themselves can, when administered into or onto the body, be converted into a compound of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include:
(i) where the compound of formula (I) contains a carboxylic acid functionality (—COOH), an ester thereof, for example, a compound wherein the hydrogen of the carboxylic acid functionality of the compound of formula (I) is replaced by (C$_1$-C$_8$)alkyl;
(ii) where the compound of formula (I) contains an alcohol functionality (—OH), an ether thereof, for example, a compound wherein the hydrogen of the alcohol functionality of the compound of formula (I) is replaced by (C$_1$-C$_6$)alkanoyloxymethyl; and
(iii) where the compound of formula (I) contains a primary or secondary amino functionality (—NH$_2$ or —NHR where R≠H), an amide thereof, for example, a compound wherein, as the case may be, one or both hydrogens of the amino functionality of the compound of formula (I) is/are replaced by (C$_1$-C$_{10}$)alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include
(i) where the compound of formula (I) contains a methyl group, an hydroxymethyl derivative thereof (—CH$_3$—>—CH$_2$OH):
(ii) where the compound of formula (I) contains an alkoxy group, an hydroxy derivative thereof (—OR—>—OH);
(iii) where the compound of formula (I) contains a tertiary amino group, a secondary amino derivative thereof (—NR$^1$R$^2$—>—NHR$^1$ or —NHR$^2$);
(iv) where the compound of formula (I) contains a secondary amino group, a primary derivative thereof (—NHR$^1$—>—NH$_2$);
(v) where the compound of formula (I) contains a phenyl moiety, a phenol derivative thereof (-Ph->-PhOH); and
(vi) where the compound of formula (I) contains an amide group, a carboxylic acid derivative thereof (—CONH$_2$—>COOH).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or I-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of formula (I) (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art. (See, for example, Smith, Roger M. Loughborough University, Loughborough, UK. Chromatographic Science Series (1998), 75(Supercritical Fluid Chromatography with Packed Columns), pp. 223-249 and references cited therein.) In the relevant examples herein, columns were obtained from Chiral Technologies, Inc, West Chester, Pa., USA, a subsidiary of Daicel® Chemical Industries, Ltd., Tokyo, Japan.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature. Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

For administration to human patients, the total daily dose of a compound of formula (I) is typically in the range of 0.01 mg to 500 mg depending, of course, on the mode of administration. In another embodiment of the present invention, the total daily dose of a compound of formula (I) is typically in the range of 0.1 mg to 300 mg. In yet another embodiment of the present invention, the total daily dose of a compound of formula (I) is typically in the range of 1 mg to 30 mg. The total daily dose may be administered in single or divided doses and may, at the physician's discretion, fall outside of the typical range given herein. These dosages are based on an average human subject having a weight of about 65 kg to 70 kg. The physician will readily be able to determine doses for subjects whose weight falls outside this range, such as infants and the elderly. In the case of aerosols, the dosage unit is determined by means of a valve which delivers a metered amount. Units in accordance with the invention are typically arranged to administer a metered dose or "puff" containing from 0.001 mg to 10 mg of a compound of the invention. The overall daily dose will typically be in the range 0.001 mg to 40 mg which may be administered in a single dose or, more usually, as divided doses throughout the day.

A compound of formula (I) can be administered per se, or in the form of a pharmaceutical composition, which, as active constituent contains an efficacious dose of at least one compound of the invention, in addition to customary pharmaceutically innocuous excipients and/or additives.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Compounds of formula (I) may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of formula (I) may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, N.Y., 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

Compounds of formula (I) may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Compounds of the invention may also be administered topically to the skin or mucosa, that is, dermally or transdermally.

The compounds of formula (I) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound of formula (I) comprising, for example, ethanol, aqueous ethanol, or a suitable alternative agent for dispersing, solubilising, or extending release of the compound, a propellant as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of formula (I) may also be administered directly to the eye or ear, typically in the form of drops of a micronised suspension or solution in isotonic, pH-adjusted, sterile saline.

Compounds of formula (I) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in international patent publications WO-A-91/11172, WO-A-94/02518 and WO-A-98/55148.

Inasmuch as it may desirable to administer a combination of active compounds, for example, for the purpose of treating a particular disease or condition, it is within the scope of the present invention that two or more pharmaceutical compositions, at least one of which contains a compound of formula (I), may conveniently be combined in the form of a kit suitable for coadministration of the compositions. Thus, a kit of the invention comprises two or more separate pharmaceutical compositions, at least one of which contains a compound of formula (I), and means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid.

All the compound of formula (I) can be made by the specific and general experimental procedures described below in combination with the common general knowledge of one skilled in the art (see, for example, Comprehensive Organic Chemistry, Ed. Barton and Ollis, Elsevier; Comprehensive Organic Transformations: A Guide to Functional Group Preparations, Larock, John Wiley and Sons).

Methods for Preparing Aryl Pyridyl Linked Compounds

Those skilled in the art will appreciate that there are many known ways of preparing aryl pyridyl linked compounds. Such methods are disclosed in patent textbooks and laboratory handbooks which constitute the common general knowledge of the skilled person, including the textbooks referenced above and references cited therein. Typically, an aryl halide (Cl, Br, I) or trifluoromethanesulphonate is stirred with an organometallic species such as a stannane, organomagnesium derivative or a boronate ester or boronic acid in the presence of a catalyst, usually a palladium derivative between 0° C. and 120° C. in solvents including tetrahydrofuran, toluene, DMF and water for 1 to 24 hours. For example, an aryl bromide may be heated to 100° C. in a mixture of water/toluene with a base such as sodium carbonate or sodium hydroxide, a palladium catalyst such as tetrakis(triphenylphosphine)palladium (0), a phase transfer catalyst such as tetra-n-butyl ammonium bromide and an aryl boronic acid or ester. As a second example, an aryl boronic ester an aryl halide (Cl, Br, I) or aryl trifluoromethanesulphonate and a fluoride source such as KF or CsF in a non-aqueous reaction medium such as 1,4-dioxane may be employed.

General Scheme for the Preparation of Amides

Those skilled in the art will appreciate that there are many known ways of preparing amides. For example, see Montalbetti, C. A. G. N and Falque, V., *Amide bond formation and peptide coupling*, Tetrahedron, (2005) 61: (46), pp. 10827-10852 and references cited therein. The examples provided herein are thus not intended to be exhaustive, but merely illustrative. The general scheme for amide formation is as follows:

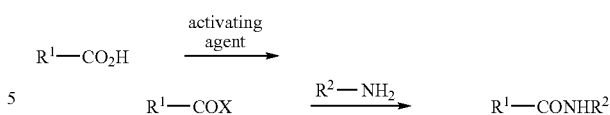

As an example:

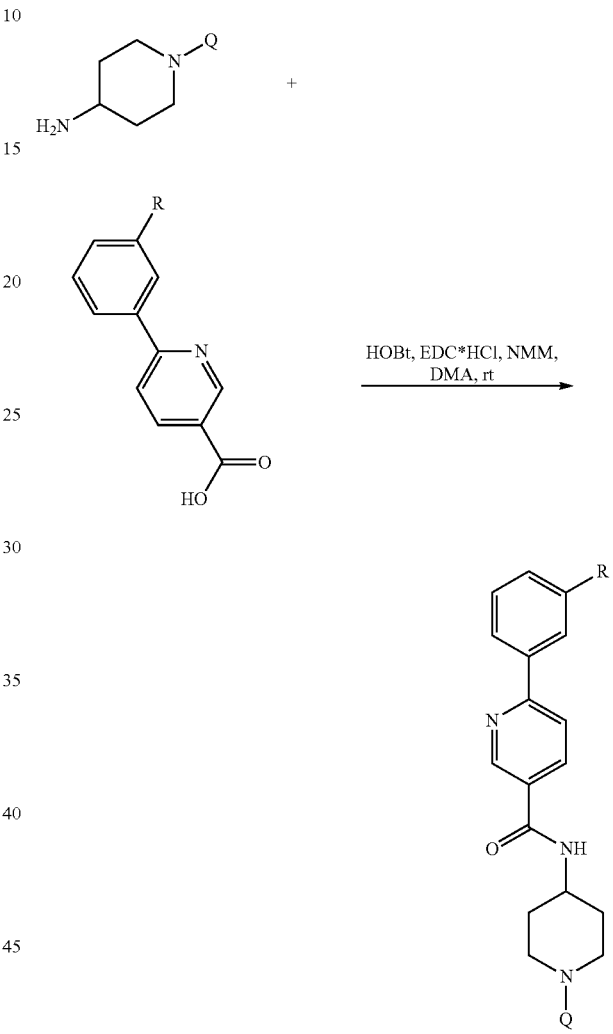

In the following Examples, unless otherwise stated, the following general method was used: To the carboxylic acid (0.15 mmol) and 1-hydroxybenzotriazole (0.3 mmol) in DMF (1.0 mL) was added 0.3.mmol of PS-Carbodiimide resin (Argonaut, 1.3 mmol/g). The mixture was shaken for 10 min and then the amine (0.1 mmol) in DMF (1 mL) was added. The mixture was allowed to agitate overnight at rt and subsequently treated with 0.60 mmole of PS-trisamine (Argonaut, 3.8 mmol/g). Reaction mixture was filtered, concentrated in vacuo and purified by reverse phase chromatography.

Where it is stated that compounds were prepared in the manner described for an earlier Example, the skilled person will appreciate that reaction times, number of equivalents of reagents and reaction temperatures may be modified for each specific reaction, and that it may nevertheless be necessary or desirable to employ different work-up or purification conditions.

EXAMPLE 1

6-Phenyl-N-(1-(2,2,2-trifluoroethyl)piperidin-4-yl) nicotinamide

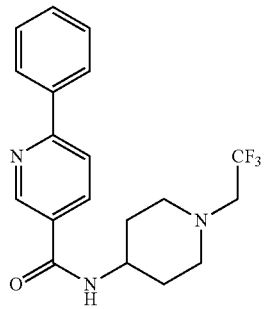

Step A: 8-(Trifluoroacetyl)-1,4-dioxa-8-azaspiro[4.5] decane

4-Piperidone ethylene ketal (127.0 g, 0.887 mol), Et₃N (145 mL, 1.044 mol), and 4-dimethylaminopyrid (DMAP, 10.5 g, 0.086 mol) were mixed in dichloromethane (1 L). A solution of trifluoroacetic anhydride (192.0 g, 0.91 mol) in dichloromethane (500 mL) was added dropwise at 0-5° C. for 1 h. The mixture was allowed to warm up to room temperature and stirred overnight. The reaction mixture was washed with 1 N aqueous HCl (2×1.2 L), water (1.2 L), 10% aqueous NaHCO₃ (1.2 L), brine (600 mL), dried over anhydrous Na₂SO₄, and evaporated under vacuum to afford 8-(trifluoroacetyl)-1,4-dioxa-8-azaspiro[4.5]decane (194.5 g).

Step B: 1-(2,2,2-Trifluoroethyl)piperidin-4-one

A solution of 8-(trifluoroacetyl)-1,4-dioxa-8-azaspiro[4.5] decane (87.0 g, 0.364 mol) in THF (375 added dropwise under argon to 1 M BH₃ in THF (800 mL, 0.8 mol) at 0-5° C. for 10 min. The cool was removed. The reaction mixture was refluxed for 5 h, cooled to 0-5° C., and quenched by adding carefully 6 N aqueous HCl (130 mL) for ~1 h under stirring. The organic solvents were removed under vacuum. The aqueous residue was alkalized with a 50% solution of NaOH (150 mL), diluted with water (500 mL), and extracted with ether (3×400 mL). The combined extracts were dried over anhydrous Na₂SO₄ and evaporated to give a mixture (98.8 g) of the intermediate 8-(2,2,2-trifluoroethyl)-1,4-dioxa-8-azaspiro [4.5]decane and butanol in 79:21 weight ratio. Water (1.1 L) and concentrated HCl (100 mL) were added, and the obtained mixture was refluxed for 3 h. After cooling to room temperature, the reaction mixture was alkalized to pH 9 by adding a 40% solution of NaOH (~150 mL) and extracted with ether (3×350 mL). The combined extracts were dried over anhydrous Na₂SO₄ and evaporated to afford a mixture (72.8 g) of 1-(2,2,2-trifluoroethyl)piperidin-4-one and butanol in 86:14 weight ratio.

Step C: 1-(2,2,2-Trifluoroethyl)piperidin-4-amine

A 25% aqueous solution of ammonia (170 mL), 10% Pd/C (7.4 g), and a solution of the above 1-(2,2,2-trifluoroethyl) piperidin-4-one /butanol mixture (72.5 g, 0.344 mol, 86:14 weight ratio) in methanol (420 mL) were placed into a 2 L glass autoclave purged with argon. The reaction mixture was hydrogenated in a Parr apparatus at a hydrogen pressure of 40 psi for 18 h. The catalyst was removed by filtration. The filtrate was concentrated in vacuo to 150 mL. Potash (46 g) and ether (200 mL) were added, and the mixture was vigorously stirred for 20 min. The organic layer was separated, and the aqueous one was extracted with ether (100 mL). The combined organic layers were dried over anhydrous Na₂SO₄ and evaporated to afford a mixture (74.4 g) of 1-(2,2,2-trifluoroethyl)piperidin-4-amine and 1-(2,2,2-trifluoroethyl)-N-[1-(2,2,2-trifluoroethyl)piperidin-4-yl]piperidin-4-amine in 72:28 weight ratio (contain butanol). This mixture was fractionated at 7-8 mmHg on a 15 cm Vigreaux column (a fraction with bp 75-95° C. was collected) to afford 1-(2,2,2-trifluoroethyl)piperidin-4-amine (38.5 g) as a colorless liquid.

Step D: 6-Phenyl-N-[1-(2,2,2-trifluoroethyl)piperidin-4-yl]nicotinamide

To a 250 mL 3-necked flask containing 2-phenyl-5-pyridinecarboxylic acid (2.75 g, 13.8 mmol) in N,N-dimethylacetamide (DMA, 35 mL) was added N-(3-dimethylaminopropyl)-N'-ethylcarbodiimide hydrochloride (EDAC/EDC*HCl, 2.95 g, 15.2 mmol), 1-hydroxybenzotriazole (HOBt. 1.89 g, 13.8 mmol), 1-(2,2,2-trifluoroethyl)piperidin-4-amine (3.36 g, 15.2 mmol) and 4-methylmorpholine (NMM, 3.8 mL, 34.5 mmol). After stirring at room temperature for 1 hour, the reaction was diluted with water (~200 mL) and the resulting solid collected by filtration. The solid was washed with H₂O (3×100 mL), collected and dried in a vacuum oven (45° C.) overnight to give the desired product (4.24 g). LCMS (ES+) 4.30 min (TIC, 75%; ¹H NMR purity >95%); ¹H NMR (400 MHz, DMSO-d₆) □ ppm 1.46-1.65 (m, 2H) 1.77 (d, J=10.80 Hz, 2 H) 2.31-2.54 (m, 4H) 2.90 (d, J=11.53 Hz, 2H) 3.65-3.86 (m, 1H) 7.36-7.56 (m, 3H) 8.01 (d, J=8.24 Hz, 1H) 8.09 (d, J=6.95 Hz, 2H) 8.22 (d, J=8.42 Hz, 1H) 8.38 (d, J=7.32 Hz, 1H) 9.02 (s, 1 H); MS(ES+) 364 (M+1); HRMS (TOF, ES+) calculated for C₁₉H₂₀F₃N₃O+H⁺: 364.1637; observed 364.1611.

EXAMPLE 2

6-(3-Fluorophenyl)-N-(1-(2,2,2-trifluoroethyl)piperidin-4-yl)nicotinamide

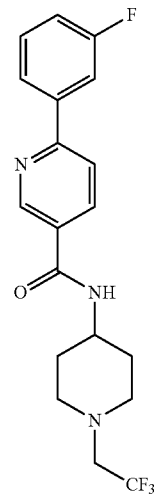

1-(2,2,2-Trifluoroethyl)piperidin-4-amine was synthesized as in steps a-c of Example 1. To a 250 mL round bottom flask containing 6-(3-fluorophenyl)pyridine-3-carboxylic acid (see Example 3, Step A)(2.01 g, 9.25 mmol) in DMA (35 mL) was added EDAC/EDC*HCl(1.95 g, 10.2 mmol), HOBt (1.38 g, 10.2 mmol), 1-(2,2,2-trifluoroethyl)piperidin-4-amine (1.85 g, 10.2 mmol) and NMM (2.23 mL, 20.4). After stirring at room temperature for 2 hours the reaction mixture was diluted with water (100 mL) and the resulting solid filtered and dried to give the desired product (2.96 g). LCMS (ES+) 4.55 min (TIC, 90%; 1H NMR purity >95%); 1H NMR (400 MHz, DMSO-$d_6$) ☐ ppm 1.60 (dq, J=11.84, 3.48 Hz, 2 H) 1.81 (d, J=10.62 Hz, 2H) 2.44 (t, J=11.16 Hz, 2H) 2.50 (br. s., 2H) 2.94 (d, J=11.53 Hz, 2H) 3.74-3.87 (m, 1H) 7.32 (dt, J=8.37, 2.29 Hz, 1H) 7.57 (q, 1H) 7.96 (d, J=10.43 Hz, 1H) 8.01 (d, J=7.69 Hz, 1H) 8.14 (d, J=8.24 Hz, 1H) 8.28 (dd, J=8.24, 2.20 Hz, 1H) 8.49 (d, J=7.50 Hz, 1H) 9.07 (d, J=1.83 Hz, 1H); MS(ES+) 382 (M+1); HRMS (TOF, ES+) calculated for $C_{19}H_{19}F_4N_3O+H^+$: 382.1542; observed 382.1548.

EXAMPLE 3

6-(3-Fluorophenyl)-N-{1-[5-(morpholin-4-ylcarbonyl)pyridin-2-yl]piperidin-4-yl}nicotinamide

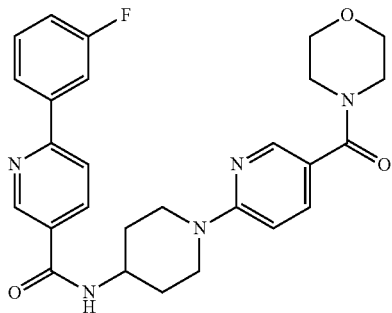

Step A: 6-(3-fluorophenyl)nicotinic acid

3-Fluorophenylboronic acid (39.5 g, 0.282 mol), a solution of $K_2CO_3$ (150 g) in water (700 mL), [$Bu_4N$]Br (3.5 g, 0.0107 mol), and Pd(PPh$_3$)$_4$ (12.4 g, 0.0107 mol) were added to a solution of 6-chloronicotinic acid (37.0 g, 0.235 mol) in toluene. The reaction mixture was stirred under reflux for 20 h. After cooling, the reaction mixture was filtered and acidified with 2 M HCl to pH 3. The formed precipitate was separated by filtration and dried to give 6-(3-fluorophenyl)nicotinic acid (49.9 g). $^1$H NMR (400 MHz, DMSO-$d_6$) δppm 7.29 (td, J=8.46, 2.42 Hz, 1H) 7.50-7.56 (m, 1H) 7.93 (dd, J=10.47, 2.15 Hz, 1H) 7.97 (d, J=7.79 Hz, 1 H) 8.11 (d, J=8.06 Hz, 1H) 8.30 (dd, J=8.32, 2.15 Hz, 1H) 9.11 (d, J=1.88 Hz, 1 H), 13.48 (bs, 1H).

Step B: tert-Butyl 4-(2-(3-fluorophenyl)nicotinamido)piperidine-1-carboxylate

1-Boc-4-aminopiperidine hydrochloride (55.9 g, 0.230 mol, 1.18 HCl), (benzotriaxol-1-yloxy)tris(dimethylamino)phosphonium hexafluorophosphate (BOP, 112 g, 0.253 mol), and N,N-diisopropylethylamine (DIPEA, 140 mL, 0.805 mol) were added to a solution of 6-(3-fluorophenyl)nicotinic acid (49.9 g, 0.230 mol) in dichloromethane (1 L). The reaction mixture was stirred at room temperature for 18 h, evaporated, and chromatographed (silica gel, ethyl acetate-hexane, 2:1). The appropriate fractions were collected and evaporated to give tert-butyl 4-(2-(3-fluorophenyl)nicotinamido)piperidine-1-carboxylate (56.4 g). MS(ES+)=400 (M+1).

Step C:
6-(3-Fluorophenyl)-N-(piperidin-4-yl)nicotinamide

4 M HCl in dioxane (400 mL) was added to a solution of tert-butyl 4-(2-(3-fluorophenyl)nicotinamido)piperidine-1-carboxylate (56.4 g, 0.14 mol) in dioxane (100 mL). The reaction mixture was stirred at room temperature for 4 h. The formed precipitate was separated by filtration, washed with ether, and dried to give 6-(3-fluorophenyl)-N-(piperidin-4-yl)nicotinamide (52 g as the HCl salt). $^1$H NMR (400 MHz, DMSO-$d_6$) δ ppm 1.77-1.93 (m, 2H) 1.93-2.06 (m, 2H) 2.91-3.12 (m, 2H) 3.31 (d, J=12.89 Hz, 2H) 4.02-4.18 (m, 1H) 7.26-7.40 (m, 1H) 7.50-7.64 (m, 1H) 7.91-8.09 (m, 2 H) 8.17 (d, J=8.59 Hz, 1H) 8.40 (dd, J=8.32, 2.15 Hz, 1H) 8.87 (d, J=7.52 Hz, 1 H) 9.13 (d, J=1.61 Hz, 2 H); HRMS (TOF, ES+) calculated for $C_{17}H_{19}FN_3O+H^+$: 300.1507; observed 300.1538.

Step D: 6-(3-Fluorophenyl)-N-{1-[5-(morpholin-4-ylcarbonyl)pyridin-2-yl]piperidin-4-yl}nicotinamide To a vial containing CsF (684 mg, 4.50 mmol) and 1-methyl-2-pyrrolidinone (NMP, 2 mL) was added 6-(3-fluorophenyl)-N-(piperidin-4-yl)nicotinamide hydrochloride (247 mg) and (6-chloropyridin-3-yl)(morpholino)methanone (170 mg, 0.750 mmol). The reaction mixture was heated to 96° C. for 24 hrs. After allowing the reaction to cool to room temperature the reaction was diluted with H$_2$O (3 mL) and the mixture extracted with ethyl acetate (3×10 mL). The organics were combined, dried (MgSO$_4$) and the solvent removed to give an oil, which after chromatography (silica, 5% MeOH:DCM) gave 6-(3-fluorophenyl)-N-{1-[5-(morpholin-4-ylcarbonyl)pyridin-2-yl]piperidin-4-yl}nicotinamide (55 mg). $^1$H NMR (400 MHz, DMSO-$d_6$) δ ppm 9.09 (1H, s), 8.53 (1H, d, J=7.7 Hz), 8.30 (1H, dd, J=8.4, 1.6 Hz), 8.23 (2 H, d, J=11.9 Hz), 8.15 (1H, d, J=8.4 Hz), 8.02 (1H, d, J=7.9 Hz), 7.98 (1H, br. s.), 7.53-7.61 (1H, m), 7.26-7.37 (1H, m), 5.02 (1H, br. s.), 4.45 (1H, br. s.), 4.24 (1H, br. s.), 3.86 (1H, br. s.) 3.73 (1H, br. s.), 3.30 (3H, br. s.), 1.87-2.05 (5H, m), 1.61 (2H, br. s.), 0.75 (3H, t, J=7.3 Hz)

EXAMPLE 3a

N-(1-Methylpiperidin-4-yl)-6-phenylnicotinamide

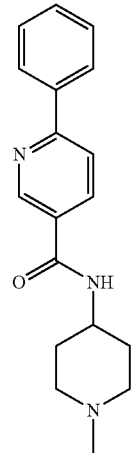

A total of 25.3 mg (86%) was obtained after chromatography: LCMS (ES+) 2.84 min (TIC, 100%); 1H NMR (400 MHz, DMSO-$d_6$) ppm 1.49-1.71 (m, 2H) 1.81 (d, J=10.62 Hz, 2H) 2.21 (t, J=11.35 Hz, 2H) 2.27 (s, 3H) 2.89 (d, J=11.16 Hz, 2H) 3.79 (br. s., 1H) 7.38-7.56 (m, 3H) 8.02 (d, J=8.24 Hz, 1H) 8.10 (d, J=6.77 Hz, 2H) 8.22 (d, J=6.04 Hz, 1H) 8.42 (d, J=6.77 Hz, 1H) 9.03 (s, 1H); MS(ES+) 296 (M+1); HRMS (TOF, ES+) calculated for $C_{18}H_{21}N_3O+H^+$: 296.1763; observed 296.1758.

The following table lists compounds of Formula (III) that have been prepared.

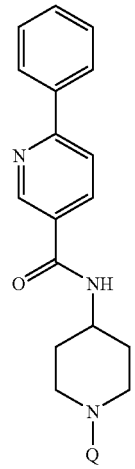

(III)

| Ex | Q | Name | MS Calc (M + H) | MS Obs (M + H) |
|---|---|---|---|---|
| 3b | CO₂Et | Ethyl 4-{[(6-phenylpyridin-3-yl)carbonyl]amino}piperidine-1-carboxylate | 354.1818 | 354.1830 |
| 4 | iPr | N-(1-Isopropylpiperidin-4-yl)-6-phenylnicotinamide | 324.2076 | 324.2108 |
| 5 | -CH₂-(2-pyridyl) | 6-Phenyl-N-[1-(pyridin-2-ylmethyl)piperidin-4-yl]nicotinamide | 373.2028 | 373.1919 |
| 6 | -CH₂-(tetrahydropyran-4-yl) | 6-Phenyl-N-[1-(tetrahydro-2H-pyran-4-ylmethyl)piperidin-4-yl]nicotinamide | 380.2338 | 380.2363 |
| 7 | -C(O)C(CH₃)₃ | N-[1-(2,2-Dimethylpropanoyl)piperidin-4-yl]-6-phenylnicotinamide | 366.2181 | 366.2227 |
| 8 | -CH₂-phenyl | N-(1-Benzylpiperidin-4-yl)-6-phenylnicotinamide | 372.2076 | 372.2028 |

EXAMPLE 9

6-(4-Fluorophenyl)-N-(1-(2,2,2-trifluoroethyl)piperidin-4-yl)nicotinamide

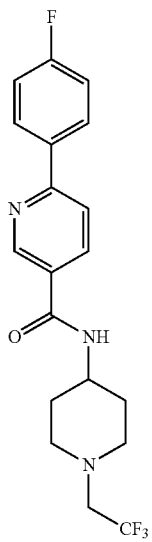

A total of 14.7 mg (39%) was obtained after chromatography: LCMS (ES+) 4.47 min (TIC, 100%); 1H NMR (400 MHz, DMSO-$d_6$) □ ppm 1.52-1.70 (m, 2H) 1.81 (d, J=11.71 Hz, 2H) 2.33-2.61 (m, 4H) 2.94 (d, J=11.35 Hz, 2H) 3.80 (br. s., 1H) 7.34 (t, J=8.69 Hz, 2H) 8.06 (d, J=8.24 Hz, 1H) 8.14-8.33 (m, 3H) 8.42 (d, J=7.14 Hz, 1H) 9.05 (br. s., 1H); MS(ES+) 382 (M+1); HRMS (TOF, ES+) calculated for $C_{19}H_{19}F_4N_3O+H^+$: 382.1542; observed 382.1529.

The following table lists compounds of formula (IV) that have been prepared.

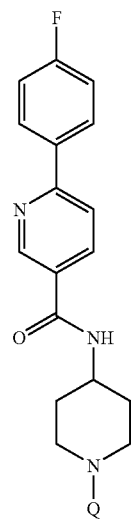

(IV)

| Ex | Q | Name | MS calc (M + H) | MS obs (M + H) |
|---|---|---|---|---|
| 10 | ![propylketone] | N-(1-Butyrylpiperidin-4-yl)-6-(4-fluorophenyl)nicotinamide | 370.1931 | 370.1918 |

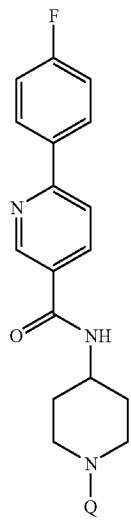

(IV)

| Ex | Q | Name | MS calc (M + H) | MS obs (M + H) |
|---|---|---|---|---|
| 11 | (2-pyridylmethyl) | 6-(4-Fluorophenyl)-N-[1-(pyridin-2-ylmethyl)piperidin-4-yl]nicotinamide | 391.1934 | 391.1955 |
| 12 | Me | 6-(4-Fluorophenyl)-N-(1-methylpiperidin-4-yl)nicotinamide | 314.1668 | 314.1661 |
| 13 | benzyl | N-(1-Benzylpiperidin-4-yl)-6-(4-fluorophenyl)nicotinamide | 390.1982 | 390.1944 |

EXAMPLE 14

6-(3-Methoxyphenyl)-N-(1-(2,2,2-trifluoroethyl)piperidin-4-yl)nicotinamide

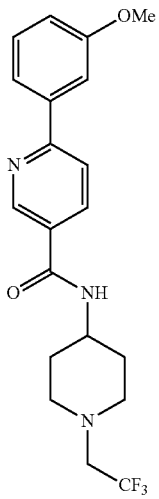

A total of 20.6 mg (52%) was obtained after chromatography: LCMS (ES+) 4.41 min (TIC, 100%); 1H NMR (400 MHz, DMSO-d$_6$) ☐ ppm 1.50-1.72 (m, 2H) 1.82 (d, J=11.35 Hz, 2H) 2.34-2.58 (m, 4H) 2.95 (d, J=10.98 Hz, 2H) 3.85 (br. s., 4H) 7.05 (d, J=6.77 Hz, 1H) 7.43 (t, J=7.87 Hz, 1H) 7.62-7.80 (m, 2H) 8.07 (d, J=8.24 Hz, 1H) 8.25 (d, J=8.42 Hz, 1H) 8.42 (d, J=7.32 Hz, 1H) 9.06 (d, J=1.28 Hz, 1 H); MS(ES+) 394 (M+1); HRMS (TOF, ES+) calculated for $C_{20}H_{22}F_3N_3O_2+H^+$: 394.1742 observed 394.1742.

The following table lists compounds of formula (V) that have been prepared.

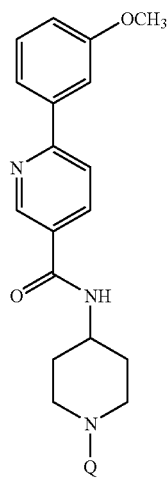

(V)

| Ex | Q | Name | MS Calc (M + H) | MS Obs (M + H) |
|---|---|---|---|---|
| 15 | (pyridin-2-ylmethyl) | 6-(3-Methoxyphenyl)-N-[1-(pyridin-2-ylmethyl)piperidin-4-yl]nicotinamide | 403.2134 | 403.2203 |
| 16 | methyl | 6-(3-Methoxyphenyl)-N-(1-methylpiperidin-4-yl)nicotinamide | 326.1869 | 326.5 |
| 17 | benzyl | N-(1-Benzylpiperidin-4-yl)-6-(3-methoxyphenyl)nicotinamide | 402.2181 | 402.2181 |
| 18 | —CO$_2$Et | Ethyl 4-({[6-(3-methoxyphenyl)pyridin-3-yl]carbonyl}amino)piperidine-1-carboxylate | 384.1923 | 384.1911 |
| 19 | butyryl | N-(1-Butyrylpiperidin-4-yl)-6-(3-methoxyphenyl)nicotinamide | 382.2130 | 382.2142 |
| 20 | isopropyl | N-(1-Isopropylpiperidin-4-yl)-6-(3-methoxyphenyl)nicotinamide | 354.2181 | 354.2247 |

EXAMPLE 21

6-m-Tolyl-N-(1-(2,2,2-trifluoroethyl)piperidin-4-yl)nicotinamide

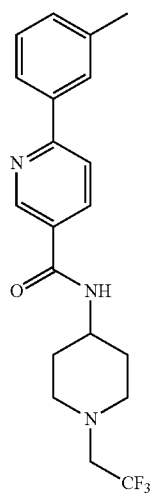

A total of 10.1 mg (27%) was obtained after chromatography: LCMS (ES+) 4.64 min (TIC, 100%); 1H NMR (400 MHz, DMSO-$d_6$) ☐ ppm 1.61 (q, J=10.01 Hz, 2H) 1.81 (d, J=10.07 Hz, 2H) 2.41 (s, 3H) 2.43-2.59 (m, 4H) 2.95 (d, J=12.45 Hz, 2H) 3.80 (br. s., 1H) 7.29 (d, J=7.14 Hz, 1 H) 7.40 (t, J=7.50 Hz, 1 H) 7.92 (d, J=8.24 Hz, 1H) 7.97 (br. s., 1H) 8.04 (d, J=8.42 Hz, 1H) 8.25 (d, J=8.05 Hz, 1H) 8.42 (d, J=7.69 Hz, 1H) 9.05 (br. s., 1H); MS(ES+) 378 (M+1); HRMS (TOF, ES+) calculated for $C_{20}H_{22}F_3N_3O+H^+$: 378.1793; observed 378.1783.

Using methods similar to the method set out in Example 21, the following compounds of formula (VI) were prepared.

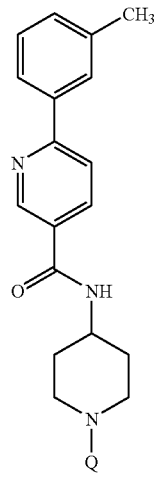

(VI)

| Ex | Q | Name | MS Calc (M + H) | MS Obs (M + H) |
|---|---|---|---|---|
| 22 | methyl | 6-(3-Methylphenyl)-N-(1-methylpiperidin-4-yl)nicotinamide | 310.1919 | 310.1935 |
| 23 | benzyl | N-(1-Benzylpiperidin-4-yl)-6-(3-methylphenyl)nicotinamide | 386.2232 | 386.2117 |
| 24 | ~~~C(=O)CH2CH2CH3 | N-(1-Butyrylpiperidin-4-yl)-6-(3-methylphenyl)nicotinamide | 366.2181 | 366.2144 |
| 25 | isopropyl | N-(1-Isopropylpiperidin-4-yl)-6-(3-methylphenyl)nicotinamide | 338.2232 | 338.2118 |

EXAMPLE 27

6-(3-Fluorophenyl)-N-(1-methylpiperidin-4-yl)nicotinamide

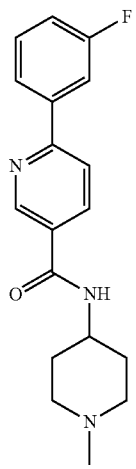

A total of 33.2 mg (quant.) was obtained after chromatography: LCMS (ES+) 2.79 min (TIC, 100%); 1H NMR (400 MHz, DMSO-d$_6$) ppm 1.57-1.72 (m, 2H) 1.85 (d, J=10.62 Hz, 2H) 2.21 (t, J=11.35 Hz, 2 H) 2.30 (s, 3H) 2.92 (d, J=11.71 Hz, 2H) 3.83 (dd, J=11.16, 3.84 Hz, 1H) 7.30-7.37 (m, 1H) 7.54-7.62 (m, 1H) 7.96 (d, J=10.62 Hz, 1H) 8.02 (d, J=8.05 Hz, 1H) 8.14 (d, J=8.24 Hz, 1H) 8.29 (dd, J=8.33, 2.10 Hz, 1H) 8.55 (d, J=7.50 Hz, 1H) 9.08 (d, J=1.83 Hz, 1H); MS(ES+) 314 (M+1); HRMS (TOF, ES+) calculated for $C_{18}H_{20}FN_3O+H^+$: 314.1668; observed 314.1696.

The following table lists compounds of formula (VII) that have been prepared.

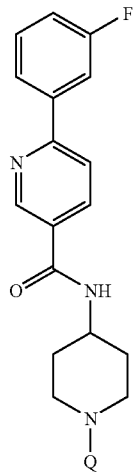

(VII)

| Ex | Q | Name | MS Calc (M + H) | MS Obs (M + H) |
|---|---|---|---|---|
| 28 | (pyridin-2-ylmethyl) | 6-(3-Fluorophenyl)-N-[1-(pyridin-2-ylmethyl)piperidin-4-yl]nicotinamide | 391.1934 | 391.1889 |
| 29 | benzyl | N-(1-Benzylpiperidin-4-yl)-6-(3-fluorophenyl)nicotinamide | 390.1982 | 390.1946 |
| 30 | isopropyl | 6-(3-Fluorophenyl)-N-(1-isopropylpiperidin-4-yl)nicotinamide | 342.1982 | 342.1932 |

(VII)

[Structure shown with Q substituent on piperidine nitrogen, connected via amide to pyridine bearing 3-fluorophenyl group]

| Ex | Q | Name | MS Calc (M + H) | MS Obs (M + H) |
|---|---|---|---|---|
| 31 | 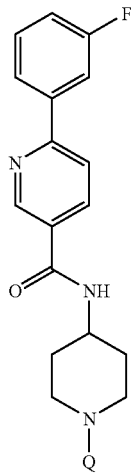 | N-(1-Butyrylpiperidin-4-yl)-6-(3-fluorophenyl)nicotinamide | 370.1911 | 370.1911 |
| 32 | —CO₂Et | Ethyl 4-({[6-(3-fluorophenyl)pyridin-3-yl]carbonyl}amino)piperidine-1-carboxylate | 372.1723 | 372.1729 |

EXAMPLE 33

Ethyl 4-({[6-(3,5-difluorophenyl)pyridin-3-yl]carbonyl}amino)piperidine-1-carboxylate

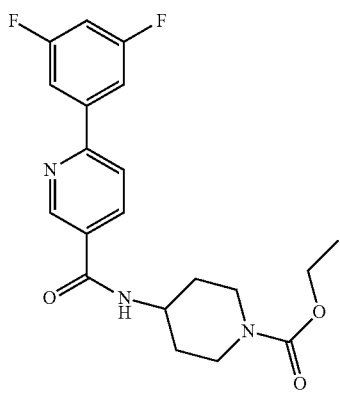

Step A: Preparation of tert-butyl 6-bromonicotinate

To a round bottom flask containing 2-bromo-5-pyridinecarboxylic acid (10.0 g, 49 mmol) in DCM (500 mL) was added oxalyl bromide (7.4 mL) and 5 drops of DMF. After some gas evolution, the reaction mixture was stirred at reflux ca 6 h, then cooled to rt and heptane 100 mL was added, followed by concentration of the mixture. The mixture was then suspended in THF 400 mL, cooled to 0° C. t-BuOK (5.8 g, 52 mmol) was then added and the rxn allowed to warm to rt and stirred for 2 h. The mixture poured into EtOAc, washed with 1 N NaOH, water, brine, dried MgSO₄ filtered and concentrated. The residue was purified by silica gel chromatography Biotage 40S Heptane EtOAc 0-80% 3 L to afford the title compound 4.2 g (36%) of as a white solid. ¹H NMR (400 MHz, DMSO-d₆) ☐ ppm 8.78-8.86 (1H, m), 8.14 (1H, dd, J=8.4, 2.4 Hz), 7.81 (1H d, J=8.4 Hz), 1.56 (9H, s).

Step B: Preparation of tert-butyl 6-(3,5-difluorophenyl)nicotinate

To round-bottom flask was added 3,5-difluoro phenylboronic acid (1.84 g, 11.6 mmol), palladium tetrakis(triphenylphosphine) (89.5 mg, 0.08 mmol) and tert-butyl 6-bromonicotinate (2.0 g, 7.75 mmol) and the mixture was evacuated 3× with N₂. The solids were dissolved in 50 mL of DMF, followed by addition of 11 mL of 2 M cesium carbonate. The resulting mixture was heated to ~90° C. until no starting bromide material was apparent by HPLC. The mixture was cooled to rt and then poured into a separatory funnel, followed by addition of EtOAc and water (1×200 mL). The layers were separated and the organic extract washed with brine (1×200 mL), dried MgSO₄, filtered and concentrated to afford an orange oil. The crude mixture was purified by silica gel column chromatography on Biotage (silica, 2-10% EtOAc in Heptane)-ca 2.5 L to afford the title compound 2.1 g (93%) as white solid. ¹H NMR (400 MHz, DMSO-d6) ☐ ppm 9.10-9.14 (1H, m), 8.29-8.35 (1H, m), 8.20-8.25 (1H, m), 7.90 (2H, dd, J=9.0, 1.5 Hz), 7.42 (1H, s), 1.59 (9H, s).

Step C: Preparation of
6-(3,5-difluoro-phenyl)-nicotinic acid

To tert-butyl 6-(3,5-difluorophenyl)nicotinate in DCM (80 mL) was added trifluroacetic acid (20 mL). After stirring at rt overnight, toluene was added (100 mL) and the solvent removed to give the crude product as a white powder. The solid was re-crystallized from MeOH to afford the title compound 1.269 g (74%) as a white solid. $^1$H NMR (400 MHz, DMSO-d6) □ ppm 9.16 (1H, d, J=1.7 Hz), 8.37 (1 H, dd, J=8.2, 2.0 Hz), 8.23 (1 H, d, J=8.2 Hz), 7.86-7.95 (2H, m), 7.36-7.47 (1H, m).

Step D: Preparation of Ethyl 4-({[6-(3,5-difluorophenyl)pyridin-3-yl]carbonyl}amino)piperidine-1-carboxylate 6-(3,5-difluoro-phenyl)-nicotinic acid (55 mg, 0.23 mmol), HOBt (40 mg, 0.29 mmol), ethyl 4-aminopiperidine-1-carboxylate (23 mg, 0.13 mmol), and PS-carbodimide (350 mg) in DCM (5 ml) was shaken 12 h. After shaking, PS-trisamine (3 mg) was added and the reaction shaken for 4 h, then filtered and washed with 15% MeOH/DCM. The organic was concentrated and purified by reversed phase automatic chromatography to provide 8.3 mg (9%) of the title compound. $^1$H NMR (400 MHz, DMSO-d6) □ ppm 9.08 (1H, d, J=1.5 Hz), 8.51 (1H, d, J=7.3 Hz), 8.31 (1H, dd, J=8.2, 2.4 Hz), 8.19 (1 h, d, J=8.8 Hz), 7.89 (2H, br. s.), 4.03 (2H, br. s.), 4.05 (4H, d, J=7.3 Hz), 2.94 (2H, br. s.), 1.85 (2H, d, J=13.5 Hz), 1.48 (2H, br. s.), 1.20 (3H, t, J=7.1 Hz).

EXAMPLE 34

6-(3,5-Difluorophenyl)-N-[1-(2,2,2-trifluoroethyl)piperidin-4-yl]nicotinamide

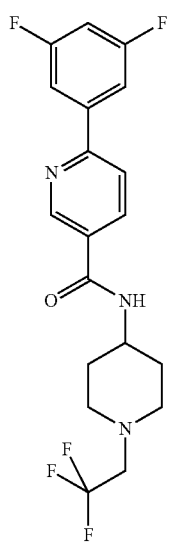

6-(3,5-Difluoro-phenyl)-nicotinic acid (50 mg, 0.21 mmol), 1-(2,2,2-trifluoroethyl)piperidin-4-amine hydrochloride (48 mg, 0.22 mmol) N,N-diisopropylethylamine (0.296 mL, 1.69 mmol), HATU (101 mg, 0.26 mmol) in acetonitrile (5 mL) was shaken at room temperature for 12 h. The reaction mixture was concentrated and the crude reaction mixture purified by automated reversed phase chromatography to provide 6 mg (7%) of the title compound. $^1$H NMR (400 MHz, DMSO-d6) □ ppm 9.08 (1H, s), 8.47 (1H, d, J=7.0 Hz), 8.30 (1H, dd, J=8.4, 2.2 Hz), 8.19 (1H, d, J=8.1 Hz), 7.88 (2H, d, J=7.0 Hz), 7.36 (1H, t, J=10.1 Hz), 3.82 (1H, br. s.), 3.11-3.23 (2H, m), 2.95 (2H, d, J=11.0 Hz), 2.42-2.48 (2H, m), 1.76-1.87 (2H, m), 1.56-1.66 (2H, m).

EXAMPLE 35

6-(3-Fluorophenyl)-N-(1-(5-methoxy-2-(pyridin-2-yl)pyrimidin-4-yl)piperidin-4-yl)nicotinamide

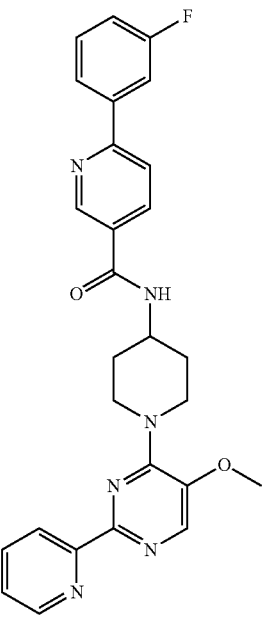

Step A: 6-(3-Fluorophenyl)nicotinic acid

3-Fluorophenylboronic acid (39.5 g, 0.282 mol), a solution of K$_2$CO$_3$ (150 g) in water (700 mL), [Bu$_4$N]Br (3.5 g, 0.0107 mol), and Pd(PPh$_3$)$_4$ (12.4 g, 0.0107 mol) were added to a solution of 6-chloronicotinic acid (37.0 g, 0.235 mol) in toluene. The reaction mixture was stirred under reflux for 20 h. After cooling, the reaction mixture was filtered and acidified with 2 M HCl to pH 3. The formed precipitate was separated by filtration and dried to give 6-(3-fluorophenyl)nicotinic acid (yield 97%, 49.9 g). $^1$H NMR (400 MHz, DMSO-d$_6$) □ ppm 7.29 (td, J=8.46, 2.42 Hz, 1H) 7.50-7.56 (m, 1H) 7.93 (dd, J=10.47, 2.15 Hz, 1H) 7.97 (d, J=7.79 Hz, 1H) 8.11 (d, J=8.06 Hz, 1H) 8.30 (dd, J=8.32, 2.15 Hz, 1H) 9.11 (d, J=1.88 Hz, 1H), 13.48 (bs, 1H).

Step B: tert-Butyl 4-(2-(3-fluorophenyl)nicotinamido)piperidine-1-carboxylate

1-Boc-4-aminopiperidine hydrochloride (55.9 g, 0.230 mol, 1.18 HCl), BOP (112 g, 0.253 mol), and DIPEA (140 mL, 0.805 mol) were added to a solution of the compound from Step 1 (49.9 g, 0.230 mol) in dichloromethane (1 L). The reaction mixture was stirred at room temperature for 18 h, evaporated, and chromatographed (silica gel, ethyl acetate-hexane, 2:1). The product was evaporated to give tert-butyl 4-(2-(3-fluorophenyl)nicotinamido)piperidine-1-carboxylate (yield 61%, 56.4 g). MS(ES+)=400 (M+H) observed, 400.20 expected.

Step C:
6-(3-Fluorophenyl)-N-(piperidin-4-yl)nicotinamide

4 M HCl in dioxane (400 mL) was added to a solution of the compound of Step 2 (56.4 g, 0.14 mol) in dioxane (100 mL). The reaction mixture was stirred at room temperature for 4 h. The formed precipitate was separated by filtration, washed with ether, and dried to give 6-(3-fluorophenyl)-N-(piperidin-4-yl)nicotinamide as an HCl salt (quantitative yield, 52 g). $^1$H NMR (400 MHz, DMSO-$d_6$) □ ppm 1.77-1.93 (m, 2H) 1.93-2.06 (m, 2H) 2.91-3.12 (m, 2H) 3.31 (d, J=12.89 Hz, 2H) 4.02-4.18 (m, 1H) 7.26-7.40 (m, 1H) 7.50-7.64 (m, 1H) 7.91-8.09 (m, 2H) 8.17 (d, J=8.59 Hz, 1H) 8.40 (dd, J=8.32, 2.15 Hz, 1H) 8.87 (d, J=7.52 Hz, 1H) 9.13 (d, J=1.61 Hz, 2H); HRMS (TOF, ES+) calculated for C17H19FN3O+H$^+$: 300.1507; observed 300.1538.

Step D: 6-(3-Fluorophenyl)-N-(1-(5-methoxy-2-(pyridin-2-yl)pyrimidin-4-yl)piperidin-4-yl)nicotinamide To a vial containing CsF (60-85 mgs, 5-7 eqs) was added (0.2 mL, 0.08 mmol) of a solution of 4-chloro-5-methoxy-2-phenylpyrimidine in DMF followed by addition of (0.22 mL, 0.088 mmol) of 6-(3-fluorophenyl)-N-(piperidin-4-yl)nicotinamide-HCl salt in DMF and triethylamine (2-3 eq). The reaction mixture was heated to 85-90° C. for 24 hrs and then allowed to cool to room temperature. The crude reaction mixture was then filtered and purified by RP-HPLC to give the desired product. $^1$H NMR (400 MHz, DMSO-$d_6$) □ ppm 1.63-1.73 (m, 2H) 1.96 (d, J=10.25 Hz, 2H) 3.11-3.19 (m, 2H) 3.94 (s, 3H) 4.18 (d, J=7.69 Hz, 1H) 4.64 (d, J=12.81 Hz, 2H) 7.31 (td, J=8.33, 2.38 Hz, 1H) 7.43 (d, J=5.12 Hz, 1H) 7.53-7.59 (m, 1H) 7.87-7.97 (m, 2H) 8.00 (d, J=7.69 Hz, 1H) 8.12 (d, J=8.42 Hz, 1H) 8.20 (s, 1H) 8.26 (d, J=8.05 Hz, 1H) 8.29 (dd, J=8.42, 1.83 Hz, 1H) 8.50 (d, J=7.69 Hz, 1H) 8.68 (d, J=4.39 Hz, 1H) 9.08 (s, 1H); LC/MS(ES+)=485.5 observed, 485.21 expected.

EXAMPLE 36

6-(3-Fluorophenyl)-N-(piperidin-4-yl)nicotinamide

See under Example 35, step 3.
Using techniques analogous to Example 35 the following compounds of Formula (VII) may be prepared.

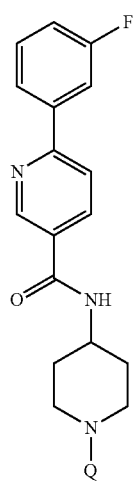

(VII)

EXAMPLE 37

N-(1-(6-(1H-Pyrazol-3-ylamino)pyrimidin-4-yl)piperidin-4-yl)-6-(3-fluorophenyl)nicotinamide

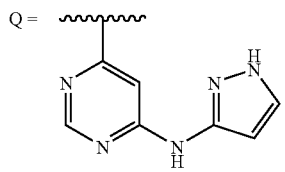

NMR: 1H NMR (400 MHz, DMSO-$d_6$) □ ppm 1.49-1.59 (m, 2H) 1.90 (br. s., 2H) 3.01 (d, J=15.37 Hz, 2H) 4.15 (br. s., 1H) 4.26 (d, J=12.45 Hz, 3H) 6.16 (br. s., 1H) 6.78 (br. s., 1H) 7.31 (d, J=2.20 Hz, 1H) 7.53-7.60 (m, 2H) 7.95 (d, J=10.98 Hz, 1H) 8.00 (d, J=8.05 Hz, 1H) 8.14 (d, J=4.39 Hz, 1H) 8.11 (s, 1H) 8.29 (dd, J=8.24, 2.01 Hz, 1H) 8.49 (d, J=7.32 Hz, 1H) 9.08 (d, J=1.46 Hz, 1H) 9.17 (br. s., 1H).
MS calc (M+H) 459.2; MS obs (M+H) 459.5.

EXAMPLE 38

N-(1-(6-Chloroquinazolin-4-yl)piperidin-4-yl)-6-(3-fluorophenyl)nicotinamide

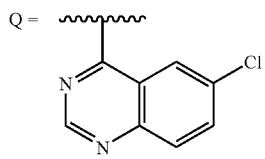

1H NMR (400 MHz, DMSO-$d_6$) □ ppm 1.68-1.87 (m, 2H) 2.01 (d, J=2.93 Hz, 2H) 3.41 (t, 2H) 4.22 (br. s., 1H) 4.32 (d, J=13.18 Hz, 2H) 7.24-7.37 (m, 1H) 7.50-7.64 (m, 1H) 7.84 (s, 2H) 7.92-7.99 (m, 2H) 8.01 (d, J=7.32 Hz, 1H) 8.14 (d, J=8.42 Hz, 1H) 8.31 (dd, J=8.24, 2.01 Hz, 1H) 8.57 (d, J=7.32 Hz, 1H) 8.65 (s, 1H) 9.10 (s, 1H).
MS calc (M+H) 462.14; MS obs (M+H) 462.5.

EXAMPLE 39

6-(3-Fluorophenyl)-N-(1-(1-phenyl-1H-tetrazol-5-yl)piperidin-4-yl)nicotinamide

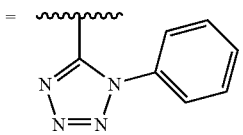

1H NMR (400 MHz, DMSO-$d_6$) □ ppm 1.57-1.73 (m, 2H) 1.83 (d, J=10.62 Hz, 2H) 3.06 (t, J=11.35 Hz, 2H) 3.50 (d, J=13.18 Hz, 2H) 4.04 (d, J=6.95 Hz, 1H) 7.52-7.59 (m, 2H) 7.59-7.72 (m, 5H) 7.95 (d, J=10.62 Hz, 1H) 8.00 (d, J=7.69 Hz, 1H) 8.12 (d, J=8.42 Hz, 1H) 8.28 (dd, J=8.60, 2.01 Hz, 1H) 8.51 (d, J=7.32 Hz, 1H) 9.07 (s, 1H).
MS calc (M+H) 444.19; MS obs (M+H) 444.8.

EXAMPLE 40

6-(3-Fluorophenyl)-N-(1-(9-(2-hydroxycyclopentyl)-9H-purin-6-yl)piperidin-4-yl)nicotinamide

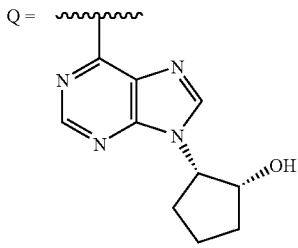

1H NMR (400 MHz, DMSO-$d_6$) ☐ ppm 1.50-1.68 (m, 4H) 1.75-1.90 (m, 2H) 1.93-2.11 (m, 5H) 2.31-2.26 (m, 1H) 4.17-4.29 (m, 1H) 4.43-4.52 (m, 1H) 4.55 (d, J=7.69 Hz, 1H) 5.13 (d, J=5.12 Hz, 1H) 5.33 (br. s., 2H) 7.23-7.37 (m, 1H) 7.49-7.64 (m, 1H) 7.93 (d, 1H) 8.00 (d, J=7.69 Hz, 1H) 8.12 (d, J=8.42 Hz, 1H) 8.18-8.26 (m, 2H) 8.29 (dd, J=8.42, 2.20 Hz, 1H) 8.49 (d, J=7.32 Hz, 1H) 9.08 (d, J=1.83 Hz, 1H).
MS calc (M+H) 502.23; MS obs (M+H) 502.6.

EXAMPLE 40

N-[1-(3-Cyano-6-methylpyridin-2-yl)piperidin-4-yl]-6-(3-fluorophenyl)nicotinamide

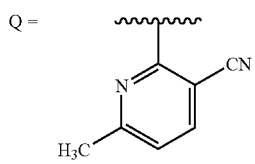

1H NMR (400 MHz, DMSO-$d_6$) ☐ ppm 1.62-1.78 (m, 2H) 1.96 (br. s., 2H) 2.41 (s, 3H) 3.09-3.21 (m, 2H) 4.15 (br. s., 1H) 4.28 (d, J=13.54 Hz, 2H) 6.78 (d, J=7.69 Hz, 1H) 7.24-7.37 (m, 1H) 7.50-7.65 (m, 1H) 7.87-7.98 (m, 2H) 8.01 (d, J=7.69 Hz, 1H) 8.13 (d, J=8.42 Hz, 1H) 8.31 (dd, J=8.24, 2.01 Hz, 1H) 8.54 (d, J=7.69 Hz, 1H) 9.10 (s, 1H).
MS calc (M+H) 416.18; MS obs (M+H) 416.5.

EXAMPLE 42

6-(3-Fluorophenyl)-N-[1-(3-phenylpyrazin-2-yl)piperidin-4-yl]nicotinamide

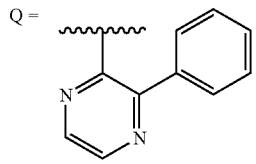

1H NMR (400 MHz, DMSO-$d_6$) ☐ ppm 1.53-1.69 (m, 2H) 1.78 (br. s., 2H) 2.81 (t, J=11.53 Hz, 2H) 3.62 (d, J=12.81 Hz, 2H) 3.98 (br. s., 1H) 7.24-7.36 (m, 1H) 7.39-7.47 (m, 1H) 7.50 (t, J=7.32 Hz, 2H) 7.53-7.61 (m, 1H) 7.84-7.98 (m, 3H) 8.01 (d, J=7.69 Hz, 1H) 8.12 (d, J=8.42 Hz, 1H) 8.15-8.21 (m, 2H) 8.29 (dd, J=8.42, 2.20 Hz, 1H) 8.52 (d, J=7.69 Hz, 1H) 9.08 (d, J=1.83 Hz, 1H).
MS calc (M+H) 454.2; MS obs (M+H) 454.5.

EXAMPLE 43

6-(3-Fluorophenyl)-N-(1-{3-[(2-hydroxyethyl)amino]quinoxalin-2-yl}piperidin-4-yl)nicotinamide

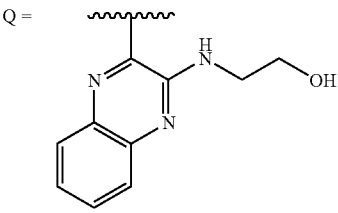

1H NMR (400 MHz, DMSO-$d_6$) ☐ ppm 1.79-1.95 (m, 2H) 2.02 (d, J=10.98 Hz, 2H) 2.91-3.04 (m, 2H) 3.56 (q, J=5.73 Hz, 2H) 3.66 (t, J=5.49 Hz, 2H) 3.69-3.78 (m, 2H) 4.08 (d, J=7.32 Hz, 1H) 4.78-4.89 (m, 1H) 6.38 (t, J=5.49 Hz, 1H) 7.22-7.35 (m, 2H) 7.38 (t, J=6.95 Hz, 1H) 7.49-7.55 (m, 1H) 7.59 (dd, J=12.99, 6.77 Hz, 2H) 7.96 (d, J=10.62 Hz, 1H) 8.01 (d, J=8.05 Hz, 1H) 8.13 (d, J=8.42 Hz, 1H) 8.32 (dd, J=8.42, 2.20 Hz, 1H) 8.61 (d, J=7.32 Hz, 1H) 9.11 (d, J=1.83 Hz, 1 H).
MS calc (M+H) 487.22; MS obs (M+H) 487.5.

EXAMPLE 44

N-{1-[5-(3,4-Dimethoxyphenyl)-2-methylpyrimidin-4-yl]piperidin-4-yl}-6-(3-fluorophenyl)nicotinamide

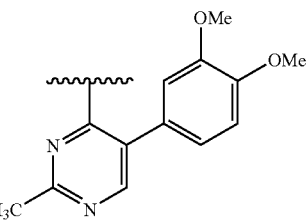

1H NMR (400 MHz, DMSO-$d_6$) ☐ ppm 1.46-1.63 (m, 2H) 1.79 (br. s., 2H) 2.58 (s, 3H) 2.87 (t, J=11.71 Hz, 2H) 3.84 (d, J=8.79 Hz, 6H) 3.90 (d, J=12.81 Hz, 2H) 4.06 (br. s., 1H) 6.98-7.12 (m, 3H) 7.30-7.41 (m, 1H) 7.53-7.66 (m, 1H) 7.97 (br. s., 1H) 8.04 (d, J=7.69 Hz, 1H) 8.10 (s, 1H) 8.15 (d, J=8.42 Hz, 1H) 8.31 (dd, J=8.24, 2.01 Hz, 1H) 8.51 (d, J=7.69 Hz, 1H) 9.10 (d, J=1.46 Hz, 1H).
MS calc (M+H) 528.23; MS obs (M+H) 528.5.

EXAMPLE 45

N-[1-(2-Amino-6-methylpyrimidin-4-yl)piperidin-4-yl]-6-(3-fluorophenyl)nicotinamide

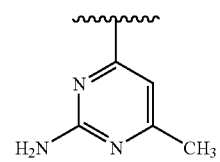

1H NMR (400 MHz, DMSO-$d_6$) ☐ ppm 1.48 (d, J=12.08 Hz, 2H) 1.86 (d, J=10.62 Hz, 2H) 2.08 (s, 3H) 2.87-3.01 (m, 2H) 4.10 (br. s., 1H) 4.29 (br. s., 2H) 5.83 (s, 2H) 5.97 (s, 1H) 7.24-7.38 (m, 1H) 7.50-7.64 (m, 1H) 7.95 (d, J=10.62 Hz, 1H) 8.00 (d, J=7.69 Hz, 1H) 8.12 (d, J=8.42 Hz, 1H) 8.29 (dd, J=8.24, 2.01 Hz, 1H) 8.47 (d, J=7.69 Hz, 1H) 9.08 (d, J=1.83 Hz, 1H).
MS calc (M+H) 407.19; MS obs (M+H) 407.5.

EXAMPLE 46

N-{1-[5,6-Dimethyl-2-(trifluoromethyl)pyrimidin-4-yl]piperidin-4-yl}-6-(3-fluorophenyl)nicotinamide

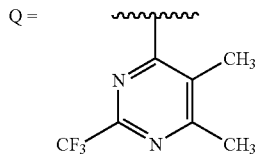

1H NMR (400 MHz, DMSO-d$_6$) ☐ ppm 1.60-1.77 (m, 2H) 1.96 (d, J=9.88 Hz, 2H) 2.21 (s, 3H) 2.42 (s, 3H) 3.10 (t, J=12.08 Hz, 2H) 3.89 (d, J=13.18 Hz, 2H) 4.05-4.21 (m, 1H) 7.24-7.37 (m, 1H) 7.50-7.61 (m, 1H) 7.95 (d, J=10.98 Hz, 1H) 8.01 (d, J=7.69 Hz, 1H) 8.13 (d, J=8.42 Hz, 1H) 8.31 (dd, J=8.42, 1.83 Hz, 1H) 8.54 (d, J=7.69 Hz, 1H) 9.09 (s, 1H).
MS calc (M+H) 474.18; MS obs (M+H) 474.6.

EXAMPLE 47

6-(3-Fluorophenyl)-N-(1-{4-[2-(5-methylisoxazol-3-yl)pyrrolidin-1-yl]pyrimidin-2-yl}piperidin-4-yl)nicotinamide

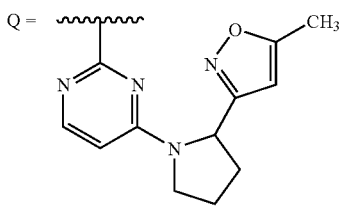

1H NMR (400 MHz, DMSO-d$_6$) ☐ ppm 1.44 (br. s., 1H) 1.78 (br. s., 2H) 1.97 (d, J=5.86 s., 2H) 2.32 (s, 4H) 2.89 (br. s., 2H) 3.47 (br. s., 1H) 3.61 (br. s., 1H) 4.08 (br. s., 1H) 4.52 (br. s., 2H) 5.14 (br. s., 1H) 5.78 (br. s., 1H) 6.07 (br. s., 1H) 7.23-7.39 (m, 1H) 7.49-7.64 (m, 1H) 7.84 (d, J=6.22 Hz, 1H) 7.95 (d, J=10.62 Hz, 1H) 8.00 (d, J=8.05 Hz, 1H) 8.12 (d, J=8.42 Hz, 1H) 8.28 (dd, J=8.05, 1.83 Hz, 1H) 8.42 (d, J=7.69 Hz, 1H) 9.07 (s, 1H).
MS calc (M+H) 528.24; MS obs (M+H) 528.8.

EXAMPLE 48

N-[1-(5-Chloro-6-methyl-2-pyridin-2-ylpyrimidin-4-yl)piperidin-4-yl]-6-(3-fluorophenyl)nicotinamide

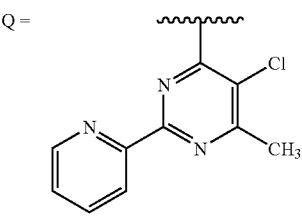

1H NMR (400 MHz, DMSO-d$_6$) ☐ ppm 1.77 (br. s., 2H) 1.99 (br. s., 2H) 2.57 (s, 3H) 3.15-3.23 (m, 2H) 4.17 (br. s., 1H) 4.35 (d, J=13.18 Hz, 2H) 7.26-7.37 (m, 1H) 7.49 (dd, J=7.14, 4.94 Hz, 1H) 7.53-7.63 (m, 1H) 7.89-7.98 (m, 2H) 8.01 (d, J=7.69 Hz, 1H) 8.13 (d, J=8.05 Hz, 1H) 8.25-8.37 (m, 2H) 8.55 (d, J=7.69 Hz, 1H) 8.72 (d, J=4.39 Hz, 1H) 9.10 (s, 1H).
MS calc (M+H) 503.17; MS obs (M+H) 503.5.

EXAMPLE 49

6-(3-Fluorophenyl)-N-[1-(6-methoxypyrimidin-4-yl)piperidin-4-yl]nicotinamide

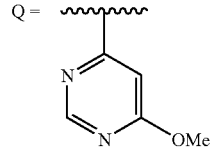

1H NMR (400 MHz, DMSO-d$_6$) ☐ ppm 1.41-1.59 (m, 2H) 1.89 (br. s., 2H) 3.00-3.11 (m, 2H) 3.83 (s, 3 H) 4.15 (br. s., 1H) 4.34 (d, J=13.18 Hz, 2H) 6.12 (s, 1H) 7.25-7.37 (m, 1H) 7.51-7.63 (m, 1H) 7.95 (d, J=10.62 Hz, 1H) 8.01 (d, J=7.69 Hz, 1H) 8.12 (d, J=8.05 Hz, 1H) 8.23-8.33 (m, 2H) 8.47 (d, J=7.69 Hz, 1H) 9.08 (d, J=1.83 Hz, 1H).
MS calc (M+H) 408.18; MS obs (M+H) 408.5.

EXAMPLE 50

6-(3-Fluorophenyl)-N-{1-[5-(morpholin-4-ylcarbonyl)pyridin-2-yl]piperidin-4-yl}nicotinamide

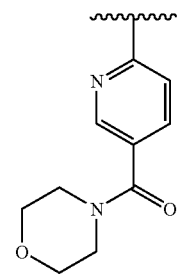

1H NMR (400 MHz, DMSO-d$_6$) ☐ ppm 9.08 (1H, d, J=2.4 Hz), 8.53 (1H, d, J=7.9 Hz), 8.29 (1H, dd, J=8.4, 2.2 Hz), 8.22 (1H, d, J=2.4 Hz), 8.14 (1H, d, J=8.5 Hz), 7.90-8.07 (2H, m) 7.50-7.65 (2H, m), 7.25-7.39 (1H, m), 6.91 (1H, d, J=8.9 Hz), 4.30-4.47 (2H, m), 4.04-4.26 (1H, m) 3.44-3.67 (8H, m), 2.97-3.14 (2H, m), 1.90 (2H, dd, J=13.1, 2.6 Hz), 1.45-1.62 (2H, m).
MS calc (M+H) 490.22; MS obs (M+H) 490.5.

EXAMPLE 51

6-(3-Fluorophenyl)-N-[1-(1-methyl-1H-tetrazol-5-yl)piperidin-4-yl]nicotinamide

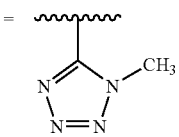

1H NMR (400 MHz, DMSO-d$_6$) F ppm 9.10 (1H, d, J=1.6 Hz), 8.61 (1H, d, J=7.4 Hz), 8.27-8.36 (1H, m), 8.15 (1H, d, J=8.2 Hz), 7.91-8.08 (2H, m), 7.51-7.64 (1H, m), 7.24-7.38 (1H, m), 4.02-4.20 (1 H, m), 3.85-3.92 (3H, m), 3.60-3.74 (2H, m), 3.07-3.22 (2H, m), 1.87-2.01 (2H, m), 1.67-1.85 (2 H, m).
MS calc (M+H) 382.17; MS obs (M+H) 382.4.

| Ex | Q | Name | MS Calc (M + H) | MS Obs (M + H) |
|---|---|---|---|---|
| 52 | 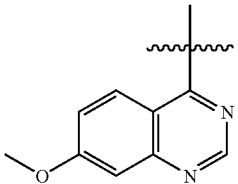 | 6-(3-Fluorophenyl)-N-[1-(7-methoxyquinazolin-4-yl)piperidin-4-yl]nicotinamide | 458.2 | 458.5 |
| 53 | 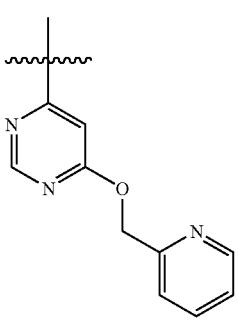 | 6-(3-Fluorophenyl)-N-{1-[6-(pyridin-2-ylmethoxy)pyrimidin-4-yl]piperidin-4-yl}nicotinamide | 485.2 | 485.5 |
| 54 | 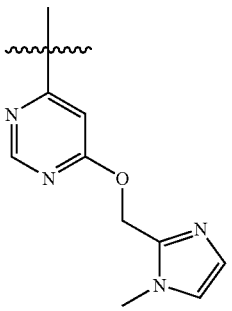 | 6-(3-Fluorophenyl)-N-(1-{6-[(1-methyl-1H-imidazol-2-yl)methoxy]pyrimidin-4-yl}piperidin-4-yl)nicotinamide | 488.2 | 488.6 |
| 55 | 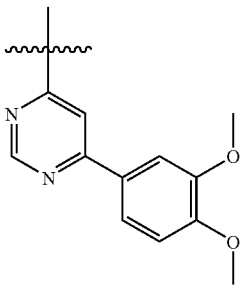 | N-{1-[6-(3,4-Dimethoxyphenyl)pyrimidin-4-yl]piperidin-4-yl}-6-(3-fluorophenyl)nicotinamide | 514.2 | 514.7 |
| 56 | 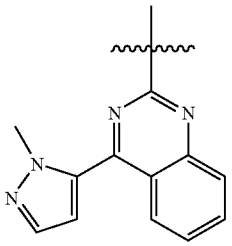 | 6-(3-Fluorophenyl)-N-{1-[4-(1-methyl-1H-pyrazol-5-yl)quinazolin-2-yl]piperidin-4-yl}nicotinamide | 508.2 | 508.1 |

-continued

| Ex | Q | Name | MS Calc (M + H) | MS Obs (M + H) |
|---|---|---|---|---|
| 57 | 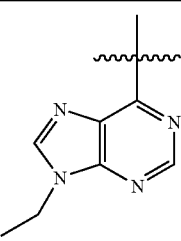 | N-[1-(9-Ethyl-9H-purin-6-yl)piperidin-4-yl]-6-(3-fluorophenyl)nicotinamide | 446.2 | 446.6 |
| 58 | 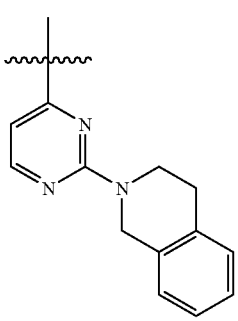 | N-{1-[2-(3,4-Dihydroisoquinolin-2(1H)-yl)pyrimidin-4-yl]piperidin-4-yl}-6-(3-fluorophenyl)nicotinamide | 509.2 | 509.6 |
| 59 | 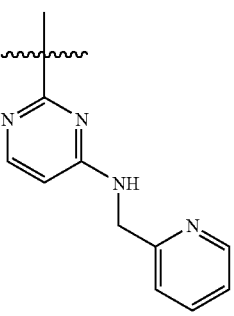 | 6-(3-Fluorophenyl)-N-(1-{4-[(pyridin-2-ylmethyl)amino]pyrimidin-2-yl}piperidin-4-yl)nicotinamide | 484.2 | 484.5 |
| 60 | 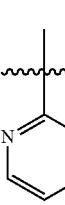 | 6-(3-Fluorophenyl)-N-(1-pyrazin-2-ylpiperidin-4-yl)nicotinamide | 378.2 | 378.3 |
| 61 | 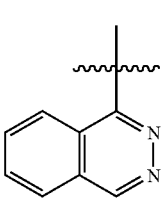 | 6-(3-Fluorophenyl)-N-(1-phthalazin-1-ylpiperidin-4-yl)nicotinamide | 428.2 | 428.4 |
| 62 | 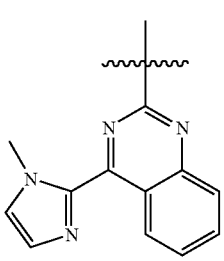 | 6-(3-Fluorophenyl)-N-{1-[4-(1-methyl-1H-imidazol-2-yl)quinazolin-2-yl]piperidin-4-yl}nicotinamide | 508.2 | 508.5 |

-continued

| Ex | Q | Name | MS Calc (M + H) | MS Obs (M + H) |
|---|---|---|---|---|
| 63 | pyrido[2,3-d]pyrimidin-4-yl | 6-(3-Fluorophenyl)-N-(1-pyrido[2,3-d]pyrimidin-4-ylpiperidin-4-yl)nicotinamide | 429.2 | 429.4 |
| 64 | 3-(aminocarbonyl)pyridin-2-yl | N-{1-[3-(Aminocarbonyl)pyridin-2-yl]piperidin-4-yl}-6-(3-fluorophenyl)nicotinamide | 420.2 | 420.5 |
| 65 | 3-chloropyridin-2-yl | N-[1-(3-Ahloropyridin-2-yl)piperidin-4-yl]-6-(3-fluorophenyl)nicotinamide | 411.1 | 411.5 |
| 66 | 3-(ethoxycarbonyl)pyridin-2-yl | Ethyl 2-[4-({[6-(3-fluorophenyl)pyridin-3-yl]carbonyl}amino)piperidin-1-yl]nicotinate | 449.2 | 449.5 |
| 67 | 3-cyano-4-methoxypyridin-2-yl | N-[1-(3-Cyano-4-methoxypyridin-2-yl)piperidin-4-yl]-6-(3-fluorophenyl)nicotinamide | 432.2 | 432.5 |
| 68 | 5-(aminocarbonyl)pyridin-2-yl | N-{1-[5-(Aminocarbonyl)pyridin-2-yl]piperidin-4-yl}-6-(3-fluorophenyl)nicotinamide | 420.2 | 420.5 |
| 69 | 3-cyano-4,6-dimethylpyridin-2-yl | N-[1-(3-Cyano-46-dimethylpyridin-2-yl)piperidin-4-yl]-6-(3-fluorophenyl)nicotinamide | 430.2 | 430.5 |

-continued

| Ex | Q | Name | MS Calc (M + H) | MS Obs (M + H) |
|---|---|---|---|---|
| 70 | 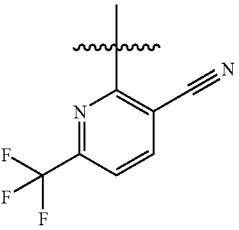 | N-{1-[3-Cyano-6-(trifluoromethyl)pyridin-2-yl]piperidin-4-yl}-6-(3-fluorophenyl)nicotinamide | 470.2 | 470.6 |
| 71 | 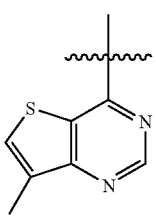 | 6-(3-Fluorophenyl)-N-[1-(7-methylthieno[3,2-d]pyrimidin-4-yl)piperidin-4-yl]nicotinamide | 448.2 | 448.5 |
| 72 | 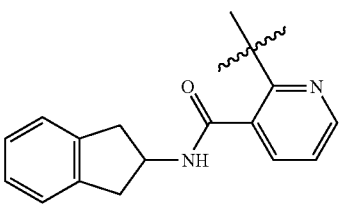 | N-(2,3-Dihydro-1H-inden-2-yl)-2-[4-({[6-(3-fluorophenyl)pyridin-3-yl]carbonyl}amino)piperidin-1-yl]nicotinamide | 536.2 | 536.5 |
| 73 | 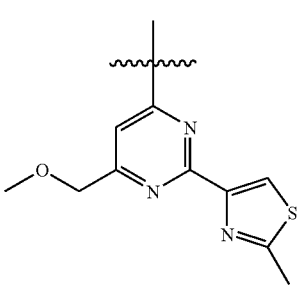 | 6-(3-Fluorophenyl)-N-{1-[6-(methoxymethyl)-2-(2-methyl-13-thiazol-4-yl)pyrimidin-4-yl]piperidin-4-yl}nicotinamide | 519.2 | 519.5 |
| 74 | 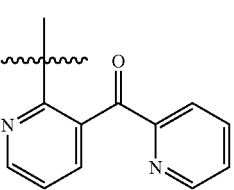 | 6-(3-Fluorophenyl)-N-{1-[3-(pyridin-2-ylcarbonyl)pyridin-2-yl]piperidin-4-yl}nicotinamide | 482.2 | 482.5 |
| 75 | 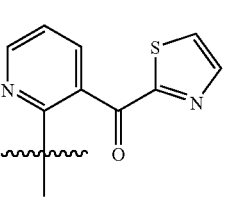 | 6-(3-Fluorophenyl)-N-{1-[3-(1,3-thiazol-2-ylcarbonyl)pyridin-2-yl]piperidin-4-yl}nicotinamide | 488.2 | 488.5 |

-continued

| Ex | Q | Name | MS Calc (M + H) | MS Obs (M + H) |
|---|---|---|---|---|
| 76 | | N-[1-(5-Acetyl-3-cyano-6-methylpyridin-2-yl)piperidin-4-yl]-6-(3-fluorophenyl)nicotinamide | 458.2 | 458.4 |
| 77 | | N-{1-[3-(2-Cyanobenzoyl)pyridin-2-yl]piperidin-4-yl}-6-(3-fluorophenyl)nicotinamide | 506.2 | 506.5 |
| 78 | | Methyl 2-amino-4-[4-({[6-(3-fluorophenyl)pyridin-3-yl]carbonyl}amino)piperidin-1-yl]pyrimidine-5-carboxylate | 451.2 | 451.5 |
| 79 | | N-[1-(3-Benzylpyrazin-2-yl)piperidin-4-yl]-6-(3-fluorophenyl)nicotinamide | 468.2 | 468.6 |
| 80 | | 6-[4-({[6-(3-Fluorophenyl)pyridin-3-yl]carbonyl}amino)piperidin-1-yl]-N-methylpyridazine-3-carboxamide | 435.2 | 435.5 |
| 81 | | N-[(1-Ethylpyrrolidin-2-yl)methyl]-6-[4-({[6-(3-fluorophenyl)pyridin-3-yl]carbonyl}amino)piperidin-1-yl]pyridazine-3-carboxamide | 532.3 | 532.5 |

-continued

| Ex | Q | Name | MS Calc (M + H) | MS Obs (M + H) |
|---|---|---|---|---|
| 82 | 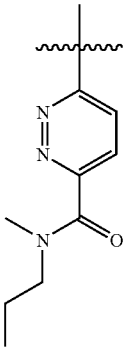 | 6-[4-({[6-(3-Fluorophenyl)pyridin-3-yl]carbonyl}amino)piperidin-1-yl]-N-methyl-N-propylpyridazine-3-carboxamide | 477.2 | 477.5 |
| 83 | 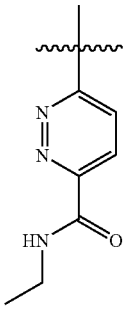 | N-Ethyl-6-[4-({[6-(3-fluorophenyl)pyridin-3-yl]carbonyl}amino)piperidin-1-yl]pyridazine-3-carboxamide | 449.2 | 449.5 |
| 84 | 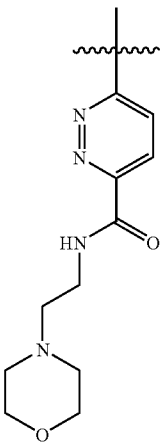 | 6-[4-({[6-(3-Fluorophenyl)pyridin-3-yl]carbonyl}amino)piperidin-1-yl]-N-(2-morpholin-4-ylethyl)pyridazine-3-carboxamide | 534.3 | 534.7 |
| 85 | 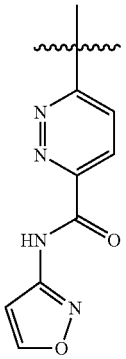 | 6-[4-({[6-(3-Fluorophenyl)pyridin-3-yl]carbonyl}amino)piperidin-1-yl]-N-isoxazol-3-ylpyridazine-3-carboxamide | 488.2 | 488.5 |

-continued

| Ex | Q | Name | MS Calc (M + H) | MS Obs (M + H) |
|---|---|---|---|---|
| 86 | (3,4-dimethylisoxazol-5-yl carbamoyl pyridazine) | N-(3,4-Dimethylisoxazol-5-yl)-6-[4-({[6-(3-fluorophenyl)pyridin-3-yl]carbonyl}amino)piperidin-1-yl]pyridazine-3-carboxamide | 516.2 | 516.5 |
| 87 | (4-ethylpiperazin-1-yl carbonyl pyridazine) | N-(1-{6-[(4-Ethylpiperazin-1-yl)carbonyl]pyridazin-3-yl}piperidin-4-yl)-6-(3-fluorophenyl)nicotinamide | 518.3 | 518.7 |
| 88 | (2-ethoxyethyl carbamoyl pyridazine) | N-(2-Ethoxyethyl)-6-[4-({[6-(3-fluorophenyl)pyridin-3-yl]carbonyl}amino)piperidin-1-yl]pyridazine-3-carboxamide | 493.2 | 493.6 |
| 89 | (1,3,5-trimethyl-1H-pyrazol-4-yl carbamoyl pyridazine) | 6-[4-({[6-(3-Fluorophenyl)pyridin-3-yl]carbonyl}amino)piperidin-1-yl]-N-(1,3,5-trimethyl-1H-pyrazol-4-yl)pyridazine-3-carboxamide | 529.2 | 529.7 |

-continued

| Ex | Q | Name | MS Calc (M + H) | MS Obs (M + H) |
|---|---|---|---|---|
| 90 | 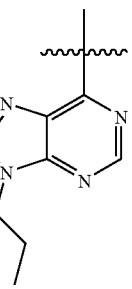 | 6-(3-Fluorophenyl)-N-(1-{9-[1-(hydroxymethyl)propyl]-9H-purin-6-yl}piperidin-4-yl)nicotinamide | 490.2 | 490.6 |
| 91 | 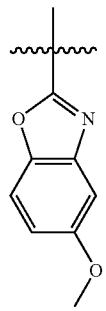 | 6-(3-Fluorophenyl)-N-[1-(5-methoxy-13-benzoxazol-2-yl)piperidin-4-yl]nicotinamide | 447.2 | 447.5 |
| 92 | 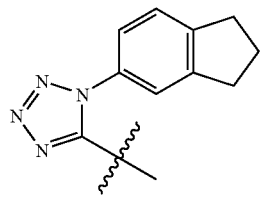 | N-{1-[1-(2,3-Dihydro-1H-inden-5-yl)-1H-tetrazol 5-yl]piperidin-4-yl}-6-(3-fluorophenyl)nicotinamide | 484.2 | 484.5 |
| 93 | 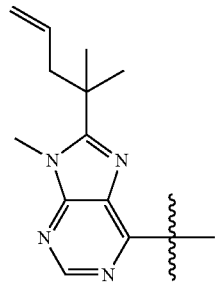 | N-{1-[8-(1,1-Dimethylbut-3-en-1-yl)-9-methyl-9H-purin-6-yl]piperidin-4-yl}-6-(3-fluorophenyl)nicotinamide | 514.3 | 514.8 |
| 94 | 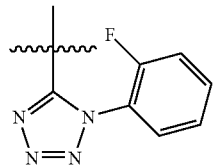 | 6-(3-Fluorophenyl)-N-{1-[1-(2-fluorophenyl)-1H-tetrazol-5-yl]piperidin-4-yl}nicotinamide | 462.2 | 461.5 |
| 95 | 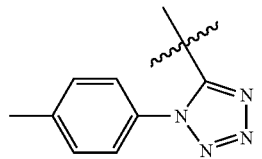 | 6-(3-Fluorophenyl)-N-{1-[1-(4-methylphenyl)-1H-tetrazol-5-yl]piperidin-4-yl}nicotinamide | 458.2 | 458.4 |

| Ex | Q | Name | MS Calc (M + H) | MS Obs (M + H) |
|---|---|---|---|---|
| 96 | 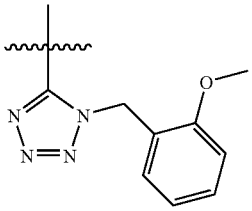 | 6-(3-Fluorophenyl)-N-{1-[1-(2-methoxybenzyl)-1H-tetrazol-5-yl]piperidin-4-yl}nicotinamide | 488.2 | 488.6 |
| 97 | 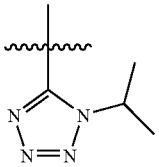 | 6-(3-Fluorophenyl)-N-[1-(1-isopropyl-1H-tetrazol-5-yl)piperidin-4-yl]nicotinamide | 410.2 | 410.5 |
| 98 | 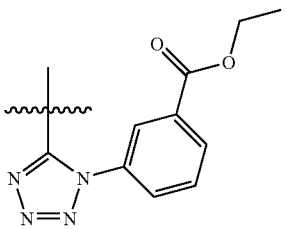 | Ethyl 3-{5-[4-({[6-(3-fluorophenyl)pyridin-3-yl]carbonyl}amino)piperidin-1-yl]-1H-tetrazol-1-yl}benzoate | 516.2 | 516.8 |
| 99 | 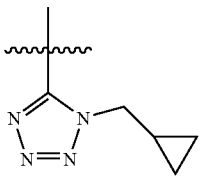 | N-{1-[1-(Cyclopropylmethyl)-1H-tetrazol-5-yl]piperidin-4-yl}-6-(3-fluorophenyl)nicotinamide | 422.2 | 422.5 |
| 100 | 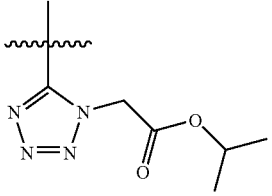 | Isopropyl {5-[4-({[6-(3-fluorophenyl)pyridin-3-yl]carbonyl}amino)piperidin-1-yl]-1H-tetrazol-1-yl}acetate | 468.2 | 468.6 |
| 101 | 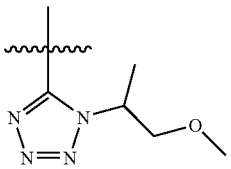 | 6-(3-fluorophenyl)-N-{1-[1-(2-methoxy-1-methylethyl)-1H-tetrazol-5-yl]piperidin-4-yl}nicotinamide | 440.2 | 440.4 |
| 102 | 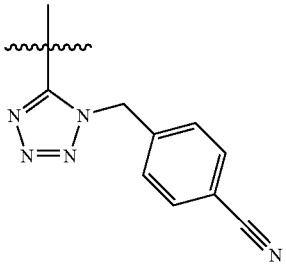 | N-{1-[1-(4-Cyanobenzyl)-1H-tetrazol-5-yl]piperidin-4-yl}-6-(3-fluorophenyl)nicotinamide | 483.2 | 483.5 |

-continued

| Ex | Q | Name | MS Calc (M + H) | MS Obs (M + H) |
|---|---|---|---|---|
| 103 | | N-{1-[1-(3-Ethoxyphenyl)-1H-tetrazol-5-yl]piperidin-4-yl}-6-(3-fluorophenyl)nicotinamide | 488.2 | 488.5 |
| 104 | | 6-(3-Fluorophenyl)-N-(1-{1-[(1R)-1-phenylethyl]-1H-tetrazol-5-yl}piperidin-4-yl)nicotinamide | 472.2 | 472.9 |
| 105 | | N-{1-[1-(2-Ethoxyphenyl)-1H-tetrazol-5-yl]piperidin-4-yl}-6-(3-fluorophenyl)nicotinamide | 440.2 | 440.4 |
| 106 | | 6-(3-Fluorophenyl)-N-{1-[9-(2,2,2-trifluoroethyl-9H-purin-6-yl]piperidin-4-yl}nicotinamide | 500.2 | 500.8 |
| 107 | | 6-(3-Fluorophenyl)-N-{1-[9-(2-piperidin-1-ylethyl)-9H-purin-6-yl]piperidin-4-yl}nicotinamide | 529.3 | 529.7 |
| 108 | | 6-(3-Fluorophenyl)-N-{1-[1-(3-methoxybenzyl)-1H-tetrazol-5-yl]piperidin-4-yl)nicotinamide | 488.2 | 488.5 |

-continued

| Ex | Q | Name | MS Calc (M + H) | MS Obs (M + H) |
|---|---|---|---|---|
| 109 | 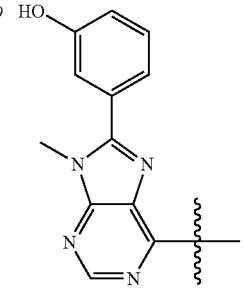 | 6-(3-Fluorophenyl)-N-{1-[8-(3-hydroxyphenyl)-9-methyl-9H-purin-6-yl]piperidin-4-yl}nicotinamide | 524.2 | 524.8 |
| 110 | 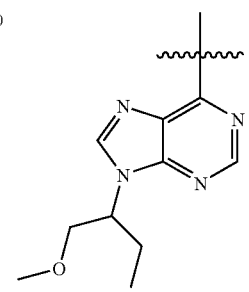 | 6-(3-Fluorophenyl)-N-(1-{9-[1-(methoxymethyl)propyl]-9H-purin-6-yl}piperidin-4-yl)nicotinamide | 504.2 | 504.5 |
| 111 | 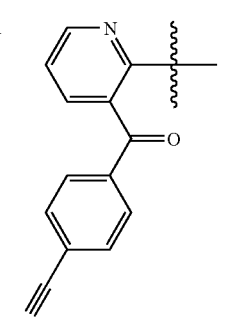 | N-{1-[3-(4-Cyanobenzoyl)pyridin-2-yl]piperidin-4-yl}-6-(3-fluorophenyl)nicotinamide | 506.2 | 506.5 |
| 112 | 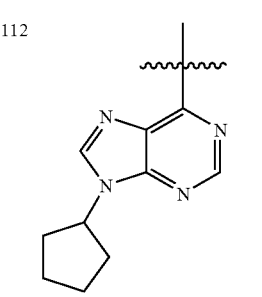 | N-[1-(9-Cyclopentyl-9H-purin-6-yl)piperidin-4-yl]-6-(3-fluorophenyl)nicotinamide | 486.2 | 486.6 |
| 113 | 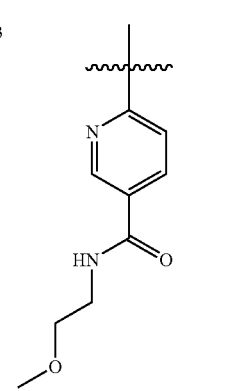 | 6-(3-Fluorophenyl)-N-[1-(5-{[(2-methoxyethyl)amino]carbonyl}pyridin-2-yl)piperidin-4-yl]nicotinamide | 478.2 | 478.5 |

| Ex | Q | Name | MS Calc (M + H) | MS Obs (M + H) |
|---|---|---|---|---|
| 114 | 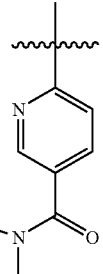 | 6-(3-Fluorophenyl)-N-{1-[5-(pyrrolidin-1-ylcarbonyl)pyridin-2-yl]piperidin-4-yl}nicotinamide | 474.2 | 474.6 |
| 115 | 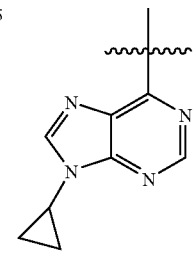 | N-[1-(9-Cyclopropyl-9H-purin-6-yl)piperidin-4-yl]-6-(3-fluorophenyl)nicotinamide | 458.2 | 458.5 |
| 116 | 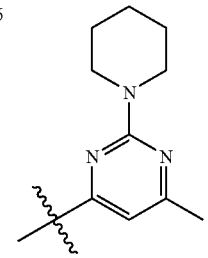 | 6-(3-Fluorophenyl)-N-[1-(6-methyl-2-piperidin-1-ylpyrimidin-4-yl)piperidin-4-yl]nicotinamide | 475.3 | 475.5 |
| 117 | 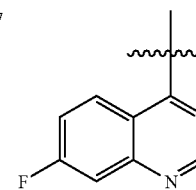 | 6-(3-Fluorophenyl)-N-[1-(7-fluoroquinazolin-4-yl)piperidin-4-yl]nicotinamide | 446.3 | 446.5 |
| 118 | 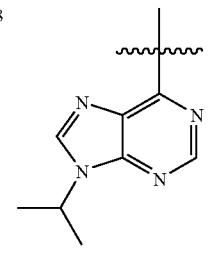 | 6-(3-Fluorophenyl)-N-[1-(9-isopropyl-9H-purin-6-yl)piperidin-4-yl]nicotinamide | 460.2 | 460.5 |
| 119 | 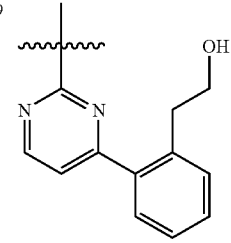 | 6-(3-Fluorophenyl)-N-(1-{4-[2-(2-hydroxyethyl)phenyl]pyrimidin-2-yl}piperidin-4-yl)nicotinamide | 498.2 | 498.8 |

-continued

| Ex | Q | Name | MS Calc (M + H) | MS Obs (M + H) |
|---|---|---|---|---|
| 120 | (pyridine with morpholine and ethyl ester substituents) | Ethyl 6-[4-({[6-(3-fluorophenyl)pyridin-3-yl]carbonyl}amino)piperidin-1-yl]-4-morpholin-4-ylnicotinate | 534.2 | 534.5 |
| 121 | (5-fluoro-6-methyl-3-cyanopyridin-2-yl) | N-[1-(3-Cyano-5-fluoro-6-methylpyridin-2-yl)piperidin-4-yl]-6-(3-fluorophenyl)nicotinamide | 434.2 | 434.5 |
| 122 | (7,8-dimethoxyquinazolin-4-yl) | N-[1-(7,8-Dimethoxyquinazolin-4-yl)piperidin-4-yl]-6-(3-fluorophenyl)nicotinamide | 488.2 | 488.5 |
| 123 | (6,7,8-trimethoxyquinazolin-4-yl) | 6-(3-Fluorophenyl)-N-[1-(678-trimethoxyquinazolin-4-yl)piperidin-4-yl]nicotinamide | 518.2 | 518.5 |
| 124 | (7H-pyrrolo[2,3-d]pyrimidin-4-yl) | 6-(3-fluorophenyl)-N-[1-(7H-pyrrolo[23-d]pyrimidin-4-yl)piperidin-4-yl]nicotinamide | 417.2 | 417.5 |
| 125 | (9-methyl-9H-purin-6-yl) | 6-(3-Fluorophenyl)-N-[1-(9-methyl-9H-purin-6-yl)piperidin-4-yl]nicotinamide | 432.2 | 432.5 |

-continued

| Ex | Q | Name | MS Calc (M + H) | MS Obs (M + H) |
|---|---|---|---|---|
| 126 | 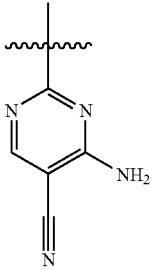 | N-[1-(4-Amino-5-cyanopyrimidin-2-yl)piperidin-4-yl]-6-(3-fluorophenyl)nicotinamide | 418.2 | 418.6 |
| 127 | 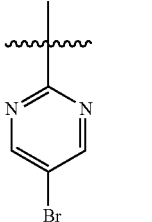 | N-[1-(5-Bromopyrimidin-2-yl)piperidin-4-yl]-6-(3-fluorophenyl)nicotinamide | 456.1 | 456.1 |
| 128 | 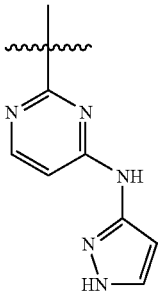 | 6-(3-Fluorophenyl)-N-{1-[4-(1H-pyrazol-3-ylamino)pyrimidin-2-yl]piperidin-4-yl}nicotinamide | 459.2 | 459.5 |
| 129 | 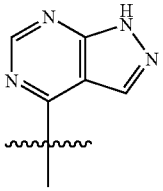 | 6-(3-Fluorophenyl)-N-[1-(1H-pyrazolo[3,4-d]pyrimidin-4-yl)piperidin-4-yl]nicotinamide | 418.2 | 418.8 |
| 130 | 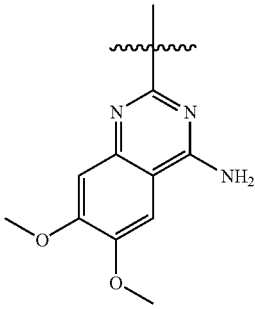 | N-[1-(4-Amino-6,7-dimethoxyquinazolin-2-yl)piperidin-4-yl]-6-(3-fluorophenyl)nicotinamide | 503.2 | 503.5 |
| 131 | 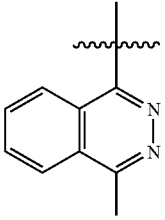 | 6-(3-Fluorophenyl)-N-[1-(4-methylphthalazin-1-yl)piperidin-4-yl]nicotinamide | 442.2 | 442.5 |

-continued

| Ex | Q | Name | MS Calc (M + H) | MS Obs (M + H) |
|---|---|---|---|---|
| 132 | 2-amino-9H-purin-6-yl | N-[1-(2-Amino-9H-purin-6-yl)piperidin-4-yl]-6-(3-fluorophenyl)nicotinamide | 433.2 | 433.5 |
| 133 | 6-amino-2-methylpyrimidin-4-yl | N-[1-(6-Amino-2-methylpyrimidin-4-yl)piperidin-4-yl]-6-(3-fluorophenyl)nicotinamide | 407.2 | 407.5 |
| 134 | 3,6-dimethylpyrazin-2-yl | N-[1-(3,6-Dimethylpyrazin-2-yl)piperidin-4-yl]-6-(3-fluorophenyl)nicotinamide | 406.2 | 406.5 |
| 135 | 3-(trifluoromethyl)pyridin-2-yl | 6-(3-Fluorophenyl)-N-{1-[3-(trifluoromethyl)pyridin-2-yl]piperidin-4-yl}nicotinamide | 445.2 | 445.8 |
| 136 | 4-(trifluoromethyl)pyrimidin-2-yl | 6-(3-Fluorophenyl)-N-{1-[4-(trifluoromethyl)pyrimidin-2-yl]piperidin-4-yl}nicotinamide | 446.2 | 446.6 |
| 137 | 5-chloropyridin-2-yl | N-[1-(5-Chloropyridin-2-yl)piperidin-4-yl]-6-(3-fluorophenyl)nicotinamide | 411.2 | 411.5 |
| 138 | quinoxalin-2-yl | 6-(3-Fluorophenyl)-N-(1-quinoxalin-2-ylpiperidin-4-yl)nicotinamide | 428.2 | 428.4 |

-continued

| Ex | Q | Name | MS Calc (M + H) | MS Obs (M + H) |
|---|---|---|---|---|
| 139 | 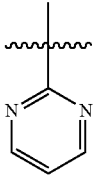 | 6-(3-Fluorophenyl)-N-(1-pyrimidin-2-ylpiperidin-4-yl)nicotinamide | 378.2 | 378.3 |
| 140 | 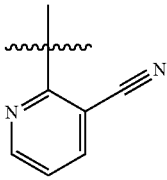 | N-[1-(3-Cyanopyridin-2-yl)piperidin-4-yl]-6-(3-fluorophenyl)nicotinamide | 402.2 | 402.5 |
| 141 | 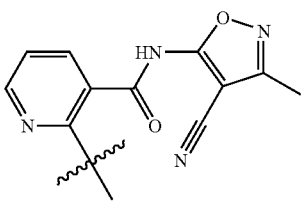 | N-(4-Cyano-3-methylisoxazol-5-yl)-2-[4-({[6-(3-fluorophenyl)pyridin-3-yl]carbonyl}amino)piperidin-1-yl]nicotinamide | 526.2 | 526.8 |
| 142 | 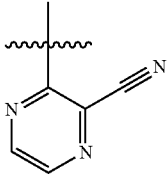 | N-[1-(3-Cyanopyrazin-2-yl)piperidin-4-yl]-6-(3-fluorophenyl)nicotinamide | 403.2 | 403.4 |
| 143 | 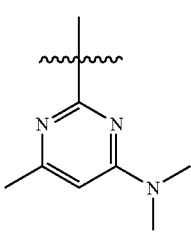 | N-{1-[4-(Dimethylamino)-6-methylpyrimidin-2-yl]piperidin-4-yl}-6-(3-fluorophenyl)nicotinamide | 435.2 | 435.5 |
| 144 | 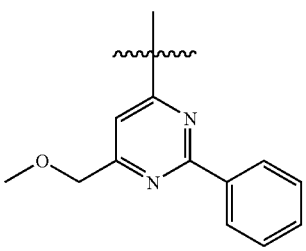 | 6-(3-Fluorophenyl)-N-{1-[6-(methoxymethyl)-2-phenylpyrimidin-4-yl]piperidin-4-yl}nicotinamide | 498.2 | 498.8 |
| 145 | 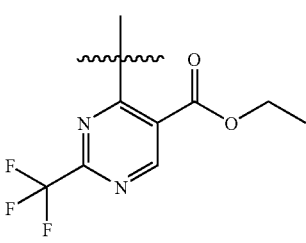 | Ethyl 4-[4-({[6-(3-fluorophenyl)pyridin-3-yl]carbonyl}amino)piperidin-1-yl]-2-(trifluoromethyl)pyrimidine-5-carboxylate | 518.2 | 518.7 |

-continued

| Ex | Q | Name | MS Calc (M + H) | MS Obs (M + H) |
|---|---|---|---|---|
| 146 | 2-methyl-pyridin-3-yl morpholine carbonyl | 6-(3-Fluorophenyl)-N-{1-[3-(morpholin-4-ylcarbonyl)pyridin-2-yl]piperidin-4-yl}nicotinamide | 490.2 | 490.5 |
| 147 | 9-(tetrahydro-2H-pyran-2-yl)-9H-purin-6-yl | 6-(3-Fluorophenyl)-N-{1-[9-(tetrahydro-2H-pyran-2-yl)-9H-purin-6-yl]piperidin-4-yl}nicotinamide | 502.2 | 502.8 |
| 148 | 3-carbamoyl-6-(trifluoromethyl)pyridin-2-yl | 2-[4-({[6-(3-Fluorophenyl)pyridin-3-yl]carbonyl}amino)piperidin-1-yl]-6-(trifluoromethyl)nicotinamide | 488.2 | 488.4 |
| 149 | 5-(pyridin-2-ylcarbonyl)pyridin-2-yl | 6-(3-Fluorophenyl)-N-{1-[5-(pyridin-2-ylcarbonyl)pyridin-2-yl]piperidin-4-yl}nicotinamide | 482.2 | 482.5 |
| 150 | 4-methyl-2-(methoxycarbonyl)pyrimidin-2-yl | Methyl 2-[4-({[6-(3-fluorophenyl)pyridin-3-yl]carbonyl}amino)piperidin-1-yl]-6-methylpyrimidine-4-carboxylate | 450.2 | 450.5 |
| 151 | 6-aminopyrimidin-4-yl | N-[1-(6-Aminopyrmidin-4-yl)piperidin-4-yl]-6-(3-fluorophenyl)nicotinamide | 393.2 | 393.4 |

-continued

| Ex | Q | Name | MS Calc (M + H) | MS Obs (M + H) |
|---|---|---|---|---|
| 152 | 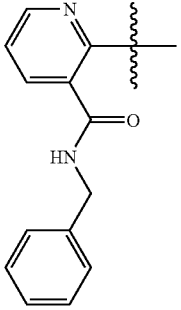 | N-Benzyl-2-[4-({[6-(3-fluorophenyl)pyridin-3-yl]carbonyl}amino)piperidin-1-yl]nicotinamide | 510.2 | 510.5 |
| 153 | 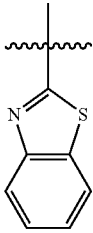 | N-[1-(1,3-Benzothiazol-2-yl)piperidin-4-yl]-6-(3-fluorophenyl)nicotinamide | 433.1 | 433.5 |
| 154 | 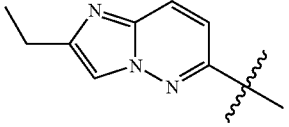 | N-[1-(2-Ethylimidazo[1,2-b]pyridazin-6-yl)piperidin-4-yl]-6-(3-fluorophenyl)nicotinamide | 445.2 | 445.8 |
| 155 | 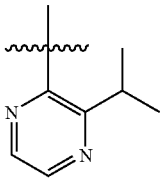 | 6-(3-Fluorophenyl)-N-[1-(3-isopropylpyrazin-2-yl)piperidin-4-yl]nicotinamide | 420.2 | 420.5 |
| 156 | 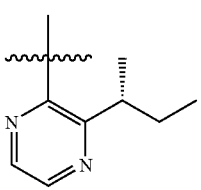 | 6-(3-Fluorophenyl)-N-(1-{3-[(1R)-1-methylpropyl]pyrazin-2-yl}piperidin-4-yl)nicotinamide | 434.2 | 434.5 |
| 157 | 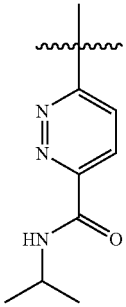 | 6-[4-({[6-(3-Fluorophenyl)pyridin-3-yl]carbonyl}amino)piperidin-1-yl]-N-isopropylpyridazine-3-carboxamide | 463.2 | 463.6 |

-continued

| Ex | Q | Name | MS Calc (M + H) | MS Obs (M + H) |
|---|---|---|---|---|
| 158 | 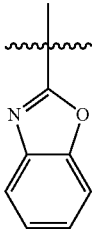 | N-[1-(1,3-Benzoxazol-2-yl)piperidin-4-yl]-6-(3-fluorophenyl)nicotinamide | 417.2 | 417.5 |
| 159 | 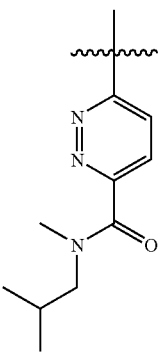 | 6-[4-({[6-(3-Fluorophenyl)pyridin-3-yl]carbonyl}amino)piperidin-1-yl]-N-isobutyl-N-methylpyridazine-3-carboxamide | 491.3 | 491.5 |
| 160 | 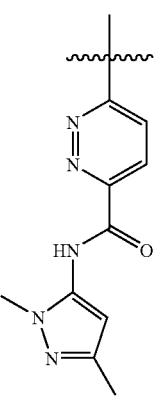 | N-(1,3-Dimethyl-1H-pyrazol-5-yl)-6-[4-({[6-(3-fluorophenyl)pyridin-3-yl]carbonyl}amino)piperidin-1-yl]pyridazine-3-carboxamide | 515.2 | 515.5 |
| 161 | 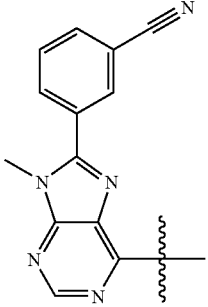 | N-{1-[8-(3-Cyanophenyl)-9-methyl-9H-purin-6-yl]piperidin-4-yl}-6-(3-fluorophenyl)nicotinamide | 533.2 | 533.5 |

| Ex | Q | Name | MS Calc (M + H) | MS Obs (M + H) |
|---|---|---|---|---|
| 162 | | 6-(3-Fluorophenyl)-N-(1-{9-[(5-methyl pyrazin-2-yl)methyl]-9H-purin-6-yl}piperidin-4-yl)nicotinamide | 524.2 | 524.5 |
| 163 | | N-(Cyclohexylmethyl)-6-[4-({[6-(3-fluorophenyl)pyridin-3-yl]carbonyl}amino)piperidin-1-yl]pyridazine-3-carboxamide | 517.3 | 517.7 |
| 164 | | 6-[4-({[6-(3-Fluorophenyl)pyridin-3-yl]carbonyl}amino)piperidin-1-yl]-N-[2-(2-oxoimidazolidin-1-yl)ethyl]pyridazine-3-carboxamide | 533.2 | 533.5 |
| 165 | | 6-(3-Fluorophenyl)-N-{1-[3-(pyrrolidin-1-ylcarbonyl)pyridin-2-yl]piperidin-4-yl}nicotinamide | 474.2 | 474.5 |
| 166 | | 6-(3-Fluorophenyl)-N-(1-quinazolin-2-ylpiperidin-4-yl)nicotinamide | 428.2 | 428.3 |

-continued

| Ex | Q | Name | MS Calc (M + H) | MS Obs (M + H) |
|---|---|---|---|---|
| 167 | (pyrazine with methyl carboxylate) | Methyl 5-[4-({[6-(3-fluorophenyl)pyridin-3-yl]carbonyl}amino)piperidin-1-yl]pyrazine-2-carboxylate | 436.2 | 436.6 |
| 168 | (pyridine with N-(5-methylisoxazol-3-yl)carboxamide) | 2-[4-({[6-(3-Fluorophenyl)pyridin-3-yl]carbonyl}amino)piperidin-1-yl]-N-(5-methylisoxazol-3-yl)nicotinamide | 501.2 | 501.6 |
| 169 | (3,6-diethylpyrazin-2-yl) | N-[1-(3,6-Diethylpyrazin-2-yl)piperidin-4-yl]-6-(3-fluorophenyl)nicotinamide | 434.2 | 434.5 |
| 170 | (6,7-dihydro-5H-cyclopenta[b]pyridine-3-carboxamide) | 2-[4-({[6-(3-Fluorophenyl)pyridin-3-yl]carbonyl}amino)piperidin-1-yl]-6,7-dihydro-5H-cyclopenta[b]pyridine-3-carboxamide | 460.2 | 460.5 |
| 171 | (pyrido[2,3-d]pyrimidin-2-yl) | 6-(3-Fluorophenyl)-N-(1-pyrido[2,3-d]pyrimidin-2-ylpiperidin-4-yl)nicotinamide | 429.2 | 429.5 |
| 172 | (4-(3-fluorophenyl)pyrimidin-2-yl) | 6-(3-Fluorophenyl)-N-{1-[4-(3-fluorophenyl)pyrimidin-2-yl]piperidin-4-yl}nicotinamide | 472.2 | 472.8 |

-continued

| Ex | Q | Name | MS Calc (M + H) | MS Obs (M + H) |
|---|---|---|---|---|
| 173 | 6,7-dimethoxyquinoxalin-2-yl | N-[1-(6,7-Dimethoxyquinoxalin-2-yl)piperidin-4-yl]-6-(3-fluorophenyl)nicotinamide | 488.2 | 488.6 |
| 174 | 7-fluoroquinazolin-2-yl | 6-(3-Fluorophenyl)-N-[1-(7-fluoroquinazolin-2-yl)piperidin-4-yl]nicotinamide | 446.2 | 446.8 |
| 175 | 5-cyano-6-methylpyridin-2-yl | N-[1-(5-Cyano-6-methylpyridin-2-yl)piperidin-4-yl]-6-(3-fluorophenyl)nicotinamide | 416.2 | 416.5 |
| 176 | 4-amino-2-methylpteridin-6-yl | N-[1-(4-Amino-2-methylpteridin-6-yl)piperidin-4-yl]-6-(3-fluorophenyl)nicotinamide | 459.2 | 459.5 |
| 177 | 4-(3-methoxyphenyl)pyrimidin-2-yl | 6-(3-Fluorophenyl)-N-{1-[4-(3-methoxyphenyl)pyrimidin-2-yl]piperidin-4-yl}nicotinamide | 484.2 | 484.5 |

-continued

| Ex | Q | Name | MS Calc (M + H) | MS Obs (M + H) |
|---|---|---|---|---|
| 178 | 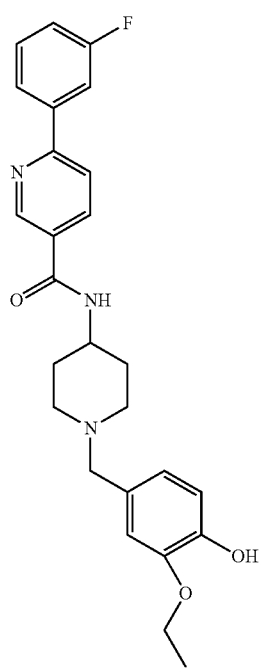 | 6-(3-Fluorophenyl)-N-[1-(6-methoxyquinazolin-4-yl)piperidin-4-yl]nicotinamide | 458.2 | 458.5 |

EXAMPLE 179

N-(1-(3-Ethoxy-4-hydroxybenzyl)piperidin-4-yl)-6-(3-fluorophenyl)nicotinamide

The following compounds of formula (VII) were prepared using methods analogous to that of Example 179.

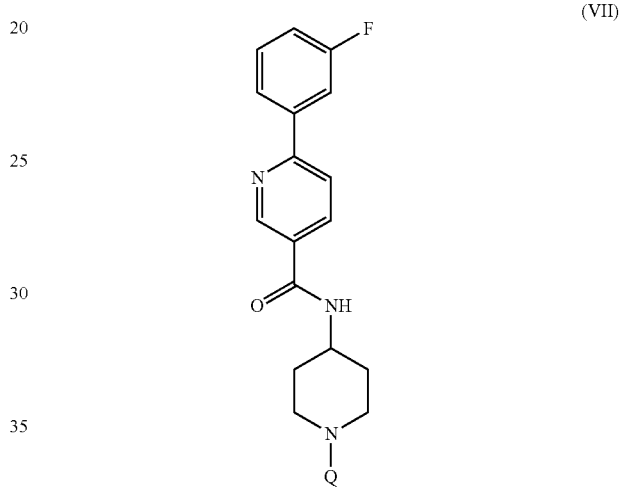

(VII)

To a solution of (0.2 mL, 0.08 mmol in 1:1 THF:DMSO) aldehyde was added the amine (in 1:1 THF:DMSO, 0.2 mL, 0.08 mmol), sodium triacetoxyborohydride dispersion (0.33 mL, 2.5 eq, in 1:1 THF:DMSO) and glacial acetic acid (0.01 mL). The reaction mixture was stirred at room temperature for 16-24 h and then aqueous $K_2CO_3$ (3 M, 0.2 mL) and ethanol (0.55 mL) was added. The reaction was shaken for 30 min and then the mixture was filtered and the filtrate concentrated and the residue purified by RP-HPLC to give the desired product. $^1$H NMR (400 MHz, DMSO-$d_6$) □ ppm 1.33 (t, J=6.95 Hz, 3H) 1.60 (d, J=10.98 Hz, 2H) 1.80 (br. s., 2H) 2.01 (br. s., 2H) 2.82 (br. s., 2H) 3.37 (br. s., 2H) 3.81 (br. s., 1H) 4.01 (q, J=6.95 Hz, 2H) 6.63-6.77 (m, 2H) 6.84 (s, 1H) 7.26-7.37 (m, 1H) 7.51-7.62 (m, 1H) 7.95 (d, J=10.62 Hz, 1H) 8.00 (d, J=8.05 Hz, 1H) 8.12 (d, J=8.42 Hz, 1H) 8.28 (dd, J=8.24, 201 Hz, 1 H) 8.44 (d, J=7.69 Hz, 1H) 8.65 (br. s., 1H) 9.07 (s, 1H). MS(ES+)=450.3 observed.

EXAMPLE 180

6-(3-Fluorophenyl)-N-{1-[2-(5-methyl-2,4-dioxo-34-dihydropyrimidin-1(2H)-yl)ethyl]piperidin-4-yl}nicotinamide Q = 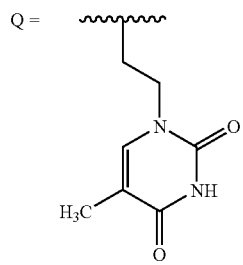

1H NMR (400 MHz, DMSO-$d_6$) □ ppm 1.46-1.65 (m, 2H) 1.77 (s, 5H) 2.10 (br. s., 2H) 2.90 (br. s., 2H) 3.39 (s, 3H) 3.74 (t, J=6.22 Hz, 2H) 7.25-7.39 (m, 1H) 7.48 (s, 1H) 7.52-7.63 (m, 1H) 7.94 (d, J=10.25 Hz, 1H) 8.00 (d, J=8.05 Hz, 1H) 8.11 (d, J=8.42 Hz, 1H) 8.28 (dd, J=8.24, 2.01 Hz, 1H) 8.45 (d, J=7.69 Hz, 1H) 9.07 (d, J=1.46 Hz, 1H).

MS calc (M+H) 452.2; MS obs (M+H) 452.0.

EXAMPLE 181

6-(3-Fluorophenyl)-N-[1-(3-pyrimidin-2-ylbenzyl)piperidin-4-yl]nicotinamide

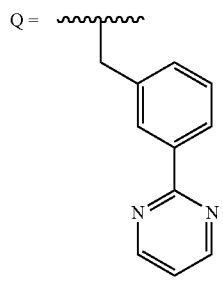

1H NMR (400 MHz, DMSO-d6) □ ppm 1.65 (br. s., 2H) 1.83 (br. s., 2H) 2.11 (br. s., 2H) 2.89 (br. s., 2 H) 3.59 (br. s., 2H) 3.84 (br. s., 1H) 7.32 (s, 1H) 7.41-7.52 (m, 4H) 7.57 (d, J=6.22 Hz, 1H) 7.97 (br. s., 1H) 8.01 (d, J=8.05 Hz, 1H) 8.12 (d, J=8.05 Hz, 1H) 8.24-8.33 (m, 2H) 8.39 (s, 1H) 8.46 (d, J=7.69 Hz, 1H) 8.91 (d, J=5.12 Hz, 1H) 9.08 (s, 1H).

MS calc (M+H) 468.21; MS obs (M+H) 468.6.

EXAMPLE 182

6-(3-Fluorophenyl)-N-{1-[(3-phenyl-1H-pyrazol-4-yl)methyl]piperidin-4-yl}nicotinamide

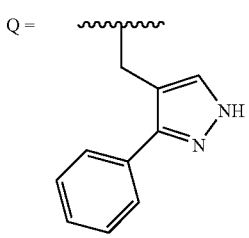

1H NMR (400 MHz, DMSO-d6) □ ppm 1.60 (d, J=9.88 Hz, 2H) 1.82 (br. s., 2H) 1.97-2.15 (m, 2H) 2.91 (br. s., 2H) 3.39 (s, 2H) 3.83 (d, J=6.95 Hz, 1H) 7.23-7.61 (m, 6H) 7.61-8.04 (m, 5H) 8.11 (d, J=8.05 Hz, 1H) 8.29 (dd, J=8.05, 2.20 Hz, 1H) 8.46 (d, J=7.69 Hz, 1H) 9.07 (s, 1H).

MS calc (M+H) 456.21; MS obs (M+H) 456.6.

EXAMPLE 183

N-{1-[(6-Fluoro-1H-indol-3-yl)methyl]piperidin-4-yl}-6-(3-fluorophenyl)nicotinamide

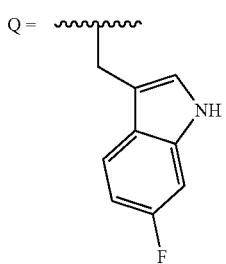

1H NMR (400 MHz, DMSO-d6) □ ppm 1.58 (d, J=12.08 Hz, 2H) 1.79 (br. s., 2H) 1.94-2.10 (m, 2H) 2.90 (d, J=11.35 Hz, 2H) 3.62 (s, 2H) 3.79 (br. s., 1H) 6.77-6.91 (m, 1H) 7.11 (dd, J=10.07, 2.01 Hz, 1 H) 7.21 (d, J=1.83 Hz, 1H) 7.26-7.35 (m, 1H) 7.50-7.61 (m, 1H) 7.64 (dd, J=8.42, 5.86 Hz, 1H) 7.94 (d, J=10.62 Hz, 1H) 8.00 (d, J=7.69 Hz, 1H) 8.11 (d, J=8.42 Hz, 1H) 8.28 (dd, J=8.42, 2.20 Hz, 1H) 8.43 (d, J=7.32 Hz, 1H) 9.06 (s, 1H) 10.93 (br. s., 1H).

MS calc (M+H) 447.19; MS obs (M+H) 447.4.

EXAMPLE 184

6-(3-Fluorophenyl)-N-[1-(4-isopropoxy-3-methoxybenzyl)piperidin-4-yl]nicotinamide

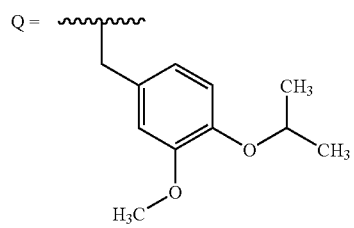

1H NMR (400 MHz, DMSO-d6) □ ppm 1.24 (d, J=6.22 Hz, 6H) 1.62 (d, J=3.66 Hz, 2H) 1.80 (br. s., 2H) 2.03 (br. s., 2H) 2.82 (br. s., 2H) 3.40 (s, 1H) 3.75 (s, 3H) 3.81 (br. s., 1H) 4.46 (d, J=5.86 Hz, 1H) 6.78 (d, J=8.05 Hz, 1H) 6.83-6.96 (m, 3H) 7.31 (s, 1H) 7.50-7.62 (m, 1H) 7.95 (br. s., 1H) 7.99 (s. 1 H) 8.12 (d, J=8.05 Hz, 1H) 8.27 (d, J=1.83 Hz, 1H) 8.46 (s, 1H) 9.07 (d, J=1.46 Hz, 1H).

MS calc (M+H) 478.24; MS obs (M+H) 478.3.

EXAMPLE 185

N-{1-[(1-Ethyl-1H-pyrazol-4-yl)methyl]piperidin-4-yl}-6-(3-fluorophenyl)nicotinamide

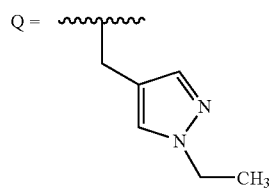

1H NMR (400 MHz, DMSO-d6) □ ppm 1.35 (t, J=7.14 Hz, 3H) 1.49-1.65 (m, 2H) 1.79 (br. s., 2H) 1.97 (t, J=10.98 Hz, 2H) 2.84 (d, J=11.35 Hz, 2H) 3.34 (s, 2H) 3.76 (d, J=7.32 Hz, 1H) 4.08 (q, J=7.08 Hz, 2 H) 7.26-7.36 (m, 2H) 7.52-7.62 (m, 2H) 7.95 (d, J=10.62 Hz, 1H) 8.00 (d, J=7.69 Hz, 1H) 8.12 (d, J=8.42 Hz, 1H) 8.28 (dd, J=8.05, 1.83 Hz, 1H) 8.43 (d, J=7.69 Hz, 1H) 9.07 (s, 1H).

MS calc (M+H) 408.21; MS obs (M+H) 408.5.

EXAMPLE 186

N-[1-(3,4-Dihydro-2H-pyran-2-ylmethyl)piperidin-4-yl]-6-(3-fluorophenyl)nicotinamide

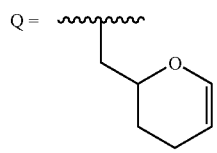

1H NMR (400 MHz, DMSO-d<sub>6</sub>) ppm 1.46-1.67 (m, 3H) 1.75-1.94 (m, 4H) 1.97-2.21 (m, 4H) 2.33-2.45 (m, 1H) 2.83-2.96 (m, 2H) 3.67-3.86 (m, 1H) 3.87-4.00 (m, 1H) 4.65 (br. s., 1H) 6.35 (br. s., 1 H) 7.25-7.37 (m, 1H) 7.50-7.64 (m, 1H) 7.95 (d, J=10.62 Hz, 1H) 8.01 (d, J=7.69 Hz, 1H) 8.12 (d, J=8.05 Hz, 1H) 8.28 (dd, J=8.42, 1.83 Hz, 1H) 8.43 (d, J=7.32 Hz, 1H) 9.07 (s, 1H).

MS calc (M+H) 396.2; MS obs (M+H) 396.4.

EXAMPLE 187

6-(3-Fluorophenyl)-N-(1-{[3-(4-fluorophenyl)-1H-pyrazol-4-yl]methyl}piperidin-4-yl)nicotinamide

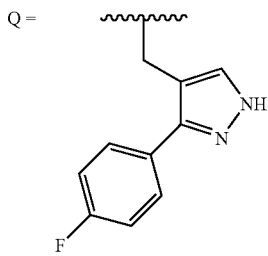

1H NMR (400 MHz, DMSO-d<sub>6</sub>) ppm 1.50-1.70 (m, 2H) 1.83 (br. s., 2H) 1.98-2.13 (m, 2H) 2.91 (br. s., 2H) 3.37 (s, 2H) 3.84 (br. s., 1H) 7.16-7.39 (m, 3H) 7.41-7.52 (m, 1H) 7.51-7.62 (m, 1H) 7.70 (br. s., 1H) 7.84 (br. s., 1H) 7.95 (d, J=10.62 Hz, 2H) 8.00 (d, J=7.32 Hz, 1H) 8.11 (d, J=8.05 Hz, 1H) 8.29 (dd, J=8.24, 2.01 Hz, 1H) 8.46 (d, J=7.69 Hz, 1H) 9.08 (s, 1H).

MS calc (M+H) 474.2; MS obs (M+H) 474.5.

EXAMPLE 188

6-(3-Fluorophenyl)-N-[1-(3-pyridin-2-ylbenzyl)piperidin-4-yl]nicotinamide

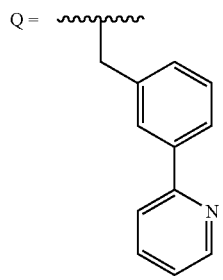

1H NMR (400 MHz, DMSO-d<sub>6</sub>) ppm 1.63 (dd, J=11.71, 2.56 Hz, 2H) 1.83 (d, J=11.71 Hz, 2H) 2.03-2.21 (m, 2H) 2.88 (d, J=11.35 Hz, 2H) 3.35 (s, 3H) 3.58 (s, 2H) 3.84 (d, J=4.76 Hz, 1H) 7.25-7.41 (m, 2H) 7.45 (t, J=7.50 Hz, 1H) 7.52-7.63 (m, 1H) 7.83-7.91 (m, 1H) 7.94 (d, J=8.42 Hz, 1H) 8.00 (d, J=7.69 Hz, 1H) 8.04 (s, 1H) 8.11 (d, J=8.42 Hz, 1H) 8.28 (dd, J=8.42, 2.20 Hz, 1H) 8.46 (d, J=7.69 Hz, 1H) 8.67 (d, J=4.03 Hz, 1H) 9.07 (d, J=1.46 Hz, 1H).

MS calc (M+H) 467.22; MS obs (M+H) 467.5.

EXAMPLE 189

6-(3-Fluorophenyl)-N-[1-(quinolin-4-ylmethyl)piperidin-4-yl]nicotinamide

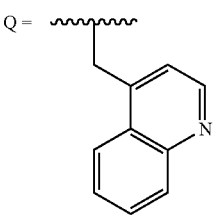

1H NMR (400 MHz, DMSO-d<sub>6</sub>) ppm 1.63 (dd, J=12.08, 2.93 Hz, 2H) 1.84 (d, J=10.25 Hz, 2H) 2.22 (t, J=10.80 Hz, 2H) 2.92 (d, J=11.35 Hz, 2H) 3.87 (br. s., 1H) 3.97 (s, 2H) 7.24-7.38 (m, 1H) 7.50 (d, J=4.03 Hz, 1H) 7.52-7.68 (m, 2H) 7.76 (t, J=7.69 Hz, 1H) 7.95 (d, J=10.98 Hz, 1H) 8.02 (dd, J=12.26, 8.24 Hz, 2H) 8.12 (d, J=8.42 Hz, 1H) 8.28 (dd, J=8.24, 2.01 Hz, 1H) 8.34 (d, J=8.42 Hz, 1H) 8.45 (d, J=7.69 Hz, 1H) 8.85 (d, J=4.03 Hz, 1H) 9.07 (s, 1H).

MS calc (M+H) 441.2; MS obs (M+H) 441.5.

EXAMPLE 190

6-(3-Fluorophenyl)-N-[1-(1H-imidazol-5-ylmethyl)piperidin-4-yl]nicotinamide

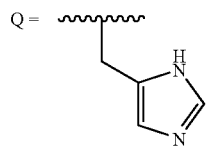

1H NMR (400 MHz, DMSO-d<sub>6</sub>) ppm 1.57 (d, J=10.25 Hz, 2H) 1.79 (br. s., 2H) 2.02 (t, J=10.98 Hz, 2 H) 2.87 (br. s., 2H) 3.40 (br. s., 2H) 3.76 (br. s., 1H) 6.75 (br. s., 1H) 6.93 (br. s., 1H) 7.26-7.37 (m, 1 H) 7.47-7.62 (m, 2H) 7.95 (d, J=10.62 Hz, 1H) 8.00 (d, J=8.05 Hz, 1H) 8.12 (d, J=8.42 Hz, 1H) 8.28 (dd, J=8.24, 2.01 Hz, 1H) 8.44 (d, J=7.32 Hz, 1H) 9.07 (d, J=1.83 Hz, 1H).

MS calc (M+H) 380.18; MS obs (M+H) 380.1.

EXAMPLE 191

N-{1-[(4-Chloro-1-methyl-1H-pyrazol-3-yl)methyl]piperidin-4-yl}-6-(3-fluorophenyl)nicotinamide

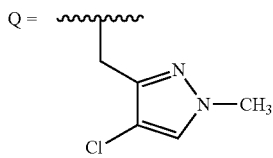

1H NMR (400 MHz, DMSO-d$_6$) ☐ ppm 1.48-1.64 (m, 2H) 1.79 (br. s., 2H) 2.09 (t, J=10.98 Hz, 2H) 2.86 (d, J=12.08 Hz, 2H) 3.42 (s, 2H) 3.74 (s, 4H) 6.31-7.43 (m, 1H) 7.49-7.64 (m, 1H) 7.85 (s, 1H) 7.95 (d, J=10.62 Hz, 1H) 8.00 (d, J=8.05 Hz, 1H) 8.11 (d, J=8.42 Hz, 1H) 8.28 (dd, J=8.42, 1.83 Hz, 1H) 8.43 (d, J=7.69 Hz, 1H) 9.06 (s, 1H).

MS calc (M+H) 428.16; MS obs (M+H) 428.3.

EXAMPLE 194

N-[1-(4-Fluoro-3-methoxybenzyl)piperidin-4-yl]-6-(3-fluorophenyl)nicotinamide

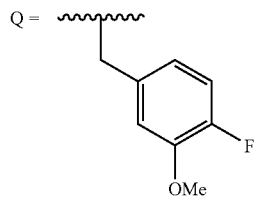

1H NMR (400 MHz, DMSO-d$_6$) ☐ ppm 1.50-1.69 (m, 2H) 1.81 (br. s., 2H) 2.06 (t, J=10.98 Hz, 2H) 2.83 (d, J=11.35 Hz, 2H) 3.45 (s, 2H) 3.84 (s, 4H) 6.87 (d, J=1.83 Hz, 1H) 7.04-7.18 (m, 2H) 7.26-7.37 (m, 1H) 7.50-7.64 (m, 1H) 7.95 (d, J=10.98 Hz, 1H) 8.01 (d, J=7.69 Hz, 1H) 8.12 (d, J=8.42 HZ, 1H) 8.28 (dd, J=8.42, 2.20 Hz, 1H) 8.45 (d, J=7.69 Hz, 1H) 9.07 (s, 1H).

MS calc (M+H) 438.19; MS obs (M+H) 438.5.

EXAMPLE 193

N-[1-(3,4-difluorobenzyl)piperidin-4-yl]-6-(3-fluorophenyl)nicotinamide

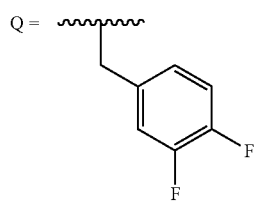

1H NMR (400 MHz, DMSO-d$_6$) ☐ ppm 1.62 (t, J=11.71 Hz, 2H) 1.82 (d, J=1.46 Hz, 2H) 2.08 (t, J=10.98 Hz, 2H) 2.80 (br. s., 2H) 3.48 (s, 2H) 3.80 (br. s., 1H) 7.16 (br. s., 1H) 7.24-7.45 (m, 3H) 7.51-7.63 (m, 1H) 7.96 (s, 1H) 8.01 (d, J=7.69 Hz, 1H) 8.12 (d, J=8.42 Hz, 1H) 8.28 (dd, J=8.24, 2.01 Hz, 1H) 8.45 (d, J=7.32 Hz, 1H) 9.07 (s, 1H).

MS calc (M+H) 426.17; MS obs (M+H) 425.9.

EXAMPLE 194

6-(3-Fluorophenyl)-N-[1-(2-oxo-2-phenylethyl)piperidin-4-yl]nicotinamide

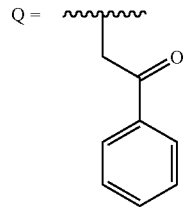

MS calc (M+H) 418.19; MS obs (M+H) 418.3.

EXAMPLE 195

N-{1-[(5-Chloro-1-methyl-3-phenyl-1H-pyrazol-4-yl)methyl]piperidin-4-yl}-6-(3-fluorophenyl)nicotinamide

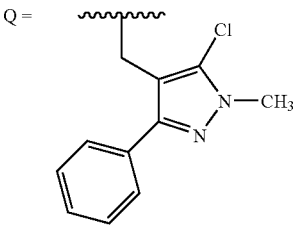

1H NMR (400 MHz, DMSO-d$_6$) ☐ ppm 1.61 (br. s., 2H) 1.83 (br. s., 2H) 2.13 (br. s., 2H) 2.90 (d, J=11.35 Hz, 2H) 3.34 (s, 1H) 3.87 (s, 4H) 7.26-7.40 (m, 3H) 7.44 (t, J=7.32 Hz, 2H) 7.51-7.62 (m, 1 H) 7.95 (d, J=8.05 Hz, 3H) 8.00 (d, J=7.69 Hz, 1H) 8.11 (d, J=8.42 Hz, 1H) 8.29 (dd, J=8.05, 1.83 Hz, 1 H) 8.46 (d, J=7.69 Hz, 1H) 9.08 (s, 1H).

MS calc (M+H) 504.19; MS obs (M+H) 504.5.

EXAMPLE 196

6-(3-Fluorophenyl)-N-{1-[(1-methyl-1H-pyrazol-4-yl)methyl]piperidin-4-yl}nicotinamide

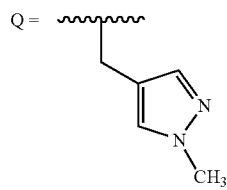

1H NMR (400 MHz, DMSO-d$_6$) ☐ ppm 1.48-1.64 (m, 2H) 1.80 (d, J=9.52 Hz, 2H) 1.90-2.04 (m, 2H) 2.84 (d, J=11.35

Hz, 2H) 3.35 (br. s., 1H) 3.75 (br. s., 1H) 3.79 (s, 3H) 7.26-7.37 (m, 2H) 7.51-7.62 (m, 3H) 7.95 (d, J=10.25 Hz, 1H) 8.00 (d, J=8.05 Hz, 1H) 8.11 (d, J=8.42 Hz, 1H) 8.28 (dd, J=8.24, 2.01 Hz, 1H) 8.44 (d, J=7.69 Hz, 1H) 9.07 (d, J=1.83 Hz, 1H).

MS calc (M+H) 394.2; MS obs (M+H) 394.1.

EXAMPLE 197

6-(3-Fluorophenyl)-N-[1-(quinolin-8-ylmethyl)piperidin-4-yl]nicotinamide

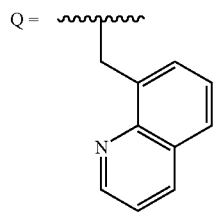

1H NMR (400 MHz, DMSO-d$_6$) ppm 1.60-1.76 (m, 2H) 1.84 (br. s., 2H) 2.13-2.29 (m, 2H) 2.89-3.03 (m, 2H) 3.84 (br. s., 1H) 4.20 (s, 2H) 7.24-7.37 (m, 1H) 7.50-7.68 (m, 3H) 7.86 (dd, J=13.54, 7.69 Hz, 2H) 7.95 (d, J=10.25 Hz, 1H) 8.01 (d, J=7.69 Hz, 1H) 8.12 (d, J=8.05 Hz, 1H) 8.29 (dd, J=8.42, 1.83 Hz, 1H) 8.36 (d, J=7.69 Hz, 1H) 8.47 (d, J=7.32 Hz, 1H) 8.93 (d, J=2.93 Hz, 1H) 9.08 (s, 1 H).

MS calc (M+H) 441.2; MS obs (M+H) 441.5.

EXAMPLE 198

6-(3-Fluorophenyl)-N-[1-(3-pyrazin-2-ylbenzyl)piperidin-4-yl]nicotinamide

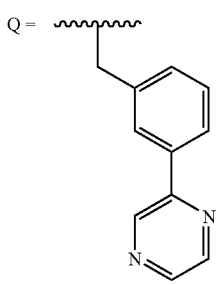

1H NMR (400 MHz, DMSO-d$_6$) ppm 1.55-1.72 (m, 2H) 1.84 (d, J=9.52 Hz, 2H) 2.11 (t, J=11.16 Hz, 2 H) 2.89 (d, J=10.98 Hz, 2H) 3.59 (s, 2H) 3.84 (br. s., 1H) 7.25-7.38 (m, 1H) 7.48-7.62 (m, 2H) 7.95 (d, J=10.98 Hz, 1H) 8.01 (t, J=7.50 Hz, 2H) 8.10 (d, J=4.76 Hz, 1H) 8.13 (s, 1H) 8.28 (dd, J=8.42, 1.83 Hz, 1H) 8.46 (d, J=7.32 Hz, 1H) 8.62 (d, J=2.20 Hz, 1H) 8.73 (s, 1H) 9.07 (s, 1 H) 9.24 (s, 1H).

MS calc (M+H) 468.21; MS obs (M+H) 468.3.

EXAMPLE 199

N-{1-[(2-Butyl-1H-imidazol-4-yl)methyl]piperidin-4-yl}-6-(3-fluorophenyl)nicotinamide

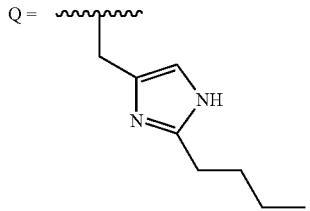

1H NMR (400 MHz, DMSO-d$_6$) ppm 0.88 (t, J=7.32 Hz, 3H) 1.21-1.36 (m, 3H) 1.49-1.66 (m , 5H) 1.79 (br. s., 2H) 2.01 (t, J=10.80 Hz, 2H) 2.57 (s, 1H) 2.85 (br. s., 2H) 3.34 (br. s., 1H) 3.77 (br. s., 1H) 7.23-7.38 (m, 1H) 7.50-7.64 (m, 1H) 7.95 (d, J=10.62 Hz, 1H) 8.00 (d, J=8.05 Hz, 1H) 8.12 (d, J=8.42 Hz, 1H) 8.28 (dd, J=8.24, 2.01 Hz, 1H) 8.43 (d, J=7.69 Hz, 1H) 9.07 (d, J=1.46 Hz, 1H) 11.39 (br. s., 1H).

MS calc (M+H) 436.24; MS obs (M+H) 436.3.

EXAMPLE 200

N-[1-(3,4-Dihydro-2H-15-benzodioxepin-7-ylmethyl)piperidin-4-yl]-6-(3-fluorophenyl)nicotinamide

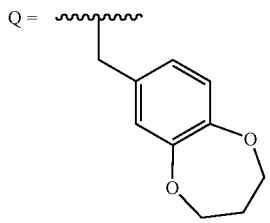

1H NMR (400 MHz, DMSO-d$_6$) ppm 1.59 (dd, J=11.71, 2.93 Hz, 2H) 1.97-2.07 (m, 2H) 2.05-2.14 (m, 2H) 2.81 (d, J=11.35 Hz, 2H) 3.38 (s, 2H) 3.81 (br. s., 1H) 4.11 (q, J=5.73 Hz, 4H) 6.82-6.95 (m, 2H) 7.31 (d, J=2.20 Hz, 1H) 7.51-7.64 (m, 1H) 7.95 (d, J=10.25 Hz, 1H) 8.00 (d, J=8.05 Hz, 1H) 8.12 (d, J=8.42 Hz, 1H) 8.28 (dd, J=8.42, 1.83 Hz, 1H) 8.44 (d, J=7.69 Hz, 1H) 9.07 (s, 1H.

MS calc (M+H) 462.21; MS obs (M+H) 462.5.

EXAMPLE 201

6-(3-Fluorophenyl)-N-[1-(4-pyridin-2-ylbenzyl)piperidin-4-yl]nicotinamide

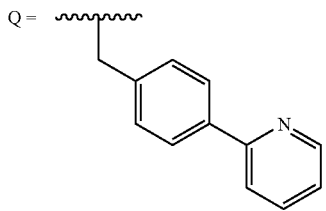

1H NMR (400 MHz, DMSO-d$_6$) ☐ ppm 1.57-1.71 (m, 2H) 1.84 (d, J=10.25 Hz, 2H) 2.02-2.16 (m, 2H) 2.87 (d, J=11.35 Hz, 2H) 3.55 (s, 2H) 3.83 (d, J=11.35 Hz, 1H) 7.26-7.39 (m, 2H) 7.43 (d, J=8.05 Hz, 2H) 7.51-7.62 (m, 1H) 7.87 (t, J=6.95 Hz, 1H) 7.91-7.98 (m, 2H) 7.99-8.09 (m, 3H) 8.12 (d, J=8.42 Hz, 1H) 8.29 (dd, J=8.42, 1.83 Hz, 1H) 8.46 (d, J=7.32 Hz, 1H) 8.66 (d, J=4.03 Hz, 1H) 9.08 (d, J=1.83 Hz, 1H).

MS calc (M+H) 467.22; MS obs (M+H) 467.5.

EXAMPLE 202

N-[1-(3-Fluoro-4-methylbenzyl)piperidin-4-yl]-6-(3-fluorophenyl)nicotinamide

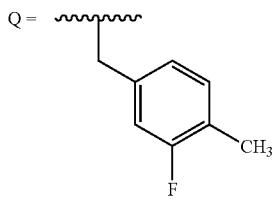

1H NMR (400 MHz, DMSO-d$_6$) ☐ ppm 1.51-1.69 (m, 2H) 1.81 (br. s., 2H) 2.05 (br. s., 2H) 2.21 (s, 3H) 2.82 (d, J=11.35 Hz, 2H) 3.45 (s, 2H) 3.81 (br. s., 1H) 7.00-7.11 (m, 2H) 7.22 (t, J=7.87 Hz, 1H) 7.27-7.36 (m, 1H) 7.51-7.63 (m, 1H) 7.95 (d, J=10.98 Hz, 1H) 8.00 (d, J=7.69 Hz, 1H) 8.12 (d, J=8.42 Hz, 1H) 8.28 (dd, J=8.42, 1.83 Hz, 1H) 8.44 (d, J=7.32 Hz, 1H) 9.07 (s, 1H).

MS calc (M+H) 422.2; MS obs (M+H) 422.0.

EXAMPLE 203 tert-Butyl(1-{[4-({[6-(3-fluorophenyl)pyridin-3-yl]carbonyl}amino)piperidin-1-yl]methyl}cyclopropyl)carbamate

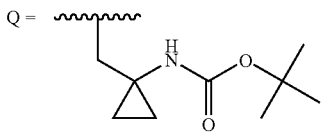

1H NMR (400 MHz, DMSO-d$_6$) ☐ ppm 0.52 (br. s., 1H) 0.64 (br. s., 1H) 1.32-1.45 (m, 10H) 1.58 (br. s., 3H) 1.78 (br. s., 3H) 1.91 (br. s., 1H) 2.07 (br. s., 2H) 2.39 (br. s., 1H) 2.99 (s, 2H) 3.77 (br. s., 2H) 7.26-7.37 (m, 1H) 7.51-7.65 (m, 1H) 7.95 (d, J=10.62 Hz, 1H) 8.01 (d, J=7.69 Hz, 1H) 8.12 (d, J=8.05 Hz, 1H) 8.24-8.34 (m, 1H) 8.43 (d, J=7.69 Hz, 1H) 9.07 (br. s., 1H).

MS calc (M+H) 469.25; MS obs (M+H) 469.5.

EXAMPLE 204

N-[1-(3-Chloro-4-methoxybenzyl)piperidin-4-yl]-6-(3-fluorophenyl)nicotinamide

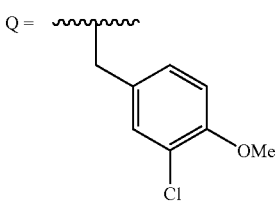

1H NMR (400 MHz, DMSO-d$_6$) ☐ ppm 1.51-1.66 (m, 2H) 1.80 (br. s., 2H) 2.04 (t, J=11.16 Hz, 2H) 2.81 (d, J=10.98 Hz, 2H) 3.42 (s, 2H) 3.74 (d, J=5.12 Hz, 1H) 3.84 (s, 3H) 7.09 (d, J=8.42 Hz, 1H) 7.18-7.26 (m, 1H) 7.27-7.39 (m, 2H) 7.52-7.64 (m, 1H) 7.96 (br. s., 1H) 8.00 (d, J=7.32 Hz, 1H) 8.12 (d, J=8.05 Hz, 1H) 8.28 (dd, J=8.24, 2.01 Hz, 1H) 8.44 (d, J=7.69 Hz, 1H) 9.07 (d, J=1.46 Hz, 1H).

MS calc (M+H) 454.16; MS obs (M+H) 454.4.

EXAMPLE 205

N-[1-(2,5-Dimethoxybenzyl)piperidin-4-yl]-6-(3-fluorophenyl)nicotinamide

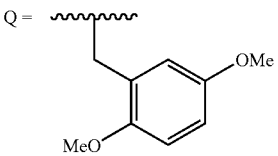

1H NMR (400 MHz, DMSO-d$_6$) ☐ ppm 1.55-1.70 (m, 2H) 1.81 (br. s., 2H) 2.10 (t, J=11.16 Hz, 2H) 2.85 (d, J=12.08 Hz, 2H) 3.46 (s, 2H) 3.71 (s, 3H) 3.73 (s, 3H) 3.81 (br. s., 1H) 6.78 (dd, J=8.79, 2.93 Hz, 1H) 6.86-6.96 (m, 2H) 7.26-7.37 (m, 1H) 7.51-7.63 (m, 1H) 7.95 (d, J=10.25 Hz, 1H) 8.01 (d, J=8.05 Hz, 1H) 8.12 (d, J=8.05 Hz, 1H) 8.29 (dd, J=8.42, 1.83 Hz, 1H) 8.45 (d, J=7.69 Hz, 1H) 9.08 (s, 1H).

MS calc (M+H) 450.21; MS obs (M+H) 450.5.

EXAMPLE 206

6-(3-Fluorophenyl)-N-[1-(3-isopropoxybenzyl)piperidin-4-yl]nicotinamide

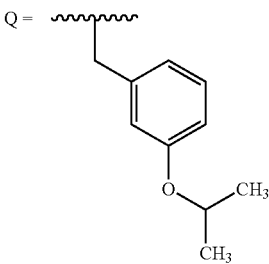

1H NMR (400 MHz, DMSO-d$_6$) ☐ ppm 1.19-1.31 (m, 6H) 1.53-1.70 (m, 2H) 1.81 (br. s., 2H) 1.98-2.14 (m, 2H) 2.83 (d, J=11.35 Hz, 2H) 3.44 (s, 2H) 3.79 (d, J=4.03 Hz, 1H) 4.49-4.66 (m, 1H) 6.78 (d, J=7.32 Hz, 1H) 6.81-6.88 (m, 2H) 7.21 (t, J=7.87 Hz, 1H) 7.27-7.37 (m, 1H) 7.51-7.62 (m, 1H) 7.95 (d, J=10.98 Hz, 1H) 8.01 (d, J=8.05 Hz, 1H) 8.12 (d, J=8.42 Hz, 1H) 8.28 (dd, J=8.24, 2.01 Hz, 1H) 8.45 (d, J=7.32 Hz, 1H) 9.07 (s, 1H).

MS calc (M+H) 448.23; MS obs (M+H) 448.5.

EXAMPLE 207

6-(3-Fluorophenyl)-N-{1-[(1-methyl-1H-indol-2-yl)methyl]piperidin-4-yl}nicotinamide

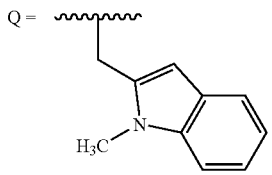

1H NMR (400 MHz, DMSO-d$_6$) □ ppm 1.51-1.68 (m, 2H) 1.83 (d, J=10.98 Hz, 2H) 2.11 (t, J=10.98 Hz, 2H) 2.91 (d, J=11.35 Hz, 2H) 3.65 (s, 2H) 3.78 (s, 3H) 3.83 (br. s., 1H) 6.34 (s, 1H) 6.99 (t, J=7.50 Hz, 1H) 7.11 (t, J=7.69 Hz, 1H) 7.26-7.35 (m, 1H) 7.40 (d, J=8.42 Hz, 1H) 7.48 (d, J=7.69 Hz, 1H) 7.51-7.63 (m, 1H) 7.95 (d, J=10.62 Hz, 1H) 8.00 (d, J=7.69 Hz, 1H) 8.11 (d, J=8.05 Hz, 1H) 8.23-8.34 (m, 1 H) 8.45 (d, J=7.69 Hz, 1H) 9.07 (s, 1H).

MS calc (M+H) 443.22; MS obs (M+H) 443.4.

EXAMPLE 208

N-{1-[(2-Ethyl-1H-imidazol-5-yl)methyl]piperidin-4-yl}-6-(3-fluorophenyl)nicotinamide

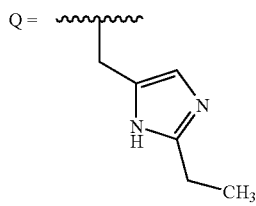

1H NMR (400 MHz, DMSO-d$_6$) □ ppm 1.18 (t, J=7.69 Hz, 3H) 1.48-1.66 (m, 2H) 1.81 (d, J=11.71 Hz, 2 H) 2.01 (t, J=10.98 Hz, 2H) 2.55-2.63 (m, 2H) 2.86 (d, J=10.25 Hz, 2H) 3.34 (br. s., 2H) 3.65-3.86 (m, 1H) 6.68 (br. s., 1H) 7.25-7.38 (m, 1H) 7.51-7.64 (m, 1H) 7.95 (d, J=10.98 Hz, 1H) 8.00 (d, J=7.69 Hz, 1H) 8.12 (d, J=8.05 Hz, 1H) 8.28 (dd, J=8.24, 2.01 Hz, 1H) 8.44 (d, J=7.69 Hz, 1H) 9.07 (d, J=1.83 Hz, 1H).

MS calc (M+H) 408.21; MS obs (M+H) 408.5.

EXAMPLE 209

N-{1-[(1-tert-Butyl-3,5-dimethyl-1H-pyrazol-4-yl)methyl]piperidin-4-yl}-6-(3-fluorophenyl)nicotinamide

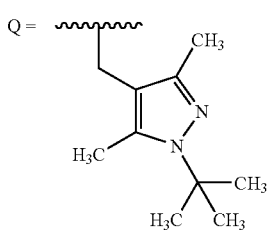

1H NMR (400 MHz, DMSO-d$_6$) □ ppm 1.53 (s, 9H) 1.79 (d, J=9.88 Hz, 2H) 1.97 (t, J=10.98 Hz, 2H) 2.06 (s, 3H) 2.32 (s, 3H) 2.78 (d, J=10.98 Hz, 2H) 3.17 (s, 2H) 3.37-3.40 (m, 2H) 3.73-3.88 (m, 1H) 7.23-7.37 (m, 1H) 7.49-7.61 (m, 1H) 7.94 (d, J=10.25 Hz, 1H) 8.00 (d, J=7.69 Hz, 1H) 8.11 (d, J=8.42 Hz, 1H) 8.27 (dd, J=8.24, 2.01 Hz, 1H) 8.42 (d, J=7.32 Hz, 1H) 9.06 (d, J=1.83 Hz, 1H).

MS calc (M+H) 464.27; MS obs (M+H) 464.6.

EXAMPLE 210

6-(3-Fluorophenyl)-N-{1-[4-(1H-pyrazol-1-yl)benzyl]piperidin-4-yl}nicotinamide

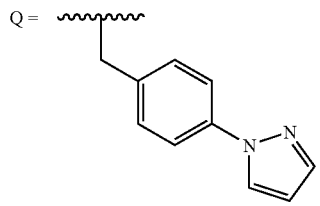

1H NMR (400 MHz, DMSO-d$_6$) □ ppm 1.54-1.71 (m, 2H) 1.84 (d, J=10.98 Hz, 2H) 2.09 (t, J=10.98 Hz, 2H) 2.86 (d, J=10.98 Hz, 2H) 3.52 (s, 2H) 3.83 (br. s., 1H) 6.53 (s, 1H) 7.26-7.36 (m, 1H) 7.42 (d, J=8.42 Hz, 2H) 7.52-7.63 (m, 1H) 7.73 (s, 1H) 7.79 (d, J=8.42 Hz, 2H) 7.95 (d, J=10.25 Hz, 1H) 8.01 (d, J=7.32 Hz, 1H) 8.12 (d, J=8.05 Hz, 1H) 8.28 (dd, J=8.05, 1.83 Hz, 1H) 8.41-8.53 (m, 2H) 9.08 (d, J=1.83 Hz, 1H).

MS calc (M+H) 456.21; MS obs (M+H) 456.5.

EXAMPLE 211

N-[1-(2-Fluoro-6-methoxybenzyl)piperidin-4-yl]-6-(3-fluorophenyl)nicotinamide

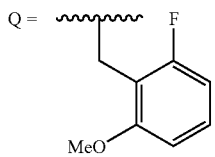

1H NMR (400 MHz, DMSO-d$_6$) □ ppm 1.44-1.63 (m, 2H) 1.78 (d, J=10.25 Hz, 2H) 2.10 (t, J=1.35 Hz, 2H) 2.82 (d, J=111.71 Hz, 2H) 3.53 (s, 2H) 3.73 (br. s., 1H) 3.82 (s, 3H) 6.78 (t, J=8.60 Hz, 1H) 6.87 (d, J=8.42 Hz, 1H) 7.24-7.37 (m, 2H) 7.49-7.63 (m, 1H) 7.94 (d, J=10.62 Hz, 1H) 8.00 (d, J=7.69 Hz, 1 H) 8.11 (d, J=8.42 Hz, 1H) 8.27 (dd, J=8.42, 1.83 Hz, 1H) 8.40 (d, J=7.69 Hz, 1H) 9.06 (d, J=1.83 Hz, 1 H).

MS calc (M+H) 438.19; MS obs (M+H) 438.5.

EXAMPLE 212

N-[2-(3,4-Dimethoxybenzyl)piperidin-4-yl]-6-(3-fluorophenyl)nicotinamide

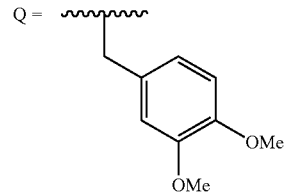

1H NMR (400 MHz, DMSO-d$_6$) ☐ ppm 1.51-1.69 (m, 2H) 1.77-1.88 (m, 2H) 2.03 (t, J=10.98 Hz, 2H) 2.83 (d, J=11.35 Hz, 2H) 3.41 (s, 2H) 3.74 (d, J=5.12 Hz, 6H) 3.81 (br. s., 1H) 6.77-6.84 (m, 1H) 6.85-6.96 (m, 2H) 7.24-7.37 (m, 1H) 7.51-7.63 (m, 1H) 7.95 (d, J=10.98 Hz, 1H) 8.00 (d, J=7.69 Hz, 1H) 8.11 (d, J=8.42 Hz, 1H) 8.28 (dd, J=8.24, 2.01 Hz, 1H) 8.45 (d, J=7.32 Hz, 1H) 9.07 (d, J=1.83 Hz, 1H).

MS calc (M+H) 450.21; MS obs (M+H) 450.4.

| Ex | Q | Name | MS Calc (M + H) | MS Obs (M + H) |
|---|---|---|---|---|
| 213 | | N-[1-(2-Cyanobenzyl)piperidin-4-yl]-6-(3-fluorophenyl)nicotinamide | 415.2 | 415.4 |
| 214 | | N-(1-{4-[3-(Dimethylamino)propoxy]benzyl}piperidin-4-yl)-6-(3-fluorophenyl)nicotinamide | 491.3 | 491.5 |
| 215 | | 6-(3-Fluorophenyl)-N-{1-[(1-methyl-1H-imidazol-2-yl)methyl]piperidin-4-yl}nicotinamide | 394.2 | 394.5 |
| 216 | | 6-(3-Fluorophenyl)-N-[1-(1,3-thiazol-2-ylmethyl)piperidin-4-yl]nicotinamide | 397.1 | 397.3 |
| 217 | | 6-(3-Fluorophenyl)-N-[1-(4-isopropoxybenzyl)piperidin-4-yl]nicotinamide | 448.2 | 448.5 |
| 218 | | 6-(3-Fluorophenyl)-N-[1-(245-trifluorobenzyl)piperidin-4-yl]nicotinamide | 444.2 | 444.5 |

-continued

| Ex | Q | Name | MS Calc (M + H) | MS Obs (M + H) |
|---|---|---|---|---|
| 219 | 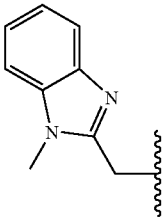 | 6-(3-Fluorophenyl)-N-{1-[(1-methyl-1H-benzimidazol-2-yl)methyl]piperidin-4-yl}nicotinamide | 444.2 | 444.5 |
| 220 | 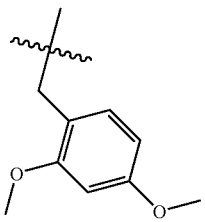 | N-[1-(2,4-Dimethoxybenzyl)piperidin-4-yl]-6-(3-fluorophenyl)nicotinamide | 450.2 | 450.5 |
| 221 |  | N-[1-(Cyclohex-3-en-1-ylmethyl)piperidin-4-yl]-6-(3-fluorophenyl)nicotinamide | 394.2 | 394.4 |
| 222 | 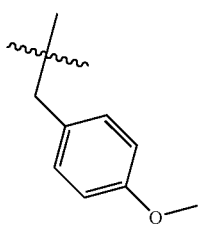 | 6-(3-Fluorophenyl)-N-[1-(4-methoxybenzyl)piperidin-4-yl]nicotinamide | 420.2 | 420.5 |
| 223 | 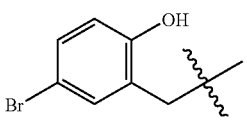 | N-[1-(5-Bromo-2-hydroxybenzyl)piperidin-4-yl]-6-(3-fluorophenyl)nicotinamide | 484.1 | 486.4 (Br iso) |
| 224 | 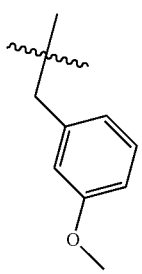 | 6-(3-Fluorophenyl)-N-[1-(3-methoxybenzyl)piperidin-4-yl]nicotinamide | 420.2 | 420.3 |
| 225 | 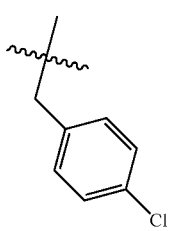 | N-[1-(4-Chlorobenzyl)piperidin-4-yl]-6-(3-fluorophenyl)nicotinamide | 424.2 | 424.1 |

-continued

| Ex | Q | Name | MS Calc (M + H) | MS Obs (M + H) |
|---|---|---|---|---|
| 226 | (3-methylene-5-methoxy-1H-indol-3-yl) | 6-(3-Fluorophenyl)-N-{1-[(5-methoxy-1H-indol-3-yl)methyl]piperidin-4-yl}nicotinamide | 459.2 | 459.5 |
| 227 | (4-cyanobenzyl) | N-[1-(4-Cyanobenzyl)piperidin-4-yl]-6-(3-fluorophenyl)nicotinamide | 415.2 | 415.4 |
| 228 | (3,4-diethoxybenzyl) | N-[1-(3,4-Diethoxybenzyl)piperidin-4-yl]-6-(3-fluorophenyl)nicotinamide | 478.2 | 478.3 |
| 229 | (2-ethoxybenzyl) | N-[1-(2-Ethoxybenzyl)piperidin-4-yl]-6-(3-fluorophenyl)nicotinamide | 434.2 | 434.4 |
| 230 | (2,3-dimethoxybenzyl) | N-[1-(2,3-Dimethoxybenzyl)piperidin-4-yl]-6-(3-fluorophenyl)nicotinamide | 450.2 | 450.4 |

| Ex | Q | Name | MS Calc (M + H) | MS Obs (M + H) |
|---|---|---|---|---|
| 231 | 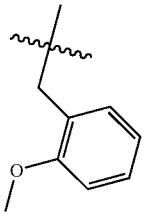 | 6-(3-Fluorophenyl)-N-[1-(2-methoxybenzyl)piperidin-4-yl]nicotinamide | 420.2 | 420.3 |
| 232 | 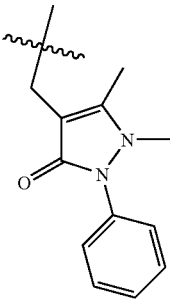 | N-{1-[(1,5-Dimethyl-3-oxo-2-phenyl-2,3-dihydro-1H-pyrazol-4-yl)methyl]piperidin-4-yl}-6-(3-fluorophenyl)nicotinamide | 500.2 | 500.5 |
| 233 | 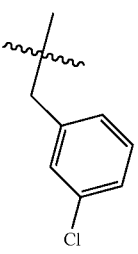 | N-[1-(3-Chlorobenzyl)piperidin-4-yl]-6-(3-fluorophenyl)nicotinamide | 424.2 | 424.3 |
| 234 | 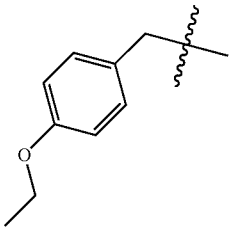 | N-[1-(4-Ethoxybenzyl)piperidin-4-yl]-6-(3-fluorophenyl)nicotinamide | 434.2 | 434.5 |
| 235 | 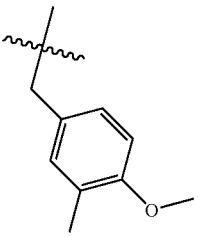 | 6-(3-Fluorophenyl)-N-[1-(4-methoxy-3-methylbenzyl)piperidin-4-yl]nicotinamide | 434.2 | 434.5 |
| 236 | 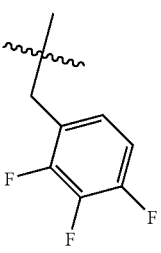 | 6-(3-Fluorophenyl)-N-[1-(2,3,4-trifluorobenzyl)piperidin-4-yl]nicotinamide | 444.2 | 444.5 |

-continued

| Ex | Q | Name | MS Calc (M + H) | MS Obs (M + H) |
|---|---|---|---|---|
| 237 | 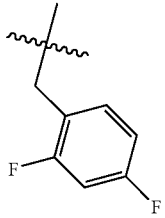 | N-[1-(2,4-Difluorobenzyl)piperidin-4-yl]-6-(3-fluorophenyl)nicotinamide | 426.2 | 426.1 |
| 238 | 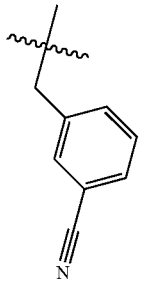 | N-[1-(3-Cyanobenzyl)piperidin-4-yl]-6-(3-fluorophenyl)nicotinamide | 415.2 | 415.1 |
| 239 | 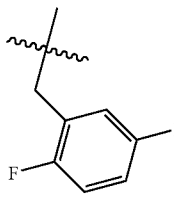 | N-[1-(2,5-Difluorobenzyl)piperidin-4-yl]-6-(3-fluorophenyl)nicotinamide | 426.2 | 426.0 |
| 240 | 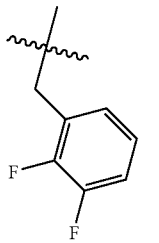 | N-[1-(2,3-Difluorobenzyl)piperidin-4-yl]-6-(3-fluorophenyl)nicotinamide | 426.2 | 425.9 |
| 241 | 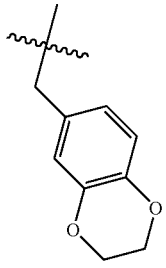 | N-[1-(2,3-Dihydro-14-benzodioxin-6-ylmethyl)piperidin-4-yl]-6-(3-fluorophenyl)nicotinamide | 448.2 | 448.5 |
| 242 | 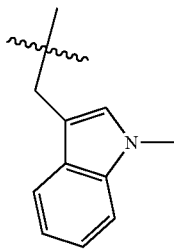 | 6-(3-Fluorophenyl)-N-{1-[(1-methyl-1H-indol-3-yl)methyl]piperidin-4-yl}nicotinamide | 443.2 | 443.6 |

| Ex | Q | Name | MS Calc (M + H) | MS Obs (M + H) |
|---|---|---|---|---|
| 243 | (1-acetylindol-3-ylmethyl) | N-{1-[(1-Acetyl-1H-indol-3-yl)methyl]piperidin-4-yl}-6-(3-fluorophenyl)nicotinamide | 471.2 | 471.3 |
| 244 | (2,6-difluorobenzyl) | N-[1-(2,6-Difluorobenzyl)piperidin-4-yl]-6-(3-fluorophenyl)nicotinamide | 426.2 | 425.9 |
| 245 | (3-bromo-4-methoxybenzyl) | N-[1-(3-Bromo-4-methoxybenzyl)piperidin-4-yl]-6-(3-fluorophenyl)nicotinamide | 498.1 | 500.1 |
| 246 | (quinolin-3-ylmethyl) | 6-(3-Fluorophenyl)-N-[1-(quinolin-3-ylmethyl)piperidin-4-yl]nicotinamide | 441.2 | 441.3 |
| 247 | (3-fluoro-4-methoxybenzyl) | N-[1-(3-Fluoro-4-methoxybenzyl)piperidin-4-yl]-6-(3-fluorophenyl)nicotinamide | 438.2 | 438.3 |
| 248 | (3,5-difluorobenzyl) | N-[1-(3,5-Difluorobenzyl)piperidin-4-yl]-6-(3-fluorophenyl)nicotinamide | 426.2 | 426.0 |

-continued

| Ex | Q | Name | MS Calc (M + H) | MS Obs (M + H) |
|---|---|---|---|---|
| 249 | (3-ethoxy-4-methoxybenzyl group) | N-[1-(3-Ethoxy-4-methoxybenzyl)piperidin-4-yl]-6-(3-fluorophenyl)nicotinamide | 464.2 | 464.4 |
| 250 | (1,3,5-trimethylpyrazol-4-ylmethyl group) | 6-(3-Fluorophenyl)-N-{1-[(1,3-trimethyl-1H-pyrazol-4-yl)methyl]piperidin-4-yl}nicotinamide | 422.2 | 422.0 |
| 251 | (2,2-dimethylpropyl group) | N-[1-(2,2-Dimethylpropyl)piperidin-4-yl]-6-(3-fluorophenyl)nicotinamide | 370.2 | 370.4 |
| 252 | (5-fluoro-1H-indol-3-ylmethyl group) | N-{1-[(5-Fluoro-1H-indol-3-yl)methyl]piperidin-4-yl}-6-(3-fluorophenyl)nicotinamide | 447.2 | 447.3 |
| 253 | (4-ethoxy-3-methoxybenzyl group) | N-[1-(4-Ethoxy-3-methoxybenzyl)piperidin-4-yl]-6-(3-fluorophenyl)nicotinamide | 464.2 | 464.5 |
| 254 | (2,4-dioxo-1,2,3,4-tetrahydropyrimidin-5-ylmethyl group) | N-{1-[(2,4-Dioxo-1234-tetrahydropyrimidin-5-yl)methyl]piperidin-4-yl}-6-(3-fluorophenyl)nicotinamide | 424.2 | 424.3 |

-continued

| Ex | Q | Name | MS Calc (M + H) | MS Obs (M + H) |
|---|---|---|---|---|
| 255 | | 6-(3-Fluorophenyl)-N-{1-[2-(2-hydroxyethoxy)benzyl]piperidin-4-yl}nicotinamide | 450.2 | 450.4 |
| 256 | | 6-(3-Fluorophenyl)-N-{1-[3-(2-hydroxyethoxy)benzyl]piperidin-4-yl}nicotinamide | 450.2 | 450.0 |
| 257 | | N-[1-(3-Chloro-4-hydroxy-5-methoxybenzyl)piperidin-4-yl]-6-(3-fluorophenyl)nicotinamide | 470.2 | 470.5 |
| 258 | | 6-(3-Fluorophenyl)-N-{1-[4-(2-hydroxyethoxy)benzyl]piperidin-4-yl}nicotinamide | 450.2 | 450.4 |
| 259 | | 6-(3-Fluorophenyl)-N-{1-[4-(methylsulfonyl)benzyl]piperidin-4-yl}nicotinamide | 468.2 | 468.1 |

| Ex | Q | Name | MS Calc (M + H) | MS Obs (M + H) |
|---|---|---|---|---|
| 260 | 2-chloro-3,4-dimethoxybenzyl group | N-[1-(2-Chloro-3,4-dimethoxybenzyl)piperidin-4-yl]-6-(3-fluorophenyl)nicotinamide | 484.2 | 484.1 |
| 261 | cinnolin-3-ylmethyl group | N-[1-(Cinnolin-3-ylmethyl)piperidin-4-yl]-6-(3-fluorophenyl)nicotinamide | 442.2 | 442.4 |
| 262 | (3-methylquinoxalin-2-yl)methyl group | 6-(3-Fluorophenyl)-N-{1-[(3-methylquinoxalin-2-yl)methyl]piperidin-4-yl}nicotinamide | 456.2 | 456.5 |
| 263 | quinoxalin-2-ylmethyl group | 6-(3-Fluorophenyl)-N-[1-(quinoxalin-2-ylmethyl)piperidin-4-yl]nicotinamide | 442.2 | 442.5 |
| 264 | (1,3-dimethyl-2,4-dioxo-1,2,3,4-tetrahydropyrimidin-5-yl)methyl group | N-{1-[(1,3-Dimethyl-2,4-dioxo-1,2,3,4-tetrahydropyrimidin-5-yl)methyl]piperidin-4-yl}-6-(3-fluorophenyl)nicotinamide | 452.2 | 452.3 |

-continued

| Ex | Q | Name | MS Calc (M + H) | MS Obs (M + H) |
|---|---|---|---|---|
| 265 | (3-methoxycarbonyl-1H-indol-3-yl)methyl group | Methyl 3-{[4-({[6-(3-fluorophenyl)pyridin-3-yl]carbonyl}amino)piperidin-1-yl]methyl}-1H-indole-6-carboxylate | 487.2 | 487.4 |
| 266 | (2-methyl-1H-imidazol-4-yl)methyl group | 6-(3-Fluorophenyl)-N-{1-[(2-methyl-1H-imidazol-4-yl)methyl]piperidin-4-yl}nicotinamide | 394.2 | 394.3 |
| 267 | 3,5-dichloro-4-hydroxybenzyl group | N-[1-(3,5-Dichloro-4-hydroxybenzyl)piperidin-4-yl]-6-(3-fluorophenyl)nicotinamide | 474.1 | 474.1 |
| 268 | 2-(tert-butoxycarbonylamino)-2-methylpropyl group | tert-Butyl {2-[4-({[6-(3-fluorophenyl)pyridin-3-yl]carbonyl}amino)piperidin-1-yl]-1,1-dimethylethyl}carbamate | 471.2 | 471.5 |
| 269 | 3-(N-methyl-tert-butoxycarbonylamino)propyl group | tert-Butyl {3-[4-({[6-(3-fluorophenyl)pyridin-3-yl]carbonyl}amino)piperidin-1-yl]propyl}methylcarbamate | 471.3 | 471.5 |

-continued

| Ex | Q | Name | MS Calc (M + H) | MS Obs (M + H) |
|---|---|---|---|---|
| 270 | | 6-(3-Fluorophenyl)-N-{1-[(1,3,6-trimethyl-2,4-dioxo-1,2,3,4-tetrahydropyrimidin-5-yl)methyl]piperidin-4-yl}nicotinamide | 466.2 | 466.5 |
| 271 | | N-(1-{4-[(Diethylamino)carbonyl]benzyl}piperidin-4-yl)-6-(3-fluorophenyl)nicotinamide | 489.3 | 489.3 |
| 272 | | 6-(3-Fluorophenyl)-N-{1-[(2-oxo-1,2-dihydropyridin-3-yl)methyl]piperidin-4-yl}nicotinamide | 407.2 | 407.1 |
| 273 | | N-(1-{2-[3-(Dimethylamino)propoxy]benzyl}piperidin-4-yl)-6-(3-fluorophenyl)nicotinamide | 491.3 | 491.6 |
| 274 | | N-{1-[(1-Ethyl-3,5-dimethyl-1H-pyrazol-4-yl)methyl]piperidin-4-yl}-6-(3-fluorophenyl)nicotinamide | 436.2 | 436.1 |

-continued

| Ex | Q | Name | MS Calc (M + H) | MS Obs (M + H) |
|---|---|---|---|---|
| 275 | 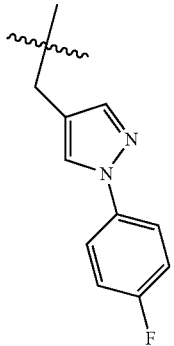 | 6-(3-Fluorophenyl)-N-(1-{[1-(4-fluorophenyl)-1H-pyrazol-4-yl]methyl}piperidin-4-yl)nicotinamide | 474.2 | 474.5 |
| 276 | 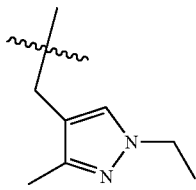 | N-{1-[(1-Ethyl-3-methyl-1H-pyrazol-4-yl)methyl]piperidin-4-yl}-6-(3-fluorophenyl)nicotinamide | 422.2 | 422.4 |
| 277 | 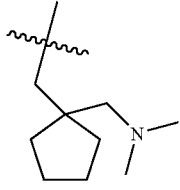 | N-[1-({1-[(Dimethylamino)methyl]cyclopentyl}methyl)piperidin-4-yl]-6-(3-fluorophenyl)nicotinamide | 439.3 | 439.4 |
| 278 | 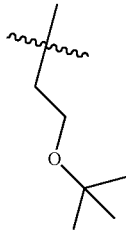 | N-[1-(2-tert-Butoxyethyl)piperidin-4-yl]-6-(3-fluorophenyl)nicotinamide | 400.2 | 400.5 |
| 279 | 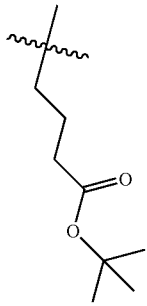 | tert-Butyl 4-[4-({[6-(3-fluorophenyl)pyridin-3-yl]carbonyl}amino)piperidin-1-yl]butanoate | 442.2 | 442.5 |
| 280 | 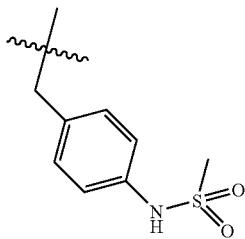 | 6-(3-Fluorophenyl)-N-(1-{4-[(methylsulfonyl)amino]benzyl}piperidin-4-yl)nicotinamide | 483.2 | 483.4 |

-continued

| Ex | Q | Name | MS Calc (M + H) | MS Obs (M + H) |
|---|---|---|---|---|
| 281 | | tert-Butyl {3-[4-({[6-(3-fluorophenyl)pyridin-3-yl]carbonyl}amino)piperidin-1-yl]propyl}carbamate | 457.3 | 457.6 |
| 282 | | 6-(3-Fluorophenyl)-N-(1-{4-[(methylamino)sulfonyl]benzyl}piperidin-4-yl)nicotinamide | 483.2 | 483.1 |
| 283 | | 6-(3-Fluorophenyl)-N-{1-[(6-methylpyridin-2-yl)methyl]piperidin-4-yl}nicotinamide | 405.2 | 405.0 |
| 284 | | Ethyl (5-{[4-({[6-(3-fluorophenyl)pyridin-3-yl]carbonyl}amino)piperidin-1-yl]methyl}-1H-indol-1-yl)acetate | 515.2 | 515.3 |
| 285 | | 6-(3-Fluorophenyl)-N-(1-{[4-(2-methoxyphenyl)tetrahydro-2H-pyran-4-yl]methyl}piperidin-4-yl)nicotinamide | 504.3 | 504.4 |

| Ex | Q | Name | MS Calc (M + H) | MS Obs (M + H) |
|---|---|---|---|---|
| 286 | | 6-(3-Fluorophenyl)-N-(1-{[4-(3-methoxyphenyl)tetrahydro-2H-pyran-4-yl]methyl}piperidin-4-yl)nicotinamide | 504.3 | 504.5 |
| 287 | | N-{1-[(1,5-dimethyl-1H-pyrazol-4-yl)methyl]piperidin-4-yl}-6-(3-fluorophenyl)nicotinamide | 408.2 | 408.5 |
| 288 | | N-[1-(2,1,3-Benzothiadiazol-5-ylmethyl)piperidin-4-yl]-6-(3-fluorophenyl)nicotinamide | 448.2 | 448.0 |
| 289 | | 6-(3-Fluorophenyl)-N-{1-[(2-phenyl-1,3-thiazol-5-yl)methyl]piperidin-4-yl}nicotinamide | 473.2 | 473.1 |
| 290 | | 6-(3-Fluorophenyl)-N-[1-(quinolin-6-ylmethyl)piperidin-4-yl]nicotinamide | 441.2 | 441.4 |

| Ex | Q | Name | MS Calc (M + H) | MS Obs (M + H) |
|---|---|---|---|---|
| 291 | 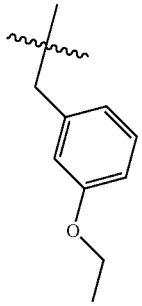 | N-[1-(3-Ethoxybenzyl)piperidin-4-yl]-6-(3-fluorophenyl)nicotinamide | 434.2 | 434.5 |
| 292 | 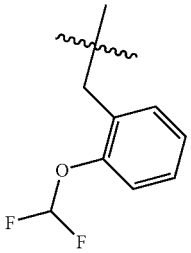 | N-{1-[2-(Difluoromethoxy)benzyl]piperidin-4-yl}-6-(3-fluorophenyl)nicotinamide | 456.2 | 456.5 |
| 293 | 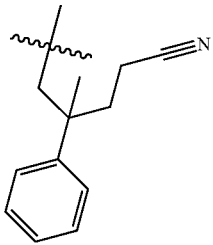 | N-[1-(4-Cyano-2-methyl-2-phenylbutyl)piperidin-4-yl]-6-(3-fluorophenyl)nicotinamide | 471.3 | 471.4 |
| 294 | 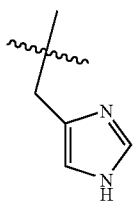 | 6-(3-Fluorophenyl)-N-[1-(1H-imidazol-4-ylmethyl)piperidin-4-yl]nicotinamide | 380.2 | 380.5 |
| 295 | 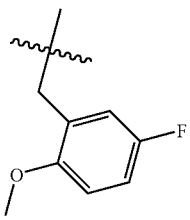 | N-[1-(5-Fluoro-2-methoxybenzyl)piperidin-4-yl]-6-(3-fluorophenyl)nicotinamide | 438.2 | 438.5 |
| 296 | 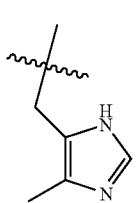 | 6-(3-Fluorophenyl)-N-{1-[(4-methyl-1H-imidazol-5-yl)methyl]piperidin-4-yl}nicotinamide | 394.2 | 394.5 |

-continued

| Ex | Q | Name | MS Calc (M + H) | MS Obs (M + H) |
|---|---|---|---|---|
| 297 | 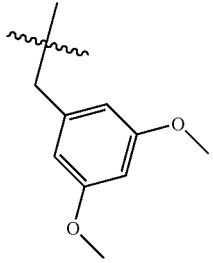 | N-[1-(3,5-Dimethoxybenzyl)piperidin-4-yl]-6-(3-fluorophenyl)nicotinamide | 450.2 | 450.1 |
| 298 |  | N-[1-(3,3-Dimethylbutyl)piperidin-4-yl]-6-(3-fluorophenyl)nicotinamide | 384.2 | 384.5 |
| 299 | 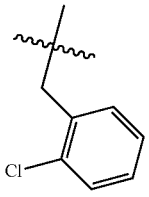 | N-[1-(2-Chlorobenzyl)piperidin-4-yl]-6-(3-fluorophenyl)nicotinamide | 424.2 | 424.0 |
| 300 | 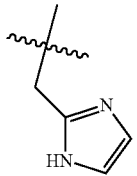 | 6-(3-Fluorophenyl)-N-[1-(1H-imidazol-2-ylmethyl)piperidin-4-yl]nicotinamide | 380.2 | 380.4 |
| 301 | 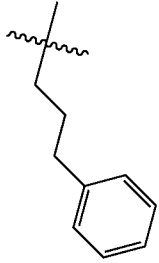 | 6-(3-Fluorophenyl)-N-[1-(3-phenylpropyl)piperidin-4-yl]nicotinamide | 418.2 | 418.3 |
| 302 | 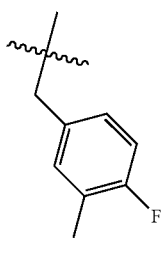 | N-[1-(4-Fluoro-3-methylbenzyl)piperidin-4-yl]-6-(3-fluorophenyl)nicotinamide | 422.2 | 422.4 |

-continued

| Ex | Q | Name | MS Calc (M + H) | MS Obs (M + H) |
|---|---|---|---|---|
| 303 | | N-[1-(3-Cyano-4-fluorobenzyl)piperidin-4-yl]-6-(3-fluorophenyl)nicotinamide | 433.2 | 433.1 |
| 304 | | 6-(3-Fluorophenyl)-N-[1-(1H-indol-5-ylmethyl)piperidin-4-yl]nicotinamide | 429.2 | 429.6 |
| 305 | | N-[1-(2,6-Dimethoxy-4-methylbenzyl)piperidin-4-yl]-6-(3-fluorophenyl)nicotinamide | 464.2 | 464.5 |
| 306 | | N-[1-(2-Ethoxy-4-methoxybenzyl)piperidin-4-yl]-6-(3-fluorophenyl)nicotinamide | 464.2 | 464.5 |
| 307 | | 6-(3-Fluorophenyl)-N-(1-{[3-(4-methylphenyl)-1H-pyrazol-4-yl]methyl}piperidin-4-yl)nicotinamide | 470.2 | 470.5 |

| Ex | Q | Name | MS Calc (M + H) | MS Obs (M + H) |
|---|---|---|---|---|
| 308 | (5-(4-cyanophenoxy)pyridin-2-yl)methyl group | N-(1-{[6-(4-Cyanophenoxy)pyridin-3-yl]methyl}piperidin-4-yl)-6-(3-fluorophenyl)nicotinamide | 508.2 | 508.1 |
| 309 | (4-chloro-6-fluoro-2H-chromen-3-yl)methyl group | N-(1-[(4-Chloro-6-fluoro-2H-chromen-3-yl)methyl]piperidin-4-yl)-6-(3-fluorophenyl)nicotinamide | 496.2 | 496.6 |
| 310 | (2,6-dioxo-tetrahydropyrimidin-4-yl)methyl group | N-{1-[(2,6-Dioxo-1,2,3,6-tetrahydropyrimidin-4-yl)methyl]piperidin-4-yl}-6-(3-fluorophenyl)nicotinamide | 424.2 | 424.1 |
| 311 | (5-methoxycarbonyl-1H-indol-3-yl)methyl group | Methyl 3-{[4-({[6-(3-fluorophenyl)pyridin-3-yl]carbonyl}amino)piperidin-1-yl]methyl}-1H-indole-5-carboxylate | 487.2 | 487.6 |
| 312 | 4,4,4-trifluorobutyl group | 6-(3-Fluorophenyl)-N-[1-(4,4,4-trifluorobutyl)piperidin-4-yl]nicotinamide | 410.2 | 410.0 |

-continued

| Ex | Q | Name | MS Calc (M + H) | MS Obs (M + H) |
|---|---|---|---|---|
| 313 | 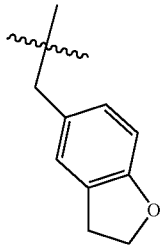 | N-[1-(2,3-Dihydro-1-benzofuran-5-ylmethyl)piperidin-4-yl]-6-(3-fluorophenyl)nicotinamide | 432.2 | 432.5 |
| 314 | 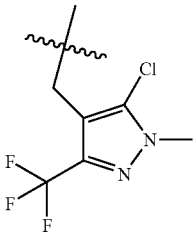 | N-(1-{[5-Chloro-1-methyl-3-(trifluoromethyl)-1H-pyrazol-4-yl]methyl}piperidin-4-yl)-6-(3-fluorophenyl)nicotinamide | 496.2 | 496.3 |
| 315 | 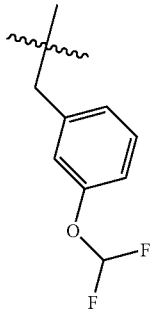 | N-{1-[3-(Difluoromethoxy)benzyl]piperidin-4-yl}-6-(3-fluorophenyl)nicotinamide | 456.2 | 456.5 |
| 316 | 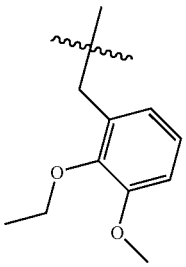 | N-[1-(2-Ethoxy-3-methoxybenzyl)piperidin-4-yl]-6-(3-fluorophenyl)nicotinamide | 464.2 | 464.4 |
| 317 | 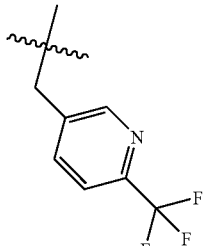 | 6-(3-Fluorophenyl)-N-(1-{[6-(trifluoromethyl)pyridin-3-yl]methyl}piperidin-4-yl)nicotinamide | 459.2 | 459.4 |

-continued

| Ex | Q | Name | MS Calc (M + H) | MS Obs (M + H) |
|---|---|---|---|---|
| 318 | 2,3-difluoro-4-methylbenzyl | N-[1-(2,3-Difluoro-4-methylbenzyl)piperidin-4-yl]-6-(3-fluorophenyl)nicotinamide | 440.2 | 440.4 |
| 319 | (5-chloro-1,3-dimethyl-1H-pyrazol-4-yl)methyl | N-{1-[(5-Chloro-1,3-dimethyl-1H-pyrazol-4-yl)methyl]piperidin-4-yl}-6-(3-fluorophenyl)nicotinamide | 442.2 | 442.5 |
| 320 | (2-phenyl-1H-imidazol-4-yl)methyl | 6-(3-Fluorophenyl)-N-{1-[(2-phenyl-1H-imidazol-4-yl)methyl]piperidin-4-yl}nicotinamide | 456.2 | 456.1 |
| 321 | (4-bromo-1-methyl-1H-pyrazol-3-yl)methyl | N-{1-[(4-Bromo-1-methyl-1H-pyrazol-3-yl)methyl]piperidin-4-yl}-6-(3-fluorophenyl)nicotinamide | 472.1 | 472.0 |
| 322 | 3-(4-methoxyphenyl)propyl | 6-(3-Fluorophenyl)-N-{1-[3-(4-methoxyphenyl)propyl]piperidin-4-yl}nicotinamide | 448.2 | 448.0 |
| 323 | 2-fluoro-5-methoxybenzyl | N-[1-(2-Fluoro-5-methoxybenzyl)piperidin-4-yl]-6-(3-fluorophenyl)nicotinamide | 438.2 | 438.1 |

-continued

| Ex | Q | Name | MS Calc (M + H) | MS Obs (M + H) |
|---|---|---|---|---|
| 324 | 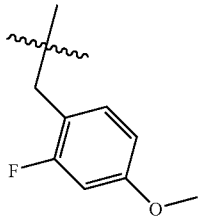 | N-[1-(2-Fluoro-4-methoxybenzyl)piperidin-4-yl]-6-(3-fluorophenyl)nicotinamide | 438.2 | 438.1 |
| 325 |  | 6-(3-Fluorophenyl)-N-(1-pentylpiperidin-4-yl)nicotinamide | 370.2 | 370.5 |
| 326 | 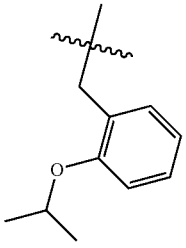 | 6-(3-Fluorophenyl)-N-[1-(2-isopropoxybenzyl)piperidin-4-yl]nicotinamide | 448.2 | 448.5 |
| 327 | 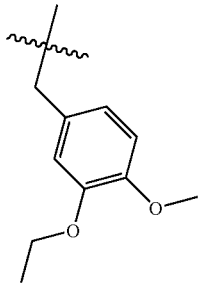 | 6-(3-Fluorophenyl)-N-{1-[4-methoxy-3-(methoxymethyl)benzyl]piperidin-4-yl}nicotinamide | 464.2 | 464.4 |
| 328 | 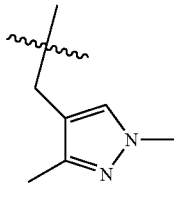 | N-{1-[(1,3-Dimethyl-1H-pyrazol-4-yl)methyl]piperidin-4-yl}-6-(3-fluorophenyl)nicotinamide | 408.2 | 408.5 |
| 329 | 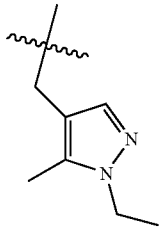 | N-{1-[(1-Ethyl-5-methyl-1H-pyrazol-4-yl)methyl]piperidin-4-yl}-6-(3-fluorophenyl)nicotinamide | 422.2 | 422.5 |

-continued

| Ex | Q | Name | MS Calc (M + H) | MS Obs (M + H) |
|---|---|---|---|---|
| 330 | | 6-(3-Fluorophenyl)-N-[1-(4-pyrimidin-2-ylbenzyl)piperidin-4-yl]nicotinamide | 468.2 | 468.8 |
| 331 | | 6-(3-Fluorophenyl)-N-[1-(2,3,5-trifluorobenzyl)piperidin-4-yl]nicotinamide | 444.2 | 444.3 |
| 332 | | 6-(3-fluorophenyl)-N-[1-(345-trifluorobenzyl)piperidin-4-yl]nicotinamide | 444.2 | 444.3 |
| 333 | | tert-Butyl 3-{[4-({[6-(3-fluorophenyl)pyridin-3-yl]carbonyl}amino)piperidin-1-yl]methyl}piperidine-1-carboxylate | 497.3 | 497.5 |
| 334 | | tert-Butyl (1-{[4-({[6-(3-fluorophenyl)pyridin-3-yl]carbonyl}amino)piperidin-1-yl]methyl}cyclobutyl)carbamate | 483.3 | 483.6 |

-continued

| Ex | Q | Name | MS Calc (M + H) | MS Obs (M + H) |
|---|---|---|---|---|
| 335 | (3,5-dimethyl-1-phenyl-1H-pyrazol-4-yl)methyl | N-{1-[(3,5-Dimethyl-1-phenyl-1H-pyrazol-4-yl)methyl]piperidin-4-yl}-6-(3-fluorophenyl)nicotinamide | 484.2 | 484.5 |
| 336 | 7-hydroxy-3,7-dimethyloctyl | 6-(3-Fluorophenyl)-N-[1-(7-hydroxy-3,7-dimethyloctyl)piperidin-4-yl]nicotinamide | 456.3 | 456.5 |
| 337 | 1H-benzimidazol-2-ylmethyl | N-[1-(1H-Benzimidazol-2-ylmethyl)piperidin-4-yl]-6-(3-fluorophenyl)nicotinamide | 430.2 | 430.3 |
| 338 | (6-ethoxyquinolin-2-yl)methyl | N-[(6-Ethoxyquinolin-2-yl)methyl]piperidin-4-yl}-6-(3-fluorophenyl)nicotinamide | 485.2 | 485.5 |
| 339 | methyl (indol-3-yl)acetate | Methyl (3-{[4-({[6-(3-fluorophenyl)pyridin-3-yl]carbonyl}amino)piperidin-1-yl]methyl}-1H-indol-1-yl)acetate | 501.2 | 501.5 |

| Ex | Q | Name | MS Calc (M + H) | MS Obs (M + H) |
|---|---|---|---|---|
| 340 | 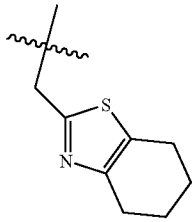 | 6-(3-Fluorophenyl)-N-[1-(4,5,6,7-tetrahydro-1,3-benzothiazol-2-ylmethyl)piperidin-4-yl]nicotinamide | 451.2 | 451.3 |
| 341 | 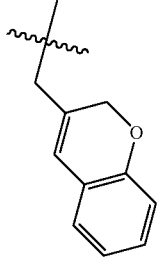 | N-[1-(2H-Chromen-3-ylmethyl)piperidin-4-yl]-6-(3-fluorophenyl)nicotinamide | 444.2 | 444.5 |
| 342 | 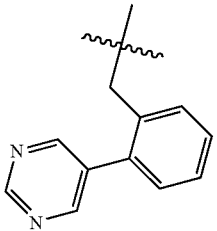 | 6-(3-Fluorophenyl)-N-[1-(2-pyrimidin-5-ylbenzyl)piperidin-4-yl]nicotinamide | 468.2 | 468.1 |
| 343 | 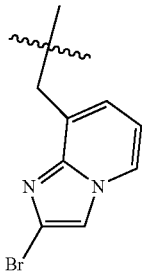 | N-{1-[(2-Bromoimidazo[1,2-a]pyridin-8-yl)methyl]piperidin-4-yl}-6-(3-fluorophenyl)nicotinamide | 508.1 | 508.5 |
| 344 | 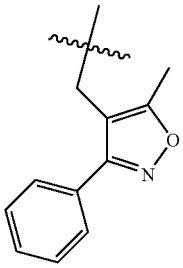 | 6-(3-Fluorophenyl)-N-{1-[(5-methyl-3-phenylisoxazol-4-yl)methyl]piperidin-4-yl}nicotinamide | 471.2 | 471.5 |

| Ex | Q | Name | MS Calc (M+H) | MS Obs (M+H) |
|---|---|---|---|---|
| 345 | 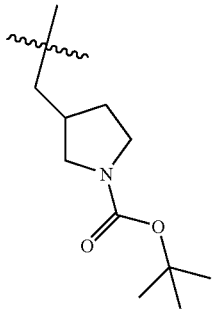 | tert-Butyl 3-{[4-({[6-(3-fluorophenyl)pyridin-3-yl]carbonyl}amino)piperidin-1-yl]methyl}pyrrolidine-1-carboxylate | 483.3 | 483.6 |
| 346 | 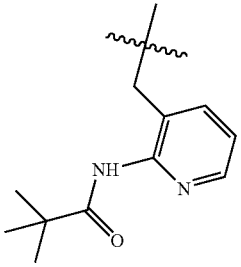 | N-[1-({2-[(2,2-Dimethylpropanoyl)amino]pyridin-3-yl}methyl)piperidin-4-yl]-6-(3-fluorophenyl)nicotinamide | 490.3 | 490.5 |
| 347 | 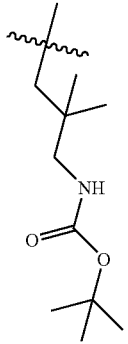 | tert-Butyl {3-[4-({[6-(3-fluorophenyl)pyridin-3-yl]carbonyl}amino)piperidin-1-yl]-2,2-dimethylpropyl}carbamate | 485.3 | 485.6 |
| 348 | 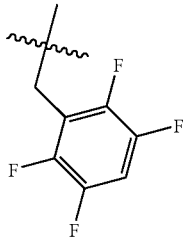 | 6-(3-Fluorophenyl)-N-[1-(2,3,5,6-tetrafluorobenzyl)piperidin-4-yl]nicotinamide | 462.2 | 462.3 |
| 349 | 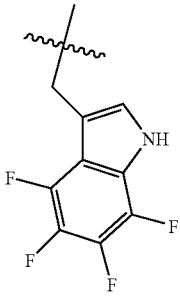 | 6-(3-Fluorophenyl)-N-{1-[(4,5,6,7-tetrafluoro-1H-indol-3-yl)methyl]piperidin-4-yl}nicotinamide | 501.2 | 501.1 |

-continued

| Ex | Q | Name | MS Calc (M + H) | MS Obs (M + H) |
|---|---|---|---|---|
| 350 | 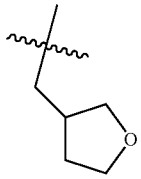 | 6-(3-Fluorophenyl)-N-[1-(tetrahydrofuran-3-ylmethyl)piperidin-4-yl]nicotinamide | 384.2 | 384.6 |
| 351 | 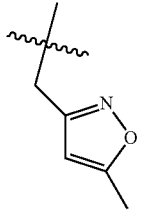 | 6-(3-Fluorophenyl)-N-{1-[(5-methylisoxazol-3-yl)methyl]piperidin-4-yl}nicotinamide | 395.2 | 394.9 |
| 352 | 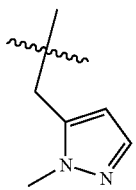 | 6-(3-Fluorophenyl)-N-{1-[(1-methyl-1H-pyrazol-5-yl)methyl]piperidin-4-yl}nicotinamide | 394.2 | 394.3 |
| 353 | 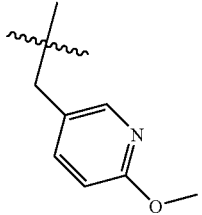 | 6-(3-Fluorophenyl)-N-{1-[(6-methoxypyridin-3-yl)methyl]piperidin-4-yl}nicotinamide | 421.2 | 421.4 |
| 354 | 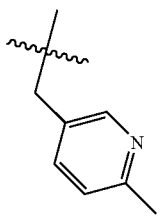 | 6-(3-Fluorophenyl)-N-{1-[(6-methylpyridin-3-yl)methyl]piperidin-4-yl}nicotinamide | 405.2 | 405.4 |
| 355 | 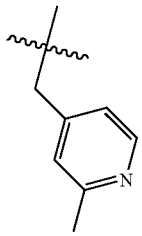 | 6-(3-Fluorophenyl)-N-{1-[(2-methylpyridin-4-yl)methyl]piperidin-4-yl}nicotinamide | 405.2 | 405.1 |

| Ex | Q | Name | MS Calc (M + H) | MS Obs (M + H) |
|---|---|---|---|---|
| 356 | 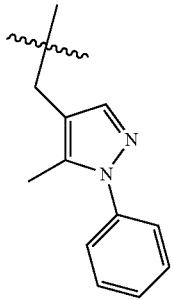 | 6-(3-Fluorophenyl)-N-{1-[(5-methyl-1-phenyl-1H-pyrazol-4-yl)methyl]piperidin-4-yl}nicotinamide | 470.2 | 470.5 |
| 357 | 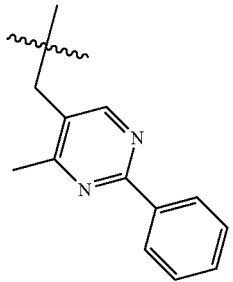 | 6-(3-Fluorophenyl)-N-{1-[(4-methyl-2-phenylpyrimidin-5-yl)methyl]piperidin-4-yl}nicotinamide | 482.2 | 482.5 |
| 358 | 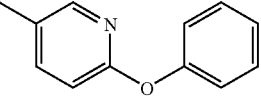 | 6-(3-Fluorophenyl)-N-{1-[(6-phenoxypyridin-3-yl)methyl]piperidin-4-yl}nicotinamide | 483.2 | 483.6 |
| 359 | 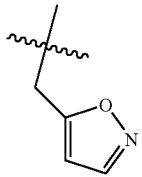 | 6-(3-Fluorophenyl)-N-[1-(isoxazol-5-ylmethyl)piperidin-4-yl]nicotinamide | 381.2 | 381.4 |
| 360 | 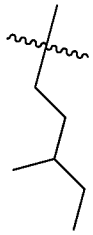 | 6-(3-Fluorophenyl)-N-[1-(3-methylpentyl)piperidin-4-yl]nicotinamide | 384.2 | 384.4 |
| 361 | 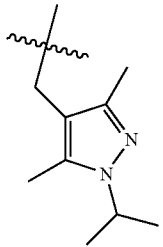 | 6-(3-Fluorophenyl)-N-{1-[(1-isopropyl-3,5-dimethyl-1H-pyrazol-4-yl)methyl]piperidin-4-yl}nicotinamide | 450.3 | 450.3 |

-continued

| Ex | Q | Name | MS Calc (M + H) | MS Obs (M + H) |
|---|---|---|---|---|
| 362 | (3,5-dimethyl-1-(4-fluorophenyl)-1H-pyrazol-4-yl)methyl | 6-(3-Fluorophenyl)-N-(1-{[1-(4-fluorophenyl)-3,5-dimethyl-1H-pyrazol-4-yl]methyl}piperidin-4-yl)nicotinamide | 502.2 | 502.5 |
| 363 | (isoxazol-3-yl)methyl | 6-(3-Fluorophenyl)-N-[1-(isoxazol-3-ylmethyl)piperidin-4-yl]nicotinamide | 381.2 | 381.4 |
| 364 | 3-[(dimethylamino)methyl]-4-methoxybenzyl | N-(1-{3-[(Dimethylamino)methyl]-4-methoxybenzyl}piperidin-4-yl)-6-(3-fluorophenyl)nicotinamide | 477.3 | 477.4 |
| 365 | [1-(4-methoxyphenyl)-1H-imidazol-2-yl]methyl | 6-(3-Fluorophenyl)-N-(1-{[1-(4-methoxyphenyl)-1H-imidazol-2-yl]methyl}piperidin-4-yl)nicotinamide | 486.2 | 486.5 |
| 366 | (5-isopropyl-1H-pyrazol-3-yl)methyl | 6-(3-Fluorophenyl)-N-{5-[(1-isopropyl-1H-pyrazol-3-yl)methyl]piperidin-4-yl}nicotinamide | 422.2 | 422.5 |

| Ex | Q | Name | MS Calc (M + H) | MS Obs (M + H) |
|---|---|---|---|---|
| 367 | | 6-(3-Fluorophenyl)-N-{1-[3-(1H-pyrazol-1-yl)benzyl]piperidin-4-yl}nicotinamide | 456.2 | 456.5 |
| 368 | | N-{1-[(2-Aminopyrimidin-5-yl)methyl]piperidin-4-yl}-6-(3-fluorophenyl)nicotinamide | 407.2 | 407.5 |
| 369 | | N-{1-[3-(3,5-Dimethyl-1H-pyrazol-1-yl)benzyl]piperidin-4-yl}-6-(3-fluorophenyl)nicotinamide | 484.2 | 484.4 |
| 370 | | N-{1-[(6-Fluoro-4H-1,3-benzodioxin-8-yl)methyl]piperidin-4-yl}-6-(3-fluorophenyl)nicotinamide | 466.2 | 466.1 |
| 371 | | N-[1-(2,1,3-Benzothiadiazol-4-ylmethyl)piperidin-4-yl]-6-(3-fluorophenyl)nicotinamide | 448.2 | 448.1 |

-continued

| Ex | Q | Name | MS Calc (M + H) | MS Obs (M + H) |
|---|---|---|---|---|
| 372 | | N-{1-[(1,3-Dimethyl-1H-pyrazol-5-yl)methyl]piperidin-4-yl}-6-(3-fluorophenyl)nicotinamide | 408.2 | 408.5 |
| 373 | | 6-(3-Fluorophenyl)-N-{1-[(2-phenyl-1,3-thiazol-4-yl)methyl]piperidin-4-yl}nicotinamide | 473.2 | 473.0 |
| 374 | | 6-(3-Fluorophenyl)-N-{1-[(1-methyl-1H-imidazol-4-yl)methyl]piperidin-4-yl}nicotinamide | 394.2 | 394.0 |
| 375 | | 6-(3-Fluorophenyl)-N-(1-{[6-(1H-pyrazol-1-yl)pyridin-2-yl]methyl}piperidin-4-yl)nicotinamide | 457.2 | 457.6 |
| 376 | | 6-(3-Fluorophenyl)-N-{1-[4-(1-methyl-1H-imidazol-2-yl)benzyl]piperidin-4-yl}nicotinamide | 470.2 | 470.4 |

-continued

| Ex | Q | Name | MS Calc (M + H) | MS Obs (M + H) |
|---|---|---|---|---|
| 377 | 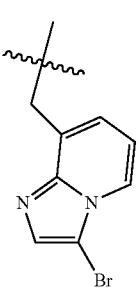 | N-{1-[(3-Bromoimidazo[1,2-a]pyridin-8-yl)methyl]piperidin-4-yl}-6-(3-fluorophenyl)nicotinamide | 508.1 | 508.4 |
| 378 | 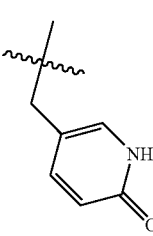 | 6-(3-Fluorophenyl)-N-{1-[(6-oxo-1,6-dihydropyridin-3-yl)methyl]piperidin-4-yl}nicotinamide | 407.2 | 407.0 |
| 379 | 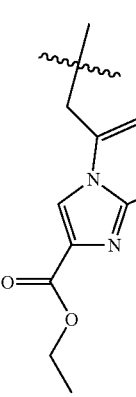 | Ethyl 5-{[4-({[6-(3-fluorophenyl)pyridin-3-yl]carbonyl}amino)piperidin-1-yl]methyl}imidazo[1,2-a]pyridine-2-carboxylate | 502.2 | 502.4 |
| 380 | 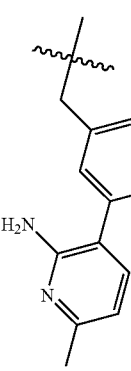 | N-{1-[3-(2-Amino-6-methylpyridin-3-yl)benzyl]piperidin-4-yl}-6-(3-fluorophenyl)nicotinamide | 496.2 | 496.5 |

| Ex | Q | Name | MS Calc (M + H) | MS Obs (M + H) |
|---|---|---|---|---|
| 381 | (3-pyrimidin-5-ylbenzyl) | 6-(3-Fluorophenyl)-N-[1-(3-pyrimidin-5-ylbenzyl)piperidin-4-yl]nicotinamide | 468.2 | 468.1 |
| 382 | [5-(2-chlorophenyl)-1H-pyrazol-4-yl]methyl | N-(1-{[5-(2-Chlorophenyl)-1H-pyrazol-4-yl]methyl}piperidin-4-yl)-6-(3-fluorophenyl)nicotinamide | 490.2 | 490.4 |
| 383 | (2,7-dimethylimidazo[1,2-a]pyridin-3-yl)methyl | N-{1-[(2,7-Dimethylimidazo[1,2,a]pyridin-3-yl)methyl]piperidin-4-yl}-6-(3-fluorophenyl)nicotinamide | 458.2 | 458.5 |
| 384 | (1H-pyrazol-5-yl)methyl | 6-(3-Fluorophenyl)-N-[1-(1H-pyrazol-5-ylmethyl)piperidin-4-yl]nicotinamide | 380.2 | 380.0 |
| 385 | [4-(1-cyanocyclopent-3-en-1-yl)benzyl] | N-{1-[4-(1-Cyanocyclopent-3-en-1-yl)benzyl]piperidin-4-yl}-6-(3-fluorophenyl)nicotinamide | 481.2 | 481.6 |

-continued

| Ex | Q | Name | MS Calc (M + H) | MS Obs (M + H) |
|---|---|---|---|---|
| 386 |  | 6-(3-Fluorophenyl)-N-[1-(4,5,6,7-tetrahydropyrazolo[1,5-a]pyridin-3-ylmethyl)piperidin-4-yl]nicotinamide | 434.2 | 434.1 |
| 387 |  | 6-(3-Fluorophenyl)-N-[1-(5,6,7,8-tetrahydro-4H-pyrazolo[1,5-a]azepin-3-ylmethyl)piperidin-4-yl]nicotinamide | 448.2 | 448.5 |
| 388 |  | N-(1-{3-[(3-Ethyl-1,2,4-oxadiazol-5-yl)methoxy]benzyl}piperidin-4-yl)-6-(3-fluorophenyl)nicotinamide | 516.2 | 516.5 |
| 389 |  | 6-(3-Fluorophenyl)-N-{1-[(2-methylpyrimidin-4-yl)methyl]piperidin-4-yl}nicotinamide | 406.2 | 406.1 |
| 390 |  | N-[1-({2-[Cyclohexyl(methyl)amino]pyrimidin-4-yl}methyl)piperidin-4-yl]-6-(3-fluorophenyl)nicotinamide | 503.3 | 503.4 |

-continued

| Ex | Q | Name | MS Calc (M + H) | MS Obs (M + H) |
|---|---|---|---|---|
| 391 | 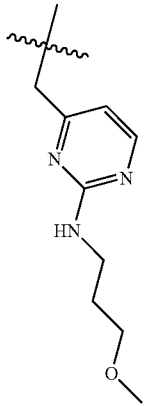 | 6-(3-Fluorophenyl)-N-[1-({2-[(3-methoxypropyl)amino]pyrimidin-4-yl}methyl)piperidin-4-yl]nicotinamide | 479.3 | 479.5 |
| 392 | 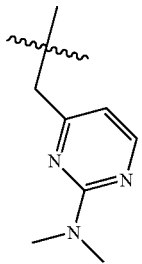 | N-(1-{[2-(Dimethylamino)pyrimidin-4-yl]methyl}piperidin-4-yl)-6-(3-fluorophenyl)nicotinamide | 435.2 | 435.3 |
| 393 | 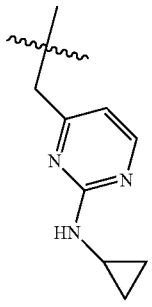 | N-(1-{[2-(Cyclopropylamino)pyrimidin-4-yl]methyl}piperidin-4-yl)-6-(3-fluorophenyl)nicotinamide | 447.2 | 447.1 |
| 394 | 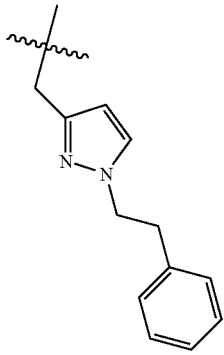 | 6-(3-Fluorophenyl)-N-(1-{[1-(2-phenylethyl)-1H-pyrazol-3-yl]methyl}piperidin-4-yl)nicotinamide | 484.2 | 484.6 |

-continued

| Ex | Q | Name | MS Calc (M + H) | MS Obs (M + H) |
|---|---|---|---|---|
| 395 | | 6-(3-Fluorophenyl)-N-(1-{[1-(2-phenylethyl)-1H-pyrazol-5-yl]methyl}piperidin-4-yl)nicotinamide | 484.2 | 484.5 |
| 396 | | 6-(3-Fluorophenyl)-N-{1-[(1-methyl-1H-pyrazol-3-yl)methyl]piperidin-4-yl}nicotinamide | 394.2 | 394.3 |
| 397 | | 6-(3-Fluorophenyl)-N-{1-[(2-morpholin-4-ylpyrimidin-4-yl)methyl]piperidin-4-yl}nicotinamide | 477.2 | 477.5 |
| 398 | | N-[1-({2-[Ethyl(methyl)amino]-5,6,7,8-tetrahydroquinazolin-6-yl}methyl)piperidin-4-yl]-6-(3-fluorophenyl)nicotinamide | 503.3 | 503.6 |

-continued

| Ex | Q | Name | MS Calc (M + H) | MS Obs (M + H) |
|---|---|---|---|---|
| 399 | | N-(1-{[2-(cyclopropylmethyl)-5,6,7,8-tetrahydroquinazolin-6-yl]methyl}piperidin-4-yl)-6-(3-fluorophenyl)nicotinamide | 500.3 | 500.5 |
| 400 | | 6-(3-Fluorophenyl)-N-{1-[(2-isopropyl-5,6,7,8-tetrahydroquinazolin-6-yl)methyl]piperidin-4-yl}nicotinamide | 488.3 | 488.5 |
| 401 | | 6-(3-Fluorophenyl)-N-{1-[(2-methyl-5,6,7,8-tetrahydroquinazolin-6-yl)methyl]piperidin-4-yl}nicotinamide | 460.2 | 460.5 |
| 402 | | N-{1-[(2-tert-Butyl-5,6,7,8-tetrahydroquinazolin-6-yl)methyl]piperidin-4-yl}-6-(3-fluorophenyl)nicotinamide | 502.3 | 502.4 |

-continued

| Ex | Q | Name | MS Calc (M + H) | MS Obs (M + H) |
|---|---|---|---|---|
| 403 | | 6-(3-Fluorophenyl)-N-{1-[(2-propyl-5,6,7,8-tetrahydroquinazolin-6-yl)methyl]piperidin-4-yl}nicotinamide | 488.3 | 488.5 |
| 404 | | 6-(3-Fluorophenyl)-N-{1-[3-methoxy-2-(2-methoxyethoxy)benzyl]piperidin-4-yl}nicotinamide | 494.2 | 494.1 |
| 405 | | N-{1-[(2,2-Difluoroethoxy)-3-methoxybenzyl]piperidin-4-yl}-6-(3-fluorophenyl)nicotinamide | 500.2 | 500.5 |
| 406 | | 6-(3-Fluorophenyl)-N-[1-(imidazo[1,2-a]pyridin-2-ylmethyl)piperidin-4-yl]nicotinamide | 430.2 | 430.4 |
| 407 | | 6-(3-Fluorophenyl)-N-(1-{[4-(4-fluorophenyl)-1,3-thiazol-2-yl]methyl}piperidin-4-yl)nicotinamide | 491.2 | 491.6 |

-continued
| Ex | Q | Name | MS Calc (M + H) | MS Obs (M + H) |
|---|---|---|---|---|
| 408 | 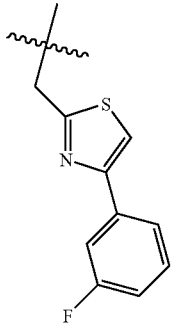 | 6-(3-Fluorophenyl)-N-(1-{[4-(3-fluorophenyl)-1,3-thiazol-2-yl]methyl}piperidin-4-yl)nicotinamide | 491.2 | 491.5 |
| 409 | 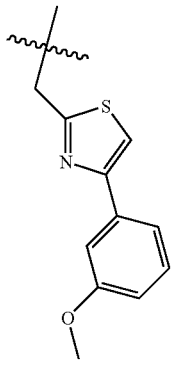 | 6-(3-Fluorophenyl)-N-(1-{[4-(3-methoxyphenyl)-1,3-thiazol-2-yl]methyl}piperidin-4-yl)nicotinamide | 503.2 | 503.4 |
| 410 |  | N-(1-{[4-(3-Cyanophenyl)-1,3-thiazol-2-yl]methyl}piperidin-4-yl)-6-(3-fluorophenyl)nicotinamide | 498.2 | 498.3 |
| 411 | 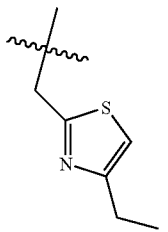 | N-{1-[(4-Ethyl-1,3-thiazol-2-yl)methyl]piperidin-4-yl}-6-(3-fluorophenyl)nicotinamide | 425.2 | 425.0 |

| Ex | Q | Name | MS Calc (M + H) | MS Obs (M + H) |
|---|---|---|---|---|
| 412 | (5-methyl-4-phenyl-1,3-thiazol-2-yl)methyl | 6-(3-Fluorophenyl)-N-{1-[(5-methyl-4-phenyl-1,3-thiazol-2-yl)methyl]piperidin-4-yl}nicotinamide | 487.2 | 487.5 |
| 413 | [4-(3,4-difluorophenyl)-1,3-thiazol-2-yl]methyl | N-(1-{[4-(3,4)-1,3-Thiazol-2-yl]methyl}piperidin-4-yl)-6-(3-fluorophenyl)nicotinamide | 509.2 | 509.4 |
| 414 | (3-bromoimidazo[1,2-a]pyridin-2-yl)methyl | N-{1-[(3-Bromoimidazo[1,2-a]pyridin-2-yl)methyl]piperidin-4-yl}-6-(3-fluorophenyl)nicotinamide | 508.1 | 508.5 |
| 415 | (3-methyl-3H-imidazo[4,5-b]pyridin-2-yl)methyl | 6-(3-Fluorophenyl)-N-{1-[(3-methyl-3H-imidazo[4,5-b]pyridin-2-yl)methyl]piperidin-4-yl}nicotinamide | 445.2 | 445.5 |
| 416 | (4-{[(tert-butoxycarbonyl)amino]}cyclohexyl)methyl | tert-Butyl (4-{[4-({[6-(3-fluorophenyl)pyridin-3-yl]carbonyl}amino)piperidin-1-yl]methyl}cyclohexyl)carbamate | 511.3 | 511.5 |

| Ex | Q | Name | MS Calc (M + H) | MS Obs (M + H) |
|---|---|---|---|---|
| 417 | | N-(1-{3-[3-(Dimethylamino)propoxy]benzyl}piperidin-4-yl)-6-(3-fluorophenyl)nicotinamide | 491.3 | 491.9 |
| 418 | | N-[1-(2,3-Dihydro-1,4-benzodioxin-5-ylmethyl)piperidin-4-yl]-6-(3-fluorophenyl)nicotinamide | 448.2 | 448.5 |
| 419 | | N-[1-(2-Fluoro-4-(1-hydroxy-1-methylethyl)benzyl]piperidin-4-yl}-6-(3-fluorophenyl)nicotinamide | 466.2 | 466.5 |
| 420 | | 6-(3-Fluorophenyl)-N-(1-{[1-(2-methoxyethyl)-1H-benzimidazol-2-yl]methyl}piperidin-4-yl)nicotinamide | 488.2 | 488.6 |
| 421 | | 6-(3-Fluorophenyl)-N-{1-[(1-methyl-1H-imidazo[4,5-b]pyridin-2-yl)methyl]piperidin-4-yl}nicotinamide | 445.2 | 445.8 |
| 422 | | N-{1-[(1-Cyclopropyl-1H-benzimidazol-2-yl)methyl]piperidin-4-yl}-6-(3-fluorophenyl)nicotinamide | 470.2 | 470.6 |

-continued

| Ex | Q | Name | MS Calc (M + H) | MS Obs (M + H) |
|---|---|---|---|---|
| 423 | | N-(1-{[(1-(2-Fluoroethyl)-1H-benzimidazol-2-yl]methyl}piperidin-4-yl)-6-(3-fluorophenyl)nicotinamide | 476.2 | 476.5 |
| 424 | | N-(1-{[(1-(Fluoromethyl)-1H-benzimidazol-2-yl]methyl}piperidin-4-yl)-6-(3-fluorophenyl)nicotinamide | 462.2 | 462.5 |
| 425 | | N-{1-[3-(2,2-Difluoroethyoxy)-4-methoxybenzyl]piperidin-4-yl}-6-(3-fluorophenyl)nicotinamide | 500.2 | 500.8 |
| 426 | | 6-(3-Fluorophenyl)-N-{1-[(2-phenyl-1,3-oxazol-4-yl)methyl]piperidin-4-yl}nicotinamide | 457.2 | 457.5 |
| 427 | | 6-(3-Fluorophenyl)-N-{1-[(3-methyl-1-propyl-1H-pyrazol-4-yl)methyl]piperidin-4-yl}nicotinamide | 436.2 | 436.6 |

-continued

| Ex | Q | Name | MS Calc (M + H) | MS Obs (M + H) |
|---|---|---|---|---|
| 428 | | 6-(3-Fluorophenyl)-N-{1-[3-(hydroxymethyl)-4-isopropoxybenzyl]piperidin-4-yl}nicotinamide | 478.2 | 478.5 |
| 429 | | 6-(3-Fluorophenyl)-N-{1-[(5-isobutyl-1H-pyrazol-3-yl)methyl]piperidin-4-yl}nicotinamide | 436.2 | 436.6 |
| 430 | | 6-(3-Fluorophenyl)-N-{1-[(8-fluoroquinolin-2-yl)methyl]piperidin-4-yl}nicotinamide | 459.2 | 459.5 |
| 431 | | N-{1-[(1-Ethyl-1H-imidazol-2-yl)methyl]piperidin-4-yl}-6-(3-fluorophenyl)nicotinamide | 408.2 | 408.5 |
| 432 | | 6-(3-Fluorophenyl)-N-{1-[(3-methylimidazo[1,2-a]pyridin-2-yl)methyl]piperidin-4-yl}nicotinamide | 444.2 | 444.9 |
| 433 | | 6-(3-Fluorophenyl)-N-{1-[(4-isopropyl-1,3-thiazol-2-yl)methyl]piperidin-4-yl}nicotinamide | 439.2 | 439.5 |

| Ex | Q | Name | MS Calc (M + H) | MS Obs (M + H) |
|---|---|---|---|---|
| 434 | 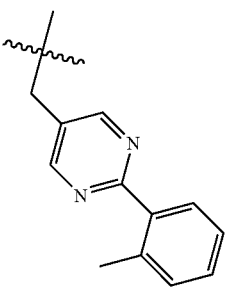 | 6-(3-Fluorophenyl)-N-(1-{[2-(2-methylphenyl)pyrimidin-5-yl]methyl}piperidin-4-yl)nicotinamide | 482.2 | 482.5 |
| 435 | 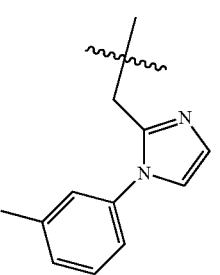 | 6-(3-Fluorophenyl)-N-(1-{[1-(3-methylphenyl)-1H-imidazol-2-yl]methyl}piperidin-4-yl)nicotinamide | 470.2 | 470.6 |
| 436 | 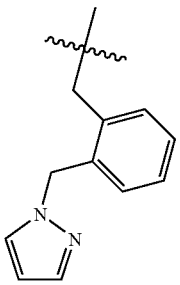 | 6-(3-Fluorophenyl)-N-{1-[2-(1H-pyrazol-1-ylmethyl)benzyl]piperidin-4-yl}nicotinamide | 470.2 | 470.8 |
| 437 | 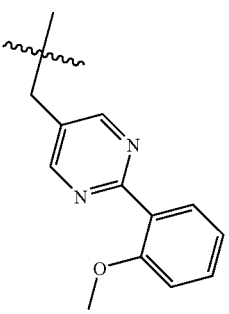 | 6-(3-Fluorophenyl)-N-(1-{[2-(2-methoxyphenyl)pyrimidin-5-yl]methyl}piperidin-4-yl)nicotinamide | 498.2 | 498.8 |
| 438 | 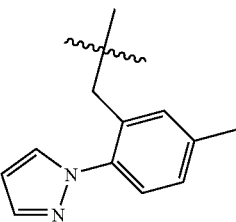 | 6-(3-Fluorophenyl)-N-{1-[5-methyl-2-(1H-pyrazol-1-yl)benzyl]piperidin-4-yl}nicotinamide | 470.2 | 470.6 |

-continued

| Ex | Q | Name | MS Calc (M + H) | MS Obs (M + H) |
|---|---|---|---|---|
| 439 | | 6-(3-Fluorophenyl)-N-(1-{[3-(3-fluorophenyl)-1H-pyrazol-4-yl]methyl}piperidin-4-yl)nicotinamide | 474.2 | 474.6 |
| 440 | | 6-(3-Fluorophenyl)-N-(1-{[2-(2-methoxyethyl)pyrimidin-5-yl]methyl}piperidin-4-yl)nicotinamide | 450.2 | 450.3 |
| 441 | | 6-(3-Fluorophenyl)-N-{1-[(2-propylpyrimidin-5-yl)methyl]piperidin-4-yl}nicotinamide | 434.2 | 434.5 |
| 442 | | N-{1-[(2-Ethylpyrimidin-5-yl)methyl]piperidin-4-yl}-6-(3-fluorophenyl)nicotinamide | 420.2 | 420.5 |
| 443 | | 6-(3-Fluorophenyl)-N-{1-[(2-methylpyrimidin-5-yl)methyl]piperidin-4-yl}nicotinamide | 406.2 | 406.5 |
| 444 | | 6-(3-Fluorophenyl)-N-{1-[(3,5,6-trimethylpyrazin-2-yl)methyl]piperidin-4-yl}nicotinamide | 434.2 | 434.6 |

-continued

| Ex | Q | Name | MS Calc (M + H) | MS Obs (M + H) |
|---|---|---|---|---|
| 445 | | N-{1-[(6-Chloro-2-methylimidazo[1,2-a]pyridin-3-yl)methyl]piperidin-4-yl}-6-(3-fluorophenyl)nicotinamide | 478.2 | 478.4 |
| 446 | | 6-(3-Fluorophenyl)-N-{1-[(2-methyl-1,3-thiazol-5-yl)methyl]piperidin-4-yl}nicotinamide | 411.2 | 411.5 |
| 447 | | 6-(3-Fluorophenyl)-N-(1-{[1-(methoxymethyl)-1H-benzimidazol-2-yl]methyl}piperidin-4-yl)nicotinamide | 474.2 | 474.6 |
| 448 | | N-[1-(5,6-Dihydro-4H-imidazo[4,5,1-ij]quinolin-2-ylmethyl)piperidin-4-yl]-6-(3-fluorophenyl)nicotinamide | 470.2 | 470.5 |
| 449 | | N-{1-[(5,6-Difluoro-1-methyl-1H-benzimidazol-2-yl)methyl]piperidin-4-yl}-6-(3-fluorophenyl)nicotinamide | 480.2 | 480.5 |
| 450 | | 6-(3-Fluorophenyl)-N-[1-(1,5-naphthyridin-4-ylmethyl)piperidin-4-yl]nicotinamide | 442.2 | 442.5 |

-continued

| Ex | Q | Name | MS Calc (M + H) | MS Obs (M + H) |
|---|---|---|---|---|
| 451 | 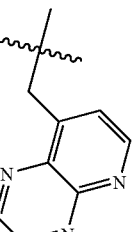 | 6-(3-Fluorophenyl)-N-[1-(pyrido[2,3-b]pyrazin-8-ylmethyl)piperidin-4-yl]nicotinamide | 443.2 | 443.8 |
| 452 | 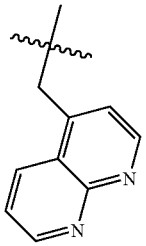 | 6-(3-Fluorophenyl)-N-[1-(1,8-naphthyridin-4-ylmethyl)piperidin-4-yl]nicotinamide | 442.2 | 442.6 |
| 453 | 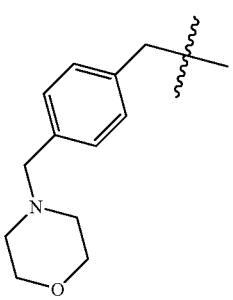 | 6-(3-Fluorophenyl)-N-{1-[4-(morpholin-4-ylmethyl)benzyl]piperidin-4-yl}nicotinamide | 489.3 | 489.5 |
| 454 | 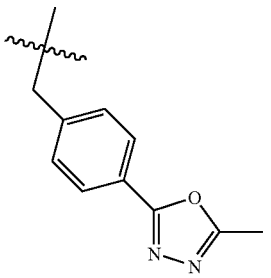 | 6-(3-Fluorophenyl)-N-{1-[4-(5-methyl-1,3,4-oxadiazol-2-yl)benzyl]piperidin-4-yl}nicotinamide | 472.2 | 472.9 |
| 455 | 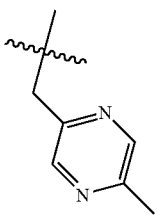 | 6-(3-Fluorophenyl)-N-{1-[(5-methylpyrazin-2-yl)methyl]piperidin-4-yl}nicotinamide | 406.2 | 406.5 |
| 456 | 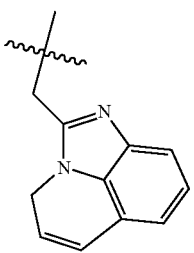 | 6-(3-Fluorophenyl)-N-[1-(4H-imidazo[4,5l-ij]quinolin-2-ylmethyl)piperidin-4-yl]nicotinamide | 468.2 | 468.6 |

-continued

| Ex | Q | Name | MS Calc (M + H) | MS Obs (M + H) |
|---|---|---|---|---|
| 457 | | Ethyl 2-{[4-({[6-(3-fluorophenyl)pyridin-3-yl]carbonyl}amino)piperidin-1-yl]methyl}-1,3-thiazole-4-carboxylate | 469.2 | 469.6 |
| 458 | RAC | (2S,3R)-5-{[4-({[6-(3-Fluorophenyl)pyridin-3-yl]carbonyl}amino)piperidin-1-yl]methyl}-2-methyl-2,3-dihydro-1-benzofuran-3-carboxylic acid | 490.2 | 490.5 |
| 459 | | N-{1-[(2-Ethoxypyridin-3-yl)methyl]piperidin-4-yl}-6-(3-fluorophenyl)nicotinamide | 435.2 | 435.6 |
| 460 | | 6-(3-Fluorophenyl)-N-{1-[(2-methoxypyridin-3-yl)methyl]piperidin-4-yl}nicotinamide | 421.2 | 421.5 |
| 461 | | 6-(3-Fluorophenyl)-N-{1-[(2-isopropoxypyridin-3-yl)methyl]piperidin-4-yl}nicotinamide | 449.2 | 449.5 |

-continued

| Ex | Q | Name | MS Calc (M + H) | MS Obs (M + H) |
|---|---|---|---|---|
| 462 | 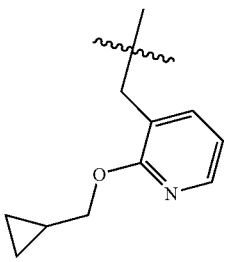 | N-(1-{[2-(Cyclopropylmethoxy)pyridin-3-yl]methyl}piperidin-4-yl)-6-(3-fluorophenyl)nicotinamide | 461.2 | 461.6 |
| 463 | 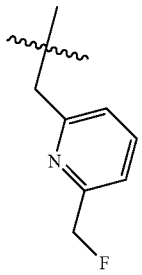 | N-(1-{[6-(Fluoromethyl)pyridin-2-yl]methyl}piperidin-4-yl)-6-(3-fluorophenyl)nicotinamide | 423.2 | 423.4 |
| 464 | 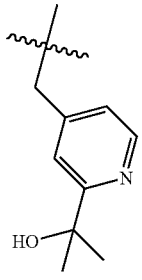 | 6-(3-Fluorophenyl)-N-(1-{[2-(1-hydroxy-1-methylethyl)pyridin-4-yl]methyl}piperidin-4-yl)nicotinamide | 449.2 | 449.6 |
| 465 | 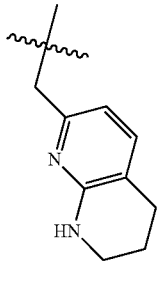 | 6-(3-Fluorophenyl)-N-[1-(5,6,7,8-tetrahydro-18-naphthyridin-2-ylmethyl)piperidin-4-yl]nicotinamide | 446.2 | 446.8 |
| 466 | 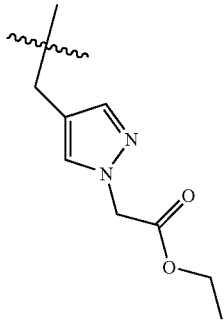 | Ethyl (4-{[4-({[6-(3-fluorophenyl)pyridin-3-yl]carbonyl}amino)piperidin-1-yl]methyl}-1H-pyrazol-1-yl)acetate | 466.2 | 466.3 |

-continued

| Ex | Q | Name | MS Calc (M + H) | MS Obs (M + H) |
|---|---|---|---|---|
| 467 | (4-chloro-2-fluoro-5-methoxybenzyl group) | N-[1-(4-Chloro-2-fluoro-5-methoxybenzyl)piperidin-4-yl]-6-(3-fluorophenyl)nicotinamide | 472.2 | 472.6 |
| 468 | (2-chloro-2-fluoro-5-methoxybenzyl group) | N-[1-(2-Chloro-2-fluoro-5-methoxybenzyl)piperidin-4-yl]-6-(3-fluorophenyl)nicotinamide | 472.2 | 472.8 |
| 469 | (6-oxo-1,6-dihydropyridazin-3-yl)methyl | 6-(3-Fluorophenyl)-N-{1-[(6-oxo-1,6-dihydropyridazin-3-yl)methyl]piperidin-4-yl}nicotinamide | 408.2 | 408.5 |
| 470 | (3-isopropyl[1,2,4]triazolo[4,3-a]pyridin-6-yl)methyl | 6-(3-Fluorophenyl)-N-{1-[(3-isopropyl[1,2,4]triazolo[4,3-a]pyridin-6-yl)methyl]piperidin-4-yl}nicotinamide | 473.2 | 473.6 |
| 471 | (6-methoxyquinolin-4-yl)methyl | 6-(3-Fluorophenyl)-N-{1-[(6-methoxyquinolin-4-yl)methyl]piperidin-4-yl}nicotinamide | 471.2 | 471.6 |
| 472 | {6-(1-hydroxy-1-methylethyl)pyridin-3-yl]methyl | 6-(3-Fluorophenyl)-N-(1-{[6-(1-hydroxy-1-methylethyl)pyridin-3-yl]methyl}piperidin-4-yl)nicotinamide | 449.2 | 449.5 |

-continued

| Ex | Q | Name | MS Calc (M + H) | MS Obs (M + H) |
|---|---|---|---|---|
| 473 | | 6-(3-Fluorophenyl)-N-{1-[4-(1-methyl-1H-pyrazol-3-yl)benzyl]piperidin-4-yl}nicotinamide | 470.2 | 470.6 |
| 474 | | 6-(3-Fluorophenyl)-N-{1-[4-(1-methyl-1H-pyrazol-5-yl)benzyl]piperidin-4-yl}nicotinamide | 470.2 | 470.6 |
| 475 | | N-{1-[(5-Bromopyridin-2-yl)methyl]piperidin-4-yl}-6-(3-fluorophenyl)nicotinamide | 469.1 | 471.5 (Br iso) |
| 476 | | N-(1-{[6-(Fluoromethyl)pyridin-3-yl]methyl}piperidin-4-yl)-6-(3-fluorophenyl)nicotinamide | 423.2 | 423.4 |
| 477 | | 6-(3-Fluorophenyl)-N-(1-{[1-methyl-3-(6-methylpyridazin-3-yl)-1H-1,2,4-triazol-5-yl]methyl}piperidin-4-yl)nicotinamide | 487.2 | 487.5 |

-continued

| Ex | Q | Name | MS Calc (M + H) | MS Obs (M + H) |
|---|---|---|---|---|
| 478 | | 6-(3-Fluorophenyl)-N-{1-[(1-methyl-3-pyridin-2-yl-1H-1,2,4-triazol-5-yl)methyl]piperidin-4-yl}nicotinamide | 472.2 | 472.9 |
| 479 | | N-(1-{[1,3-Dimethyl-5-(1,4-oxazepan-4-yl)-1H-pyrazol-4-yl]methyl}piperidin-4-yl)-6-(3-fluorophenyl)nicotinamide | 507.3 | 507.5 |
| 480 | | 6-(3-Fluorophenyl)-N-(1-{[1-methyl-5-(1-methyl-1H-pyrazol-5-yl)-1H-1,2,4-triazol-3-yl]methyl}piperidin-4-yl)nicotinamide | 475.2 | 475.5 |
| 481 | | 6-(3-Fluorophenyl)-N-{1-[(1-methyl-3-pyrimidin-2-yl-1H-1,2,4-triazol-5-yl)methyl]piperidin-4-yl}nicotinamide | 473.2 | 473.6 |
| 482 | | 6-(3-Fluorophenyl)-N-(1-{[5-(2-fluorophenyl)-1-methyl-1H-1,2,4-triazol-3-yl]methyl}piperidin-4-yl)nicotinamide | 489.2 | 489.6 |

-continued

| Ex | Q | Name | MS Calc (M + H) | MS Obs (M + H) |
|---|---|---|---|---|
| 483 | | 6-(3-Fluorophenyl)-N-(1-{[3-(3-fluorophenyl)-1-methyl-1H-1,2,4-triazol-5-yl]methyl}piperidin-4-yl)nicotinamide | 489.2 | 489.5 |
| 484 | | 6-(3-Fluorophenyl)-N-(1-{[5-(4-fluorophenyl)-1-methyl-1H-1,2,4-triazol-3-yl]methyl}piperidin-4-yl)nicotinamide | 489.2 | 489.5 |
| 485 | | 6-(3-Fluorophenyl)-N-{1-[(1-methyl-5-pyridin-2-yl-1H-1,2,4-triazol-3-yl)methyl]piperidin-4-yl}nicotinamide | 472.2 | 472.9 |
| 486 | | N-{1-[3-(Cyclopropyloxy)-4-(difluoromethoxy)benzyl]piperidin-4-yl}-6-(3-fluorophenyl)nicotinamide | 512.2 | 512.7 |
| 487 | | 6-(3-Fluorophenyl)-N-(1-{[5-(4-methoxy-3,5-dimethylpyridin-2-yl)methyl]piperidin-4-yl)nicotinamide | 449.2 | 449.5 |

-continued

| Ex | Q | Name | MS Calc (M + H) | MS Obs (M + H) |
|---|---|---|---|---|
| 488 | 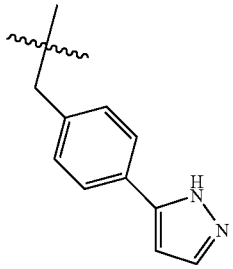 | 6-(3-Fluorophenyl)-N-{1-[4-(1H-pyrazol-5-yl)benzyl]piperidin-4-yl}nicotinamide | 456.2 | 456.5 |
| 489 | 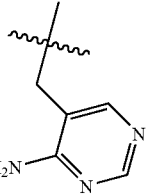 | N-{1-[(4-Aminopyrimidin-5-yl)methyl]piperidin-4-yl}-6-(3-fluorophenyl)nicotinamide | 407.2 | 407.5 |
| 490 | 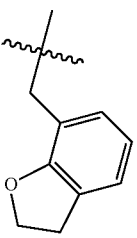 | N-[1-(2,3-Dihydro-1-benzofuran-7-ylmethyl)piperidin-4-yl]-6-(3-fluorophenyl)nicotinamide | 432.2 | 432.5 |
| 491 | 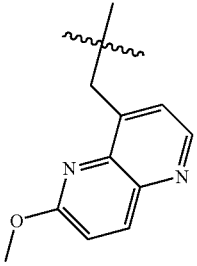 | 6-(3-Fluorophenyl)-N-{1-[(6-methoxy-1,5-naphthyridin-4-yl)methyl]piperidin-4-yl}nicotinamide | 472.2 | 472.9 |
| 492 | 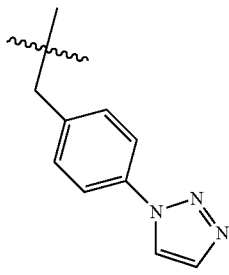 | 6-(3-Fluorophenyl)-N-{1-[4-(1H-1,2,3-triazol-1-yl)benzyl]piperidin-4-yl}nicotinamide | 457.2 | 457.5 |
| 493 | 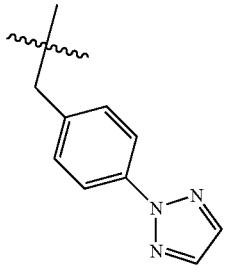 | 6-(3-Fluorophenyl)-N-{1-[4-(2H-1,2,3-triazol-2-yl)benzyl]piperidin-4-yl}nicotinamide | 457.2 | 457.5 |

-continued

| Ex | Q | Name | MS Calc (M + H) | MS Obs (M + H) |
|---|---|---|---|---|
| 494 | | 6-(3-Fluorophenyl)-N-{1-[(8-methoxy-2,3-dihydro-1,4-benzodioxin-6-yl)methyl]piperidin-4-yl}nicotinamide | 478.2 | 478.6 |
| 495 | | 6-(3-Fluorophenyl)-N-{1-[(1-methyl-1H-1,2,3-triazol-5-yl)methyl]piperidin-4-yl}nicotinamide | 395.2 | 395.4 |
| 496 | | 6-(3-Fluorophenyl)-N-[1-(3-methoxy-4-methylbenzyl)piperidin-4-yl]nicotinamide | 434.2 | 434.5 |
| 497 | | 6-(3-Fluorophenyl)-N-{1-[(3-oxo-3,4-dihydro-2H-14-benzoxazin-6-yl)methyl]piperidin-4-yl}nicotinamide | 461.2 | 461.5 |
| 498 | | 6-(3-Fluorophenyl)-N-{1-[(1-methyl-5-phenyl-1H-pyrazol-4-yl)methyl]piperidin-4-yl}nicotinamide | 470.2 | 470.6 |

-continued

| Ex | Q | Name | MS Calc (M + H) | MS Obs (M + H) |
|---|---|---|---|---|
| 499 | | 6-(3-Fluorophenyl)-N-(1-{[5-(4-methoxyphenyl)-1-methyl-1H-pyrazol-4-yl]methyl}piperidin-4-yl)nicotinamide | 500.2 | 500.8 |
| 500 | | 6-(3-Fluorophenyl)-N-(1-{[5-(4-fluorophenyl)-1-methyl-1H-pyrazol-4-yl]methyl}piperidin-4-yl)nicotinamide | 488.2 | 488.5 |
| 501 | | 6-(3-Fluorophenyl)-N-(1-{3-[(methylsulfonyl)amino]benzyl}piperidin-4-yl)nicotinamide | 483.2 | 483.6 |
| 502 | | 6-(3-Fluorophenyl)-N-[1-(1H-indol-6-ylmethyl)piperidin-4-yl]nicotinamide | 429.2 | 429.5 |
| 503 | | N-[1-(2-Fluoro-4-methylbenzyl)piperidin-4-yl]-6-(3-fluorophenyl)nicotinamide | 422.2 | 422.0 |

-continued

| Ex | Q | Name | MS Calc (M + H) | MS Obs (M + H) |
|---|---|---|---|---|
| 504 |  | N-{1-[(5,7-Dimethyl[1,2,4]triazolo[1,5-a]pyrimidin-2-yl)methyl]piperidin-4-yl}-6-(3-fluorophenyl)nicotinamide | 460.2 | 460.6 |
| 505 |  | 6-(3-Fluorophenyl)-N-{1-[(1-methylcyclopropyl)methyl]piperidin-4-yl}nicotinamide | 368.2 | 368.1 |
| 506 |  | 6-(3-Fluorophenyl)-N-(1-{[5-(3-methoxyphenyl)-1-methyl-1H-pyrazol-4-yl]methyl}piperidin-4-yl)nicotinamide | 500.2 | 500.5 |
| 507 |  | 6-(3-Fluorophenyl)-N-(1-{[5-(3-fluorophenyl)-1-methyl-1H-pyrazol-4-yl]methyl}piperidin-4-yl)nicotinamide | 488.2 | 488.3 |
| 508 |  | 6-(3-Fluorophenyl)-N-(1-{[5-(2-methoxyphenyl)-1-methyl-1H-pyrazol-4-yl]methyl}piperidin-4-yl)nicotinamide | 500.2 | 500.5 |

| Ex | Q | Name | MS Calc (M + H) | MS Obs (M + H) |
|---|---|---|---|---|
| 509 | 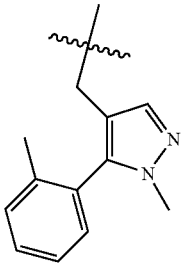 | 6-(3-Fluorophenyl)-N-(1-{[1-methyl-5-(2-methylphenyl)-1H-pyrazol-4-yl]methyl}piperidin-4-yl)nicotinamide | 484.2 | 484.6 |
| 510 | 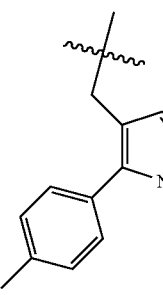 | 6-(3-Fluorophenyl)-N-(1-{[1-methyl-5-(4-methylphenyl)-1H-pyrazol-4-yl]methyl}piperidin-4-yl)nicotinamide | 484.2 | 484.3 |
| 511 | 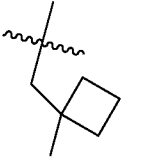 | 6-(3-Fluorophenyl)-N-{1-[(1-methylcyclobutyl)methyl]piperidin-4-yl}nicotinamide | 382.2 | 382.5 |
| 512 | 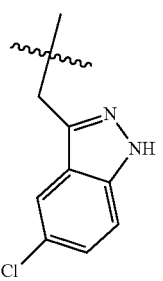 | N-{1-[(5-Chloro-1H-indazol-3-yl)methyl]piperidin-4-yl}-6-(3-fluorophenyl)nicotinamide | 464.2 | 464.0 |
| 513 | 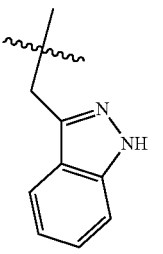 | 6-(3-Fluorophenyl)-N-[1-(1H-indazol-3-ylmethyl)piperidin-4-yl]nicotinamide | 430.2 | 430.5 |

-continued

| Ex | Q | Name | MS Calc (M + H) | MS Obs (M + H) |
|---|---|---|---|---|
| 514 | | 6-(3-Fluorophenyl)-N-{1-[(2-oxo-2,3-dihydro-1H-pyrido[2,3-b][1,4]oxazin-7-yl)methyl]piperidin-4-yl}nicotinamide | 462.2 | 462.5 |
| 515 | | 6-(3-Fluorophenyl)-N-[1-(2-methoxy-5-methylbenzyl)piperidin-4-yl]nicotinamide | 434.2 | 434.5 |
| 516 | | 6-(3-Fluorophenyl)-N-{1-[(1-propyl-1H-pyrazol-4-yl)methyl]piperidin-4-yl}nicotinamide | 422.2 | 422.5 |
| 517 | | 6-(3-Fluorophenyl)-N-{1-[(1-propyl-1H-pyrazol-5-yl)methyl]piperidin-4-yl}nicotinamide | 422.2 | 422.5 |
| 518 | | N-[1-(1-Benzofuran-3-ylmethyl)piperidin-4-yl]-6-(3-fluorophenyl)nicotinamide | 430.2 | 430.5 |

| Ex | Q | Name | MS Calc (M + H) | MS Obs (M + H) |
|---|---|---|---|---|
| 519 | 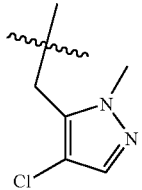 | N-{1-[(4-Chloro-1-methyl-1H-pyrazol-5-yl)methyl]piperidin-4-yl}-6-(3-fluorophenyl)nicotinamide | 428.2 | 428.4 |
| 520 | 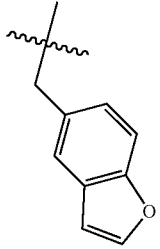 | N-[1-(1-Benzofuran-5-ylmethyl)piperidin-4-yl]-6-(3-fluorophenyl)nicotinamide | 430.2 | 430.0 |

EXAMPLE 521

Benzyl 4-({[6-(3-fluorophenyl)pyridin-3-yl]carbonyl}amino)piperidine-1-carboxylate

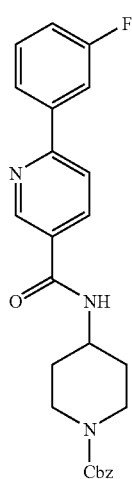

Benzyl 4-aminopiperidine-1-carboxylate (11 g, 46.9 mmol), EDAC (9.94 g, 51.9 mmol), NMM (20.7 mL, 189 mmol) and HOBt*H2O (7.22 g, 47 mmol) were added to a solution of 6-(3-fluorophenyl)nicotinic acid (10.2 g, 47 mmol) in dichloromethane:DMF (200 mL:2 mL). The reaction mixture was stirred at room temperature for 18 h, evaporated, and chromatographed (silica gel, ethyl acetate-hexane, 2:1). The solvent was evaporated to give tert-butyl 4-(2-(3-fluorophenyl)nicotinamido)piperidine-1-carboxylate (yield 61%, 12.7 g). LC/MS=434 observed, 434.19 expected The following compounds of formula (VII) were prepared in a manner analogous to Example 521.

(VII)
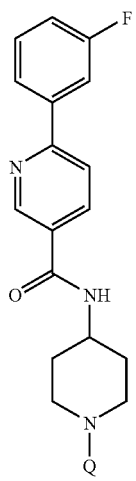
| Ex | Q | Name | MS calc (M) | MS obs (M + H) |
|---|---|---|---|---|
| 522 | 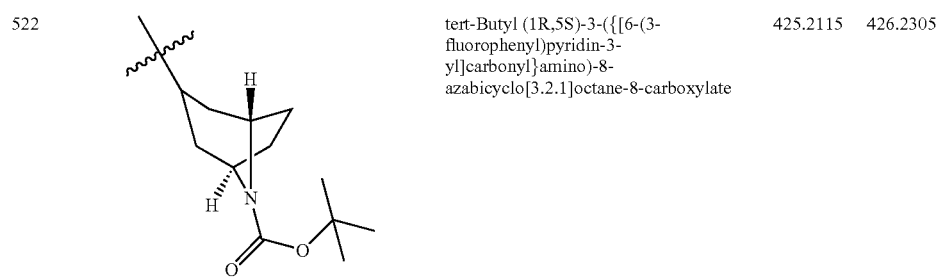 | tert-Butyl (1R,5S)-3-({[6-(3-fluorophenyl)pyridin-3-yl]carbonyl}amino)-8-azabicyclo[3.2.1]octane-8-carboxylate | 425.2115 | 426.2305 |
| 523 | 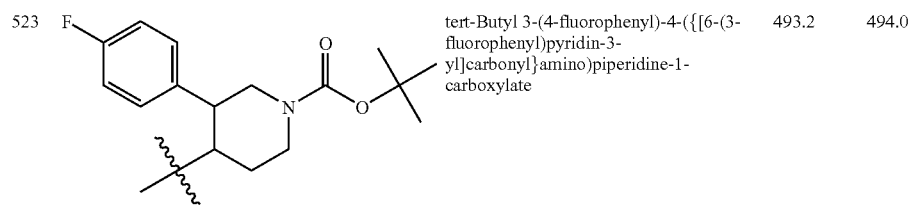 | tert-Butyl 3-(4-fluorophenyl)-4-({[6-(3-fluorophenyl)pyridin-3-yl]carbonyl}amino)piperidine-1-carboxylate | 493.2 | 494.0 |
| 524 | 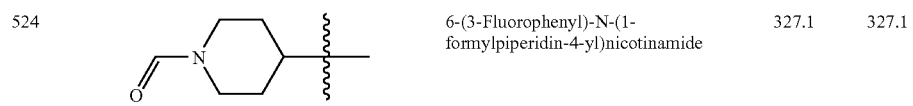 | 6-(3-Fluorophenyl)-N-(1-formylpiperidin-4-yl)nicotinamide | 327.1 | 327.1 |

EXAMPLE 525

6-(3-Fluorophenyl)-N-[3-(4-fluorophenyl)piperidin-4-yl]nicotinamide

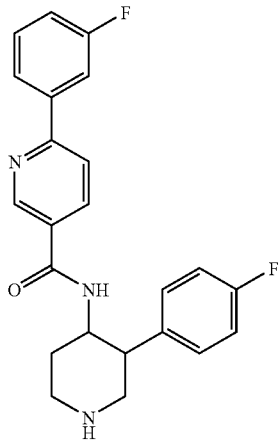

To a solution of tert-butyl 3-(4-fluorophenyl)-4-({[6-(3-fluorophenyl)pyridin-3-yl]carbonyl}amino)piperidine-1-carboxylate (348 mg, 0.71 mmol) in CH$_2$Cl$_2$ (5 mL) at 0° C. was added TFA (1.2 mL). After stirring overnight at rt the the reaction was diluted with toluene (5 mL) and then the solvent removed and the residue purified by chromatography (silica, 10% MeOH/DCM) to give the desired product, 6-(3-fluorophenyl)-N-[3-(4-fluorophenyl)piperidin-4-yl]nicotinamide. (168 mg, 61% yield). 1H NMR (400 MHz, DMSO-d6) ☐ ppm 8.87 (1H, d, J=2.0 Hz), 8.52 (1H, s), 8.04-8.15 (2H, m), 8.00 (2H, d, J=7.9 Hz), 7.58 (1H, d, J=6.1 Hz), 7.35 (4H, dd, J=9.0, 3.5 Hz), 7.08-7.22 (2H, m), 4.60-4.72 (1H, m), 3.81 (1H, t), 3.05-3.27 (4H, m), 1.91 (1H, s). LC/MS= (M+H)=394.1 observed, 394.17 expected.

EXAMPLE 526

N-Acetyl-3-(4-fluorophenyl)piperidin-4-yl]-6-(3-fluorophenyl)nicotinamide

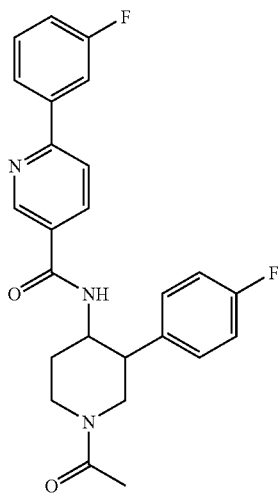

To a solution of 6-(3-fluorophenyl)-N-[3-(4-fluorophenyl)piperidin-4-yl]nicotinamide (250 mg, 0.64 mmol) in DCM (5 mL) at 0° C. was added TEA (0.11 mL, 0.76 mmol), DMAP (7.76 mg, 0.064 mmol) and acetic anhydride (97.3 mg, 0.95 mmol). After stirring at rt for 1 hr the reaction was diluted with water and then extracted with dcm. The organic extracts were combined, dried (Na$_2$SO$_4$) and solvent removed to give an oil, which after chromatography gave the desired product, N-[1-acetyl-3-(4-fluorophenyl)piperidin-4-yl]-6-(3-fluorophenyl)nicotinamide (235 mg, 85% yield). 1H NMR (400 MHz, DMSO-d6) ☐ ppm 8.76-8.89 (1 H, m), 8.27-8.51 (1H, m), 8.03-8.17 (2H, m), 7.87-8.02 (2H, m), 7.50-7.62 (1H, m), 7.22-7.46 (3 H, m), 7.03-7.17 (2H, m), 4.33-4.62 (1H, m), 3.89-4.12 (1H, m), 3.54-3.86 (2H, m), 3.34-3.44 (1 H, m), 2.63-2.92 (1H, m), 2.05-2.14 (3H, m), 1.94-2.04 (1H, m), 1.71-1.92 (1H, m). LC/MS (M+H)=436.0 observed, 436.18 expected.

EXAMPLE 527

N-[1-(2-Cyclopropyl-1-methylethyl)piperidin-4-yl]-6-(3-fluorophenyl)nicotinamide

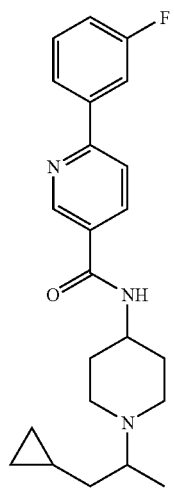

To a solution of 1-cyclopropylpropan-2-one (0.2 mL, 0.08 mmol in 1:1 THF:DMSO) was added 6-(3-fluorophenyl)-N-(piperidin-4-yl)nicotinamide (in 1:1 THF:DMSO, 0.2 mL, 0.08 mmol), sodium triacetoxyborohydride dispersion (0.33 mL, 2.5 eq, in 1:1 THF:DMSO) and glacial acetic acid (0.01 mL). The reaction mixture was stirred at room temperature for 16-24 h and then aqueous K$_2$CO$_3$ (3 M, 0.2 mL) and ethanol (0.55 mL) was added. The reaction was shaken for 30 min and then the mixture was filtered and the filtrate concentrated and the residue purified by RP-HPLC to give the desired product. LC/MS=382.4 (M+H) observed, 382.23 expected.

The following compounds of formula (VII) were prepared by methods analogous to the method described for Example 527.

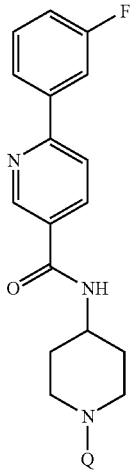

(VII)

| Ex | Q | Name | MS calc (M) | MS obs (M + H) |
|---|---|---|---|---|
| 528 | | 6-(3-Fluorophenyl)-N-[1-(5-methoxy-2,3-dihydro-1H-inden-1-yl)piperidin-4-yl]nicotinamide | 445.2 | 446.4 |
| 529 | | 6-(3-Fluorophenyl)-N-{1-[1-methyl-2-(1-methylcyclopropyl)ethyl]piperidin-4-yl}nicotinamide | 395.2 | 396.5 |
| 530 | | 6-(3-Fluorophenyl)-N-{1-[1-(2-methoxyphenyl)ethyl]piperidin-4-yl}nicotinamide | 433.2 | 434.4 |
| 531 | | 6-(3-Fluorophenyl)-N-[1-(1-phenylethyl)piperidin-4-yl]nicotinamide | 403.2 | 404.4 |
| 532 | | 6-(3-Fluorophenyl)-N-{1-[1-(3-methoxyphenyl)ethyl]piperidin-4-yl}nicotinamide | 433.2 | 434.1 |
| 533 | | N-{1-[1-(2,6-Dimethoxyphenyl)ethyl]piperidin-4-yl}-6-(3-fluorophenyl)nicotinamide | 463.2 | 464.5 |

-continued (VII)

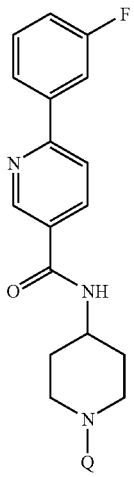

| Ex | Q | Name | MS calc (M) | MS obs (M + H) |
|---|---|---|---|---|
| 534 | | 6-(3-Fluorophenyl)-N-{1-[2-(4-methoxyphenyl)-1-methylethyl]piperidin-4-yl}nicotinamide | 447.2 | 448.1 |
| 535 | | 6-(3-Fluorophenyl)-N-{1-[1-(4-methoxyphenyl)ethyl]piperidin-4-yl}nicotinamide | 433.2 | 434.5 |
| 536 | | N-{1-[1-(3,4-Dimethoxyphenyl)ethyl]piperidin-4-yl}-6-(3-fluorophenyl)nicotinamide | 463.2 | 464.4 |
| 537 | | N-{1-[1-(Cyclopropylmethyl)-7-oxoazepan-4-yl]piperidin-4-yl}-6-(3-fluorophenyl)nicotinamide | 464.2 | 465.5 |
| 538 | | 6-(3-Fluorophenyl)-N-[1-(1-isobutyl-7-oxoazepan-4-yl)piperidin-4-yl]nicotinamide | 466.2 | 467.5 |
| 539 | | 6-(3-Fluorophenyl)-N-{1-[1-(2-methoxyethyl)-7-oxoazepan-4-yl]piperidin-4-yl}nicotinamide | 468.3 | 469.6 |
| 540 | | 6-(3-Fluorophenyl)-N-{1-[1-(1-phenyl-1H-pyrazol-4-yl)ethyl]piperidin-4-yl}nicotinamide | 469.2 | 470.6 |

-continued

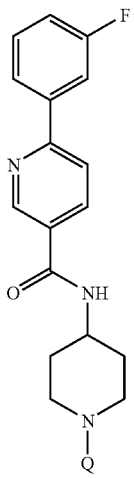

(VII)

| Ex | Q | Name | MS calc (M) | MS obs (M + H) |
|---|---|---|---|---|
| 541 | | N-{1-[1-(3,4-Dimethoxyphenyl)propyl]piperidin-4-yl}-6-(3-fluorophenyl)nicotinamide | 477.2 | 478.4 |
| 542 | | N-{1-[1-(Cyclobutylmethyl)-7-oxoazepan-4-yl]piperidin-4-yl}-6-(3-fluorophenyl)nicotinamide | 478.3 | 479.5 |
| 543 | | N-{1-[1-(2,4-Dimethoxyphenyl)ethyl]piperidin-4-yl}-6-(3-fluorophenyl)nicotinamide | 463.2 | 464.0 |
| 544 | | N-{1-[1-(3,5-Dimethoxyphenyl)ethyl]piperidin-4-yl}-6-(3-fluorophenyl)nicotinamide | 463.2 | 464.5 |
| 545 | | N-(1-sec-Butylpiperidin-4-yl)-6-(3-fluorophenyl)nicotinamide | 355.2 | 356.1 |

-continued (VII)

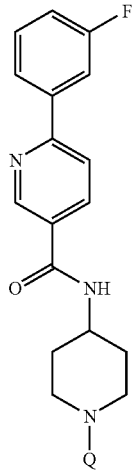

| Ex | Q | Name | MS calc (M) | MS obs (M + H) |
|---|---|---|---|---|
| 546 | | N-{1-[4-(Acetylamino)cyclohexyl]piperidin-4-yl}-6-(3-fluorophenyl)nicotinamide | 438.2 | 439.4 |
| 547 | | 6-(3-Fluorophenyl)-N-[1-(tetrahydro-2H-pyran-4-yl)piperidin-4-yl]nicotinamide | 383.2 | 384.5 |
| 548 | | 6-(3-Fluorophenyl)-N-{1-[1-methyl-3-(1H-pyrazol-1-yl)propyl]piperidin-4-yl}nicotinamide | 421.2 | 422.3 |
| 549 | | 6-(3-Fluorophenyl)-N-[1-(3-methoxycyclohexyl)piperidin-4-yl]nicotinamide | 411.2 | 412.1 |
| 550 | | 6-(3-Fluorophenyl)-N-[1-(3-hydroxy-1-methylpropyl)piperidin-4-yl]nicotinamide | 371.2 | 372.4 |
| 551 | | N-(1-Cyclopentylpiperidin-4-yl)-6-(3-fluorophenyl)nicotinamide | 367.2 | 368.4 |
| 552 | | N-(1-Azetidin-3-ylpiperidin-4-yl)-6-(3-fluorophenyl)nicotinamide | 354.2 | 355.0 |
| 553 | | 6-(3-Fluorophenyl)-N-{1-[2-(2-methoxyphenoxy)-1-methylethyl]piperidin-4-yl}nicotinamide | 463.2 | 464.4 |

-continued

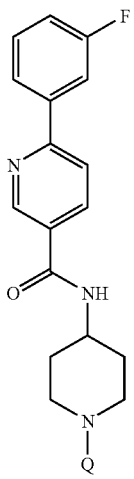

(VII)

| Ex | Q | Name | MS calc (M) | MS obs (M + H) |
|---|---|---|---|---|
| 554 | 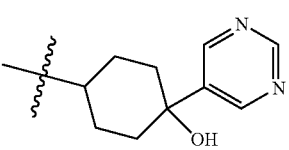 | 6-(3-Fluorophenyl)-N-[1-(4-hydroxy-4-pyrimidin-5-ylcyclohexyl)piperidin-4-yl]nicotinamide | 475.2 | 476.3 |
| 555 | 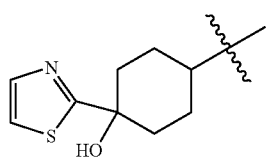 | 6-(3-Fluorophenyl)-N-{1-[4-hydroxy-4-(1,3-thiazol-2-yl)cyclohexyl]piperidin-4-yl}nicotinamide | 480.2 | 481.1 |
| 556 | 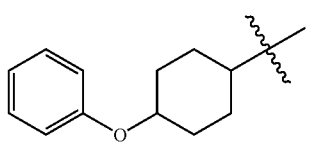 | 6-(3-Fluorophenyl)-N-[1-(4-phenoxycyclohexyl)piperidin-4-yl]nicotinamide | 473.2 | 474.5 |
| 557 | 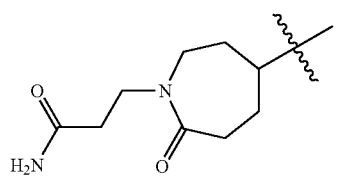 | N-{1-[1-(3-Amino-3-oxopropyl)-7-oxoazepan-4-yl]piperidin-4-yl}-6-(3-fluorophenyl)nicotinamide | 481.2 | 482.5 |
| 558 | 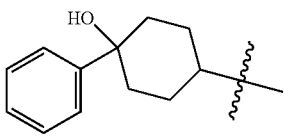 | 6-(3-Fluorophenyl)-N-[1-(4-hydroxy-4-phenylcyclohexyl)piperidin-4-yl]nicotinamide | 473.2 | 474.4 |

EXAMPLE 579 tert-Butyl 6-[4-({[6-(3-fluorophenyl)pyridin-3-yl]carbonyl}amino)piperidin-1-yl]nicotinate

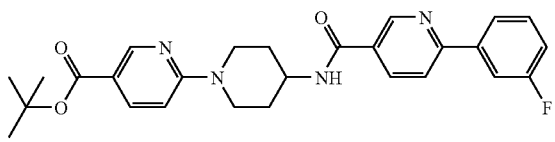

To a microwave tube was added 6-(3-fluorophenyl)-N-(piperidin-4-yl)nicotinamide (2.2 g, 7.35 mmol, tert-butyl 6-bromonicotinate (2.85 g, 11 mmol), DMA (5 mL), CsF (6.70 g, 44.1 mmol) and TEA (5 drops). After heating the reaction mixture on CEM microwave at fullpower (100° C. for 45 min), the solution was extracted with ethyl acetate and washed with water. The solvent was removed and the residue purified by chromatography (silica, 50% EtOAc: Hep) to give the desired product, tert-butyl 6-[4-({[6-(3-fluorophenyl)pyridin-3-yl]carbonyl}amino)piperidin-1-yl]nicotinate (3.39 g, 97%). 1H NMR (400 MHz, DMSO-d6) □ ppm 9.06 (1H, d, J=1.1 Hz), 8.58 (1H, d, J=1.6 Hz), 8.47 (1H, d, J=7.9 Hz), 8.27 (1H, d, J=8.4 Hz), 8.10 (1H, d, J=8.2 Hz), 7.98 (1H, d, J=8.4 Hz), 7.93 (1H, d, J=10.8 Hz), 7.86 (1H, d, J=9.1 Hz), 7.54 (1H, q), 7.29 (1H, t, J=8.6 Hz), 6.88 (1H, d, J=9.1 Hz), 4.41 (2H, d, J=13.5 Hz, 4.15 (1H, d, J=4.8 Hz), 3.10 (2H, t, J=12.3 Hz), 2.48 (2H, br. s.), 1.91 (2H, d, J=13.4 Hz), 1.50 (9H, s), HRMS (TOF, ES+) calculated 477.2302; observed 477.2515.

EXAMPLE 560

6-[4-({[6-(3-Fluorophenyl)pyridin-3-yl]carbonyl}amino)piperidin-1-yl]nicotinic acid

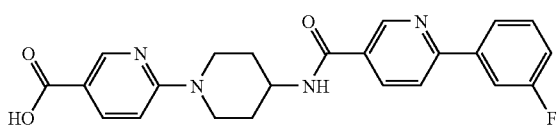

To a round-bottom flask containing tert-butyl 6-[4-({[6-(3-fluorophenyl)pyridin-3-yl]carbonyl}amino)piperidin-1-yl]nicotinate was added DCM (50 mL) and TFA (18 mL). After stirring at rt overnight the reaction was diluted with toluene (10 mL) and the solvent removed to give 6-[4-({[6-(3-fluorophenyl)pyridin-3-yl]carbonyl}amino)piperidin-1-yl]nicotinic acid, as a white solid (30 mg, 78%). 1H NMR (400 MHz, DMSO-d6) □ ppm 9.06 (1H, s), 8.62 (1H, s), 8.47 (1H, d, J=7.9 Hz), 8.22-8.32 (1H, m), 8.10 (1H, d, J=8.1 Hz), 7.85-8.01 (3H, m), 7.47-7.60 (1H, m), 7.29 (1H, t, J=7.8 Hz), 6.89 (1H, d, J=9.3 Hz), 4.42 (2H, d, J=13.2 Hz), 3.10 (2H, t, J=12.7 Hz), 2.33-2.54 (2H, m), 1.91 (2 h, d, J=13.2 Hz), 1.41-1.63 (2H, m). HRMS (TOF, ES+) calculated: 421.1676; observed 421.1722.

EXAMPLE 561

N-Ethyl-6-[4-({[6-(3-fluorophenyl)pyridin-3-yl]carbonyl}amino)piperidin-1-yl]-N-(2-hydroxyethyl)nicotinamide

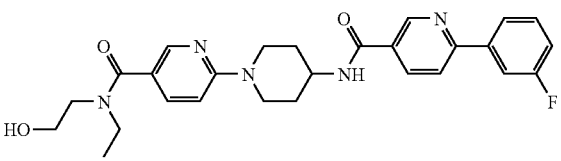

To a vial containing 6-[4-({[6-(3-fluorophenyl)pyridin-3-yl]carbonyl}amino)piperidin-1-yl]nicotinic acid (63.07 mg, 0.15 mmol) was added 0.375 mL of DMA, EDC (31.6 mg, 0.16 mmol), HOBt (20.3 mg, 0.15 mmol), NMM (0.04 mL, 0.37 mmol) and 2-(ethylamino)ethanol (13.4 mg, 0.15 mmol). The reaction mixture was stirred at room temperature for 12 hours and then diluted with water and ethyl acetate. The layers were separated and the organic layer collected and concentrated to give an oil, which was purified by RP-HPLC to give N-ethyl-6-[4-({[6-(3-fluorophenyl)pyridin-3-yl]carbonyl}amino)piperidin-1-yl]-N-(2-hydroxyethyl)nicotinamide (32 mg, 43%). HRMS (TOF, ES+) calculated for $C_{27}H_{30}FN_5O+H$: 492.2333; observed 492.2611.

The following compounds of formula (VII) were prepared using a method analogous to Example 561.

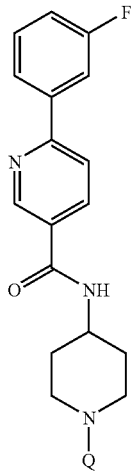

(VII)

| Ex | Q | Name | MS calc (M + H) | MS obs (M + H) |
|---|---|---|---|---|
| 562 | | 6-[4-({[6-(3-Fluorophenyl)pyridin-3-yl]carbonyl}amino)piperidin-1-yl]-N-methyl-N-(2-methylprop-2-en-1-yl)nicotinamide | 488.2462 | 488.2553 |
| 563 | | N-Allyl-6-[4-({[6-(3-fluorophenyl)pyridin-3-yl]carbonyl}amino)piperidin-1-yl]-N-methylnicotinamide | 474.2305 | 474.2396 |
| 564 | | N-{1-[5-(Azetidin-1-ylcarbonyl)pyridin-2-yl]piperidin-4-yl}-6-(3-fluorophenyl)nicotinamide | 460.2149 | 460.2224 |
| 565 | | 6-[4-({[6-(3-Fluorophenyl)pyridin-3-yl]carbonyl}amino)piperidin-1-yl]-N-methyl-N-prop-2-yn-1-ylnicotinamide | 472.2149 | 472.2223 |

-continued

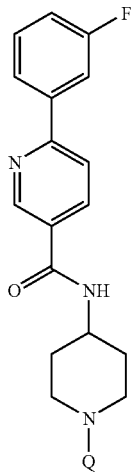
(VII)

| Ex | Q | Name | MS calc (M + H) | MS obs (M + H) |
|---|---|---|---|---|
| 566 | | N-Ethyl-6-[4-({[6-(3-fluorophenyl)pyridin-3-yl]carbonyl}amino)piperidin-1-yl]-N-methylnicotinamide | 462.2305 | 462.2389 |
| 567 | | 6-[4-({[6-(3-Fluorophenyl)pyridin-3-yl]carbonyl}amino)piperidin-1-yl]-N-(2-hydroxy-1-methylethyl)-N-methylnicotinamide | 492.2411 | 492.2495 |
| 568 | | 6-(3-Fluorophenyl)-N-(1-{5-[(3-fluoropyrrolidin-1-yl)carbonyl]pyridin-2-yl}piperidin-4-yl)nicotinamide | 492.2211 | 492.2303 |
| 569 | | N-Cyclobutyl-6-[4-({[6-(3-fluorophenyl)pyridin-3-yl]carbonyl}amino)piperidin-1-yl]-N-methylnicotinamide | 488.2462 | 488.2545 |
| 570 | | N,N-Diethyl-6-[4-({[6-(3-fluorophenyl)pyridin-3-yl]carbonyl}amino)piperidin-1-yl]nicotinamide | 476.2462 | 476.2496 |

-continued

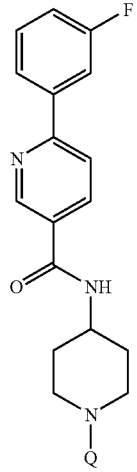

(VII)

| Ex | Q | Name | MS calc (M + H) | MS obs (M + H) |
|---|---|---|---|---|
| 571 | | N-{1-[5-(2,5-Dihydro-1H-pyrrol-1-ylcarbonyl)pyridin-2-yl]piperidin-4-yl)-6-(3-fluorophenyl)nicotinamide | 472.2149 | 472.2187 |
| 572 | | 6-[4-({[6-(3-Fluorophenyl)pyridin-3-yl]carbonyl}amino)piperidin-1-yl]-N-methyl-N-propylnicotinamide | 476.2462 | 476.2497 |
| 573 | | 6-(3-Fluorophenyl)-N-{1-[5-(1,3-thiazolidin-3-ylcarbonyl)pyridin-2-yl]piperidin-4-yl}nicotinamide | 492.1870 | 492.1910 |
| 574 | | N-(Cyclopropylmethyl)-6-[4-({[6-(3-fluorophenyl)pyridin-3-yl]carbonyl}amino)piperidin-1-yl]-N-methylnicotinamide | 488.2462 | 488.2582 |
| 575 | | 6-[4-({[6-(3-Fluorophenyl)pyridin-3-yl]carbonyl}amino)piperidin-1-yl]-N-isobutyl-N-methylnicotinamide | 490.2618 | 490.2657 |

(VII)

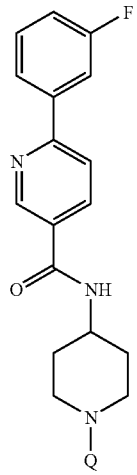

| Ex | Q | Name | MS calc (M + H) | MS obs (M + H) |
|---|---|---|---|---|
| 576 | ![](pyridine-N-methyl-cyanoethyl amide) | N-(2-Cyanoethyl)-6-[4-({[6-(3-fluorophenyl)pyridin-3-yl]carbonyl}amino)piperidin-1-yl]-N-methylnicotinamide | 487.2258 | 487.2419 |
| 577 | ![](pyridine-amide-piperidine-trifluoroethyl) | 6-(3-Fluorophenyl)-N-{1-[5-({[1-(2,2,2-trifluoroethyl)piperidin-4-yl]amino}carbonyl)pyridin-2-yl]piperidin-4-yl}nicotinamide | 585.2601 | 585.2723 |
| 578 | ![](pyridine-dimethyldihydropyrrole carbonyl) | N-(1-{5-[(2,5-Dimethyl-2,5-dihydro-1H-pyrrol-1-yl)carbonyl]pyridin-2-yl}piperidin-4-yl)-6-(3-fluorophenyl)nicotinamide | 500.1 | 500.1 |

EXAMPLE 579

N-[1-(7,8-Dihydro-5H-pyrano[4,3-d]pyrimidin-2-yl)piperidin-4-yl]-6-(3-fluorophenyl)nicotinamide

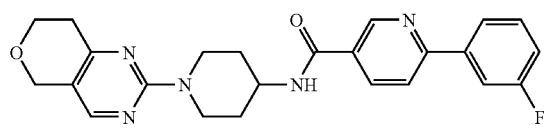

To a vial was added, 6-(3-fluorophenyl)nicotinic acid (46.4 mg, 0.213 mmol), 1-(7,8-dihydro-5H-pyrano[4,3-d]pyrimidin-2-yl)piperidin-4-amine (50 mg, 0.21 mmol), EDAC (45.0 mg, 0.235 mmol), HOBT (28.8 mg, 0.213 mmol), and DMA (1 mL) followed by NMM (0.058 mL, 0.534 mmol). The reaction was stirred overnight at room temperature and then diluted with $H_2O$ and the resulting solid filtered and collected to give the desired product, N-(1-{5-[(2,5-dimethyl-2,5-dihydro-1H-pyrrol-1-yl)carbonyl]pyridin-2-yl}piperidin-4-yl)-6-(3-fluorophenyl)nicotinamide (81 mg, 88%). 1H NMR (400 MHz, DMSO-d6) ppm 9.06 (1H, s), 8.45 (1H, d, J=7.5 Hz), 8.21-8.30 (1H, m), 8.04-8.14 (2H, m), 7.89-8.02 (2H, m) 7.49-7.59 (1H, m), 7.29 (1H, t), 4.49-4.64 (5H, m), 4.11 (1H, br. s.), 3.89 (2H, t, J=5.9 Hz), 2.94-3.07 (2 H, m), 1.88 (2H, d, J=10.1 Hz), 1.42-1.56 (3H, m). HRMS (TOF, ES+) calculated for M+H: 434.1992; observed 434.2165.

EXAMPLE 580

6-(3-Fluorophenyl)-N-(1-pyridazin-3-ylpiperidin-4-yl)nicotinamide

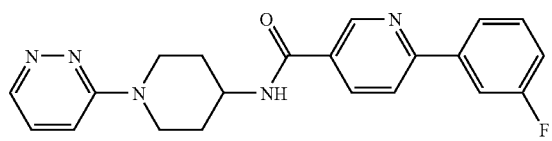

6-(3-fluorophenyl)-N-(1-pyridazin-3-ylpiperidin-4-yl)nicotinamide was prepared analogous to N-(1-{5-[(2,5-dimethyl-2,5-dihydro-1H-pyrrol-1-yl)carbonyl]pyridin-2-yl}piperidin-4-yl)-6-(3-fluorophenyl)nicotinamide, except 1-(pyridazin-3-yl)piperidin-4-amine was used as R—NH2. M+H=378.3 observed, 378.17 expected.

EXAMPLE 88

EXAMPLE 581

EXAMPLE 582

6-(3-Fluorophenyl)-N-(1-{9-[1-(hydroxymethyl)propyl]-9H-purin-6-yl}piperidin-4-yl)nicotinamide

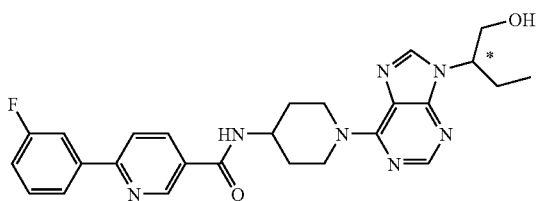

6-(3-fluorophenyl)-N-(piperidin-4-yl)nicotinamide (2.0 g, 5.37 mmol) and 2-(6-chloro-9H-purin-9-yl)butan-1-ol (1.58 g, 6.98 mmol) were placed in a flask along with 10 mL of butanol, 10 mL of water and 10 mL of triethylamine. The mixture was heated to 85° C. for 2 hours. The reaction mixture was partitioned between ethyl acetate and brine. The ethyl acetate was washed 3× with brine and then dried over MgSO$_4$, filtered and concentrated. The residue was purified by chromatography (silica, 1.5% EtOH/EtOAc) to give the desired racemic product (Example 88, 1.34 g, 57%). The material was purified by chiral chromatography-SFC (50% iPrOH in CO$_2$, AD-H 30×250 mm col) to give the two peaks (enantiomeric pair)

Example 581. Peak 1: 1H NMR (400 MHz, DMSO-d$_6$) □ ppm 9.08 (1H, d, J=2.0 Hz), 8.52 (1H, d, J=7.9 Hz), 8.29 (1H, dd, J=8.4, 2.2 Hz), 8.24 (1H, s), 8.21 (1H, s), 8.14 (1H, d, J=8.5 Hz), 7.91-8.04 (2 H, m), 7.52-7.62 (1H, m), 7.27-7.38 (1H, m), 5.36 (1H, s), 5.02 (1H, t, J=5.5 Hz), 4.38-3.50 (1H, m), 4.16-4.29 (1H, m), 3.80-3.90 (1H, m), 3.66-3.76 (1H, m), 3.21-3.37 (2H, m) 1.84-2.04 (4H, m), 1.51-1.67 (2H, m), 0.74 (3H, t, J=7.3 Hz). wt=0.66 g; M+H=490.2368 expected, 490.2406 observed; [□]$^{25}_D$=+10 (ethanol, 0.01) where c=g/00 mL Example 582. Peak 2: 1H NMR (400 MHz, DMSO-d$_6$) □ ppm 9.08 (1H, d, J=2.4 Hz), 8.53 (1H, d, J=7.9 Hz), 8.29 (1H, dd, J=8.4, 2.2 Hz), 8.23-8.26 (1H, m), 8.21 (1H, s), 8.14 (1H, d, J=8.5 Hz), 7.90-8.07 (2H, m), 7.48-7.64 (1H, m), 7.24-7.40 (1H, m), 5.35 (1H, d, J=12.6 Hz), 5.02 (1H, t, J=5.5 Hz), 4.35-4.53 (1H, m), 4.10-4.33 (1H, m), 3.79-3.93 (1H, m), 3.62-3.78 (1H, m), 3.19-3.39 (2H, m), 1.82-2.11 (4H, m), 1.48-1.70 (2H, m), 0.74 (3H, t, J=7.3 Hz). wt=0.64 g; M+H=490.2367 expected, 490.2361 observed; [□]$^{25}_D$=−10 (ethanol, 0.01) where c=g/100 mL

EXAMPLE 583

6-(2,5-Difluorophenyl)-N-[1-(2,2,2-trifluoroethyl)piperidin-4-yl]nicotinamide

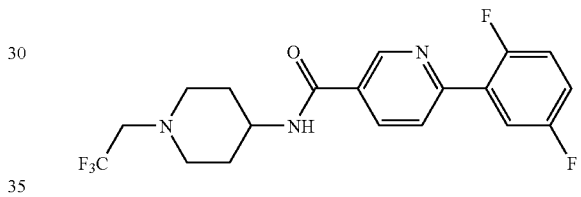

Step A: Preparation of tert-butyl 6-(2,5-difluorophenyl)nicotinate

To round-bottom flask was added 2,5-difluoro phenylboronic acid (306 mg, 1.94 mmol), palladium tetrakis(triphenylphosphine) (22.4 mg, 0.0194 mmol)) and tert-butyl 6-bromonicotinate (500 mg, 1.94 mmol) and the mixture was evacuated 3× with N$_2$. The solids were dissolved in 25 mL of DMF, followed by addition of 2.9 mL of 2 M cesium carbonate. The resulting mixture was heated to ~90° C. The mixture was cooled to rt and then poured into a sep. funnel, followed by addition of EtOAc and water (1×200 mL). The layers were separated and the organic extract washed with brine (1×200 mL), dried MgSO$_4$, filtered and concentrated to afford an orange oil. The crude mixture was purified by chromatography (silica, 10% EtOAc:Heptane) to afford the desired product (224 mg, 40%). 1H NMR (400 MHz, DMSO-d6) □ ppm 9.07-9.19 (1H, m), 8.36 (1H, dd, J=8.2, 2.2 Hz), 7.99 (1H, dd, J=8.3, 1.8 Hz), 7.75-7.86 (1H, m), 7.36-7.52 (1H, m), 7.36-7.52 (2H, m), 1.59 (9H, s). LC/MS (M+H)=292.1 observed, 292.11 expected.

Step B: 6-(2,5-difluorophenyl)nicotinic acid

To tert-butyl 6-(2,5-difluorophenyl)nicotinate in DCM (12 mL) at 0° C. was added TFA (5 mL). After stirring at room temperature overnight, toluene was added (10 mL) and the solvent removed to give a white solid (176 mg, 97%), 6-(2,5-difluorophenyl)nicotinic acid. LC/MS (M+H)=236.0 observed, 236.05 expected

Step C: Preparation of 6-(2,5-difluorophenyl)-N-[1-(2,2,2-trifluoroethyl)piperidin-4-yl]nicotinamide To a 50 mL flask was added 6-(2,5-difluorophenyl)nicotinic acid (100 mg, 0.46 mmol), 1-(2,2,2-trifluoroethyl)piperidin-4-amine (77.5 mg, 0.46 mmol), EDAC (89.7 mg, 0.468 mmol), HOBT (57.5 mg, 0.46 mmol), and DMA (2 mL) followed by NMM (0.117 mL, 1.06 mmol). The reaction was stirred for 1 hour at room temperature and then diluted with EtOAc (0.2 mL) followed by $H_2O$ (4 mL). The resulting solids were washed in $H_2O$ and collected by filtration. 1H NMR (400 MHz, DMSO-d6) ☐ ppm 9.12 (1H, d, J=2.2 Hz), 8.55 (1H, d, J=7.5 Hz), 8.31 (1H, dd, J=8.3, 2.3 Hz), 7.95 (1 H, dd, J=8.2, 1.5 Hz), 7.73-7.84 (1H, m), 7.35-7.51 (2H, m), 3.73-3.90 (1H, m), 3.19 (2H, q, J=10.3 Hz), 2.95 (2H, d, J=11.9 Hz), 2.39-2.50 (2H, m), 1.82 (2H, dd, J=14.0, 3.2 Hz), 1.53-1.68 (2H, m). LC/MS (M+H)=400.36 expected, 400.0 observed.

EXAMPLE 584

Ethyl 4-({[6-(2,5-Difluorophenyl)pyridine-3-yl]carbonyl}amino)piperidine-1-carboxylate

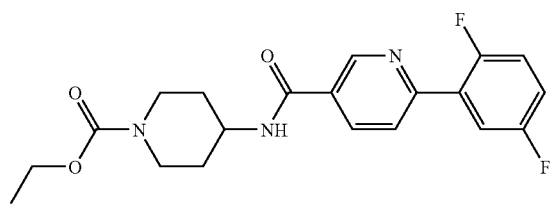

Ethyl 4-({[6-(2,5-difluorophenyl)pyridin-3-yl]carbonyl}amino)piperidine-1-carboxylate was prepared analogously to 6-(2,5-difluorophenyl)-N-[1-(2,2,2-trifluoroethyl)piperidin-4-yl]nicotinamide. 1H NMR (400 MHz, DMSO-d6) ☐ ppm 9.12 (1H, d, J=1.7 Hz), 8.58 (1H, d, J=7.5 Hz), 8.31 (1H, dd, J=8.3, 2.3 Hz), 7.95 (1H, dd, J=8.2, 1.4 Hz), 7.74-7.85 (1H, m), 7.36-7.52 (2H, m), 3.93-4.09 (6H, m) 2.97 (2H, br. s.), 1.86 (2H, dd, J=12.4, 2.5 Hz), 1.37-1.54 (2H, m), 1.20 (4H, t, J=7.1 Hz). LC/MS (M+H)=390.16 expected, 390.1 observed.

EXAMPLE 585

6-(2-Fluorophenyl)-N-[1-(2,2,2-trifluoroethyl)piperidin-4-yl]nicotinamide

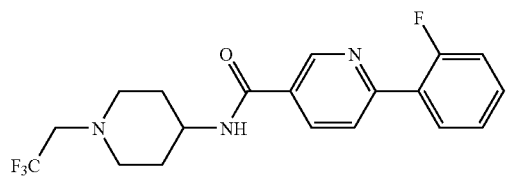

Step A: Preparation of tert-butyl 6-(2-fluorophenyl)nicotinate

To a round-bottom flask was added 2-fluoro phenylboronic acid (271 mg, 1.94 mmol), palladium tetrakis(triphenylphosphine) (22.4 mg, 0.0194 mmol)) and tert-butyl 6-bromonicotinate (500 mg, 1.94 mmol) and the mixture was evacuated 3× with $N_2$. The solids were dissolved in 25 mL of DMF, followed by addition of 2.9 mL of 2 M cesium carbonate. The resulting mixture was heated to ~90° C. The mixture was cooled to room temperature and then poured into a seperatory funnel, followed by addition of EtOAc and water (1×200 mL). The layers were separated and the organic extract washed with brine (1×200 mL), dried $MgSO_4$, filtered and concentrated to afford an orange oil. The crude mixture was purified by chromatography (silica, 10% EtOAc:Heptane) to afford the desired product (224 mg, 40%). 1H NMR (400 MHz, DMSO-d6) ☐ ppm 9.16 (1H, d, J=2.2 Hz), 8.34 (1H, dd, J=8.3, 2.3 Hz), 7.90-8.05 (2H, m), 7.50-7.62 (1H, m), 7.33-7.44 (2H, m) 1.59 (9 H, s).

Step B: 6-(2-Fluorophenyl)nicotinic acid

To tert-butyl 6-(2-fluorophenyl)nicotinate (479 mg, 1.75 mmol) in DCM (12 mL) at 0° C. was added TFA (2.5 mL). After stirring at rt overnight, toluene was added (10 mL) and the solvent removed to give a white solid (375 mg, 98%), 6-(2-fluorophenyl)nicotinic acid. LC/MS (M+H)=218.0 observed, 218.06 expected.

Step C: 6-(2-Fluorophenyl)-N-[1-(2,2,2-trifluoroethyl)piperidin-4-yl]nicotinamide To a vial was added 6-(2-fluorophenyl)nicotinic acid (100 mg, 0.46 mmol), 1-(2,2,2-trifluoroethyl)piperidin-4-amine (83.8 mg, 0.46 mmol), EDAC (97.1 mg, 0.51 mmol), HOBT (62.2 mg, 0.46 mmol), DMA (2 mL) and NMM (0.127 mL, 1.15 mmol). The reaction was stirred for 1 hour at room temperature and then diluted with EtOAc (0.2 mL) followed by $H_2O$ (4 mL). The resulting solids were washed in $H_2O$ and collected by filtration. 1H NMR (400 MHz, DMSO-d6) ☐ ppm 9.11 (1H, d, J=1.9 Hz), 8.52 (1H, d, J=7.5 Hz), 8.28 (1H, dd, J=8.3, 2.3 Hz), 7.94-8.05 (1H, m), 7.90 (1H, dd, J=8.4, 1.5 Hz), 7.50-7.58 (1H, m), 3.72-3.89 (1H, m), 3.19 (2H, q, J=10.3 Hz), 2.95 (2H, d, J=11.9 Hz), 2.40-2.48 (2H, m) 1.82 (2H, d, J=13.1 Hz), 1.52-1.67 (2H, m).

The following compounds of formula (X) were prepared using methods analogous to the method of Example 585.

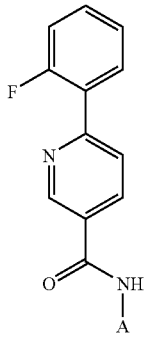

(X)

| Ex | A | Name | MS calc (M + H) | MS obs (M + H) |
|---|---|---|---|---|
| 586 | ethyl piperidine-1-carboxylate (4-yl attachment) | Ethyl 4-({[6-(2-fluorophenyl)pyridin-3-yl]carbonyl}amino)piperidine-1-carboxylate | 372.2 | 372.0 |
| 587 | 1-(pyridin-2-ylmethyl)piperidin-4-yl | 6-(2-Fluorophenyl)-N-[1-(pyridin-2-ylmethyl)piperidin-4-yl]nicotinamide | 391.2 | 391.0 |
| 588 | 1-(3-fluorobenzyl)piperidin-4-yl | N-[1-(3-Fluorobenzyl)piperidin-4-yl]-6-(2-fluorophenyl)nicotinamide | 407.2 | 408.0 |

The compounds of the following formula were also prepared using methods analogous to the method of Example 585.

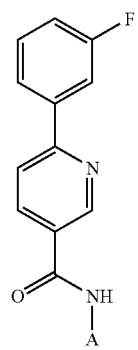

| Ex | A | Name | MS calc (M) | MS obs (M + H) |
|---|---|---|---|---|
| 589 | 1-isopropylpyrrolidin-3-yl | 6-(3-Fluorophenyl)-N-(1-isopropylpyrrolidin-3-yl)nicotinamide | 327.2 | 328.1 |

-continued

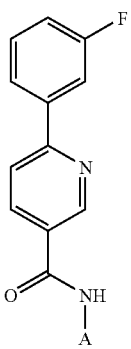

| Ex | A | Name | MS calc (M) | MS obs (M + H) |
|---|---|---|---|---|
| 590 | (7,8-Dihydro-5H-pyrano[4,3-d]pyrimidin-2-yl)pyrrolidin-3-yl | N-[1-(7,8-Dihydro-5H-pyrano[43-d]pyrimidin-2-yl)pyrrolidin-3-yl]-6-(3-fluorophenyl)nicotinamide | 419.2 | 420.3 |
| 591 | 1-propylpiperidin-4-yl | 6-(3-Fluorophenyl)-N-(1-propylpiperidin-4-yl)nicotinamide | 341.2 | 342.1 |
| 592 | 1-[(methylamino)carbonyl]piperidin-4-yl | 6-(3-Fluorophenyl)-N-{1-[(methylamino)carbonyl]piperidin-4-yl}nicotinamide | 356.2 | 357.3 |
| 593 | 1-(tetrahydro-2H-pyran-4-ylmethyl)piperidin-4-yl | 6-(3-Fluorophenyl)-N-[1-(tetrahydro-2H-pyran-4-ylmethyl)piperidin-4-yl]nicotinamide | 397.2 | 398.0 |
| 594 | 1-(ethoxycarbonyl)pyrrolidin-3-yl | Ethyl 3-({[6-(3-fluorophenyl)pyridin-3-yl]carbonyl}amino)pyrrolidine-1-carboxylate | 357.1 | 358.1 |
| 595 | 1-(6,7-Dihydro-5H-cyclopenta[d]pyrimidin-2-yl)pyrrolidin-3-yl | N-[1-(6,7-Dihydro-5H-cyclopenta[d]pyrimidin-2-yl)pyrrolidin-3-yl]-6-(3-fluorophenyl)nicotinamide | 403.2 | 404.3 |
| 596 | 1-(Cyclopropylmethyl)piperidin-4-yl | N-[1-(Cyclopropylmethyl)piperidin-4-yl]-6-(3-fluorophenyl)nicotinamide | 353.2 | 354.3 |

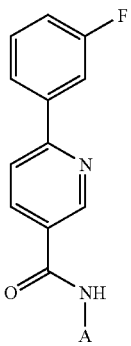

| Ex | A | Name | MS calc (M) | MS obs (M + H) |
|---|---|---|---|---|
| 597 | 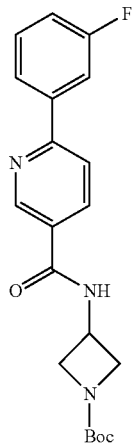 | 6-(3-Fluorophenyl)-N-[1-(6-methyl-5,6,7,8-tetrahydropyrido[4.3-d]pyrimidin-2-yl)pyrrolidin-3-yl]nicotinamide | 432.2 | 433.4 |
| 598 | 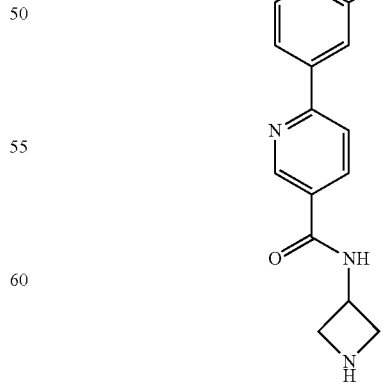 | tert-Butyl 4-({[6-(3-fluorophenyl)pyridin-3-yl]carbonyl}amino)piperidine-1-carboxylate | 399.2 | 400.3 |

EXAMPLE 599 tert-Butyl 3-(2-(3-fluorophenyl)nicotinamido)azetidine-1-carboxylate

To a solution of 6-(3-fluorophenyl)nicotinic acid (0.50 g, 2.30 mmol) in DMF (10 mL) was added HBTU (0.96 g, 2.53 mmol) and DIPEA (0.52 mL, 2.99 mmol). After 1 hr at room temperature, tert-butyl 3-aminoazetidine-1-carboxylate was added and the reaction stirred overnight. The solvent was removed and the residue was partitioned between ethyl acetate and sodium bicarbonate (aqueous saturated). The organic layer was washed with brine (2×), dried (MgSO$_4$), filtered and concentrated to give the desired product, tert-butyl 3-(2-(3-fluorophenyl)nicotinamido)azetidine-1-carboxylate (630 mg, 74%). LC/MS (M+H)=372.2 observed, 372.17 expected

EXAMPLE 600

N-Azetidin-3-yl-6-(3-fluorophenyl)nicotinamide

To a solution of tert-butyl 3-(2-(3-fluorophenyl)nicotinamido)azetidine-1-carboxylate (570 mg, 1.53 mmol) in methanol (1 mL) was added 4N HCl/dioxane (3 mL). The reaction mixture was stirred at room temperature overnight and then diluted with ether to give a solid, which was filtered and collected to give the desired product as the hydrochloride salt, N-azetidin-3-yl-6-(3-fluorophenyl)nicotinamide (480 mg, 92%). LC/MS (M+H)=272.9 observed, 272.12 expected.

EXAMPLE 601

N-[1-(2,2-Dimethylpropanoyl)azetidin-3-yl]-6-(3-fluorophenyl)nicotinamide

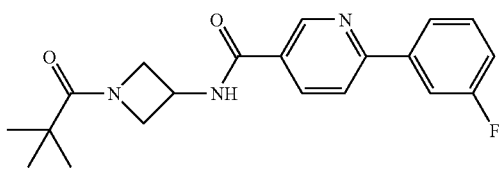

To a solution of N-azetidin-3-yl-6-(3-fluorophenyl)nicotinamide (50 mg, 0.12 mmol) in DMF (1 mL) was added DIPEA (0.06 mL, 0.32 mmol) and pivaloyl chloride (29.4 mg, 0.24 mmol). The reaction mixture was stirred at room temperature overnight and then diluted with ethyl acetate and water. The layers were separated and the organic layer washed with brine, dried (MgSO$_4$) and the solvent removed to give a solid, which was purified by chromatography (silica, 80% etoac:hex) to give the desired product, N-[1-(2,2-dimethylpropanoyl)azetidin-3-yl]-6-(3-fluorophenyl)nicotinamide (50 mg, 86%). HRMS (M+H)=356.1856 observed, 356.1774 expected.

EXAMPLE 602

N-[1-(3-Cyano-4,6-dimethylpyridin-2-yl)azetidin-3-yl]-6-(3-fluorophenyl)nicotinamide

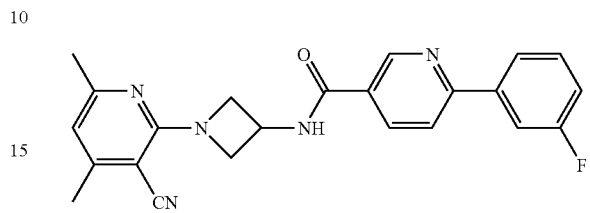

To a vial containing N-azetidin-3-yl-6-(3-fluorophenyl)nicotinamide (40 mg, 0.13 mmol) was added 2-chloro-4,6-dimethyinicotinonitrile (32 mg, 0.19), n-butanol (0.3 mL) and TEA (4 drops). The mixture was heated to 90° C. overnight and then cooled to room temperature. The mixture was diluted with water and CH$_2$Cl$_2$ and the layers separated. The organic layer was collected and the solvent removed to give an oil, which was purified by RP-HPLC to give the desired product, N-[1-(3-cyano-4,6-dimethylpyridin-2-yl)azetidin-3-yl]-6-(3-fluorophenyl) nicotinamide (40 mg, 77%). HRMS (M+H) expected 402.1730, (M+H) observed 402.1832.

The following compounds of formula were prepared using methods analogous to the method of Example 602.

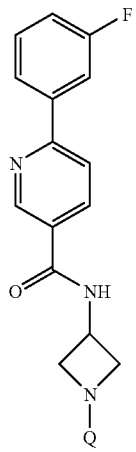

| Ex | R | Name | MS calc (M + H) | MS obs (M + H) |
|---|---|---|---|---|
| 603 | ![] | N-[1-(2-Ethylimidazo[1,2-b]pyridazin-6-yl)azetidin-3-yl]-6-(3-fluorophenyl)nicotinamide | 417.1839 | 417.1864 |
| 604 | ![] | 6-(3-Fluorophenyl)-N-{1-[3-(trifluoromethyl)pyridin-2-yl]azetidin-3-yl}nicotinamide | 417.1339 | 417.1357 |

-continued
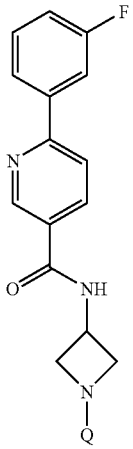
| Ex | R | Name | MS calc (M + H) | MS obs (M + H) |
|---|---|---|---|---|
| 605 | quinoxalin-2-yl | 6-(3-Fluorophenyl)-N-(1-quinoxalin-2-ylazetidin-3-yl)nicotinamide | 400.1573 | 400.1758 |
| 606 | 1,3-benzoxazol-2-yl | N-[1-(1,3-Benzoxazol-2-yl)azetidin-3-yl]-6-(3-fluorophenyl)nicotinamide | 389.1414 | 389.1473 |
| 607 | 3-cyano-6-methylpyridin-2-yl | N-[1-(3-Cyano-6-methylpyridin-2-yl)azetidin-3-yl]-6-(3-fluorophenyl)nicotinamide | 388.1573 | 388.1648 |
| 608 | 1-phenyl-1H-tetrazol-5-yl | 6-(3-Fluorophenyl)-N-[1-(1-phenyl-1H-tetrazol-5-yl)azetidin-3-yl]nicotinamide | 416.1635 | 416.1653 |

EXAMPLE 609 cis-tert-Butyl 3-({[6-(3-fluorophenyl)pyridin-3-yl]carbonyl}amino)-4-hydroxypyrrolidine-1-carboxylate

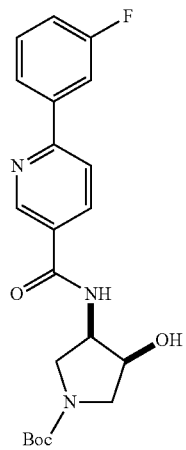

To a solution of 6-(3-fluorophenyl)nicotinic acid (391 mg, 1.8 mmol) in DMF (10 mL) at 0° C. was added HATU (753 mg, 1.98 mmol) and DIPEA (0.47 mL, 2.07 mmol). After 15 min, cis-tert-butyl 3-amino-4-hydroxypyrrolidine-1-carboxylate was added and the reaction stirred at room temperature for 5 hrs. The solvent was removed in vacuo and the residue diluted with ethyl acetate and water. The layers were separated and the organic layer washed with brine, dried (MgSO$_4$) and the solvent removed to give an oil, which after chromatography (silica, 65% ethyl acetate:hex) to give the desired product, cis-tert-butyl-3-({[6-(3-fluorophenyl)pyridin-3-yl]carbonyl}amino)-4-hydroxypyrrolidine-1-carboxylate (420 mg, 58%). LC/MS (M+H)=401.9 observed, 402.18 expected.

EXAMPLE 610

Trans-tert-Butyl 3-({[6-(3-fluorophenyl)pyridin-3-yl]carbonyl}amino)-4-hydroxypyrrolidine-1-carboxylate was synthesized analogous to the above, except using the trans-derivative of tert-butyl 3-amino-4-hydroxypyrrolidine-1-carboxylate. LC/MS (M+H)=401.9 observed, 402.18 expected.

EXAMPLE 611 trans-6-(3-Fluorophenyl)-N-[4-hydroxypyrrolidin-3-yl]nicotinamide

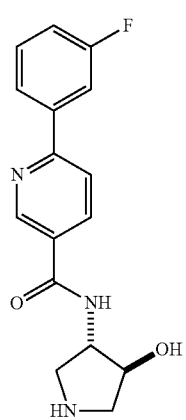

To a solution of trans-tert-butyl 3-({[6-(3-fluorophenyl)pyridin-3-yl]carbonyl}amino)-4-hydroxypyrrolidine-1-carboxylate (500 mg, 1.24 mmol) in dioxane was added 4N HCl in dioxane (10 mL). The reaction was stirred at room temperature for ~4 hrs and then diluted with ether to give a white solid, which was filtered and collected to give the desired product as the hydrochloride salt, trans-6-(3-fluorophenyl)-N-[4-hydroxypyrrolidin-3-yl]nicotinamide (390 mg, 92%). LC/MS (M+H)=301.9 observed, 302.13 expected.

EXAMPLE 612

Trans-N-[1-(2,2-dimethylpropanoyl)-4-hydroxypyrrolidin-3-yl]-6-(3-fluorophenyl)nicotinamide

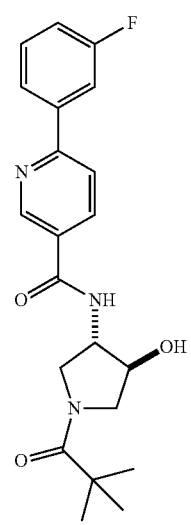

To a solution of trans-6-(3-fluorophenyl)-N-[4-hydroxypyrrolidin-3-yl]nicotinamide (50 mg, 0.15 mmol) in DMF (1.0 mL) was added DIPEA (95 mg, 0.32 mmol) and pivaloyl chloride (66 mg, 0.24 mmol). After stirring at rt overnight the mixture was partitioned between ethyl acetate and brine. The organic layer was dried (MgSO$_4$), filtered and the solvent removed to give an oil, which after chromatography (silica, 1% MeOH/EtOAc) gave the product (36 mg, 63%). HRMS (M+H)=386.1880 expected, 386.1914 observed.

EXAMPLE 613 trans-6-(3-Fluorophenyl)-N-[4-hydroxy-1-quinoxalin-2-ylpyrrolidin-3-yl]nicotinamide

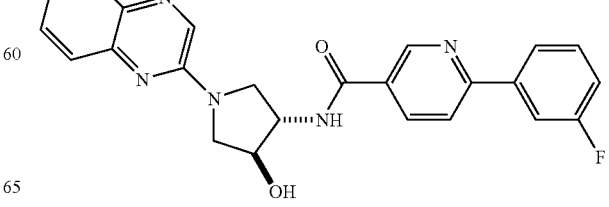

To a vial was added trans-6-(3-fluorophenyl)-N-[4-hydroxypyrrolidin-3-yl]nicotinamide (40 mg, 0.12 mmol 2-chloroquinoxaline (29.2 mg, 0.18 mmol), n-butanol, water and triethylamine (0.3 mL of each). The reaction mixture was heated to 90° C. overnight and then cooled to room temperature and the solvent removed. The residue was taken up in DMSO and purified by RP-HPLC to give the desired product, trans-6-(3-fluorophenyl)-N-[4-hydroxy-1-quinoxalin-2-ylpyrrolidin-3-yl]nicotinamide (40 mg, 79%). HRMS (M+H) expected 430.1679, observed 430.1793

The following compounds of Formula (XII) were prepared using methods analogous to the method of Example 613.

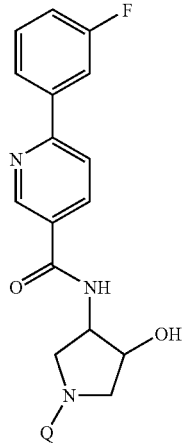

(XII)

| Ex | Q | Name | MS calc (M + H) | MS obs (M + H) |
|---|---|---|---|---|
| 614 | | Trans-N-[1-(2-ethylimidazo[12-b]pyridazin-6-yl)-4-hydroxypyrrolidin-3-yl]-6-(3-fluorophenyl)nicotinamide | 447.1945 | 447.2054 |
| 615 | | Trans-N-[1-(3-cyano-4,6-dimethylpyridin-2-yl)-4-hydroxypyrrolidin-3-yl]-6-(3-fluorophenyl)nicotinamide | 432.1836 | 432.1868 |
| 616 | | Trans-N-[1-(1,3-benzoxazol-2-yl)-4-hydroxypyrrolidin-3-yl]-6-(3-fluorophenyl)nicotinamide | 419.1519 | 419.1589 |
| 617 | | Trans-N-[(1-(3-cyano-6-methylpyridin-2-yl)-4-hydroxypyrrolidin-3-yl]-6-(3-fluorophenyl)nicotinamide | 418.1679 | 418.1645 |
| 618 | | Trans-6-(3-fluorophenyl)-N-[1-(7-fluoroquinazolin-2-yl)-4-hydroxypyrrolidin-3-yl]nicotinamide | 448.1585 | 448.1792 |
| 619 | | Trans-6-(3-fluorophenyl)-N-[4-hydroxy-1-(1-phenyl-1H-tetrazol-5-yl)pyrrolidin-3-yl]nicotinamide | 446.1741 | 446.1854 |

Preparation of 5-chloro-6-(3-fluorophenyl)nicotinic acid

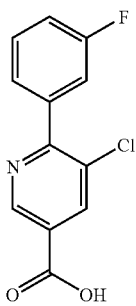

To a round bottom flask was added 5,6-dichloronicotinic acid (500 mg, 2.60 mmol), 3-fluorophenylboronic acid (364 mg, 2.60 mmol), DMF (25 mL), 2 M $Cs_2CO_3$ (6 mL) and $Pd(Ph_3)_4$ (30.1 mg, 0.0026 mmol). The reaction mixture was heated to 90° C. for 3 hrs and then allowed to cool to rt. The mixture was diluted with ethyl acetate/water and the layers separated. The organic layer was washed with brine, dried ($MgSO_4$) and the solvent removed to give a solid, which was purified by chromatography (silica, DCM/MeOH) to give the desired product, 5-chloro-6-(3-fluorophenyl)nicotinic acid (623 mg, 95%). LC/MS (M+H)=252 observed, 252.02 expected.

The following compounds of formula (XIII) were synthesized using methods analogous to the method of Example 585 (preparation of 6-(2-fluorophenyl)-N-[1-(2,2,2-trifluoroethyl)piperidin-4-yl]nicotinamide).

EXAMPLE 51

Alternative Preparation

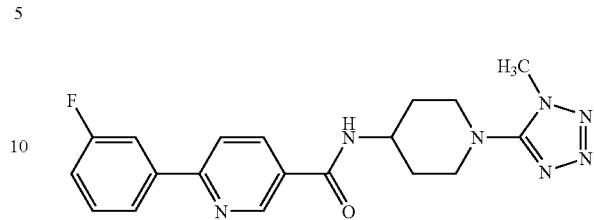

Step A: Tert-butyl[1-(1-Methyl-1H-tetrazol-5-yl)-piperidin-4-yl]-carbamate

Piperidin-4-yl-carbamic acid tert-butyl ester (30.0 g, 0.189 mol), 5-chloro-1-methyl-1H-tetrazole (28.8 g, 0.242 mol) and triethylamine (80 mL, 0.573 mol) were added to a mixture of n-butanol (80 mL) and water (80 mL) and the reaction mixture heated to 80° C. for 5 hours. The reaction was cooled to room temperature and stirred at this temperature overnight. The resulting precipitate was filtered off and washed with water (2×25 mL) and then dried to give tert-butyl[1-(1-methyl-1H-tetrazol-5-yl)-piperidin-4-yl]-carbamate as a white powder (41.8 g). $^1$H NMR (300 MHz, DMSO-$d_6$) ppm 1.39 (s, 9H) 1.44-1.65 (qd, J=12, 4 Hz, 2H) 1.75-1.92)dd, J=13, 3

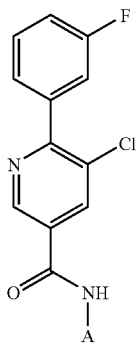

(XIII)

| Ex | A | Name | MS calc (M + H) | MS obs (M + H) |
|---|---|---|---|---|
| 620 | ![F3C-CH2-N-piperidine] | 5-Chloro-6-(3-fluorophenyl)-N-[1-(2,2,2-trifluoroethyl)piperidin-4-yl]nicotinamide | 416.1153 | 416.0 |
| 621 | ![pyridazin-3-yl-piperidine] | 5-Chloro-6-(3-fluorophenyl)-N-(1-pyridazin-3-ylpiperidin-4-yl)nicotinamide | 411.1262 | 411.1 |
| 622 | ![pivaloyl-piperidine] | 5-Chloro-6-(3-fluorophenyl)-N-(1-pivaloylpiperidin-4-yl)nicotinamide | 418.1697 | 418.1801 |

Hz, 2H) 2.95-3.16 (td, J=13, 3 Hz, 2H) 3.34-3.50 (broad s, 1H) 3.50-3.65 (dt, J=13, 3 Hz, 2H) 3.85 (s, 3H) 6.83-7.04 (m, 1H).

Step B: 1-(1-Methyl-1H-tetrazol-5-yl)-piperidin-4-amine methanesulphonic acid salt A mixture of tert-butyl[1-(1-methyl-1H-tetrazol-5-yl)-piperidin-4-yl]-carbamate (39.0 g, 0.138 mol) and methanesulphonic acid (23 mL, 0.354 mol) in isopropanol (290 mL) was stirred at 44° C. over night. The reaction mixture was cooled slowly to 0° C. and stirred for 2 hours. The precipitate was washed with cold isopropanol (2×25 mL) and dried to give 1-(1-methyl-1H-tetrazol-5-yl)-piperidin-4-amine methanesulphonic acid salt as a white powder (35.0 g). $^1$H NMR (300 MHz, MeOH-d$_4$) ppm 1.75-1.94 (qd, J=12, 3 Hz, 2H) 2.03-2.19 (d, J=12 Hz, 2H) 2.71 (s, 3H), 3.08-3.26 (t, J=13 Hz, 2H) 3.37-3.50 (m, 1H) 3.63-3.87 (d, J=13 Hz, 2H) 3.94 (s, 3H) 4.74-4.90 (d, J=1 Hz, 3H).

Step C: 6-(3-Fluorophenyl)nicotinicacid

6-Chloronicotinic acid (25.4 g, 161 mmol) and 3-fluorophenylboronic acid (33.9 g, 242 mmol) were dissolved in dimethylformamide (300 mL) and the mixture degassed with nitrogen. Tetrakis(triphenylphosphine)palladium (0) (1.0 g, 0.87 mmol) was added followed by a solution of sodium carbonate (34.0 g in 160 mL of water) drop wise. The reaction was heated overnight at 90° C. The reaction was cooled to room temperature and then water (200 mL) was added. The reaction mixture was filtered over celite and then the filtrate was washed with a mixture of ethyl acetate (50 mL) and heptane (50 mL). The phases were separated and the aqueous layer was acidified to pH 2 with 6M HCl. The yellow precipitate was filtered off and dried to give 6-(3-fluorophenyinicotinic acid) 27.9 g. $^1$H NMR (400 MHz, DMSO-d$_6$) ppm 7.36 (dt, J=2.3, 8.3 Hz, 1H) 7.79 (m, 1H) 8.01 (m, 2H) 8.18 (d, J=8.3 Hz, 1H) 8.36 (dd, J=2.3, 8.3 Hz, 1H) 9.16 (d, J=1.8 Hz, 1H).

Step D: 6-(3-Fluoro-phenyl)-N-[1-(1-methyl-1H-tetrazol-5-yl)-piperidin-4-yl]-nicotinamide To a slurry of 6-(3-fluorophenyl)nicotinic acid (20.4 g, 94.0 mmol) and 1-methylimidazole (30 mL, 376 mmol) in acetonitrile (140 mL) was added a solution of p-toluenesulphonyl chloride (27.3 g, 143 mmol) in acetonitrile (40 mL) over a period of 40 minutes keeping the internal temperature below 34° C. The reaction was stirred at room temperature for 2.5 hours and then 1-(1-methyl-1H-tetrazol-5-yl)-piperidin-4-amine methane sulphonic acid salt (26.1 g, 94 mmol) was added drop wise over 40 minutes keeping the temperature below 33° C. At the end of the addition the reaction mixture was heated to 42° C. for 2 hours and then cooled to room temperature overnight. The reaction was then cooled to 0-5° C. for approximately 1 hour and then the precipitate was filtered off, washed with cold acetonitrile (2×40 mL) to give the product as a white solid. This solid was refluxed in ethanol (530 mL) for 2 hours and then stirred at room temperature for approximately 2 hours. The precipitate was filtered, washed with ethanol (3×100 mL) and dried to give 6-(3-fluoro-phenyl)-N-[1-(1-methyl-1H-tetrazol-5-yl)-piperidin-4-yl]-nicotinamide as a white powder (43.3 g). $^1$H NMR (300 MHz, DMSO-d$_6$) ppm 1.66-1.86 (qd, J=12, 4 Hz, 2H), 1.86-2.01 (dd, J=13, 3 Hz, 2H) 3.06-3.22 (td, J=12, 2 Hz, 2H) 3.59-3.74 (d, J=13 Hz, 2H) 3.90 (s, 3H) 4.03-4.18 (m, 1H) 7.27-7.37 (tdd, J=6, 3, 1 Hz, 1H) 7.51-7.63 (m, 1H) 7.91-8.00 (dt, J=10, 2 Hz, 1H) 8.00-8.06 (d, J=8 Hz, 1H) 8.10-8.19 (dd, J=8, 1 Hz, 1H) 8.26-8.35 (dd, J=8, 2 Hz, 1H) 8.53-8.65 (d, J=8 Hz, 1H) 9.07-9.13 (d, J=2 Hz, 1H).

EXAMPLE 623

6-(3-Cyanophenyl)-N-[1-(2,2,2-trifluoroethyl)piperidin-4-yl]nicotinamide

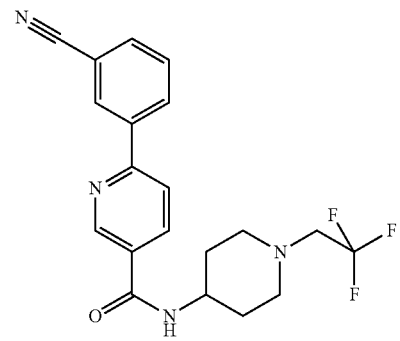

Step A: Methyl 6-(3-cyanophenyl)nicotinate

Methyl 6-chloronicotinate (467 mg, 2.72 mmol) and (3-cyanophenyl)boronic acid (400 mg, 2.72 mmol) were added to 1,4-dioxane (25 mL). To this was added 6.80 mL of a 2 M solution of aqueous potassium carbonate and tetrakis(triphenylphosphine)palladium(0) (157 mg, 0.136 mmol). The above reagents were heated at reflux for 5 hours. The reaction was cooled to room temperature and partitioned between ethyl acetate (50 mL) and water (20 mL), the phases were separated and the organic layer was dried over anhydrous MgSO$_4$, filtered and evaporated to a pale yellow solid. The solid was purified using chromatography on silica eluting with a mixture of heptane: ethyl acetate 90:10, 80:20, 70:30. The product fractions were combined and evaporated to give methyl 6-(3-cyanophenyl)nicotinate as a white solid (278 mg). LCMS (ES+) 239 (M+1) $^1$H NMR (400 MHz CDCl$_3$) ppm 4.00 (s, 3H) 7.62 (t, J=8.2 Hz, 1H) 7.76 (m, 1H) 7.83 (d, J=10.6 Hz, 1H) 8.31 (m, 1H) 8.40 (m, 2H) 9.30 (s, 1H).

Step B: 6-(3-Cyanophenyl)nicotinic acid

A mixture of methyl 6-(3-cyanophenyl)nicotinate (300 mg, 1.26 mmol) and 2 M lithium hydroxide solution (1.89 mL) in tetrahydrofuran (30 mL) was heated at 40° C. overnight. The tetrahydrofuran was evaporated off, water (5 mL) was added and the reaction mixture was acidified to pH 6 with 2N aqueous HCl. The precipitated solid was filtered off and dried under vacuum to give 6-(3-cyanophenyl)nicotinic acid (208 mg). $^1$H NMR (400 MHz, DMSO-d6) ppm 7.74 (t, J=7.8 Hz, 1H), 7.96 (m, 1H), 8.23 (m, 1H), 8.36 (m, 1H), 8.49 (m, 1H), 8.55 (m, 1H), 9.15 (m, 1H), 13.5 (broad s, 1H) LCMS 225 (M+1) ELSD 1.33 minutes.

Step C: 6-(3-Cyanophenyl)-N-[1-(2,2,2-trifluoroethyl)piperidin-4-yl]nicotinamide To a solution of 6-(3-cyanophenyl)nicotinic acid (50 mg, 0.222 mmol) in dimethylformamide (1 mL) was added 1,1¹-carbonylbis(1H-imidazole) (36.3 mg, 0.224 mmol) and the reaction mixture stirred at room temperature for 1 hour. A solution of 1-(2,2,2-trifluoroethyl)piperidin-4-amine (49 mg, 0.269 mmol) in dimethylformamide (0.5 mL) was then added and the reaction stirred overnight at room temperature. Further 1,1¹-carbonylbis(1H-imidazole) (18 mg, 0.132 mmol) was added and the reaction stirred for 30 minutes and then further 1-(2,2,2-trifluoroethyl)piperidin-4-amine (25 mg, 0.134 mmol) in dimethylformamide (0.5 mL) was added and the solution stirred for one hour. The dimethylformamide was evaporated off and the residue partitioned between ethyl acetate (10 mL) and water (3 mL). The organic layer was separated, dried over anhydrous MgSO$_4$, filtered and evaporated to a white solid. This was triturated with t-butyl methyl ether and the white solid was filtered off and dried to give 6-(3-cyanophenyl)-N-[1-(2,2,2-trifluoroethyl)piperidin-4-yl]nicotinamide 53 mg 1H NMR (400 MHz, DMSO-d6) ppm 1.57-1.67 (m, 2H) 1.80-1.87 (m, 2H) 2.43-2.54 (m, 2H) 2.93-2.99 (m, 2H) 3.20 (q, J=10.1 Hz, 2H) 3.83 (m , 1H) 7.76 (t, J=8.2 Hz, 1H) 7.97 (m, 1H) 8.24 (m, 1H) 8.34 (dd, J=6.2, 2.4 Hz, 1H) 8.52 (m, 2H) 8.61*m, 1H) 9.12 (m, 1H) LCMS 389 (M+1) ELSD 1.27 minutes.

EXAMPLE 624

6-(2-Cyanophenyl)-N-[1-(2,2,2-trifluoroethyl)piperidin-4-yl]nicotinamide

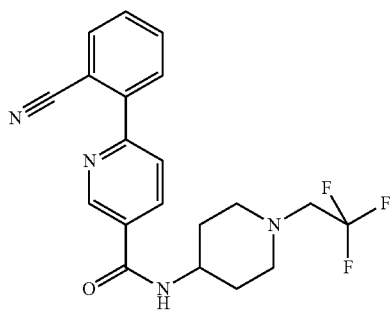

Step A: Methyl 6-(2-cyanophenyl)nicotinate

Methyl 6-chloronicotinate (1.00 g, 5.83 mmol) and (2-cyanophenyl)boronic acid (856 mg, 5.83 mmol) were added to 1,4-dioxane (50 mL). To this was added 14.6 mL of a 2 M solution of aqueous potassium carbonate and tetrakis(triphenylphosphine)palladium(0) (337 mg, 0.291 mmol). The above reagents were heated at reflux for 5 hours. The reaction was cooled to room temperature and partitioned between ethyl acetate (50 mL) and water (20 mL), the phases were separated and the organic layer was dried over anhydrous MgSO$_4$, filtered and evaporated to a gum. The solid was purified using chromatography on silica eluting with a mixture of heptane: ethyl acetate 80:20, 70:30, 30:70. The product fractions were combined and evaporated to give methyl 6-(2-cyanophenyl)nicotinate as a white solid (195 mg). LCMS (ES+) 239 (M+1), 1.37 minutes; ¹H NMR (400 MHz CDCl$_3$) ppm 4.00 (s, 3H) 7.58 (t, J=7.4 Hz, 1H) 7.74 (d, J=6.2 Hz, 1H) 7.85 (d, J=7.8 Hz, 1H) 7.90 (m, 2H) 8.45 (dd, J=5.8, 2.4 Hz, 1H) 9.37 (d, J=2.0, Hz, 1H).

Step B: 6-(2-Cyanophenyl)nicotinic acid

A mixture of methyl 6-(2-cyanophenyl)nicotinate (195 mg, 0.818 mmol) and 2 M lithium hydroxide solution (1.23 mL) in tetrahydrofuran (15 mL) was heated at 40° C. overnight. The tetrahydrofuran was evaporated off, water (5 mL) was added and the reaction mixture was acidified to pH 6 with 2N HCl. The precipitated solid was filtered off and dried under vacuum to give 6-(3-cyanophenyl)nicotinic acid (55 mg) ppm ¹H NMR (400 MHz, DMSO-d6) 7.71 (td, J=6.3, 1.5 Hz, 1H), 7.87 (td, J=7.8, 1.6 Hz, 1H) 7.96 (d, J=7.8 Hz, 1H) 8.02 (m, 2H) 8.45 (dd, J=5.8, 2.4 Hz, 1H) 9.20 (d, J=2.3 Hz, 1H), 13.55 (broad s, 1H) LCMS 225 (M+1) ELSD 1.20 minutes.

Step C: 6-(2-Cyanophenyl)-N-[1-(2,2,2-trifluoroethyl)piperidin-4-yl]nicotinamide To a solution of 6-(2-cyanophenyl)nicotinic acid (50.2 mg, 0.224 mmol) in dimethylformamide (1 mL) was added 1,1¹-carbonylbis(1H-imidazole) (36.3 mg, 0.224 mmol) and the reaction mixture stirred at room temperature for 1 hour. A solution of 1-(2,2,2-trifluoroethyl)piperidin-4-amine (49 mg, 0.269 mmol) in dimethylformamide (0.5 mL) was then added and the reaction stirred overnight at room temperature. Further 1-(2,2,2-trifluoroethyl)piperidin-4-amine (25 mg, 0.134 mmol) in dimethylformamide (0.5 mL) was added and stirred for a further 48 hours. The dimethylformamide was evaporated off and the residue partitioned between ethyl acetate (10 mL) and water (3 mL). The organic layer was separated, dried over anhydrous MgSO$_4$, filtered and evaporated to a buff coloured solid. This was triturated with a mixture of heptane and t-butyl methyl ether and the white solid was filtered off and dried to give 6-(2-cyanophenyl)-N-[1-(2,2,2-trifluoroethyl)piperidin-4-yl]nicotinamide (44 mg) 1H NMR (400 MHz, DMSO-d6) ppm 1.58-1.68 (m, 2H) 1.82-1.86 (m, 2H) 2.47-2.54 (m, 2H) 2.97 (m, 2H) 3.20 (q, J=10.25 Hz, 2H) 3.84 (m, 1H) 7.71 (td, J=6.2, 1.6 Hz, 1H) 7.87 (td, J=6.2, 1.6 Hz, 1H) 7.99 (m, 3H) 8.37 (dd, J=13.0, 2.4 Hz, 1H) 8.59 (d, J=7.4 Hz, 1H) 9.15 (dd, J=1.3, 0.8 Hz, 1H) LCMS 389 (M+1) ELSD 1.19 minutes.

EXAMPLE 625

6-(2-Hydroxyphenyl)-N-(1-pyrimidin-2-ylpiperidin-4-yl)nicotinamide

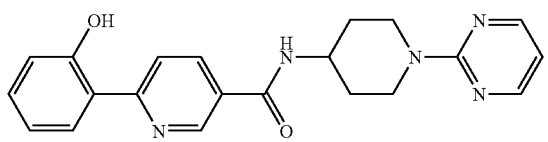

Step A: Preparation of methyl 6-(2-hydroxyphenyl)nicotinate

To a round bottom flask containing (2-hydroxyphenyl)boronic acid (1.37 g, 9.9 mmol) in 1,4-dioxane:water (8:1, 40 ml) was added methyl 6-chloronicotinate (1.71 g, 10.0 mmol), potassium carbonate (4.14 g, 30.0 mmol) and tetrakis (triphenylphosphine)palladium(0) (0.3 g, 0.26 mmol) and the resulting mixture stirred at 80° C. for 10 h, then stood at r.t. for 72 h. The solution was acidified to pH 1 with aqueous 2 N HCl and concentrated in vacuo to a volume of approximately 5 ml. This solution was then partitioned between saturated sodium hydrogen carbonate (30 ml) and dichloromethane:methanol (95:5, 150 ml). The layers were separated and the aqueous layer extracted with dichloromethane (50 ml). The organic layers were combined and dried with anhydrous MgSO₄, filtered and concentrated to afford a yellow solid. The solid was recrystallised from ethyl acetate/methanol to give the title compound as a yellow solid (1.14 g) (50%). $^{1}$H NMR (400 MHz, CDCl₃) ☐ ppm 9.16 (1H, s), 8.46-8.40 (1H, m), 8.02-7.96 (1H, m ), 7.86-7.80 (1H, m), 7.39-7.33 (1H, m), 7.10-7.04 (1H, m), 6.96-6.90 (1H, m), 4.00 (3H, s). LRMS: AP m/z 230 [M+H]⁺.

Step B: Preparation of 6-(2-hydroxyphenyl)nicotinic acid

Methyl 6-(2-hydroxyphenyl)nicotinate (1.13 g, 4.9 mmol) was dissolved in 1,4-dioxane (10.0 ml) and 1N aqueous NaOH (12.0 ml) added. The resulting solution was stirred at r.t. for 16 h. This solution was then acidified to pH 4-5 with glacial acetic acid and concentrated under reduced pressure to 5 ml volume. This solution was diluted with water (30 ml) and the resulting precipitate filtered, washed with water (10 ml) and dried to give the title compound as a yellow solid (0.77 g) (72%). $^{1}$H NMR (400 MHz, DMSO-d6) ☐ ppm 9.07 (1H, s), 8.39-8.34 (1H, m), 8.30-8.25 (1H, m), 8.06-7.99 (1H, m), 7.36-7.29 (1H, m), 6.96-6.89 (2H, m). LRMS: ES m/z 216 [M+H]⁺.

Step C: Preparation of 6-(2-hydroxyphenyl)-N-(1-pyrimidin-2-ylpiperidin-4-yl)nicotinamide 1-pyrimidin-2-ylpiperidin-4-amine (45 mg, 0.25 mmol) was added to a solution of 6-(2-hydroxyphenyl)nicotinic acid (50 mg, 0.23 mmol) in DMF (0.25 ml) and triethylamine (0.176 ml, 1.26 mmol). O-(1H-Benzotriazol-1-yl)-N,N,N',N'-tetramethyluronium hexafluorophosphate (125 mgs, 0.33 mmol) in DMF (0.5 ml) was then added and the reaction sealed. The reaction was shaken at 50° C. for 16 hours. The reaction was then evaporated to dryness in vacuo. Dichloromethane (2 ml) and saturated aqueous sodium hydrogen carbonate (0.5 ml) were added, the sealed reaction was shaken vigorously for 2 h. After this time the plates were opened and the biphasic mixture filtered through an Isolute SPE phase separation tube. The organic layer (filtrate) was evaporated to dryness in vacuo. DMSO (1 ml) was then added and the plate sealed and shaken at 50° C. until all the residue had dissolved then purified by reverse phase preparative HPLC using method B as defined below. R.T. 3.06 MS ES m/z 376 [M+H]⁺. This gave the title compound.

Examples 626-634, listed below, were similarly prepared according to the method described above for example 625, starting from 6-(2-hydroxyphenyl)nicotinic acid and the appropriate amine. HPLC purification was conducted according to Method A or Method B as indicated in the Table.

Method A:

| HPLC separation conditions: | | Preparative |
| --- | --- | --- |
| | Analytical (QC) | Acidic conditions |
| Column | XTerra C18 | Sunfire Prep C18 OBD |
| | 5 μm 4.6 × 50 mm | 5 μm 19 × 100 mm |
| Temperature | Ambient | Ambient |
| Detection | UV 225 nm - ELSD-MS | ELSD-MS |
| System/Data file | CTC - MUX1 | Fractionlynx 4 |
| Injection volume | 5 μL | 1000 μL |
| Flow rate | 1.5 mL/min | 18 mL/min |
| Mobile phase | A: H2O + 0.1% ammonia | A: H2O + 0.1% formic acid |
| | B: MeCN + 0.1% ammonia | B: MeCN + 0.1% formic acid |

| Gradient | Time (min) | % B | Time (min) | % B |
| --- | --- | --- | --- | --- |
| | 0 | 5 | 0-1.0 | 5 |
| | 0-3.0 | 5-95 | 1.0-7.0 | 5-98 |
| | 3.0-4.0 | 95 | 7.0-9.0 | 98 |
| | 4.0-4.1 | 95-5 | 9.0-9.10 | 98-5 |
| | 4.1-5.0 | 5 | 9.10-10 | 5 |

Method B:

| HPLC separation conditions: | | Preparative |
| --- | --- | --- |
| | Analytical (QC) | Basic conditions |
| Column | XTerra C18 | Xterra Prep MS C18 |
| | 5 μm 4.6 × 50 mm | 5 μm 19 × 100 mm |
| Temperature | Ambient | Ambient |
| Detection | UV 225 nm - ELSD-MS | ELSD-MS |
| System/Data file | CTC - MUX1 | Fractionlynx 4 |
| Injection volume | 5 μL | 1000 μL |
| Flow rate | 1.5 mL/min | 18 mL/min |
| Mobile phase | A: H2O + 0.1% ammonia | A: H2O + 0.1% DEA |
| | B: MeCN + 0.1% ammonia | B: MeCN + 0.1% DEA |

| Gradient | Time (min) | % B | Time (min) | % B |
| --- | --- | --- | --- | --- |
| | 0 | 5 | 0-1.0 | 5 |
| | 0-3.0 | 5-95 | 1.0-7.0 | 5-98 |
| | 3.0-4.0 | 95 | 7.0-9.0 | 98 |
| | 4.0-4.1 | 95-5 | 9.0-9.10 | 98-5 |
| | 4.1-5.0 | 5 | 9.10-10 | 5 |

| Example | Q¹ | HPLC Method | Data |
| --- | --- | --- | --- |
| 626 | CF₃-C(F)(F)- group | B | R.T. 3.06<br>ES m/z 376 [M + H]⁺ |
| 627 | tert-butyl C(=O) group | A | R.T. 3.06<br>ES m/z 382 [M + H]⁺ |
| 628 | ethyl-O-C(=O) group | A | R.T. 3.12<br>ES m/z 370 [M + H]⁺ |
| 629 | cyclopropyl group | B | R.T. 3.17<br>ES m/z 352 [M + H]⁺ |

-continued

| Example | Q¹ | HPLC Method | Data |
|---|---|---|---|
| 630 |  | B | R.T. 2.84<br>ES m/z 356 [M + H]⁺ |
| 631 | 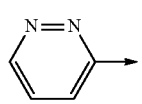 | B | R.T. 3.14<br>ES m/z 340 [M + H]⁺ |
| 632 | 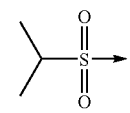 | B | R.T. 2.75<br>ES m/z 376 [M + H]⁺ |
| 633 | 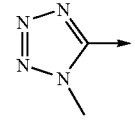 | A | R.T. 3.20<br>ES m/z 404 [M + H]⁺ |
| 634 | 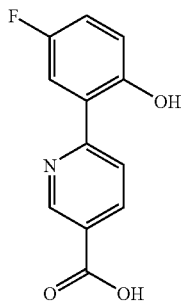 | A | R.T. 2.77<br>ES m/z 380 [M + H]⁺ |

Preparation of
6-(5-fluoro-2-hydroxyphenyl)nicotinic acid

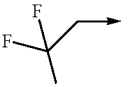

Step A: Methyl
6-(5-fluoro-2-hydroxyphenyl)nicotinate

To a degassed mixture of 1,4-dioxane:water (4:1, 15 mls) was added (5-fluoro-2-hydroxyphenyl)boronic acid (0.781 g, 5.0 mmol), methyl 6-chloronicotinate (0.86 g, 5.0 mmol), potassium carbonate (2.08 g, 15.0 mmol) and tetrakis(triphenylphosphine)palladium(0) (0.29 g, 0.05 mmol) and the resulting mixture stirred at 80° C. for 2 h. After this time additional tetrakis(triphenylphosphine)palladium(0) (0.29 g, 0.05 mmol) was added and then heating continued at 80° C. for 3 h. The mixture was then stirred at room temperature overnight. The solvent was evaporated in vacuo and the residue suspended in ethyl acetate (50 ml). The suspension was filtered through a plug of arbocel and the filtrate concentrated in vacuo. The resulting residue was dissolved in ethyl acetate (100 ml) and washed with saturated aqueous sodium carbonate (3×100 ml). The aqueous washings were combined and extracted with ethyl acetate (3×50 ml). The ethyl acetate layers were combined, dried with anhydrous MgSO₄ and concentrated in vacuo to afford a solid which was recrystallised from dichloromethane/heptane to afford the title compound as a yellow solid (0.71 g) (57%). ¹H NMR (400 MHz, CDCl₃) □ ppm 9.14 (1H, s), 8.46-8.40 (1H, m), 7.91-7.86 (1H, m) 7.53-7.46 (1H, m), 7.11-7.03 (1H, m), 7.02-6.96 (1H, m), 3.99 (3H, s). LRMS: AP m/z 248 [M+H]⁺.

Step B: 6-(5-Fluoro-2-hydroxyphenyl)nicotinic acid methyl 6-(5-fluoro-2-hydroxyphenyl)nicotinate (1.47 g, 6.0 mmol) was dissolved in MeOH (35 ml) and cooled to 0° C. Lithium hydroxide (0.71 g, 30.0 mmol) was then added and the mixture stirred at 0° C. for 0.5 h. The mixture was then allowed to warm to room temperature. Additional lithium hydroxide (0.43 g, 18.0 mmol) was added and the allowed to stir at room temperature for 72 h. The mixture was then concentrated in vacuo and the resulting yellow solid dissolved in water (150 ml). Acidified to pH 1 by addition of 1 N aqueous HCl and the resulting precipitate was filtered and washed with 0.5 M aqueous HCl to afford the title compound as a yellow powder (1.15 g) (72%). ¹H NMR (400 MHz, DMSO-d6) □ ppm 9.11 (1H, s), 8.42-8.28 (2H, m) 7.94-7.84 (1H, m), 7.26-7.15 (1H, m), 7.02-6.92 (1H, m). LRMS: ES m/z 234 [M+H]⁺.

Examples 635-644, listed below, were similarly prepared according to the method described above for example 625, starting from 6-(5-fluoro-2-hydroxyphenyl)nicotinic acid and the appropriate amine. HPLC purification was conducted according to Method A or Method B (see above) as indicated in the Table.

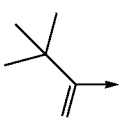

| Example | Q | HPLC method | Data |
|---|---|---|---|
| 635 | 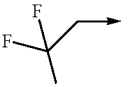 | B | R.T. 3.29<br>ES m/z 398 [M + H]⁺ |
| 636 | 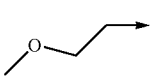 | B | R.T. 3.42<br>ES m/z 400 [M + H]⁺ |
| 637 | 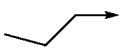 | B | R.T. 2.37<br>ES m/z 374 [M + H]⁺ |
| 638 | 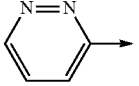 | B | R.T. 2.30<br>ES m/z 358 [M + H]⁺ |
| 639 | 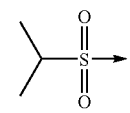 | B | R.T. 2.38<br>ES m/z 394 [M + H]⁺ |

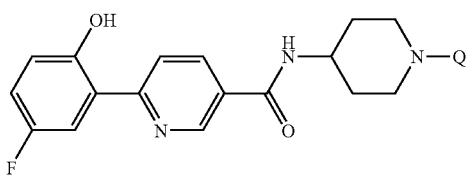

| Example | Q | HPLC method | Data |
|---|---|---|---|
| 640 | (propyl) | B | R.T. 2.29<br>ES m/z 344 [M + H]+ |
| 641 | (cyclopropylmethyl) | B | R.T. 2.36<br>ES m/z 370 [M + H]+ |
| 642 | (isopropylsulfonyl) | A | R.T. 3.43<br>ES m/z 422 [M + H]+ |
| 643 | (1-methyltetrazol-5-yl) | A | R.T. 3.07<br>ES m/z 398 [M + H]+ |
| 644 | (pyrimidin-2-yl) | A | R.T. 3.36<br>ES m/z 394 [M + H]+ |

The following specific compounds also fall within the scope of formula (I):

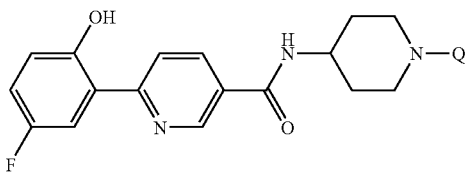

EXAMPLE 645

Q=(CH₃)NHCO—

EXAMPLE 646

Q=CH₃CH₂OCO—

EXAMPLE 647

Q=(CH₃CH₂)₂CH—

Further examples of compounds that are useful according to the invention are:

EXAMPLE 648 ethyl (3R,4S)-4-({[6-(3-fluorophenyl)pyridin-3-yl]carbonyl}amino)-3-methylpiperidine-1-carboxylate; and

EXAMPLE 649

N-(1-ethyl-7-methyl-1,2,3,4-tetrahydro-1,8-naphthyridin-4-yl)-6-(3-fluorophenyl)nicotinamide.

EXAMPLE 650

6-(3-Fluorophenyl)-N-(2-oxo-1,2,3,4-tetrahydro-quinolin-4-yl)nicotinamide

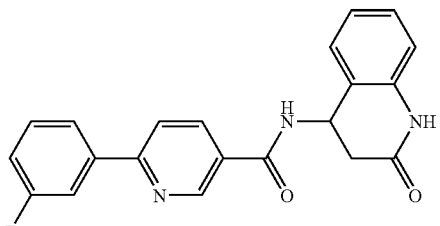

This compound was made using a method analogous to those described above. 1H NMR (400 MHz, DMSO-d6) □ ppm 2.68-2.78 (m, 2H) 5.34-5.42 (m, 1H) 6.89-7.02 (m, 2H) 7.18-7.34 (m, 3H) 7.52-7.60 (m, 1H) 7.90-8.02 (m, 2H) 8.13 (dd, 1H) 8.33 (dd, 1H) 9.11 (d, J=2.01 Hz, 2 H) 10.21 (s, 1H). MS calc (M+H)=362.13, obs (M+H)=362.13.

EXAMPLE 651

6-(3-Fluorophenyl)-N-((1R,5S,6S)-3-(2,2,2-trifluoroethyl)-3-aza-bicyclo[3.1.0]hexan-6-yl)nicotinamide

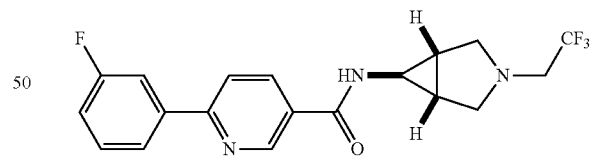

To a solution of N-((1R,5S,6S)-3-aza-bicyclo[3.1.0]hexan-6-yl)-6-(3-fluorophenyl)nicotinamide (40 mg, 0.13 mmoL) in toluene (2 mL) was added 2,2,2-trifluoroethyl-trichloromethane suflonate (45.4 mg, 0.16 mmol) and TEA (0.06 mL, 0.40 mmol). The reaction mixture was heated to reflux for 4 hrs and then cooled to room temperature and the solvent removed. The residue was taken up into DMSO and purified by RP-HPLC to give the product, 6-(3-fluorophenyl)-N-((1R,5S,6S)-3-(2,2,2-trifluoroethyl)-3-aza-bicyclo [3.1.0]hexan-6-yl)nicotinamide (20 mg, 39%). HRMS (M+H) expected 380.1386, 380.1538 observed. 1H NMR (400 MHz, DMSO-d6) □ ppm 1.19 (s, 1H) 1.71 (br. s., 1H) 2.46 (br. s., 1H) 2.59 (br. s., 1H) 2.70 (br. s., 1H) 3.02 (br. s., 1H) 3.17 (br. s., 4H) 3.40 (br. s., 2H) 7.28-7.34 (m, 1H) 7.54 (br. s., 1H) 7.97 (br. s., 1H) 8.13 (br. s., 1H) 8.24 (br. s., 1H).

EXAMPLE 652

Tert-butyl(1R,5S,6s)-6-({[6-(3-fluorophenylpyridine-3-yl]carbonyl}amino)3-azabicyclo[3.1.0]hexane-3-carboxylate

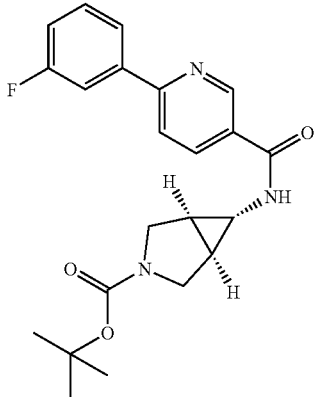

6-(3-Fluorophenyl)nicotinic acid (1.00 g, 4.60 mmol) was dissolved in dimethylformamide (5 mL) and 1,1'-carbonylbis(1H-imidazole) (746 mg, 4.60 mmol) was added and the reaction was stirred at room temperature for 1.5 hours. Tert-butyl(1R,5S,6s)-6-amino-3-azabicyclo[3.1.0]hexane-3-carboxylate (913 mg, 4.60 mmol) which can be prepared by the method of de Meijere, Chem. Eur. J. 2002, 8, No. 16, 3789-3801 was then added and the reaction stirred at room temperature overnight. The solvent was evaporated off and the residue partitioned between ethyl acetate (20 mL) and water (5 mL). The organic layer was separated and dried over anhydrous MgSO$_4$, filtered and evaporated to orange oil which crystallised on standing. The solid was triturated with tert-butyl methyl ether and the pale buff coloured solid was filtered off and dried to give tert-butyl(1R,5S,6s)-6-({[6-(3-fluorophenylpyridine-3-yl]carbonyl}amino)3-azabicyclo[3.1.0]hexane-3-carboxylate (1.13 g) $^1$H NMR (400 MHz, CDCl$_3$) ppm 1.46 (s, 9H) 1.84 (m, 2H) 2.67 (m, 1H) 3.46 (t, J=9.7 Hz, 2H) 3.79 (m, 2H) 6.30 (s, 1H) 7.16 (m, 1H) 7.47 (m, 1H) 7.80 (m, 3H) 8.18 (dd, J=5.8, 2.4 Hz, 1H) 8.99 (dd, J=1.6, 0.7 Hz, 1H).

EXAMPLE 653

N-[(1R,5S,6s)-3-azabicyclo[3.1.0]hex-6-yl]-6-(3-fluorophenyl)nicotinamide di-hydrochloride

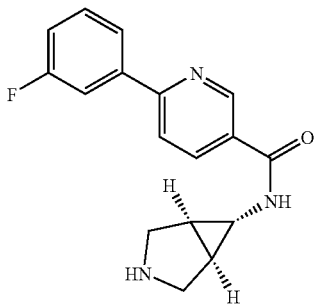

Tert-butyl(1R,5S,6s)-6-({[6-(3-fluorophenylpyridine-3-yl]carbonyl}amino)3-azabicyclo[3.1.0]hexane-3-carboxylate (900 mg, 2.26 mmol) was dissolved in methanol (15 mL) and a 4M solution of HCl in 1,4,dioxane (5.66 mL) was added and the reaction stirred at room temperature for 48 hours. The solvent was evaporated off and the residue triturated with a mixture of tert-butyl methyl ether and methanol in a ratio of approximately 3:1. The buff coloured solid was filtered off and dried to give the product N-[(1R,5S,6s)-3-azabicyclo[3.1.0]hex-6-yl]-6-(3-fluorophenyl)nicotinamide dihydrochloride as a buff coloured solid (720 mg) $^1$H NMR (400 MHz, DMSO-d6) ppm 3.09 (m, 1H) 3.40 (m, 4H) 7.35 (m, 1H) 7.59 (m, 1H) 8.01 (m, 2H), 8.17 (dd, J=1.5, 0.8 Hz, 1H) 8.31 (dd, J=7.7, 1.3 Hz, 1H) 8.91 (d, J=3.9 Hz, 1H) 9.10 (m, 2H) 9.60 (m, 2H).

EXAMPLE 654

N-[(1R,5S,6s)-3-acetyl-3-azabicyclo[3.1.0]hex-6-yl]-6-(3-fluorophenyl)nicotinamide

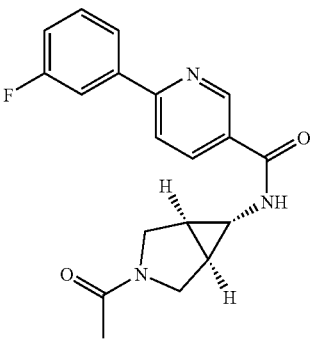

N-[(1R,5S,6s)-3-azabicyclo[3.1.0]hex-6-yl]-6-(3-fluorophenyl)nicotinamide hydrochloride(100 mg, 0.270 mmol) was suspended in dichloromethane (5 mL) and N-ethyl-N-isopropylpropan-2-amine (0.165 mL, 0.165 mL) was added. The reaction mixture was cooled in ice and then acetyl chloride (0.023 mL, 0.324 mmol) was added and the reaction stirred with cooling for 15 minutes and then at room temperature overnight. Further acetyl chloride (0.006 mL, 0.084 mmol) was added and stirred at room temperature for 2 hours. The reaction was diluted with dichloromethane (5 mL) and washed with water (5 mL). The organic layer was separated off and dried over anhydrous MgSO$_4$, filtered and evaporated to a white solid. This was triturated with tert-butyl methyl ether and the solid filtered off and dried to give N-[(1R,5S,6s)-3-acetyl-3-azabicyclo[3.1.0]hex-6-yl]-6-(3-fluorophenyl)nicotinamide as a white solid (72 mg) LCMS 340 (M+1) ELSD 1.26 minutes $^1$H NMR (400 MHz, DMSO-d6) ppm 1.86 (m, 1H) 1.94 (m, 4H) 2.61 (m, 1H) 3.86 (m, 1H) 3.67 (m, 3H) 7.35 (td, J=10.0, 3.5 Hz, 1H) 7.59 (m, 1H) 8.00 (m, 2H) 8.17 (dd, J=9.0, 0.8 Hz, 1H) 8.28 (dd, J=5.8, 2.4 Hz, 1H) 8.01 (d, J=3.8 Hz, 1H) 9.08 (d, J=1.5 Hz, 1H).

EXAMPLE 655

6-(3-Fluorophenyl)-N-[1R,5S,6S)-3-propyl-3-azabicyclo[3.1.0]hex-6-yl]nicotinamide

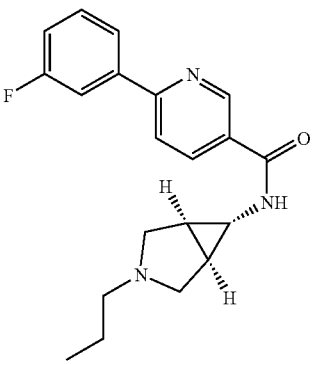

N-[(1R,5S,6s)-3-azabicyclo[3.1.0]hex-6-yl]-6-(3-fluorophenyl)nicotinamide di-hydrochloride (100 mg, 0.270 mmol), potassium carbonate (130 mg, 0.945 mmol) and 1-iodopropane (0.029 mL, 0.0297 mmol) were added to 2-propanol and the mixture heated at 55° C. overnight in a reactivial™. Further 1-iodopropane (0.029 mL, 0.0297 mmol) was added and heated at 70° C. for 20 hours. The reaction was cooled to room temperature and partitioned between ethyl acetate (10 mL) and water (5 mL). The organic layer was separated, dried over anhydrous MgSO$_4$, filtered and evaporated to a white solid. This was triturated with tert-butyl methyl ether and the solid filtered off and dried to give 6-(3-fluorophenyl)-N-[1R,5S,6s)-3-propyl-3-azabicyclo[3.1.0]hex-6-yl]nicotinamide as a white solid (43 mg) LCMS 340 (M+1) ELSD 0.90 minutes $^1$H NMR (400 MHz, DMSO-d6) ppm 0.87 (t, J=7.4 Hz, 3H) 1.43 (m, 2H) 1.66 (m, 2H) 2.33 (q, J=7.4 Hz, 4H) 3.09 (m, 3H) 7.34 (m, 1H) 7.59 (m, 1H) 7.97 (m, 1H) 7.99 (m, 1H) 8.14 (dd, J=7.5, 0.7 Hz, 1H) 8.26 (dd, J=6.2, 0.7 Hz, 1H) 8.61 (d, J=4.7 Hz, 1H) 9.06 (d, J=1.1 Hz, 1H).

EXAMPLE 656

6-(3-Fluorophenyl)-N-[1R,5S,6s)-3-(isopropylsulfonyl)-3-azabicyclo[3.1.0]hex-6-yl]nicotinamide

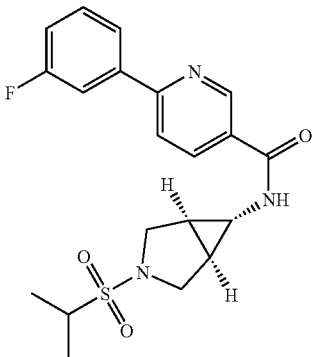

N-[(1R,5S,6s)-3-azabicyclo[3.1.0]hex-6-yl]-6-(3-fluorophenyl)nicotinamide di-hydrochloride (100 mg, 0.270 mmol) and pyridine (0.076 mL, 0.945 mmol) were added to dichloromethane (5 mL) and the reaction mixture cooled in ice. Propane-2-sulfonyl chloride (0.036 mL, 0.324 mmol) was added and the reaction stirred for 30 minutes with cooling and then at room temperature overnight. After this time the dichloromethane was evaporated off and pyridine (2 mL) was added along with further propane-2-sulfonyl chloride (0.036 mL, 0.324 mmol) and the resulting mixture stirred at room temperature overnight. Further propane-2-sulfonyl chloride (0.036 mL, 0.324 mmol) was added and stirred at room temperature for 24 hours. The pyridine was evaporated off and the residue was partitioned between ethyl acetate (10 mL) and dilute sodium bicarbonate solution (5 mL), some insoluble material was filtered off at the interface and then the organic layer was evaporated to a bright pink solid. This was purified, giving 6-(3-fluorophenyl)-N-[1R,5S,6s)-3-(isopropylsulfonyl)-3-azabicyclo[3.1.0]hex-6-yl]nicotinamide (17.6 mg) LCMS Method A (acidic conditions) RT 2.97 (100% area) min ES m/z 404 [M+H]$^+$.

Biological Data
Fluorescence Intensity h-PGDSTBA Enzyme Assay

Prostaglandin D Synthase (PGDS) converts the substrate prostaglandin H$_2$ (PGH$_2$) to prostaglandin D$_2$. The depletion of PGH$_2$ was measured via an Fe(II) reduction of the remaining PGH$_2$ to malondialdehyde (MDA) and 12-HHT. The enzyme assay is based on the quantitative formation of a fluorescent complex from the non-fluorescent compounds MDA and 2-thiobarbituric acid (TBA), substantially as described in U.S. patent application publication US-2004/152148 by Lambalot.

The enzyme assay (31 μls) contained 100 mM Tris base pH 8.0, 100 μM MgCl$_2$, 0.1 mg/ml IgG Rabbit serum, 5.0 μM PGH2 (Cayman; ethanol solution, #17020), 2.5 mM L-Glutathione (Sigma; reduced form #G4251), 1:175,000 human recombinant H-PGDS (from 1 mg/ml), 0.5% DMSO and inhibitor (varying concentration). Three μls of diluted inhibitor (dissolved in DMSO) was plated into a 384-well assay plate followed by a 25 μl addition of an enzyme solution containing h-PGDS, Tris, MgCl$_2$, IgG and L-Glutathione. After preincubation of inhibitor and enzyme solution for 10 minutes at room temperature, the reaction was initiated with a 3 μl addition of substrate solution in 10 mM HCl. The reaction was terminated after 42 second by the addition (3 μl) of stop buffer containing FeCl$_2$ and citric acid. After addition of 45.5 μls of TBA plates were heated for one hour in a 70° C. oven. Plates were cooled at room temperature overnight and read on a plate reader the next day with excitation @ 530 nm and emission @ 565 nm. IC$_{50}$'s of inhibitors were calculated with a 4-parameter fit using 11 inhibitor concentrations in duplicate with 3-fold serial dilutions. Controls on each plate included no inhibitor (zero % effect) and an inhibitor 10-fold in excess of its' IC$_{50}$ (100% effect). The highest inhibitor concentration tested was typically 1 μM.

Examples 623 onwards were tested in a slightly modified assay: The enzyme assay (30 μls during biological process) contained 100 mM Trizma pH 8.0, 100 μM MgCl$_2$, 0.1 mg/ml IgG Rabbit serum, 5.0 μM PGH2 (Cayman; ethanol solution, #17020), 2.5 mM L-Glutathione (Sigma; reduced form #G4251), 1:40,000 human recombinant H-PGDS (from 1 mg/ml), 0.5% DMSO and inhibitor (varying concentration). 3 μls of diluted inhibitor (dissolved in DMSO) was plated into a 384-well assay plate followed by a 24 μl addition of an enzyme solution containing h-PGDS, Trizma, MgCl$_2$, IgG and L-Glutathione. After pre-incubation of inhibitor and enzyme solution for 10 minutes at room temperature, the reaction was initiated with a 3 μl addition of substrate solution in 10 mM HCl. The reaction was terminated after 40 second by the addition of 3 μl stop buffer containing FeCl$_2$ and citric acid. After addition of 45 μl of TBA plates were heated for one hour in a 70° C. oven. Plates were cooled at room temperature overnight and read on a plate reader the next day with excitation @ 530 nm and emission @ 560 nm. IC$_{50}$'s of inhibitors were calculated with a 4-parameter fit using 11 inhibitor concentrations in duplicate with 1/2 log serial dilutions. Controls on each plate included no inhibitor (zero % effect) and an inhibitor 500-fold in excess of its' IC$_{50}$ (100% effect). The highest inhibitor concentration tested was typically 10 μM.

Table II shows the IC$_{50}$ values thus obtained.

TABLE II

| Example | IC$_{50}$ (nM) |
| --- | --- |
| 1 | 0.204 |
| 2 | 0.852 |
| 3 | 0.343 |

TABLE II-continued

| Example | IC$_{50}$ (nM) |
|---|---|
| 4 | 2.58 |
| 5 | 0.665 |
| 6 | 0.377 |
| 7 | 0.351 |
| 8 | 1.57 |
| 9 | 23.6 |
| 10 | 78.4 |
| 11 | 39.4 |
| 12 | 694 |
| 13 | 58 |
| 14 | 4.29 |
| 15 | 2.91 |
| 16 | 146 |
| 17 | 11.7 |
| 18 | 3.94 |
| 19 | 36.2 |
| 20 | 1000 |
| 21 | 0.898 |
| 22 | 73.3 |
| 23 | 1.72 |
| 24 | 2.64 |
| 25 | 7.66 |
| 27 | 19.1 |
| 28 | 1.72 |
| 29 | 0.946 |
| 30 | 3.79 |
| 31 | 19.9 |
| 32 | 0.387 |
| 33 | 2.41 |
| 34 | 1.85 |
| 35 | 2.95 |
| 36 | 7.11 |
| 37 | 0.478 |
| 38 | 1.04 |
| 39 | 0.924 |
| 40 | 0.556 |
| 41 | 0.893 |
| 42 | 8.58 |
| 43 | 2.18 |
| 44 | 1.36 |
| 45 | 0.773 |
| 46 | 1.73 |
| 47 | 2.92 |
| 48 | 2.9 |
| 49 | 0.619 |
| 50 | 0.681 |
| 51 | 0.266 |
| 52 | 0.332 |
| 53 | 1.03 |
| 54 | 1.31 |
| 55 | 1.67 |
| 56 | 12.8 |
| 57 | 0.285 |
| 58 | 8.25 |
| 59 | 0.822 |
| 60 | 0.593 |
| 61 | 0.365 |
| 62 | 3.33 |
| 63 | 0.183 |
| 64 | 0.246 |
| 65 | 0.354 |
| 66 | 0.627 |
| 67 | 0.955 |
| 68 | 0.361 |
| 69 | 1.21 |
| 70 | 3.26 |
| 71 | 2.18 |
| 72 | 4.97 |
| 73 | 2.89 |
| 74 | 0.293 |
| 75 | 0.314 |
| 76 | 1.35 |
| 77 | 0.425 |
| 78 | 0.148 |
| 79 | 2.28 |
| 80 | 0.408 |
| 81 | 0.947 |
| 82 | 1.05 |
| 83 | 0.37 |
| 84 | 0.635 |
| 85 | 0.72 |
| 86 | 0.876 |
| 87 | 0.538 |
| 88 | 0.694 |
| 89 | 0.365 |
| 90 | 0.305 |
| 91 | 0.603 |
| 92 | 5.15 |
| 93 | 17.9 |
| 94 | 0.426 |
| 95 | 0.764 |
| 96 | 1.19 |
| 97 | 0.319 |
| 98 | 3.7 |
| 99 | 2.08 |
| 100 | 1.53 |
| 101 | 1.4 |
| 102 | 0.943 |
| 103 | 2.15 |
| 104 | 3.18 |
| 105 | 0.655 |
| 106 | 0.873 |
| 107 | 0.804 |
| 108 | 1.29 |
| 109 | 2.74 |
| 110 | 1.61 |
| 111 | 1.62 |
| 112 | 1.87 |
| 113 | 0.263 |
| 114 | 2.3 |
| 115 | 0.241 |
| 116 | 2.56 |
| 117 | 0.429 |
| 118 | 0.89 |
| 119 | 3.74 |
| 120 | 3.49 |
| 121 | 1.21 |
| 122 | 0.168 |
| 123 | 4.66 |
| 124 | 0.345 |
| 125 | 0.176 |
| 126 | 0.656 |
| 127 | 4.01 |
| 128 | 0.687 |
| 129 | 6.24 |
| 130 | 4.57 |
| 131 | 0.463 |
| 132 | 0.365 |
| 133 | 0.395 |
| 134 | 1.81 |
| 135 | 1.47 |
| 136 | 5.12 |
| 137 | 1.41 |
| 138 | 1.23 |
| 139 | 0.222 |
| 140 | 0.628 |
| 141 | 0.721 |
| 142 | 0.33 |
| 143 | 0.688 |
| 144 | 9.56 |
| 145 | 5.94 |
| 146 | 1.55 |
| 147 | 0.737 |
| 148 | 1.75 |
| 149 | 1.82 |
| 150 | 1.8 |
| 151 | 0.519 |
| 152 | 3.35 |
| 153 | 1.89 |
| 154 | 0.96 |
| 155 | 2.3 |
| 156 | 3.15 |
| 157 | 0.678 |
| 158 | 1.58 |
| 159 | 1.59 |
| 160 | 0.483 |

TABLE II-continued

| Example | IC$_{50}$ (nM) |
|---|---|
| 161 | 3.85 |
| 162 | 1.1 |
| 163 | 14.5 |
| 164 | 0.422 |
| 165 | 1.16 |
| 166 | 3.44 |
| 167 | 3.13 |
| 168 | 2.53 |
| 169 | 23.2 |
| 170 | 1.77 |
| 171 | 1.41 |
| 172 | 35 |
| 173 | 16 |
| 174 | 8.97 |
| 175 | 5.4 |
| 176 | 0.759 |
| 177 | 68.4 |
| 178 | 0.735 |
| 179 | 2.26 |
| 180 | 0.372 |
| 181 | 3.4 |
| 182 | 0.424 |
| 183 | 1.12 |
| 184 | 3.67 |
| 185 | 11 |
| 186 | 1.79 |
| 187 | 2.59 |
| 188 | 2.25 |
| 189 | 0.502 |
| 190 | 1.83 |
| 191 | 0.171 |
| 192 | 0.701 |
| 193 | 0.768 |
| 194 | 3.5 |
| 195 | 0.194 |
| 196 | 1.35 |
| 197 | 0.578 |
| 198 | 1.04 |
| 199 | 2.7 |
| 200 | 1.61 |
| 201 | 1.93 |
| 202 | 1.17 |
| 203 | 2.17 |
| 204 | 0.067 |
| 205 | 0.238 |
| 206 | 1.84 |
| 207 | 1.59 |
| 208 | 5.98 |
| 209 | 1.37 |
| 210 | 0.46 |
| 211 | 0.453 |
| 212 | 1.4 |
| 213 | 0.469 |
| 214 | 5.55 |
| 215 | 0.38 |
| 216 | 0.36 |
| 217 | 1.51 |
| 218 | 0.448 |
| 219 | 0.749 |
| 220 | 2.42 |
| 221 | 0.446 |
| 222 | 6.64 |
| 223 | 0.928 |
| 224 | 0.342 |
| 225 | 2.48 |
| 226 | 1.42 |
| 227 | 0.815 |
| 228 | 2.5 |
| 229 | 0.509 |
| 230 | 0.53 |
| 231 | 0.552 |
| 232 | 2.71 |
| 233 | 0.352 |
| 234 | 1.65 |
| 235 | 1.98 |
| 236 | 0.577 |
| 237 | 0.698 |
| 238 | 0.135 |
| 239 | 0.245 |
| 240 | 0.181 |
| 241 | 2.19 |
| 242 | 0.781 |
| 243 | 1.03 |
| 244 | 0.288 |
| 245 | 1.2 |
| 246 | 1.97 |
| 247 | 0.653 |
| 248 | 1.05 |
| 249 | 1.17 |
| 250 | 0.409 |
| 251 | 0.623 |
| 252 | 0.865 |
| 253 | 1.45 |
| 254 | 1.68 |
| 255 | 0.738 |
| 256 | 0.397 |
| 257 | 0.58 |
| 258 | 1.24 |
| 259 | 1.68 |
| 260 | 0.578 |
| 261 | 1.48 |
| 262 | 3.86 |
| 263 | 1.16 |
| 264 | 2 |
| 265 | 4.29 |
| 266 | 2.15 |
| 267 | 0.994 |
| 268 | 8.08 |
| 269 | 3.5 |
| 270 | 0.507 |
| 271 | 5.62 |
| 272 | 0.816 |
| 273 | 1.11 |
| 274 | 2.57 |
| 275 | 5.49 |
| 276 | 0.743 |
| 277 | 5.72 |
| 278 | 5.01 |
| 279 | 4.17 |
| 280 | 0.851 |
| 281 | 1.8 |
| 282 | 0.629 |
| 283 | 0.5 |
| 284 | 1.43 |
| 285 | 1.53 |
| 286 | 1.21 |
| 287 | 3 |
| 288 | 1.25 |
| 289 | 2.09 |
| 290 | 0.843 |
| 291 | 1.17 |
| 292 | 0.465 |
| 293 | 0.592 |
| 294 | 1.76 |
| 295 | 0.506 |
| 296 | 1.4 |
| 297 | 1.25 |
| 298 | 0.939 |
| 299 | 0.308 |
| 300 | 0.362 |
| 301 | 1.16 |
| 302 | 0.636 |
| 303 | 0.662 |
| 304 | 2.11 |
| 305 | 2.7 |
| 306 | 2.71 |
| 307 | 0.784 |
| 308 | 2.03 |
| 309 | 4.32 |
| 310 | 4.78 |
| 311 | 1.72 |
| 312 | 1.08 |
| 313 | 2.15 |
| 314 | 0.24 |
| 315 | 0.549 |
| 316 | 1.36 |

TABLE II-continued

| Example | IC$_{50}$ (nM) |
|---|---|
| 317 | 2.07 |
| 318 | 1.18 |
| 319 | 0.384 |
| 320 | 2.34 |
| 321 | 0.365 |
| 322 | 0.748 |
| 323 | 0.622 |
| 324 | 0.531 |
| 325 | 4.01 |
| 326 | 2.45 |
| 327 | 1.55 |
| 328 | 0.566 |
| 329 | 1.94 |
| 330 | 1.71 |
| 331 | 2.71 |
| 332 | 1.19 |
| 333 | 1.04 |
| 334 | 2.74 |
| 335 | 0.776 |
| 336 | 1.82 |
| 337 | 1.42 |
| 338 | 62.7 |
| 339 | 1.17 |
| 340 | 1.17 |
| 341 | 0.485 |
| 342 | 0.281 |
| 343 | 1.9 |
| 344 | 0.174 |
| 345 | 0.508 |
| 346 | 4.07 |
| 347 | 0.578 |
| 348 | 0.612 |
| 349 | 2.96 |
| 350 | 0.247 |
| 351 | 0.531 |
| 352 | 0.625 |
| 353 | 0.959 |
| 354 | 2.92 |
| 355 | 0.513 |
| 356 | 2 |
| 357 | 6.66 |
| 358 | 1.72 |
| 359 | 0.443 |
| 360 | 2.76 |
| 361 | 1.35 |
| 362 | 1.05 |
| 363 | 0.299 |
| 364 | 4.03 |
| 365 | 0.13 |
| 366 | 2.42 |
| 367 | 0.707 |
| 368 | 2.03 |
| 369 | 1.36 |
| 370 | 0.456 |
| 371 | 0.438 |
| 372 | 0.981 |
| 373 | 2.36 |
| 374 | 2.99 |
| 375 | 0.667 |
| 376 | 0.876 |
| 377 | 0.491 |
| 378 | 1.41 |
| 379 | 1.43 |
| 380 | 1.25 |
| 381 | 0.0854 |
| 382 | 0.681 |
| 383 | 1.25 |
| 384 | 0.959 |
| 385 | 11.7 |
| 386 | 1.2 |
| 387 | 1.85 |
| 388 | 0.951 |
| 389 | 2.23 |
| 390 | 11.6 |
| 391 | 1.2 |
| 392 | 0.849 |
| 393 | 1.18 |
| 394 | 0.379 |
| 395 | 1.43 |
| 396 | 1.45 |
| 397 | 1.47 |
| 398 | 8.56 |
| 399 | 1.02 |
| 400 | 1.04 |
| 401 | 0.574 |
| 402 | 1.64 |
| 403 | 0.121 |
| 404 | 0.469 |
| 405 | 0.483 |
| 406 | 2.36 |
| 407 | 5.4 |
| 408 | 61.9 |
| 409 | 2.25 |
| 410 | 16.3 |
| 411 | 1.36 |
| 412 | 4.12 |
| 413 | 1000 |
| 414 | 0.35 |
| 415 | 1.96 |
| 416 | 1.68 |
| 417 | 1.1 |
| 418 | 0.427 |
| 419 | 1.03 |
| 420 | 3.4 |
| 421 | 1.34 |
| 422 | 2.53 |
| 423 | 0.931 |
| 424 | 1.3 |
| 425 | 2.81 |
| 426 | 5.53 |
| 427 | 0.656 |
| 428 | 0.926 |
| 429 | 1.12 |
| 430 | 1.2 |
| 431 | 0.822 |
| 432 | 0.962 |
| 433 | 0.401 |
| 434 | 1.51 |
| 435 | 0.908 |
| 436 | 0.885 |
| 437 | 3.52 |
| 438 | 0.417 |
| 439 | 0.762 |
| 440 | 1.96 |
| 441 | 2.58 |
| 442 | 2.78 |
| 443 | 1.59 |
| 444 | 0.135 |
| 445 | 4.24 |
| 446 | 0.891 |
| 447 | 1.1 |
| 448 | 2.45 |
| 449 | 2.8 |
| 450 | 2.05 |
| 451 | 0.88 |
| 452 | 0.724 |
| 453 | 1.42 |
| 454 | 0.82 |
| 455 | 1.34 |
| 456 | 2.05 |
| 457 | 0.76 |
| 458 | 1.78 |
| 459 | 0.721 |
| 460 | 1.28 |
| 461 | 0.239 |
| 462 | 0.264 |
| 463 | 0.385 |
| 464 | 1.02 |
| 465 | 0.881 |
| 466 | 1.49 |
| 467 | 0.257 |
| 468 | 0.375 |
| 469 | 0.855 |
| 470 | 4.14 |
| 471 | 2.68 |
| 472 | 0.491 |

TABLE II-continued

| Example | IC$_{50}$ (nM) |
|---|---|
| 473 | 2.36 |
| 474 | 1.44 |
| 475 | 4.07 |
| 476 | 0.935 |
| 477 | 4.04 |
| 478 | 2.01 |
| 479 | 0.421 |
| 480 | 2.69 |
| 481 | 2.45 |
| 482 | 2.39 |
| 483 | 3.58 |
| 484 | 2.68 |
| 485 | 2.77 |
| 486 | 2.32 |
| 487 | 0.372 |
| 488 | 0.489 |
| 489 | 1.18 |
| 490 | 0.601 |
| 491 | 2.4 |
| 492 | 0.285 |
| 493 | 1.1 |
| 494 | 0.817 |
| 495 | 0.409 |
| 496 | 0.569 |
| 497 | 1.06 |
| 498 | 0.3 |
| 499 | 1.64 |
| 500 | 0.633 |
| 501 | 0.432 |
| 502 | 1.99 |
| 503 | 2.7 |
| 504 | 2.84 |
| 505 | 0.418 |
| 506 | 1.25 |
| 507 | 0.551 |
| 508 | 0.551 |
| 509 | 0.665 |
| 510 | 2.74 |
| 511 | 1.09 |
| 512 | 0.391 |
| 513 | 0.363 |
| 514 | 0.348 |
| 515 | 1.1 |
| 516 | 2.2 |
| 517 | 0.41 |
| 518 | 0.96 |
| 519 | 0.445 |
| 520 | 1.93 |
| 521 | 556 |
| 522 | 6.54 |
| 523 | 217 |
| 524 | 1.76 |
| 525 | 14.8 |
| 526 | 76.3 |
| 527 | 2.84 |
| 528 | 2.49 |
| 529 | 2.5 |
| 530 | 2.71 |
| 531 | 1.15 |
| 532 | 1.3 |
| 533 | 2.42 |
| 534 | 0.234 |
| 535 | 2.11 |
| 536 | 1.75 |
| 537 | 2.68 |
| 538 | 1.94 |
| 539 | 2.71 |
| 540 | 1.99 |
| 541 | 0.951 |
| 542 | 1.68 |
| 543 | 3.27 |
| 544 | 1.27 |
| 545 | 2.65 |

TABLE II-continued

| Example | IC$_{50}$ (nM) |
|---|---|
| 546 | 2.83 |
| 547 | 1.14 |
| 548 | 2.07 |
| 549 | 2.26 |
| 550 | 2.38 |
| 551 | 1.32 |
| 552 | 2.37 |
| 553 | 1.78 |
| 554 | 1.72 |
| 555 | 0.928 |
| 556 | 0.364 |
| 557 | 6.56 |
| 558 | 0.345 |
| 559 | 10.6 |
| 560 | 0.641 |
| 561 | 1.14 |
| 562 | 1.74 |
| 563 | 0.981 |
| 564 | 1.09 |
| 565 | 1.05 |
| 566 | 1.82 |
| 567 | 0.867 |
| 568 | 0.649 |
| 569 | 2.13 |
| 570 | 1.41 |
| 571 | 1.04 |
| 572 | 5.25 |
| 573 | 1.35 |
| 574 | 1.24 |
| 575 | 2.24 |
| 576 | 0.561 |
| 577 | 1.48 |
| 578 | 3.1 |
| 579 | 1.05 |
| 580 | 0.35 |
| 581 | 0.69 |
| 582 | 1.22 |
| 583 | 1.05 |
| 584 | 1.38 |
| 585 | 0.734 |
| 586 | 0.787 |
| 587 | 1.19 |
| 588 | 0.621 |
| 589 | 33.3 |
| 590 | 0.74 |
| 591 | 5.57 |
| 592 | 2.44 |
| 593 | 2.0 |
| 594 | 2.7 |
| 595 | 1.06 |
| 596 | 1.93 |
| 597 | 0.85 |
| 598 | 3.79 |
| 599 | 2.92 |
| 600 | |
| 601 | 6.76 |
| 602 | 2.98 |
| 603 | 2.29 |
| 604 | 11.5 |
| 605 | 2.9 |
| 606 | 10.8 |
| 607 | 4.44 |
| 608 | |
| 609 | 5.43 |
| 610 | 6.92 |
| 611 | |
| 612 | 12 |
| 613 | 3.57 |
| 614 | 52.5 |
| 615 | 5.1 |
| 616 | 5.12 |
| 617 | 4.1 |
| 618 | 7.33 |
| 619 | 1.19 |
| 620 | 3.66 |
| 621 | 1.59 |
| 622 | 3.48 |
| 623 | 104 |

TABLE II-continued

| Example | IC$_{50}$ (nM) |
| --- | --- |
| 624 | 36 |
| 625 | 4.06 |
| 626 | 11.5 |
| 627 | 6.75 |
| 628 | 6.22 |
| 629 | 22.2 |
| 630 | 32.8 |
| 631 | 82.4 |
| 632 | 5.57 |
| 633 | 16.6 |
| 634 | 6.13 |
| 635 | 10.9 |
| 636 | 17.2 |
| 637 | 62.4 |
| 638 | 83.3 |
| 639 | 10000 |
| 640 | 129 |
| 641 | |
| 642 | 13.9 |
| 643 | 7.77 |
| 644 | |
| 645 | |
| 646 | |
| 647 | |
| 648 | |
| 649 | |
| 650 | 0.568 |
| 651 | 2.01 |
| 652 | |
| 653 | 177 |
| 654 | 33.8 |
| 655 | 66.8 |
| 656 | |
| 3a | 6.86 |
| 3b | 0.403 |

In vivo Assay—Anti-Asthmatic Effects in a Sheep Model of Asthma

A validated model of *A. suum* antigen-induced asthmatic response in conscious sheep was used to evaluate the pharmacokinetic properties, inhibition of antigen-induced early and late airway bronchoconstriction in the lung by compound (Abraham, W. M., et al., Am Rev Respir Dis 1991; 143:787-796).

Sheep used in these studies exhibit both early and late airway responses to inhalation challenge with *A. suum* antigen as well as antigen-induced airway hyper-responsiveness to inhaled carbachol. An aerosol of *A. suum* extract, generated using a disposable medical nebulizer (Raindrop®, Puritan Bennett) was delivered in at a tidal volume of 500 mL and a rate of 20 breaths/min.

A compound of Example 2 was delivered by i.v. infusion over the interval t=0-20 min prior to antigen challenge. A single dose of 1, 0.3 or 0.1 mg//kg was evaluated. Baseline and post-drug measurements of specific lung resistance ($R_L$) were obtained immediately prior to challenge (t=30 min) with *A. suum* antigen, immediately after challenge and then hourly from 1 to 6 h post challenge and on the half-hour from 6.5, 5-8 h post challenge. Measurements of $R_L$ were obtained 24 h post challenge, followed by the 24 h post-challenge dose-response curve for carbachol.

To determine the effect of the compound of Example 2 on antigen-induced airway hyper-responsiveness, measurements of $R_L$ were repeated immediately after inhalation of buffer and after each administration of 10 breaths of increasing concentrations of carbachol solution (0.25%, 0.5%, 1.0%, 2.0%, and 4.0% wt/vol). To assess airway responsiveness, the cumulative carbachol dose in breath units (BU) that increased $R_L$ 400% over the post-buffer value (i.e., PC$_{400}$) were calculated from the dose-response curve. One breath unit is defined as one breath of a 1% wt/vol carbachol solution. Measurements of PC$_{400}$ obtained after antigen were compared with those obtained before antigen challenge to determine if antigen challenge induced airway hyper-responsiveness.

The early airway response (0-2 h after allergen challenge) was not reduced but the late airway response (4-8 h after antigen challenge) was inhibited by approximately 60%.

The invention claimed is:

1. A compound of formula (I):

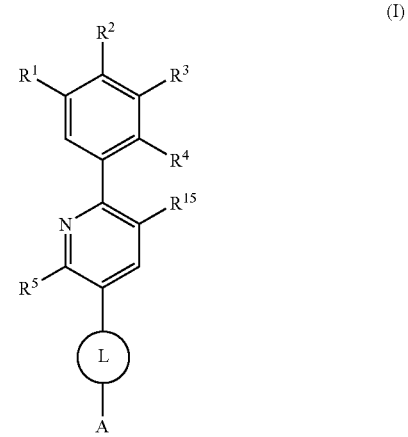

or a pharmaceutically acceptable salt thereof, wherein:

R$^1$, R$^3$ and R$^4$ are independently H, F, Cl, —CHF$_2$, —CF$_3$, —OH, —CH$_2$OH, —CH$_2$CH$_2$OH, —C≡N, —CH$_2$C≡N, —CH$_2$CH$_2$C≡N, C$_1$-C$_5$ alkyl, —C(O)OR$^{16}$, —NC(O)R$^{16}$, —NSO$_2$R$^{16}$, —C(O)R$^{16}$, or —OCH$_3$;

R$^2$ is H or F;

R$^5$ is H, —NH$_2$, —OH or —CH$_3$;

R$^{15}$ is H, F, Cl, —CH$_3$ or —OCH$_3$;

R$^{16}$ is C$_1$-C$_5$ alkyl;

L is —C(O)NH—, —NHC(O)— or —CH$_2$NHC(O)—;

A is:

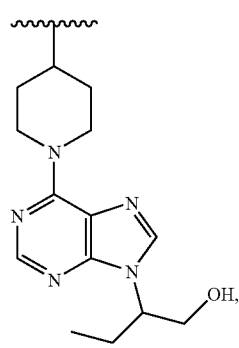 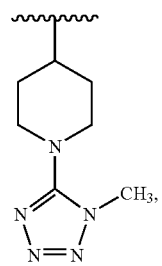

-continued

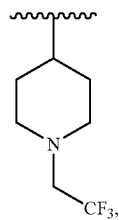 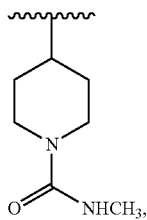

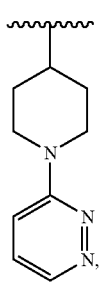 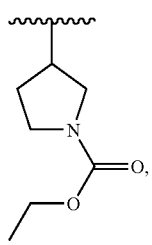 or

-continued

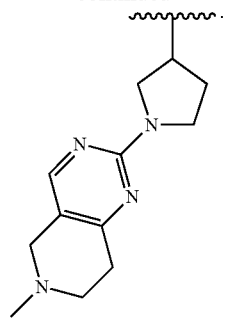

2. A compound of claim 1 wherein said compound is:
6-(3-fluorophenyl)-N-(1-{9-[1-(hydroxymethyl)propyl]-9H-purin-6-yl}piperidin-4-yl)nicotinamide; or 6-(3-fluorophenyl)-N-[1-(1-methyl-1H-tetrazol-5-yl)piperidin-4-yl]nicotinamide;
or a pharmaceutically acceptable salt thereof.

3. A pharmaceutical composition comprising a compound of claim 1, or a pharmaceutically acceptable salt thereof, and a pharmaceutically acceptable excipient.

4. A method of treating asthma in a subject in need of such treatment, which method comprises administering to said subject a therapeutically effective amount of a compound of claim 1, or a pharmaceutically acceptable salt thereof.

5. 6-(3-fluorophenyl)-N-[1-(1-methyl-1H-tetrazol-5-yl)piperidin-4-yl]nicotinamide.

6. 6-(3-Fluoro-phenyl)-N-[1-(2,2,2-trifluoro-ethyl)-piperidin-4-yl]-nicotinamide.

* * * * *